(12) United States Patent
Bihain

(10) Patent No.: US 8,288,091 B2
(45) Date of Patent: Oct. 16, 2012

(54) TRANSCRIPTION INFIDELITY, DETECTION AND USES THEREOF

(75) Inventor: Bernard Bihain, Nancy (FR)

(73) Assignee: Transmedi SA, Paris (FR)

( * ) Notice: Subject to any disclaimer, the term of this patent is extended or adjusted under 35 U.S.C. 154(b) by 234 days.

(21) Appl. No.: 12/374,431

(22) PCT Filed: Jul. 20, 2007

(86) PCT No.: PCT/EP2007/057541
§ 371 (c)(1),
(2), (4) Date: Mar. 18, 2009

(87) PCT Pub. No.: WO2008/009751
PCT Pub. Date: Jan. 24, 2008

(65) Prior Publication Data
US 2009/0317386 A1    Dec. 24, 2009

(30) Foreign Application Priority Data
Jul. 20, 2006    (EP) .................................... 06291176

(51) Int. Cl.
*C12Q 1/68*    (2006.01)
(52) U.S. Cl. ........................................................ 435/6
(58) Field of Classification Search .................. None
See application file for complete search history.

(56) References Cited

FOREIGN PATENT DOCUMENTS
WO    WO 01/40804    *    6/2001

OTHER PUBLICATIONS

Maas et al (PNAS, 2001, 98:14687-14692, IDS).*
Cappione et al (Am J Human Genetics, 1997; 60, 305-312, IDS).*
Khan et al (Clinical Cancer Research, 2000, 6:3499-3504).*
van Leeuwen et al (Science, 1998, 279:242-247).*
Ahrendt et al (PNAS, 1999, 96:7382-7387).*
Fischer, D. F. et al. "Disease-specific accumulation of mutant ubiquitin as a marker for proteasomal dysfunction in the brain" *FASEB J.*, 2003, pp. 2014-2024, vol. 17.
Gerez, L. et al. "Molecular misreading: the frequency of dinucleotide deletions in neuronal mRNAs for β-amyloid precursor protein and ubiquitin B" *Neurobiology of Aging*, 2005, pp. 145-155, vol. 26.
Hol, E. M. et al. "Frameshifted β-Amyloid Precursor Protein (APP[+1]) Is a Secretory Protein and the Level of APP[+1] in Cerebrospinal Fluid Is Linked to Alzheimer Pathology" *The Journal of Biological Chemistry*, Oct. 10, 2003, pp. 39637-39643, vol. 278, No. 41.
Laxminarayana, D. et al. "mRNA mutatations of type I protein kinase A regulatory subunit α in T lymphocytes of a subject with systemic lupus erythematosus" *International Immunology*, 2000, pp. 1521-1529, vol. 12, No. 11.

Van Den Hurk, W. H. et al. "Novel Frameshift Mutations near Short Simple Repeats" *The Journal of Biological Chemistry*, Apr. 13, 2001, pp. 11496-11498, vol. 276, No. 15.
Klimek-Tomczak, K. et al. "Editing of hnRNP K protein mRNA in colorectal adenocarcinoma and surrounding mucosa" *British Journal of Cancer*, 2006, pp. 586-592, vol. 94, XP-002411595.
Cappione, A. J. et al. "A Potential Role for NF1 mRNA Editing in the Pathogenesis of NF1 Tumors" *Am. J. Hum. Genet.*, 1997, pp. 305-312, vol. 60, XP-008072803.
Maas, S. et al. "Underediting of glutamate receptor GluR-B mRNA in malignant gliomas" PNAS, Dec. 4, 2001, pp. 14687-14692, vol. 98, No. 25, XP-002974829.
Mansfield, S. G. et al. "Repair of CFTR mRNA by spliceosome-mediated RNA trans-splicing" *Gene Therapy*, 2000, pp. 1885-1895, vol. 7, XP-000979769.
Eisenberg, E. et al. "Identification of RNA editing sites in the SNP database" *Nucleic Acids Research*, 2005, pp. 4612-4617, vol. 33, No. 14, XP-002411596.
Jeon, C. et al. "Fidelity of RNA polymerase II transcription controlled by elongation factor TFIIS" *Proc. Natl. Acad. Sci. USA*, Nov. 1996, pp. 13677-13682, vol. 93, XP-002411599.
Anant, S. et al. "Hydrolytic nucleoside and nucleotide deamination, and genetic instability: a possible link between RNA-editing enzymes and cancer?" *Trends in Molecular Medicine*, Apr. 2003, pp. 1471-4914, vol. 9, No. 4, XP-002411597.
Database EMBL, Accession No. BE169024, "QV1-HT0518-240400-172-a01 HT0518 *Homo sapiens* cDNA, mRNA sequence", Jul. 2, 2000, XP-002479542, pp. 1-2.
Database EMBL, Accession No. BF875211, "QV3-ET00099-101100-382-g10 ET0099 *Homo sapiens* cDNA, mRNA sequence", Jan. 19, 2001, XP-002479543, pp. 1-2.
Database EMBL, Accession No. BE698272, "RC2-UT0021-290700-011-g12 UT0021 *Homo sapiens* cDNA, mRNA sequence", Sep. 14, 2000, XP-002479544, pp. 1-2.
Database Geneseq, Accession No. ABG27171, "Novel human diagnostic protein #27162", Feb. 18, 2002, XP-002479540, pp. 1-2.
Database Geneseq, Accession No. AAU31084, "Novel human secreted protein #1575", Dec. 18, 2001, XP-002479541, pp. 1-2.
Brulliard, M. "Nonrandom variations in human cancer ESTs indicate that mRNA heterogeneity increases during carcinogenesis" *PNAS*, May 1, 2007, pp. 7522-7527, vol. 104, No. 18.

* cited by examiner

*Primary Examiner* — Laura B Goddard
(74) *Attorney, Agent, or Firm* — Saliwanchik, Lloyd & Eisenschenk

(57) ABSTRACT

The present invention relates to the identification of a novel mechanism of transcription infidelity in cells. The invention provides compositions and methods to detect the level of transcript ion infidelity in a sample, as well as the use thereof, e.g., for therapeutic, diagnostic, pharmacogenomic or drug design. As will be disclosed, the invention is particularly suited for detecting, monitoring or treating proliferative cell disorders, for the design and/or screening of drugs, for patient or disease profiling, prediction of disease severity and evaluation of drug efficacy.

15 Claims, 106 Drawing Sheets

Figure 2a

Figure 1A:
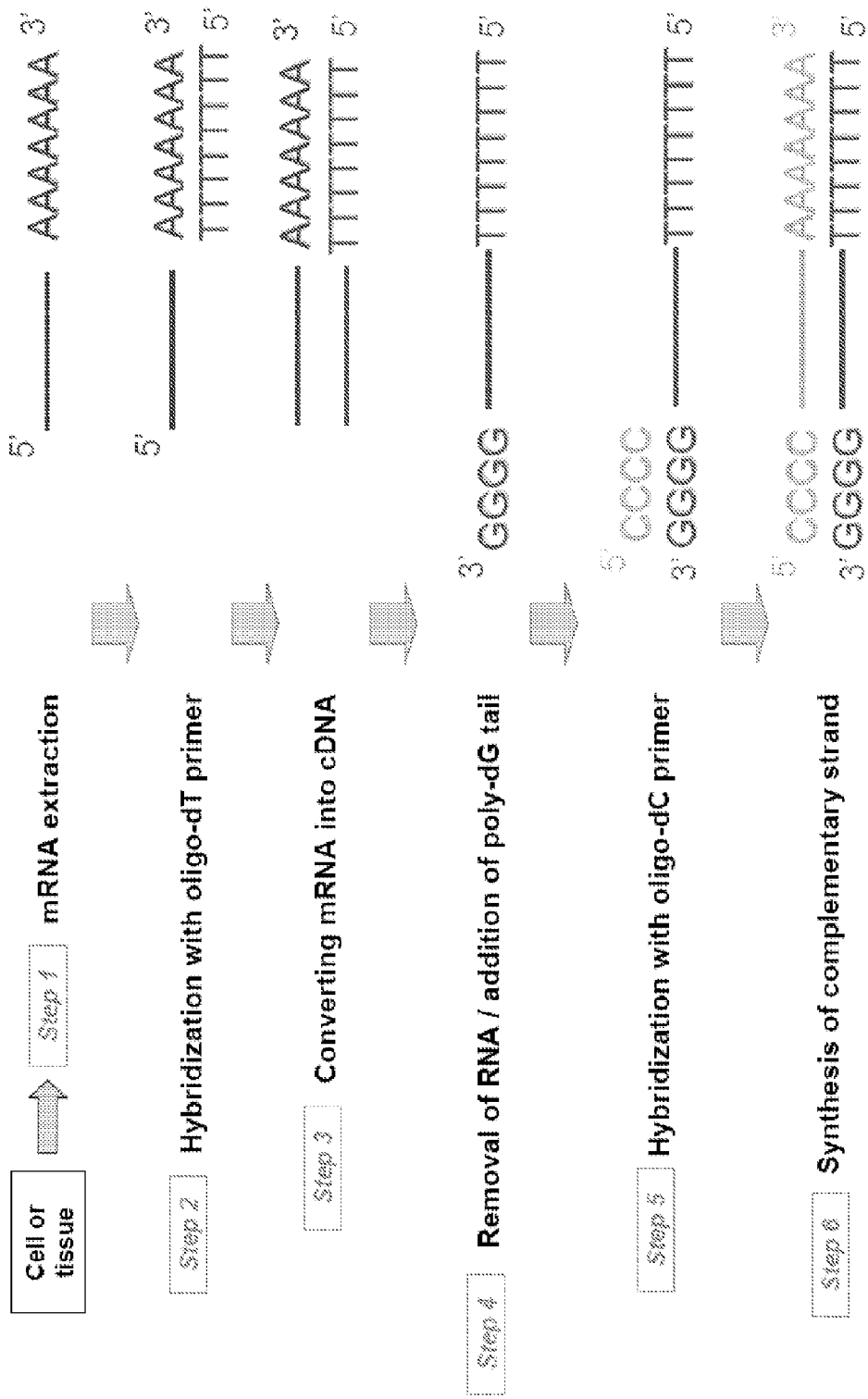
Figure 1B:
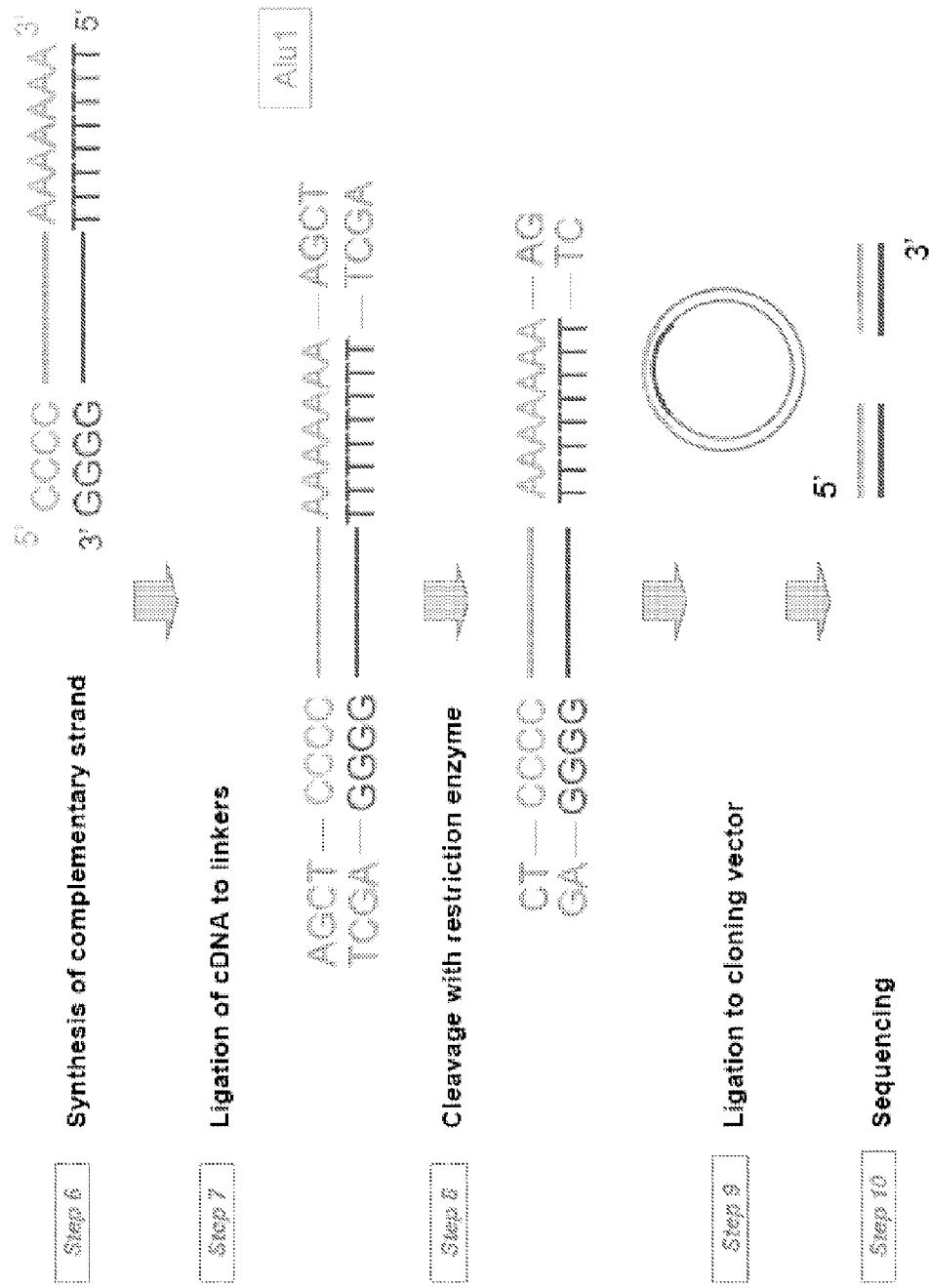

>gi|56682958|ref|NM_002032.2| Homo sapiens ferritin, heavy polypeptide 1 (FTH1), mRNA ATAAGAGACCACAAGCGACCCGCAGGGCCAGACGTTCTTCGCCGAGAGTCGTCGGGGTTTCCTGCTTCAACAGTGCTTGGACGGAAC
CGGGCGCTCGTTCCCCAACCCCGGCCGGCCGCCTATAGCCAGCCCTCTTCACGTCTCACCCTCGCAGCCCTGCCCAAGGCCCC
GCCGCCGCGCTCCAGCGCCGCGGCAGCCAGGACTCAGAGCGCGATGATGTGTCAGGCCTTTGAAGAACTTGCCCAAATACTTTC
GCTTACTACTTTGACCGCGATGATGTGGCTTTGAAGAACTTGCCCAAATACTTCTTCCACCAATCTCAGGAGAGGGAACATGC
TGAGAAACTGATGAAGCTGCAGAACCAAGAGGTGCATTACATTTCAGGATATCAGTCACTACTGGAACTGCACAACTGGCACTG
CGGGCTGAATGCAATGGAGTGAGTGACTTCATTGAGACACATTACCTGAATGAGCAGGTGAAAGCCATCAAAGAGCTGGGAGAC
CACGTGACCAACTTGCGCAAGATGGGAGCGCCCGAATCTGGCTTGGCGGAATATCTCTTTGACAAGCACACACCCTGGGAGACACAGTGGGGTTTCCTTTACCT
CAACTTGACCCTCGGGGCAAGATGGGAGCGCCCGAATTTCCCATAGCCGTGGACATTCCACCACTTAAGTCTGCATGCAGTCATACCAGGTGT
TTCTATAAGTTGTACACAGGAAAACTCCACTAAGTCTGCATGCCACATTCCATTGCTGTACCAGGAAATTGGTACCAGGTGT
CTTGAGGTCTTTGGGATGAATCAAGAAATCTATCCAGGCTATCTCCAGATTCCTTAAGTGCCGTTGTTCAGTTCTTAATCACACTAAT
CAAAAGAAACGAGTATTTGTATTTATTAAACTCATTAGTTGGCAGTAGATATAGTAGGTGTGCTGTCTTGGATTCAGATAGAACTA
AGGGTTCCCGACTCTGAATCCAGAGTCTGAGTTAAATGTTCCAATGGTTTCACAGTTTTATGAATAAAAGGCAT
TAAAGGCTGA

Figure 2b

>gi|56682960|ref|NM_000146.3| Homo sapiens ferritin, light polypeptide (FTL), mRNA GAAGTTCGGCGGTCCCGCGGTCTGTCTCTTGCTTCAACAGTGTTTGGACGGAACAGATCCGGGGACTCTCTTCCAGCCTCCGACCGC
CCTCCGATTCCTCTCCGCGTTGCAACCTCGGACGTTGATGCCATCTCTGCTTCCCAGCACCGTTTTGTGGT
TAGCCTCCTTGCCAACCATGAGCTCCCAGATTCGTCAGAATTATTCCACCGACGTGGAGGCAGCCGTCAACAGCCTGGTCAA
TTTGTACCTGCAGGCCTCCTACACCTACCTCTCTCTGGGCTTCTATTTCGACCGCGATGATGTGGCTCTGGAAGGCGTGAGCCACTTC
TTCCGCGAATTGGCCGAGGAGAAGCGCGAGGGCTACGAGCGTCTCCTGAAGATGCAAAACCAGCGAGGTGGCCGGGCTCTTCCAGG
ACATCAAGAAGCCAGCTGAGGATGAGTGGGGTAAAACCCCAGACGCCATGAAAGCCGCCATGGCCCTGGAGAAGAAACTGAACCAGGC
CCTTTTGGATCTTCATGCCCTGGGTTCCGCCCGCACCGACCCCCATCTGTGTGACTTCCTGGAGACTCACTTCCTAGATGAGGAAGTG
AAGCTTATCAAGAAGATGGGTGACCACCTGACCAACCTCCACAGACTGGGTGGCCCAGAGGCTGGCCTGGGCGAGTATCTCTTCGAAA
GGCTCACTCTCAAGCACGACTAAGAGCTTTCTTAAGAGAGCAGCCTTTCTTAACTATTCCTAACAAGCCCTGGGACCAAATGGAATAAAGCTTTTTGATGC
TCTCCCTCCAGGCAATAGGCAGCCTTTCTTAACTATTCCTAACAAGCCCTGGGACCAAATGGAATAAAGCTTTTTGATGC

Figure 2c

>gi|83641890|ref|NM_002046.3| Homo sapiens glyceraldehyde-3-phosphate dehydrogenase (GAPDH), mRNA
AAATTGAGCCCGCAGCCTCCCGCTTCGCTCTCTGCTCCTCCTGTTCGACAGTCAGCCGCATCTTCTTTTGCGTCGCCAGCCGAGCCACA
CGCTCAGACACCATGGGGAAGGTGAAGGTCGGAGTCAACGGATTTGGTCGTATTGGGCGCCTGGTCACCAGGGCTGCTTTTAACTCTG
GTAAAGTGGATATTGTTGCCATCAATGACCCCTTCATTGACCTCAACTACATGGTTTACATGTTCCAATATGATTCCACCCATGGCAAA
TTCCATGGCACCGTCAAGGCTGAGAACGGGAAGCTTGTCATCAATGGAAATCCCATCACCATCTTCCAGGAGCGAGATCCCTCAAAAT
CAAGTGGGGCGATGCTGGCGCTGAGTACGTCGTGGAGTCCACTGGCGTCTTCACCACCATGGGGCTGTGGGTCATTGACAAGGGGG
GAGCCAAAAGGGTCATCATCTCTGCCCCCTCTGCTGATGCCCCCATGTTCGTCATGGGTGTGAACCATGAGAAGTATGACAACTTTGGTATCGTGGAAGGACT
CATGACCACAGTCCATGCCATCAATGACCCCTTCGACAACACTGCCCTCTACTGCCTCTGCTCCTCTGCTGATGCCCCCATGTTCGTCATGGGGTGAGCC
AGAACATCATCCCTGCCTCTACTGGCGCTGCCAAGGCTGTGGGCAAGGTCATCCTGAGCCGGTTTCCTCTTGGAGTGTTCGGCCTCATGATGCCGAAACTG
ATGTGGAGGCAAGGCAGCCGCCATCGCCCGCCGCCACCAGGCAACTGTCATCATCTGCCCTTCCAGACCACAGTGCCCCAGGCTGCCCCAGGCT
CGACCAGCTTCCAGCCGCAGGTCAATGCAGTGTGCCCCCAAGAACCCAAGGCAGGCGGCCGGTAGGCGCCTGTGCCCAAGTGGTTGTGTCCCATCAATCAA
AGGGCCCTCCACAGCGGTGGGGCTCATGGGCGCCTGGGAGCCAGCACTGGGGGTGGAGACCTGGGTAGGTGTTGGGACCCCTTGAAG
AGGGGAGGGGCCTAGGGAGCCGCACCTTGTCATGTACCATCAATAAAGTACCCTGTGCTCAACC

Figure 2d

Figure 2e

>gi|18390348|ref|NM_000972.2| Homo sapiens ribosomal protein L7a (RPL7A), mRNA

TTCCTTTCTCTCCTCCGCCGCCCAAGATGCCGAAGGGCGAAAGAAGGCCAAGGGAAAGAAGGTGGCTTCGGCCCCAGCTGTCGTGAA
GAAGCAGGAGGCTAAGAAGGTGGTCAATCCCCTGTTTGAGAAAAGGCCTAAGAACTTTGGCATTGGAGAATTTGGCATGCCAAAGAG
ACCTCACCGCTTTGTGACCCAGGCCCTGGGCCCCGGCTATATCAGGTTGCAGCGGCAGAGCAGAGCTACTCAGCCCAAACAGTAGCG
ATTAACCAGTTCAGAGACTTCAGCCCTGGGCCCGGGGGCCGAGAAGCAGAAGAAGGCCCGAGAAGGGCCGTTGATTGCACAGGACGTGATTGCAGGAAAGGCAGAAGGCTTCACAGGAAGAC
GAAGAAGCAGAGACTGTTGCACCACCGTCAACCTTGTGGTGGAGAACAAGAAGTCAGTCCCTTACTGCATTATCAGGGAAAGGCAGAAGGCTAAGCCTGGGCTGTGGCCTCGTATCGTGTGGCCAAGCTCGAAAAGGCAAAG
ACAGATACGATGAGATGCCCACTAACTGGGTTAAATGTAGTTCCTACATAAAAATAATTGAATAATACAAATTTCCTTC

Figure 2f

>gi|39812410|ref|NM_001007.3| Homo sapiens ribosomal protein S4, X-linked (RPS4X), mRNA
GGGCGGGAGCAGCTGAAAAATCCGGCGCGCGGCCAGTCTCCAGCCCAATTTCTACGGCACCGGAGACGGAGGTCCTCTTTCCTTGCCT
AACGCAGCCATGGCTCGCTGCCGTCCGGTCCCCAAGAAGCATCTGAAGCGCGGGTGCTCCAAAGCATTGGATGCTGGATAAATTGACCGGTGTG
TTTGCTTCCTGTCCATCCATCGGTTCCCACACAGTTGAGAGAGTTGCCAGCGGGTTCATTAAAATCGATCATCATTTCCTGAGGACAGATCATTAAGTATGCC
CTGACAGGAGATGAAGTAAAGAAGATTCATCAGCATTGACCAAGACGGGAGAGAATTCGTCTGATCTATGACACCAAAGGTCGCTTGCTGTACATCGT
GGATTCATGGATGTCATCAGCAAGAGCCAAGTACAAGATTTGTGCAAAGTGAGAAGATCCTTTGTGGGCACACAAAAGATTGATTGGGCAAGATTACTGAT
ATTACACCTGAGGAGCGCACCATCCGCTACCCGATCCCCTCATCCAGGTGATAAACCCATTCAGATGATACCTAACCTGGAGGTGCTAACCACAGATGAGG
GATGCCGCCAAGTTCGACACCTGGTAACCTGTGTATGGTGACTGGACTTTCACGTGAAAGATGCCAATGGCACTTGATCAACAGCTTTGATCCAACAGAGAGG
CACCCTGGATCTCTTTTGAGGATTTCTTCCCCGAGGAAATGGGTCCCTGGGTGACATGTCCAGATCTCAGATGTACGTAATTAAAAAATATTGTGGCAGGATTAATAGC
AAGGGCAACAACAAACCATGGCGGTGAAATGGCTGGGTGAAATGGC

Figure 2g

Figure 2h

>gi|71158043|ref|NM_001010.2| Homo sapiens ribosomal protein S6 (RPS6), mRNA

```
CCTCTTTCCGTGGCGCCTCGGAGGCGTTCAGCTGCTTCAGTTGCTTCCAGCCACTGGCTGCCAGAACTCA
TTGAAGTGGACGATGAAGCAAACGTCGTACTTCGTACTTTCTATGAGAAGCGTATGGCCACAGAAGTCG
GAAGGGTTATGTGGTCCGAATCAGTGGTGGGAACGACAACAAGGTTTCCCGGAGCAGGGTGTCTTGACC
CTGCTACTGAGTAAGGGCGTTCCAACTTGGTTATTGTAAAAAAGGAGAAGAAGGATATTCTGGACTGAA
CAAATCTGACGCGTTCCAACTTGGTTATTGTAAAAAAGGAGAAGAAGGATATTCTGGACTGATACTCGA
GGGCCCAAATGAGAGCTAGAGAAACCTAGGACCAAAGCACCCAAGATCCCAAACTTTTCGAATCTCTCT
AATAAGAAGGTAAGAAGCAGAATCCGCAAATTTTCAATCTCTAAGAAGATGATGTCCGCCAGTATGTTG
TTGCTCCTGAAGCAGAAATCGAAGAAAATAAAGAGAGGCTGCAGAATATGCTAAACTTTGGCCAAGAGA
GGAGAAGCCAGGACAAATTCCGAAGAGAGGACCAGAAATAAGATCAGACTCTG
GATTTTTGAGTAACAAATAATAAGATCAGACTCTG
```

>gi|34328943|ref|NM_021109.2| Homo sapiens thymosin, beta 4, X-linked (TMSB4X), mRNA ACAACTCGGTGGTGGCCACTGGCAGACCAGACTTCGCTCGTACTCGTCGCGCTCGCTTTCCTCCGCAACCATGTCTGACAAACCC
GATATGGCTGAGATCGAGAAATTCGATAAGTCGAAACTGAAGAAGACAGAGACTCAAGAGAAAAATCCACTGCCTTCCAAAGAGACGATTGA
ACAGGAGAAGCAAGCAGGCGAATCGTAATGAGGCGGTGCGCCGCCAATATGCACTGTGTCCCTCTTCCACAAGCATTCCACGACATTCTTTCT
TTAGCTGTTGTTGCCCTTTAACTTGTAAGTCAAAGAGGTTGGATGCAAAGAGAGGTTAAATGAAGGAAGAACTACTGACAACGAA
GCCGCGCGTGCCTTTCCATCTGTCTATCTATCTGCTGGCAGGGAAGGAAGAACTTGCATGTGGTGAAGAAGAAGTGGGTGGAAGA
AGTGGGTGGACGAGACGAATCTAGAGTAAAACAAGCTGGCCCAAGGTGCCTGCAGGGTGTAATGCAGTTAATCAGTTAAAACTT
TTTTTTGTTCAAATGATTTTAATTATTGGAATGCACAATTTTTTTAATATGCAATAAAAAGTTTAAAACTT

Figure 2i

>gi|4507668|ref|NM_003295.1| Homo sapiens tumor protein, translationally-controlled 1 (TPT1), mRNA CGCCCCGAGCGGCGCTCCGGCTGCACCGCGCTCCGAGTTTCAGGCTCGTGCTAAGCTAGCGCCGTCGTGTCTCCCTTCAGT
CGGCCATCATGATTATCTACCGGGACCTCATCAGCCACGATGAGATGTTCTCCGACATCTACAAGATCCGAGAGATCGCGG
GTGCCTGGAGGTGGAGGGGAAGATGGTCAGTAGGACACAGAAGGTAACATTGATGACTCGCTCATTGTGTGGAAATGGCTC
CCCCGAGGGCGAAGGTACCGAAAGCACAGAAGATTACAGTGAAATCAATGACACATCGTGTAATTCACACCAGTCTCTTTA
AGAGCCTACAGAGAAGTACAGAGAAGTACAGAAGCAGAACAAATCAAGCACACGCCGTGACCGGAAGCTCCGAAGACTTAAGA
TATGACAGGGGCCTGCCAGAACAAATCAAGCACACGCCGTGACCGGAAGCTCCGAAGACTTAAGGTGAAACATGAATCGAGA
TGGCATGGTTGCTCTATTGGACTATCTATTTGGATCTATCACCGTCATCATAACTCATAACTGGCTTCTGCTGTCATCCGAAGA
TTAACAAATGGCAATTATTATTTGCAATTCATCCGGAGAGCTCTTCATTATTTGACTGTGATTTATTTGGAGTGGAGGCATTGTTTTAAGAAAACATG
CAAATGGGACTGATGTCATCTGAGCTCTTCATTATTTGACTGTGATTTATTTGGAGTGGAGGCATTGTTTTAAGAAAACATG
TCATGTAGGTTGTCTAAAATAAAATGCATTAAACTCATTGGAGAG

>gi|34577108|ref|NM_000034.2| Homo sapiens aldolase A, fructose-bisphosphate (ALDOA), transcript variant 1, mRNA
CCTAGCTGGCCGGATCGTGAATTGCCCGCGGAGGTGCAGCTGAAGCTCCCGAGCTCCCGACTGACTGGCTCTGCCCTTCCCATGCGACGCCCT
CTAGCCCGTGGAATCAACCGGCTCCTTGTCAGCAGGCCTGCCTGCTGCCATGTCTGCCGCCATGTCTTCATGCTGTGGGCATCTA
TTTGTTGCTGCTGCGGGCCCCAGACTGCTAGTCCGCTGAGAAGCTGACTGGAGGTGCTGCCCACTTCCTCTGCAGGAAGCAA
GGTTCCTCCAGCCCCACCAGAGCTGCCTGTCGAGAAGCCTGTGACCTGGCCACTTGCCACTGCCAGGCCCCACTTCGTGCTGCT
GCCCCCAGCCTCAACTGTCTGTCCTGAGATCAAGCTGGACCAAGGTGTGCCCACTGGTGCCGAGCCCCAGCCCTTGGGGACTG
CAGAGAGCCTCAACTGTCTGTCCTGAGATCAAGCTGGACCAAGGTGTGCCCACTGGTGCCGAGCCCCAGCCCTTGGGGACTG
TGTGCCCCTCCTCCCTGAAGAGCCTTTCCCAGGAGAACCAGATCAAGCGGCTGGAACCACAGAGGCGTGGGAACTGGCAAGT
GCAGGGCCTGGCCTCCGCAGGCAGGCACTCTTGGCGTCAAGTTCTGGGCAGAGCGGCAGAAGAGAGGCCAGAATGGTCTGGGCAGC
CAGGTGCCCTGGCCTCCCTTCCCTGCAGGCAGGCACTCTTGGCGTCAAGTTCTGGGCAGAGCGGCAGAAGAGAGGCCAGAATGGTCTGGGCAGC
ATAGGAGGAGTCTGGCCTGAGTACCGGGTACCCAAGCACTCCGTCAAGAATTTCCTGGATTCCAAGGAGAAGAATTCCTCGAAGCACCGGAACTGCACTACC
GGCAAGAGATTATTCTTGAGACAACAAGGGCTCCTCCGGTCAGTCTGGAGCAGAGAAGGAGTCTGACATGGCAGACTGGCACTGTGGCACTGCGAGG
AGCACCTGGCTGCAGATGAGTCACTGCAGAGATCCACTGGGAGACCACTCACCTGCCAGTCCCATTGCCAAGCGGCTCCAGTCAGTGCCAGTCCAGATCCAGTCACTGGGAGAACCGGCTGGTCGATGCAGCAGGA
CCGCAGCTGGCTGCAGATGAGTGACCTGACTGAGAGACGCGGCAGTTACTCCGGGAACATCGCCAATGGGGTGCATCATGAGACACTCATCAAGGCGGAT
GATGGGCGCGCCCTTCCCCCARGTTATCAAATCAACCGGCCACCCAGCGAGGCCGTCTGAGCGCCTGTGAGCCCAGTGCCCAAGTTGATACCTGACTTGCAGCCCGTTG
ATGGCGAGACTACCACCCCAGGGTTGGATGGGGACCCGGAGCTCCGCTGAGATGGTCGGCCCATCATGGAAAATGCCAATGACTGGAAGCCAATTCATGTACCAAGGCCAGAGTGCTGG
TGTGCTGAAGATTGTGCCACACGAAGCTCCGATGAGTGACTGGCTGCAGGAACACACCTGCCAGTGACGCAGATGCACCTTGCGCGGCACATGCCGCGCACATGTCACCCACCACCCTGCTGAAGCCCTGGAAGCCCTGACCTTCCTG
AATGGCATGCTGCTGTGACAAGGCTCCATGCAGGAGTGACGAGAGATTGCCAGGAGAAGCCCATCACCATGCCCCGCACTGGCGAGAGGACTGCCAACAGTCGGGTCCTCACTGGGCGTCACTTCCTG
CTGCTGCTGCTGCTCACAAGGCTCCCATGCAGGAGTGACGAGGATTGCCAGGGAGAAGCCCATCACCATGCCCCGCACTGGCGAGAGGACTGCCAACAGTCGGGTCCTCACTGGGCGTCACTTCCTG
TCAGAAGTTTCTCACAGTGGCCCTGTCAAGGAAAGCTACTCCAACTGCAAGCTGCCGGAGGCCTGGAAGGGTTCCAGAGGCCTGGAAGCGGGCCCTGACCTTCCTG
TCAGAAGTTTCTCATGATGAGGAGATTGCCAAGGTCCTGCCTGCAGCCACACTGGGGAAGCTGCGCTGGCAGCACTCGGCCGCATGCCGGAGGCCTGGAAGCGGGCCCTGACCTTCCTG
TCTGGAGGCCAGAGTGAGGGTGGAAGGGCGTCCCCGAGCCCTGCAGGCCCTGTCCAGGGCCCTCGAGGCCTGCCCGAGGTCCTGGCCCAGGTGTCCAGGGCCCCCGGAGTCCTCACTCTTGTCGTCTAACCAC
ACGGCCGAGCACAGCCCTTGCCTGGCCAGCGATCCTGCCCCCAACACTCCAACACACTCCAGGCCTGCCCGAGGTGCTGCCCAGGCCCCGAGGCCCCCGGAGTCCTCACTCTTGTCGTCTAACCAC
GCCTATTAAGCGGGTTGCCGGGCTTGCCTTCTTTCCCTGCGGCTCTTCTTTCCCACGGCTGTGATGGAGAGGAGGATCCCGCCCTGGGCT
CCAGGCTGGGCTTGCCGAGTGGTTCCCAGGCCCGGGCTCTTCTTTCCCCTGCGGCTCTTCTTTCCCACGGCTGTGATGGAGAGGAGGATCCCGCCCTGGGCT
CTGCCAAGTAAACAGCTATTAAGGGGG

Figure 2m

>gi|50345983|ref|NM_001001937.1| Homo sapiens ATP synthase, H+ transporting, mitochondrial F1 complex, alpha subunit 1, cardiac muscle (ATP5A1), nuclear gene encoding mitochondrial protein, transcript variant 1, mRNA

```
TCTGGCATTGCAAGCCTCGCTCGTTGCCACTTCCCAGCTCTTCCGCGGTATAATCAACACTAGAGAGATAGAGCGGCTAG
AACCAGTCGGAGCTGCGGCCGGAGAGTACGGGCCAGAAGTAATGCAAACATGCTGTCCGGCGTTCCTGGGCCGTGGTCCG
CCCTTCCTCGCGGGGGCCGACTGGTCTCCAGAAATGCTTTGGGTTCATCTTTCATTGCTGCAAGGAACTTCCATGCCTCTAACACTCATCT
TCAAAAGACTGGACTGCTGAGATGTCCTCTATTCCTGAAGAGAGCTATTCTTCTGAAGCTGATACCTCTGTGATCTTGAAGAAACTGGCGT
GTCTTAAGTGTCCTGAACTTGGAACCTGGTCGTGTCGTGTTTGGAAATGATAAACTAATTAAGGAGAGATATAGTGAAGAGGAC
GTATGTGCTTGAACTTGGAACCTGGTCGTGTCGTGTTTGGTGTTGGGTCGTTGGGTCGTTAGTTCCTGGTAATGCGAATTGATGGAAAGGTCCAATT
AGGAGCCATTGTGGACGTTCCAGTGGCGAGCGCCCGGTATCATTCCTGAATTTGACCGACAGACTTCAGTGCGGGAACCAATCGAATTGCTATTGACAC
GGTTCAAGACCCTGAGCGAGTGGTCCAATTGGTGCCAGCTGATGAAAGGAGCTACACCATTGTCGGCTACGCCTGGATGCTGCCCACTTC
CGTGGATAGCTTGGTGCCAATTGGTGCAGACTCGGCTGATGAAGAGAGTATTTTAGAGACGAGTGACAAACATGCCTATCCGATGCTTTGATCATCGATGCGACTTATCGAA
AGTACCTGGCTCCTTGGCTCGAGATGTCTCGCCGCAAATGAACGATGCAGCCAAAAATGAACGATCAGCATACCAAGGTATCCGCCCTGC
TGTCTGCTTACAGTCCTGAGGAGAGCAGCCAAACAAAATGAACGATGCAGCCAAAATGACGATCATTTCCATCACTGACCGATGCCCAAAACCAGGTACCTGGAAACACGATCAGCATACCAAGGTACCAAGGTATCCGCCCTGC
AATTAACGTTGGTCTCGTCGTTCGTATCCGTGTGCGTGTGCCCAGTTCGGTCTATTGGATCGATGCCAAACTGAAGTCCACTGCCACTGCCGACTGCCACCAAGAACTGAGCTGAGAAGCTGGAATTG
GCTCAGTATGTCGAGGTTCGTGTTGCTGCAAGGACAGTATTCCCAGTGGTTCGCCCAGTTCCCAGCTGCAAGAACAAGTGGCCTGTTATCTATCCGGGTGTAAGGGGATATCTTGATAA
CTGAGTGCTGAAGCAAGCAAGATTACCAAGTTTGAGAATGCTTTCTCATGTCGTGATCATGCGCACCAAGCCCTGTTGTTGGGCACTATCAGGGCT
ACTGGAGCCAGCAAGCAAGATTACCAAGTTTGAACAATGCTTTCTCATGTCGTGATCATGCGCACCAAGCCCTGTTGTTGGGCACTATCAGGGCT
GATGGAAAGATCTGAAGCTGAAGATGCAAAGCTGAAGACTGTAACAAATTCTTGTGGCTGGATTGAAGCTTAAACTCCTATGCTGTGATT
CACATCAAATAACACTTCACTTCTCATTCTCTACTAAATTAGTTCATTTCTAAAGGCTTCATCTGTATACTCCTATGCTGTAATGCATAGTT
CACATGAAAAAATAAAGGTTCCATAATGCATAGTT
```

Figure 2n

>gi|20428653|ref|NM_001743.3| Homo sapiens calmodulin 2 (phosphorylase kinase, delta) (CALM2), mRNA AGTCGAGTGGAGAGAGCGAGCTGAGTGGTTGTGTGGTGCGTCGGAAACGCGGTAGCGCTTGCAGTGCATGGCTGACCAACTGACTGAAGA
GCAGATTGCAGAATTCAAAGAAGCTTTTTCACTATTTGACAAAGATGGTGATGGAACTATAACAACAAAGGAATTGGGAACTGTAATGAGA
TCTCTTGGGCAGAATCCCACAGAAGCAGAGTTACAGGACACATGCTGATGAAGTAGATGCTGATGGCAATGGCACAATTGACTTCCCTGAA
TTCTGACAATGATGGCAGAGCTCGCAGAAGCACAAAAATCCTCGCAGAACAAATGAGAGAAGCATTCCGTGTGTTTGATAAGGATGGCAATGG
CTATATTAGTGCTGCAGAACTTCGCCATGTGATGACAAACCTGGGAGAGAAGTTAACAGATGAAGAAGTTGATGAAATGATCAGGGAAGCA
GATATTGATGGTGATGGTCAAGTAAACTATGAAGAGTTTGTACAGATGATGACAGCAAAGTGAAGACCTTGTCAAAAAATATGCATGAATTTC
TTGTACAAAATGTTATTGCCTTTGTCCTTTGTTCCCTTATCTGTTACTTACTGTCAATTGTCCTAAAACCTTATTTGAGAAAATGATCAAGTATGA
ATTAGGACTTCATTCCTCCATGTTTCTGGATATATCTAAGAACTGTAAGCCCTTCTGCACAGTGTTGTGTGAAGTTGGTGTAACTCGGGTTATGCCTT
CATGTGGCTACTCTTTTAGGATAGTTTTCTTTAAGAACTGTCAAAGACTGTCAAAGGGTGATTATGGTGGAGTGGTACCACCTATTTTTTCAGG
TTTAAGTAGTTTCTTTTAAAGTGCACTATTGCAAAACGGGTGTATTATCCAGGTACTCGTACCACTATTGCTTATGGCACAATTTGCCTC
GTACTTACTGGTCCACTTTAAACTTGCCTTTTTAAACTGCTTGTTAAGTTAGGTCCACTTAAATCGAATTCCAAGTTGT
ATATTTGTTTCCAATAAAAAAATTACAATTAGCC

Figure 2o

>gi|5031856|ref|NM_005566.1| Homo sapiens lactate dehydrogenase A (LDHA), mRNA
TGCTGCAGCCGCCTGCCGCCGATTCCGGATCCATTGCCAGCATTCCCGATTCCTTTGGTTCCAAG
TCCAATATGGCAACTCTAAGGATCAGCTGATTTATAATCTTAATGAAGGACTTCTAGAGGAAGACGCCCGAGTGCATTGAGGACAGCTTGGGTTG
GTCTGTGTGGATGGCATGGCCTGTGCCATATCAGTCAGCCCTTTCCTTAGAACACCAAAGATTGTCTCTGGCAAAGTCTTGTGATGTCGAAGACAAATGAA
GGGAGAGATGATAATCACGGTCCAACATGGCAGCCTTCCAACAGATTGTCCTTAGAACAGGAAAGCCGTCTTATTGGTCAACTATAATGAACATGCAAACTCC
AAGTGGTCATTATCTGTTATTGGGACTGGTGCTGTGGGCACTCAGCCCGAACTGGATACAGCCCGAACTTGCTTATTGCTTCAAATGCTGGACTTACGTGGCTTGGAAGAT
TCATTCCTAATGTTGTAAAATAACCGGTCTTATTGGAAGTTGCTTATGTTGGCAATCCAGTGGATATCCTTGACCTACGTGGCTTGGAAGAT
AAGTGGTTTTCCCAAAGCTGTCACCCAGATTCAGTGGGTGTTGCAATCTGGAGAACAGGAACAGTGGAAAGATAAGGAACAGTGGAAAGAAGGTTCACAACGACAGGTTCACCAGAGGTTCACAGAGGT
TGAAGACTCTGCAACCTCAAAGGCTACACATCCTGGGCTATTGGACTCCTGTGCAGAGTCTCTGTAGACATCAGAGAGGTTGGCAGAGATAATGAAGAATCCTAGGCGGTGCAC
CCAGTTTCCACCATGATTAAGGGTCTTTACGAGGAAGAGGCCCGTTGAACACAGAGTGCAGATACACTTGGAGGTGGCATGTTGTCCTTTATCTGATCT
ACCTGTTCGATGTCTGATGTCATATCATTTAAGATCATTTAAGATCATTTGACACTTCACTGCTGTCTAGGTGGACATGCGATGTCTTGTCCTTTATCTGATCT
TTAAAGTCTCTAGCAGTGGATGGCTCGATCGTAAAAACATCAACACTCCTGAGTTAGACATAGCTCTGCCACCTCTGACGCACCACTGCCAATGCT
GTGATTAAAGCCAGTGGTCATGTTATCAGTTGTCTCTCAACTGGTCTCTTCAACTGTGAATAGTTCTGCCACCTCTGACGCACCACTGCCAATGCT
ATCCTGATGCACTGGTCATTTGCCCCTGAGCCAGGCCAGTGGTGTCCATGTTACCGTGTGTTATACTTCCGGTGTCCACGTGCACCACTGCCAATGCT
GTACTGCTGATGTCTGATGGCAGTCATTACCATAACCATATAATTCCAATATCATGCCTGTGCATATATCTTCCAAGGATCTATTTGTG
ATTTTCCAGTGAGTGTACATTACCATAATGATAAAAGATCTAGAACCTACACATACACAACTATCAACCAATGCAACCAATCCAGTGTTATACCAACTAAAA
CCCCCAATAATAAACCTTGAACAGTG

Figure 2p

>gi|52851446|ref|NM_000365.4| Homo sapiens triosephosphate isomerase 1 (TPI1), mRNA
CCTTCAGCGCCTCGGCTCCAGCGGCATGGCGCCCTCCAGGAAGTTCTTCGTTGGGGGGAACTGGAAGATGAACGGGGAGAAGCAGAGTCTG
GGGGAGCTCATCGGCACTCTGAATGCGGCCAAGGTGCCGGCGGACACCGAGGTGGTTTGTGCCCCCCCTACTGCCTATATCGACTTCGCCC
GGCAGAAGCTAGATCCCAAGATTGCTGTGGCTGCCCAGAACTGCTACAAAGTGACTAATGGGGCTTTTACTGGGGAGATCAGCCCTGGCAT
GATCAAAGACTGCGGGGCCACGTGGGTCGTGGTCCTGCACGAGAGGAGCCATGTCTTTGGGGAGTCAGATGAGCTGATTGGGCAGAAA
GTGGCCCATGCTCTGGCAGAGGGACTGGGAGTAATCGCCTGCATTGGGGAGAAGCTAGATGAAGGGGAGACTGGCATCACTGAGAAGGTTG
TTTTCGAGCAGACAAAGGTCATCGCAGATAACGTGAAGGACTGGAGCAAGGTGGTCTGGGCAGAAGTCGTGGAGCTGCTGGCTCAGAGC
AGGACTCCAACAGCCCAACACCCAGTGGTAGCCATCGGCGAGAAGCTGGATGAGCGCGAAGCCGGAATCACTGAGAAGGTGGTCTTCGAGCAG
ACCGTATCATTATGGAGCCCGTGTGGGCCATCATCAATGCCAAACATGCCGAAATGCGCGCAATATGCTTCTGATGGTGTCATCGGCTCA
CTCCCCTCAAGCCCAGAATTCGTGGACATAATCAATGCTAAGCAGTAAAGCAGTAACTGTAGGCCTCGTGGCCTCATCGGCAAACTGTATCT
GCAGCCCAGAAGCCCAGTACTGCCTGCCTCCACCCGCCAGTCCCTATGGTGGACCAATCCCTCCTCCCACTTACTATAATGGTTGGAACTAAACGTCACCA
TCCTTTACTGTTATATCTTCTCACCCTTGGCTGAGAGATGCTAAATGGAAGCGGTGGGTGGTGGGATTTGCTCCTGGGATTCCAAAGCCCCAGTATGAGGCCCTAGGC
AGGTGGCTTCCTTCCCTTACACCGTGAGGGCAAGATCCCCTCAGAAGGCAGGAGTGTGTCGCCCCTGCGTGCCGTGCCCTCGTGCCTGCTGAGAAACCATC
TGAACCACCATGTGAGGGAATAAACCTGGCACTAGG

Figure 2q

TPT1 = Tumor protein, translationally controlled, 1, 830bp, chr 13 q12-q14.

VIM = Vimentin, 1847bp, chr 10 p13.

FTH1 = Ferritin, heavy polypeptide 1, 1228bp, chr 11 q13.

RPS4X = Ribosomal proteinS4, X-linked, 955bp, chr X q13.1.

RPL7A = Ribosomal protein L7a, 890bp, chr 9 q34.

ENO1 = Enolase 1, 1812bp, chr 1 p36.3-p36.2.

HSPA8 = Heat shock 70kDa protein 8, 2260bp, chr 11 q24.1.

GAPDH = Glyceraldehyde-3-phosphate dehydrogenase, 1310bp, chr 12p13.

TMSB4X = Thymosin, beta 4, X linked, 627bp, chr X q21.3-q22.

RPS6 = Ribosomal protein S6, 829bp, chr 9 p21.

FTL = Ferritin, light polypeptide, 870bp, chr 19 q 13.3-q13.4.

ALB = Albumin, 2215bp, chr 4 q11-q13.

ALDOA = Aldolase A, fructose-bisphosphate, 2303bp, chr 16q22-q24.

ATP5A1 = ATP synthase, H+ transporting, mitochondrial F1 complex, alpha subunit 1, cardiac muscle, 1945bp, chr 18q12-q21.

CALM2 = Calmodulin 2 (phosphorylase kinase, delta), 1128bp, chr 2p21.

LDHA = Lactate dehydrogenase A, 1661bp, chr 11p15.4.

TPI1 = Triosephosphate isomerase 1, 1220bp, chr 12p13.

Figure 2r

```
>gi|47009767|emb|BX437546.2| BX437546 Homo sapiens THYMUS Homo sapiens cDNA clone CS0CAP007YK05
 5-PRIME, mRNA sequence.
 Length = 868

Score = 1531 bits (829), Expect = 0.0
 Identities = 829/829 (100%)
 Strand = Plus / Plus Query: 2    cccccgagcgcgtccgctgcaccggctcgctccgagtttcaggctctgctaagc   61
            ||||||||||||||||||||||||||||||||||||||||||||||||||||||
Sbjct: 12   cccccgagcgcgtccgctgcaccggctcgctccgagtttcaggctctgctaagc   71

Query: 62   cagcgcgtcgtcgtctccttcagtgcatcatgattatcggacttcatcagc      121
            ||||||||||||||||||||||||||||||||||||||||||||||||||||||
Sbjct: 72   cagcgcgtcgtcgtctccttcagtgcatcatgattatcggacttcatcagc      131

Query: 122  cacgatgagatgttctccgacatcacaagatccggagagatcggagacggttgtgcctg  181
            ||||||||||||||||||||||||||||||||||||||||||||||||||||||
Sbjct: 132  cacgatgagatgttctccgacatcacaagatccggagagatcggagacggttgtgcctg  191

Query: 182  gaggtggagggggaagatggtcagtggagacagaaggtcagaagcattgatgactcattggt  241
            ||||||||||||||||||||||||||||||||||||||||||||||||||||||
Sbjct: 192  gaggtggagggggaagatggtcagtggagacagaaggtcagaagcattgatgactcattggt  251

Query: 242  ggaaatgccttccgctgaagcccaaggagaacaagtaccgaataatactggt      301
            ||||||||||||||||||||||||||||||||||||||||||||||||||||||
Sbjct: 252  ggaaatgccttccgctgaagcccaaggagaacaagtaccgaataatactggt      311

Query: 302  gtcgatattgtcatgaaccatcacctgcaggaaacaagtttcacaaagaagcttacaag   361
            ||||||||||||||||||||||||||||||||||||||||||||||||||||||
Sbjct: 312  gtcgatattgtcatgaaccatcacctgcaggaaacaagtttcacaaagaagcttacaag   371
```

Figure 3a

```
Query: 362  aagtacatcatgaattacatgaaatcaaggaatcagagacagagaccagaa  421
             |||||||||||||||||||||||||||||||||||||||||||||||||||
Sbjct: 372  aagtacatcatgaattacatgaaatcaaggaatcagagacagagaccagaa  431

Query: 422  agagtaaaaacttctatgacacagggctgatcatcctgttaattc  481
             ||||||||||||||||||||||||||||||||||||||||||||||||||
Sbjct: 432  agagtaaaaacttctatgacacagggctgatcatcctgttaattc  491

Query: 482  aaaaacttaccagtttattgtgaaacatgaaaactccagatgctctctattg  541
             ||||||||||||||||||||||||||||||||||||||||||||||||||
Sbjct: 492  aaaaacttaccagtttattgtgaaacatgaaaactccagatgctctctattg  551

Query: 542  gactaccgtgagatgtgtgtgacccatatatctttcttaaggatgtttagaaatg  601
             ||||||||||||||||||||||||||||||||||||||||||||||||||
Sbjct: 552  gactaccgtgagatgtgtgtgacccatatatctttcttaaggatgtttagaaatg  611

Query: 602  gaaaaatgttaacaatggcaacaaccagtcattgtcacctgtcatcaactggct  661
             ||||||||||||||||||||||||||||||||||||||||||||||||||
Sbjct: 612  gaaaaatgttaacaatggcaacaaccagtcattgtcacctgtcatcaactggct  671

Query: 662  tctgttgtcatttgactattggactgttattggagactggagtcatcttgag  721
             ||||||||||||||||||||||||||||||||||||||||||||||||||
Sbjct: 672  tctgttgtcatttgactattggactgttattggagactggagtcatcttgag  731

Query: 722  cttcattcattgactgttattgactgtggagcattgttttaagaaaaaca  781
             ||||||||||||||||||||||||||||||||||||||||||||||||||
Sbjct: 732  cttcattcattgactgttattgactgtggagcattgttttaagaaaaaca  791

Query: 782  tgtcatgtaggttgtctaaaaataaaatgcattaaactcatttgagag  830
             ||||||||||||||||||||||||||||||||||||||||||||||||||
Sbjct: 792  tgtcatgtaggttgtctaaaaataaaatgcattaaactcattgagag  840
```

Figure 3b

```
>gi|45716222|emb|AL540618.3| AL540618 Homo sapiens PLACENTA Homo sapiens cDNA clone C50DE002YF24
  5-PRIME, mRNA sequence.
  Length = 952

Score = 1531 bits (829), Expect = 0.0
 Identities = 829/829 (100%)
 Strand = Plus/Plus Query: 2    ccccccgagcgcgtcgtccgaccgctgctgctccgagttctttcagctgctgctaagc    61
            |||||||||||||||||||||||||||||||||||||||||||||||||||||||||||
Sbjct: 18   ccccccgagcgcgtcgtccgaccgctgctgctccgagttctttcagctgctgctaagc    77

Query: 62   tagcgccgtcgtcgtgtctcccttcagtcgccatctgccattatctcggactttatcagc   121
            ||||||||||||||||||||||||||||||||||||||||||||||||||||||||||||
Sbjct: 78   tagcgccgtcgtcgtgtctcccttcagtcgccatctgccattatctcggactttatcagc   137

Query: 122  cacgatgcagatgttcttcgacatctacaagatctgggagatctggattgtgttg       181
            ||||||||||||||||||||||||||||||||||||||||||||||||||||||
Sbjct: 138  cacgatgcagatgttcttcgacatctacaagatctgggagatctggattgtgttg       197

Query: 182  gagtgagggaagatggtcagtggacaagtaacaagtttcacagaacttatcgttcattggt   241
            ||||||||||||||||||||||||||||||||||||||||||||||||||||||||||||
Sbjct: 198  gagtgagggaagatggtcagtggacaagtaacaagtttcacagaacttatcgttcattggt   257

Query: 242  ggaaatgctcttccgaggccccgaggccgaaggtaccgaaagcacagtacagtaatcactggt   301
            ||||||||||||||||||||||||||||||||||||||||||||||||||||||||||||||
Sbjct: 258  ggaaatgctcttccgaggccccgaggccgaaggtaccgaaagcacagtacagtaatcactggt   317

Query: 302  gtcgatatgtcatgaacattaccatcctgcaggaactgcagaagttcacaaagttcacacaag   361
            |||||||||||||||||||||||||||||||||||||||||||||||||||||||||||||||
Sbjct: 318  gtcgatatgtcatgaacattaccatcctgcaggaactgcagaagttcacaaagttcacacaag   377

Query: 362  aagtacatcaaagattacatgaaatcaatcaaagggaaacttgaagaacagaccagaa         421
            |||||||||||||||||||||||||||||||||||||||||||||||||||||||||||
Sbjct: 378  aagtacatcaaagattacatgaaatcaatcaaagggaaacttgaagaacagaccagaa         437
```

Figure 3c

```
Query:  482  aaaaactacttatttttatggtgaaaaactgaatccagatggtatggtattgttgttctattg  541
Sbjct:  498  aaaaactaccagtttttatggtgaaaaacaacatgaatccagatggtatggtattgttgttctattg  557

Query:  542  gactactgtaggatgtg-gactacttaagatgtttttaagatgtttagaaatg  601
Sbjct:  558  gactactgtaggatgtg-gactacttaagatgtttttaagatgtttagaaatg  617

Query:  602  gaaaaatgttaacaaatggcaattattggcattattgatttggt-ttcatcat-ttattcatataatgct  661
Sbjct:  618  gaaaaatgttaacaaatggcaattattggcattattgatttggt-ttcatcat-ttattcatataatgct  677

Query:  662  tctgcttcatccacacacaacaccaggacttaagacaaatggacttccattgatgtcattgat-ttcattgag  721
Sbjct:  678  tctgcttcatccacacacaacaccaggacttaagacaaatggacttccattgatgtcattgat-ttcattgag  737

Query:  722  cttcattattgactgt-gattattggagtgagggcattttaagaaaaaca  781
Sbjct:  738  cttcattattgactgt-gattattggagtgagggcattttaagaaaaaca  797

Query:  782  tgtcatgtaggttgtcaaaaataaaatgcattaaactcattgagag  830
Sbjct:  798  tgtcatgtaggttgtcaaaaataaaatgcattaaactcattgagag  846
```

Figure 3d

>gi|45696213|emb|AL520698.3| AL520698 Homo sapiens NEUROBLASTOMA COT 10-NORMALIZED Homo sapiens cDNA clone CS0DB002YF24 5-PRIME, mRNA sequence.
Length = 909

Score = 1530 bits (828), Expect = 0.0
Identities = 828/829 (99%)
Strand = Plus / Plus

```
Query: 2    cccccgagcgcgtccgcgtgcaccgcgcctccgagctcgttttcagcttcgtgctaagc   61
            ||||||||||||||||||||||||||||||||||||||||||||||||||||||||||||
Sbjct: 18   cccccgagcgcgtccgcgtgcaccgcgcctccgagctcgttttcagcttcgtgctaagc   77

Query: 62   tagcgcgtcgtcgcgtccctccttcagtcgcatcgcatgatattaccggacttcatcagc  121
            ||||||||||||||||||||||||||||||||||||||||||||||||||||||||||||
Sbjct: 78   tagcgcgtcgtcgcgtccctccttcagtcgcatcgcatgatattaccggacttcatcagc  137

Query: 122  cacgatgagatgttcttccgacatctacaaatccgggacatgcgacggttgtgcttg    181
            ||||||||||||||||||||||||||||||||||||||||||||||||||||||||||||
Sbjct: 138  cacgatgagatgttcttccgacatctacaaatccgggacatgcgacggttgtgcttg    197

Query: 182  gaggcggagggagggagggaagatggtcagtaggacagaaggtaacactgatgactcgccattggt  241
            ||||||||||||||||||||||||||||||||||||||||||||||||||||||||||||
Sbjct: 198  gaggcggagggagggagggaagatggtcagtaggacagaaggtaacactgatgactcgccattggt  257

Query: 242  ggaaatgccttccgttccgagagccccgagggtaccgaaagcacagtaatcactggt   301
            ||||||||||||||||||||||||||||||||||||||||||||||||||||||||||||
Sbjct: 258  ggaaatgccttccgttccgagagccccgagggtaccgaaagcacagtaatcactggt   317

Query: 302  gtcgatattgtcatgaactgacctgcaggaaacaagttcacaaagaggccttacaag    361
            ||||||||||||||||||||||||||||||||||||||||||||||||||||||||||||
Sbjct: 318  gtcgatattgtcatgaactgacctgcaggaaacaagttcacaaagaggccttacaag    377

Query: 362  aagtacatcaaagattacatgaaatcaatcaaaggaagggaaacagagaaccagaa     421
            ||||||||||||||||||||||||||||||||||||||||||||||||||||||||||||
Sbjct: 378  aagtacatcaaagattacatgaaatcaatcaaaggaagggaaacagagaaccagaa     437
```

Figure 3e

Figure 3f

```
>gi|10105790|gb|BE717525.1| RC4-HT0778-190700-014-e04 HT0778 Homo sapiens cDNA, mRNA sequence
          Length = 341

Score =  564 bits (305), Expect = e-158
 Identities = 314/318 (98%), Gaps = 1/318 (0%)
 Strand = Plus / Plus Query: 347  aagaagctataagaagaagtacatcaagagattaatgaatcaaagagaaattgaa   406
            |||||||||||||||||||||||||||||||||||||||||||||||||||||||||||
Sbjct: 12   aagaagcataagaagaagtacatcaagagattaatgaatcaaagagaaattgaa    70

Query: 407  gaacagagaccagagaaaagtaaaaccttttatgacagaggctcagaacaaatcaagcac  466
            ||||||||||||||||||||||||||||||||||||||||||||||||||||||||||||
Sbjct: 71   gaacagagaccagagaaaagtaaaaccttttatgacagaggctcagaacaaatcaagcac  130

Query: 467  atccttgctaattctttttttattggtaaaacatgaattcagatgc                526
            |||||||||||||||||||||||||| ||||||||||||||||||||
Sbjct: 131  atccttgctaattctttttcttattggt-taaacatgaattccagatgc              190

Query: 527  atggttgctttattggagatcgagagatggacccatatatgattttttttaag        586
            ||||||||||||||||||||||||||||||||||||||||||||||||||||||
Sbjct: 191  atggttgctttattggagatcgtgagatgg.atgtgaccatatatgattttttttaag   250

Query: 587  gatggtttagaaatgaaatggaaaatgttaacaaatggcaattattttggatctattacctg  646
            |||||||||||||||||||||||||||||||||||||||||||||||||||||||||||||
Sbjct: 251  gatggtttagaaatgaaatggaaaatgttaacaaatggcaattattttggatctattacctg  310

Query: 647  tcatcataactggcttct  664
            ||||||||||||||||||
Sbjct: 311  tcatcataactggcttct  328
```

Figure 3g

Figure 3h

```
>gi|10246833|gb|BE814599.1| MRO-BN0070-070800-033-b04_1 BN0070 Homo sapiens cDNA, mRNA
    sequence.
    Length = 140

Score = 259 bits (140), Expect = 2e-066
Identities = 140/140 (100%)
Strand = Plus / Plus Query: 451 agacaaatcaagcacatccttgctaattcaaaaactaccagtccttattggtgtgaaaa 510
            ||||||||||||||||||||||||||||||||||||||||||||||||||||||||||||
Sbjct: 1   agacaaatcaagcacatccttgctaattcaaaaactaccagtccttattggtgtgaaaa 60

Query: 511 catgaatccagatggcatggttgctctattgacttaccgtgaggatggtgtgacccata 570
            ||||||||||||||||||||||||||||||||||||||||||||||||||||||||||||
Sbjct: 19  catgaatccagatggcatggttgctctattgacttaccgtgaggatggtgtgacccata 120

Query: 571 tatgatttctttaaggatg 590
            |||||||||||||||||||
Sbjct: 121 tatgatttctttaaggatg 140
```

Figure 3i

Figures 1, 4A:
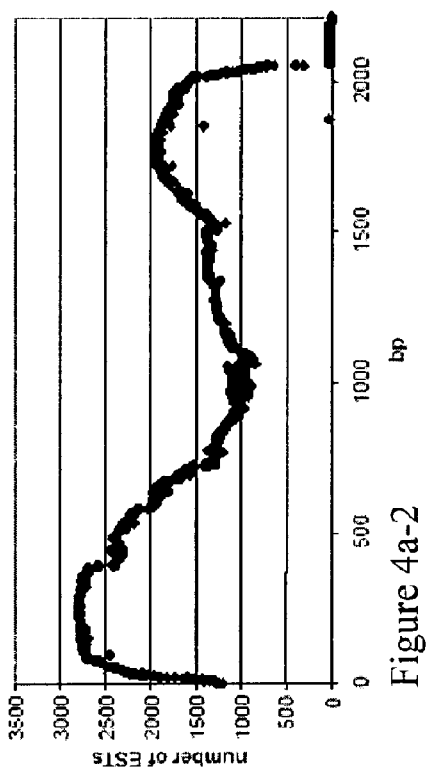

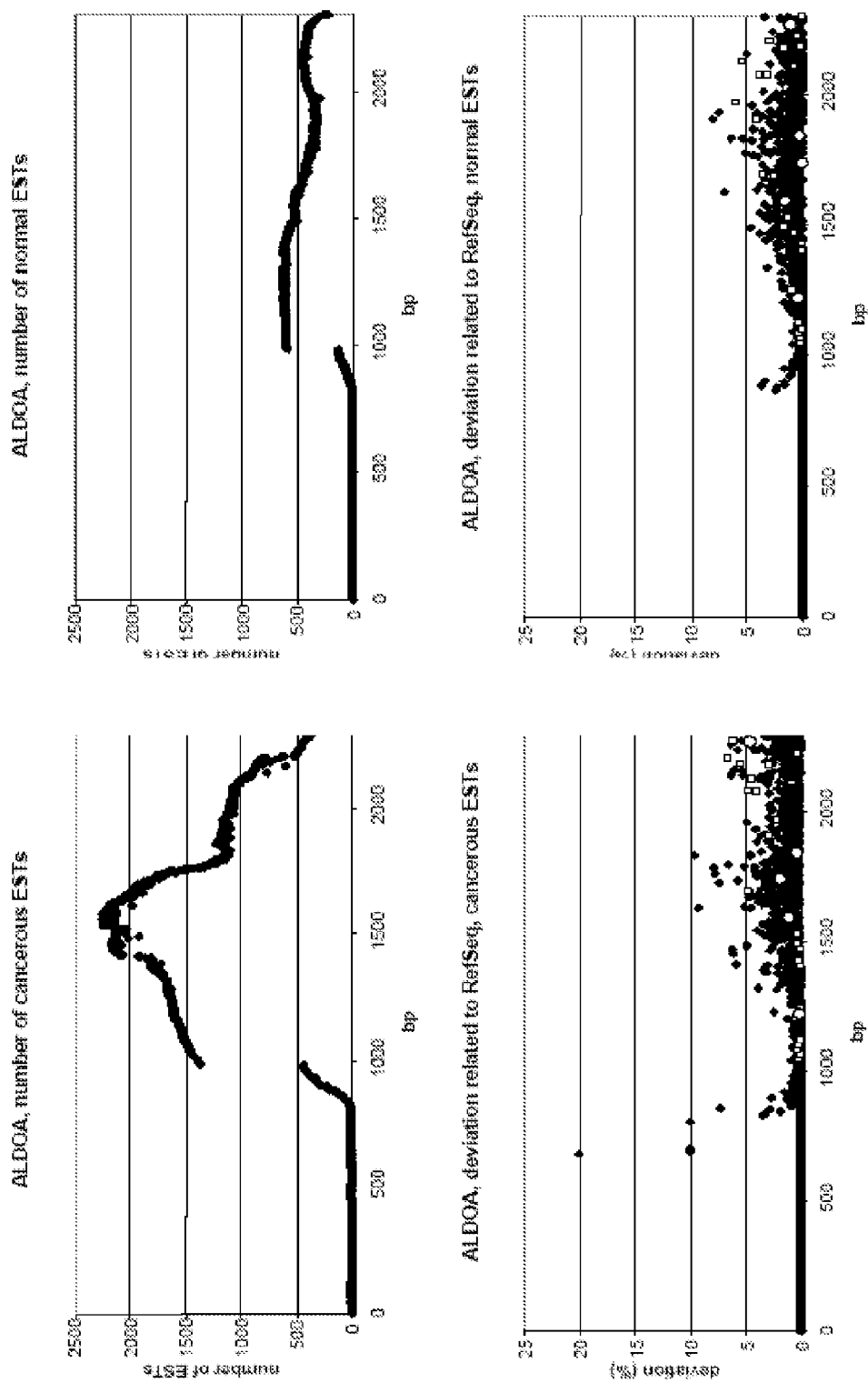
Figure 4a (following)

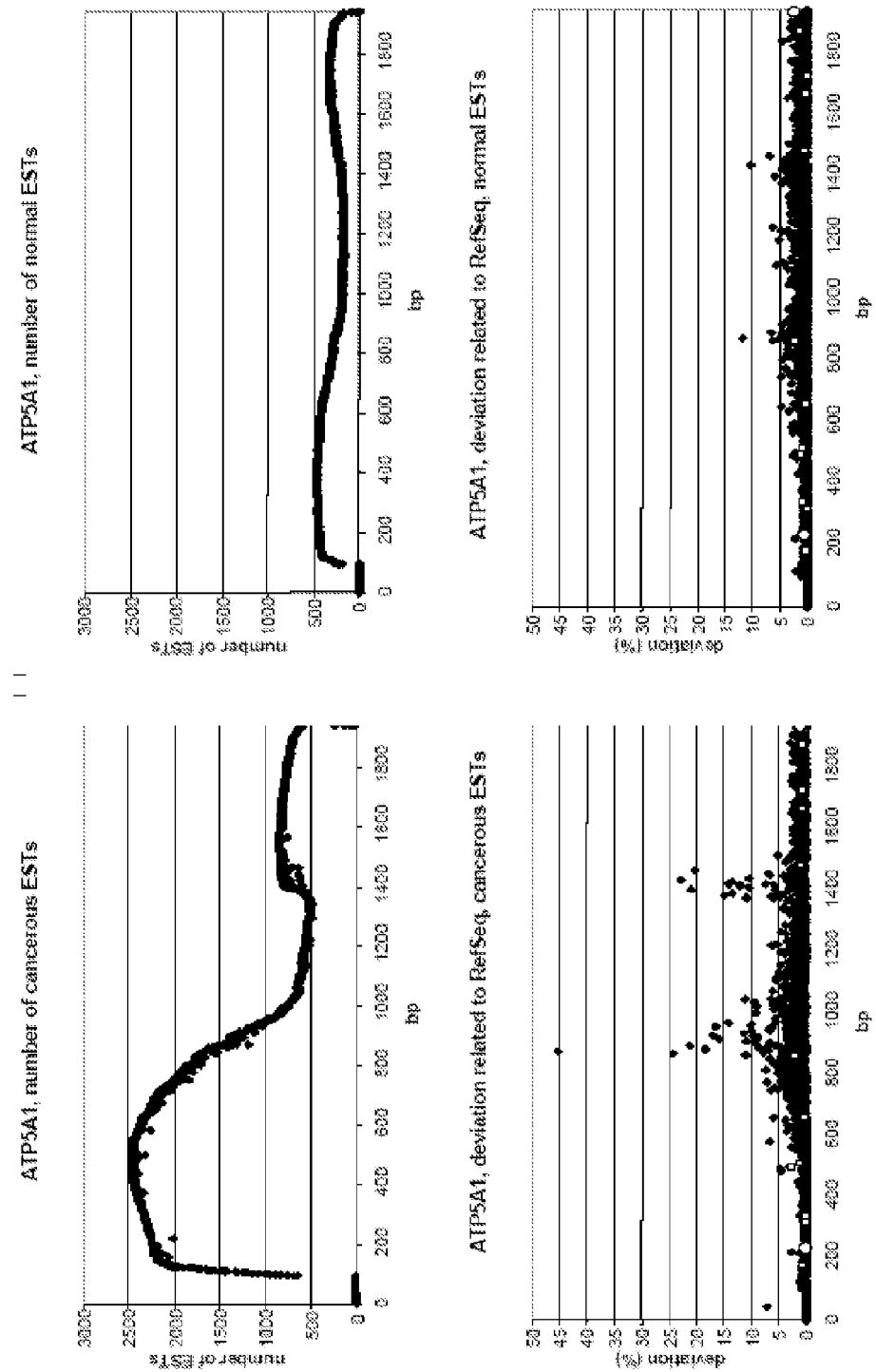
Figure 4a (following)

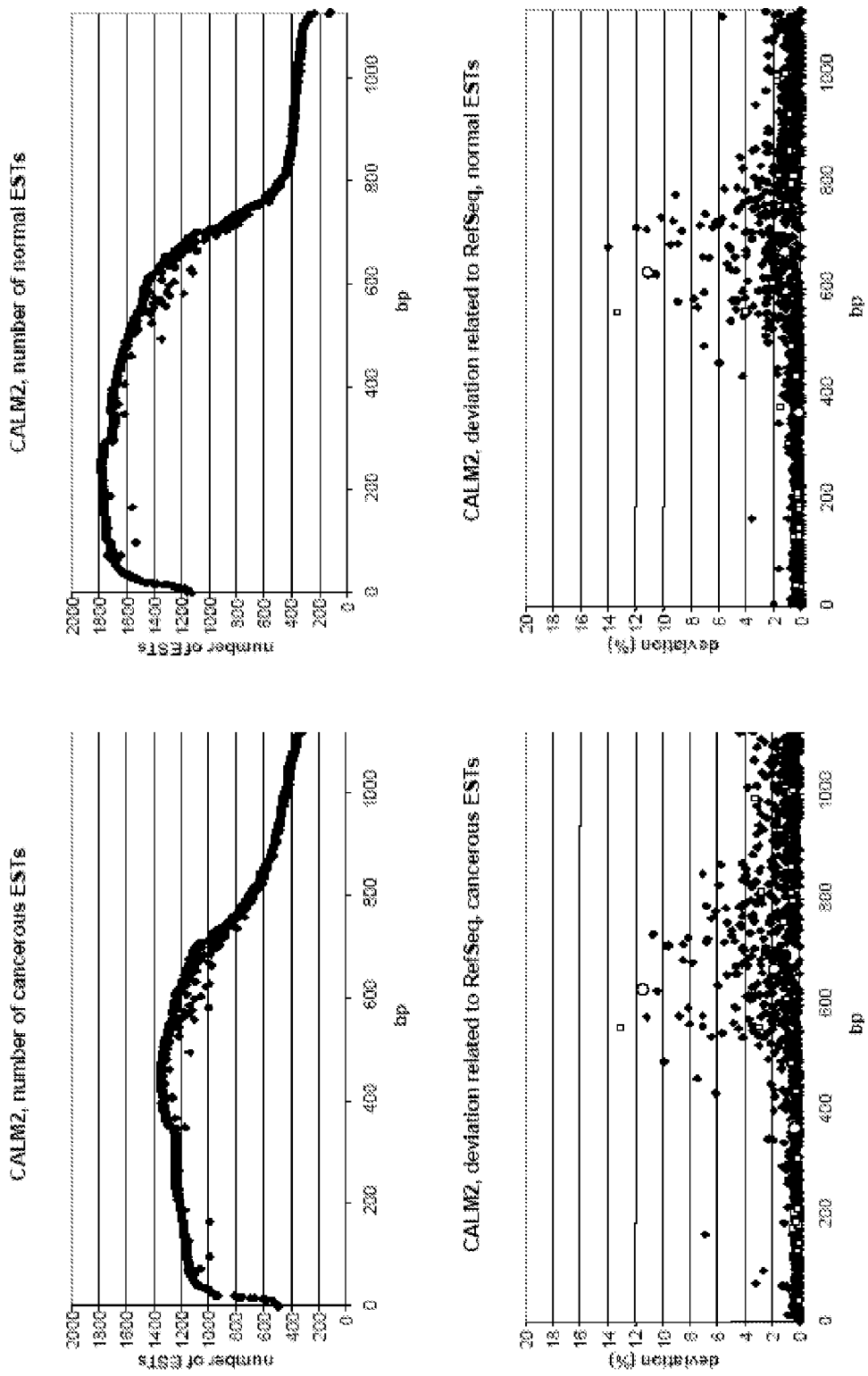
Figure 4a (following)

Figures 2, 4A:
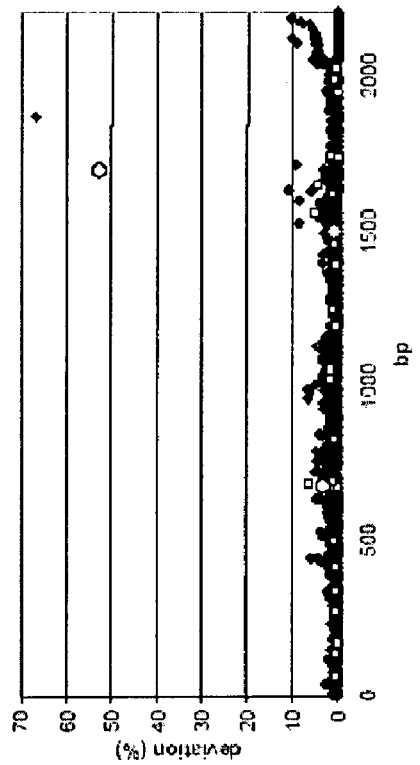
Figures 3, 4A:
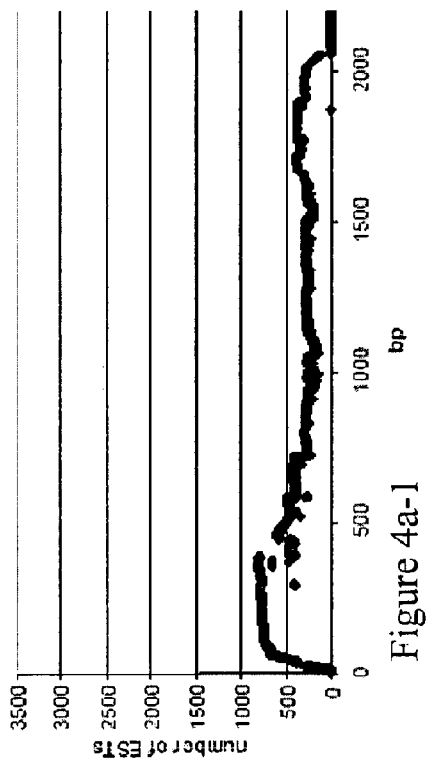
Figures 4, 4A:
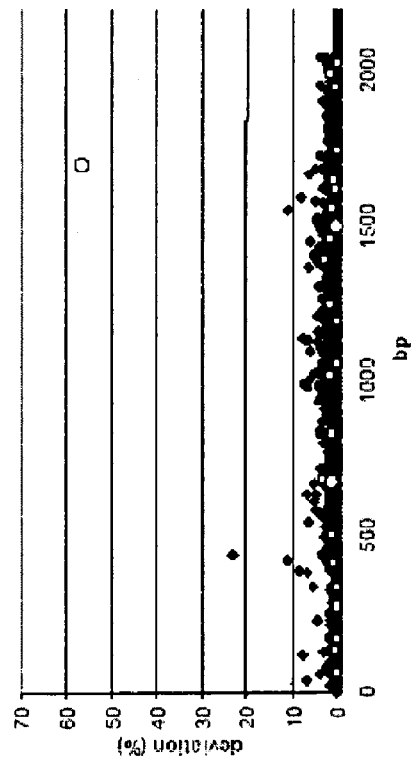
Figure 4B:
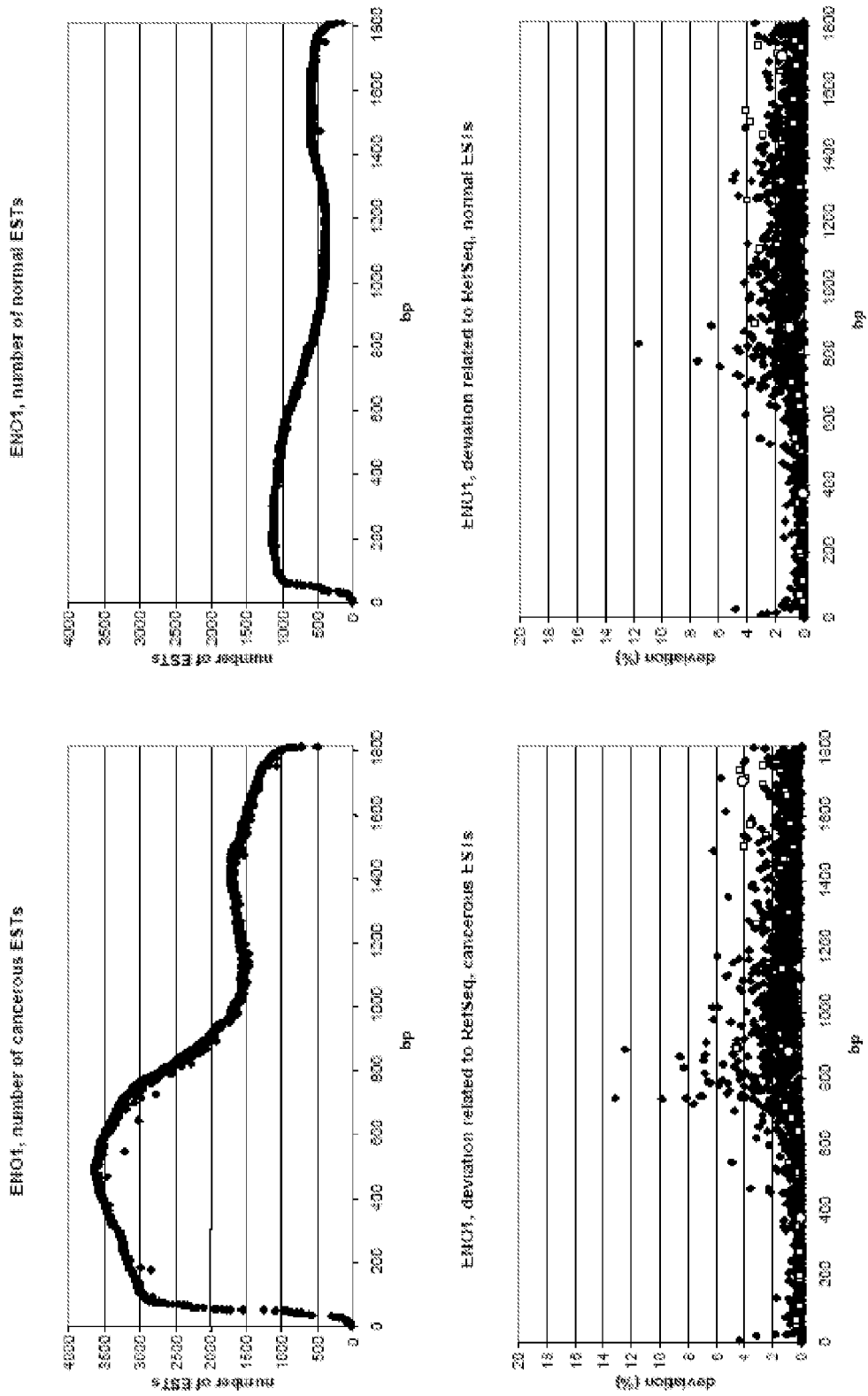

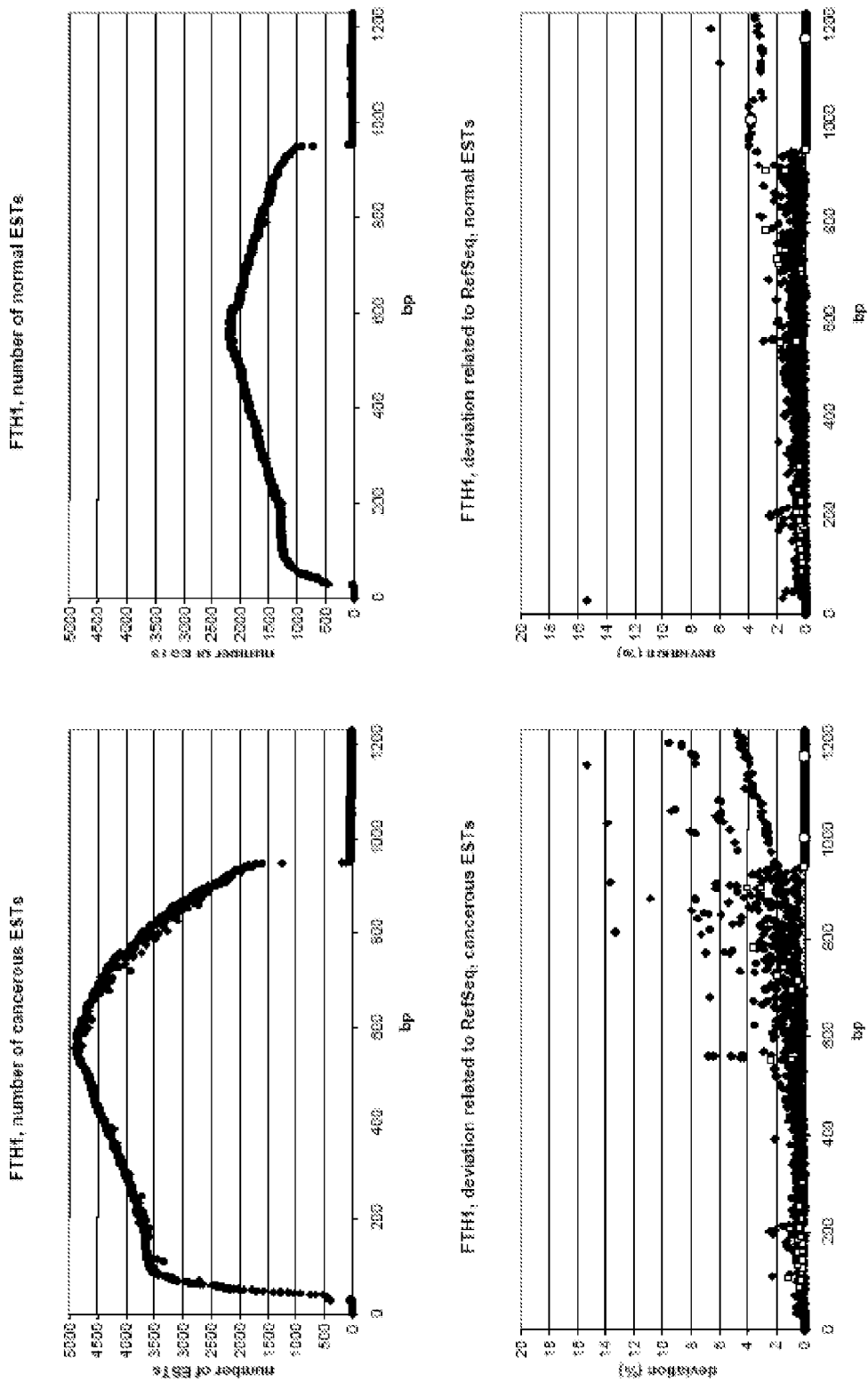
Figure 4b (following)

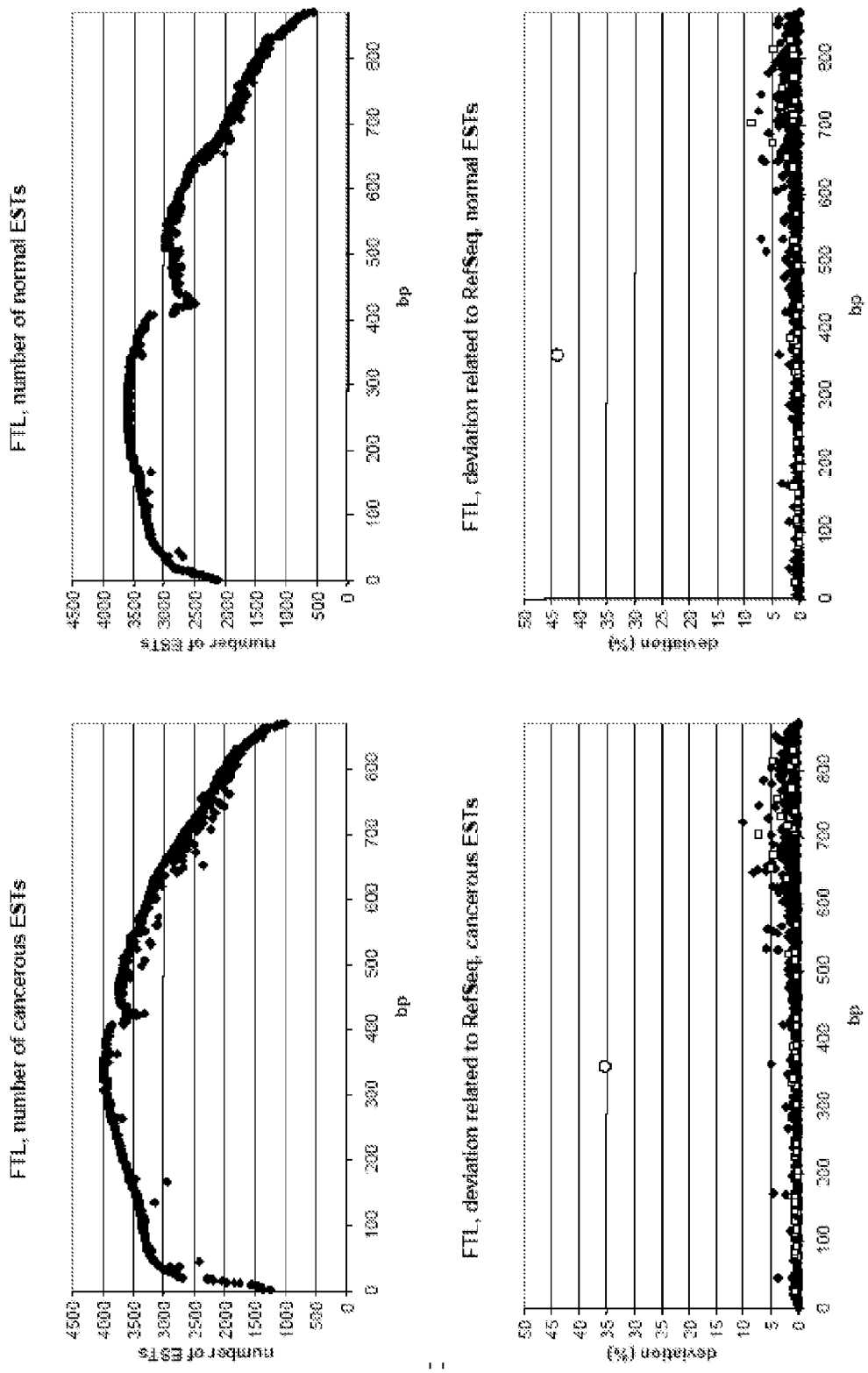
Figure 4b (following)

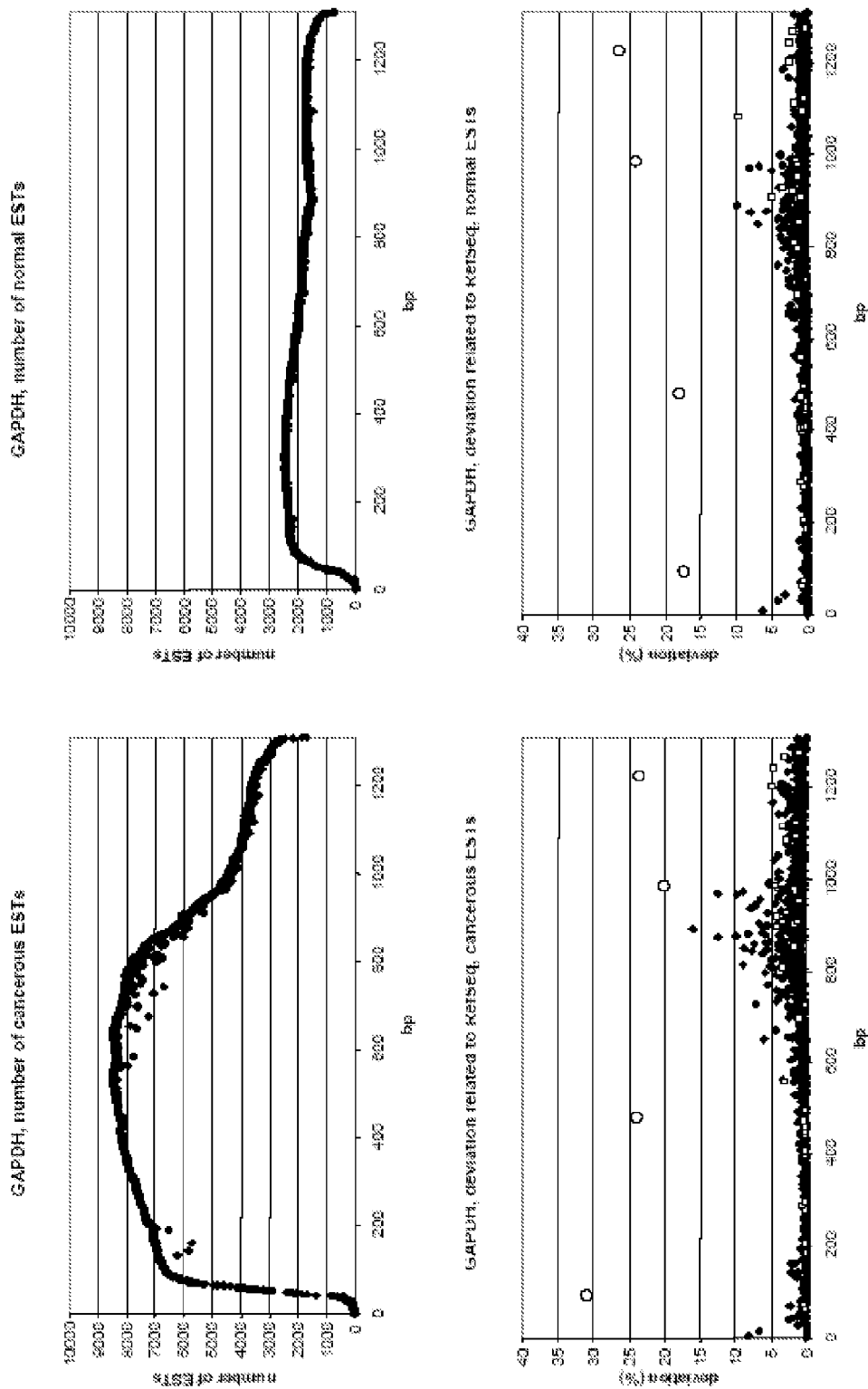
Figure 4b (following)

Figure 4C:
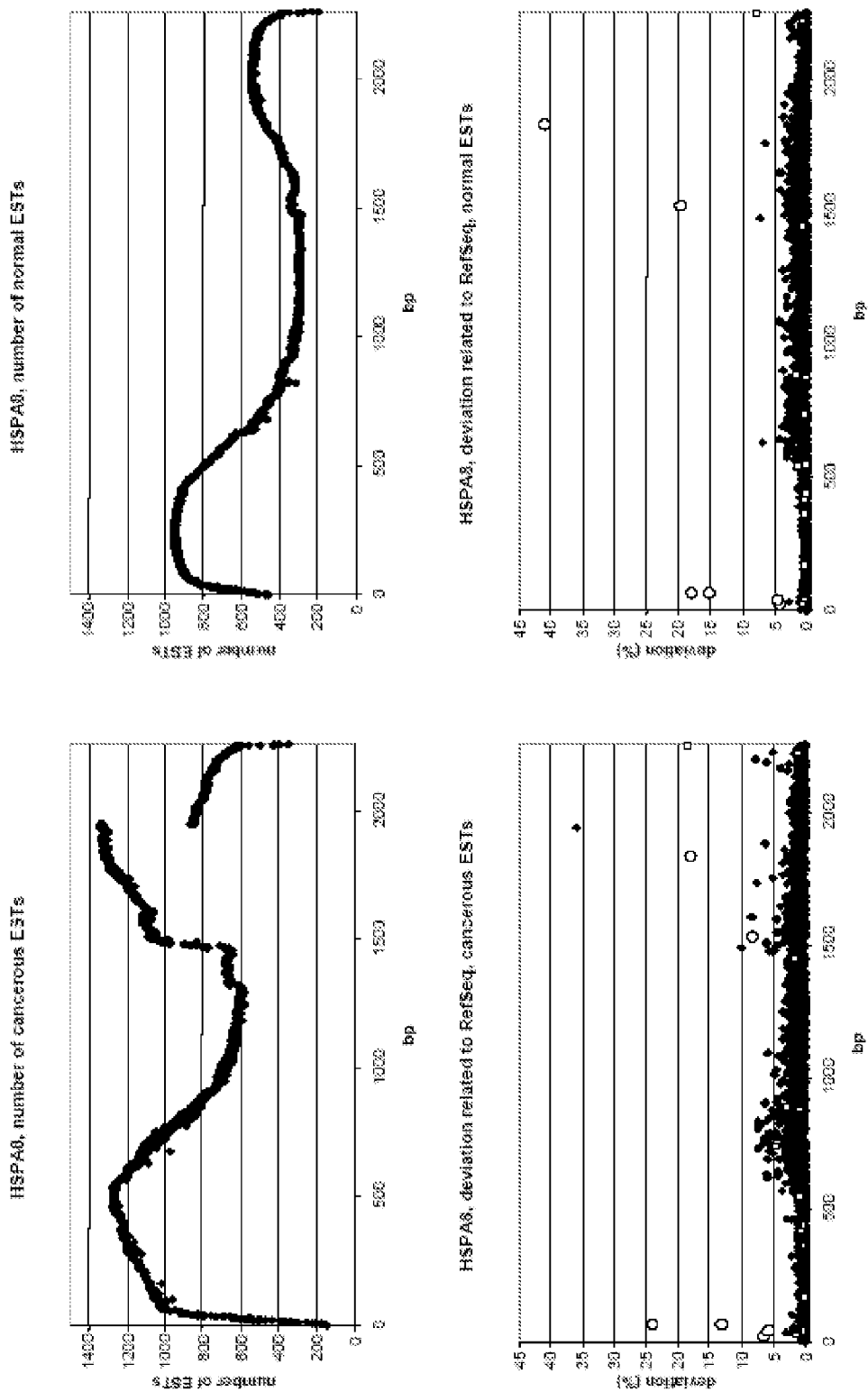

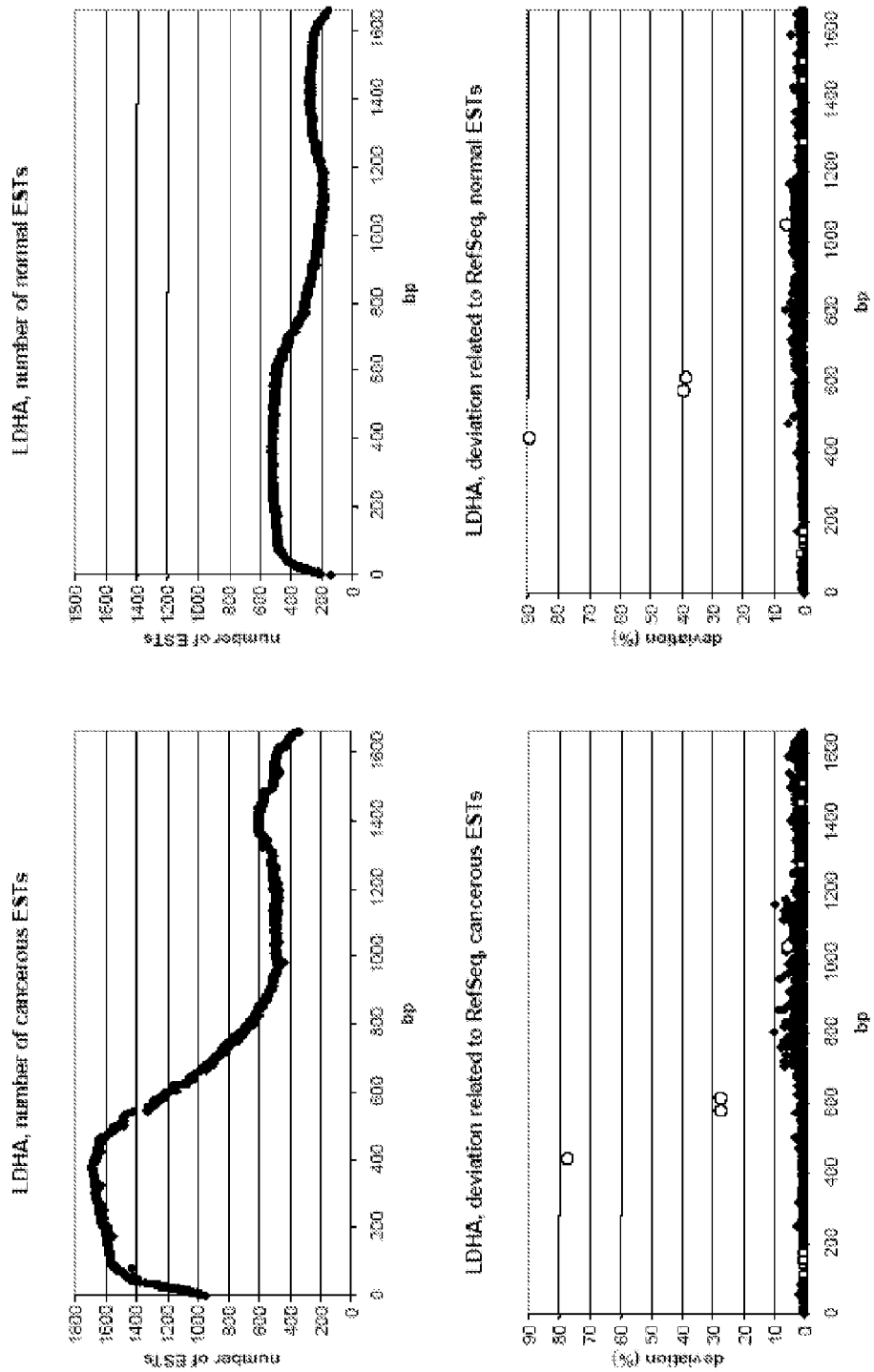
Figure 4c (following)

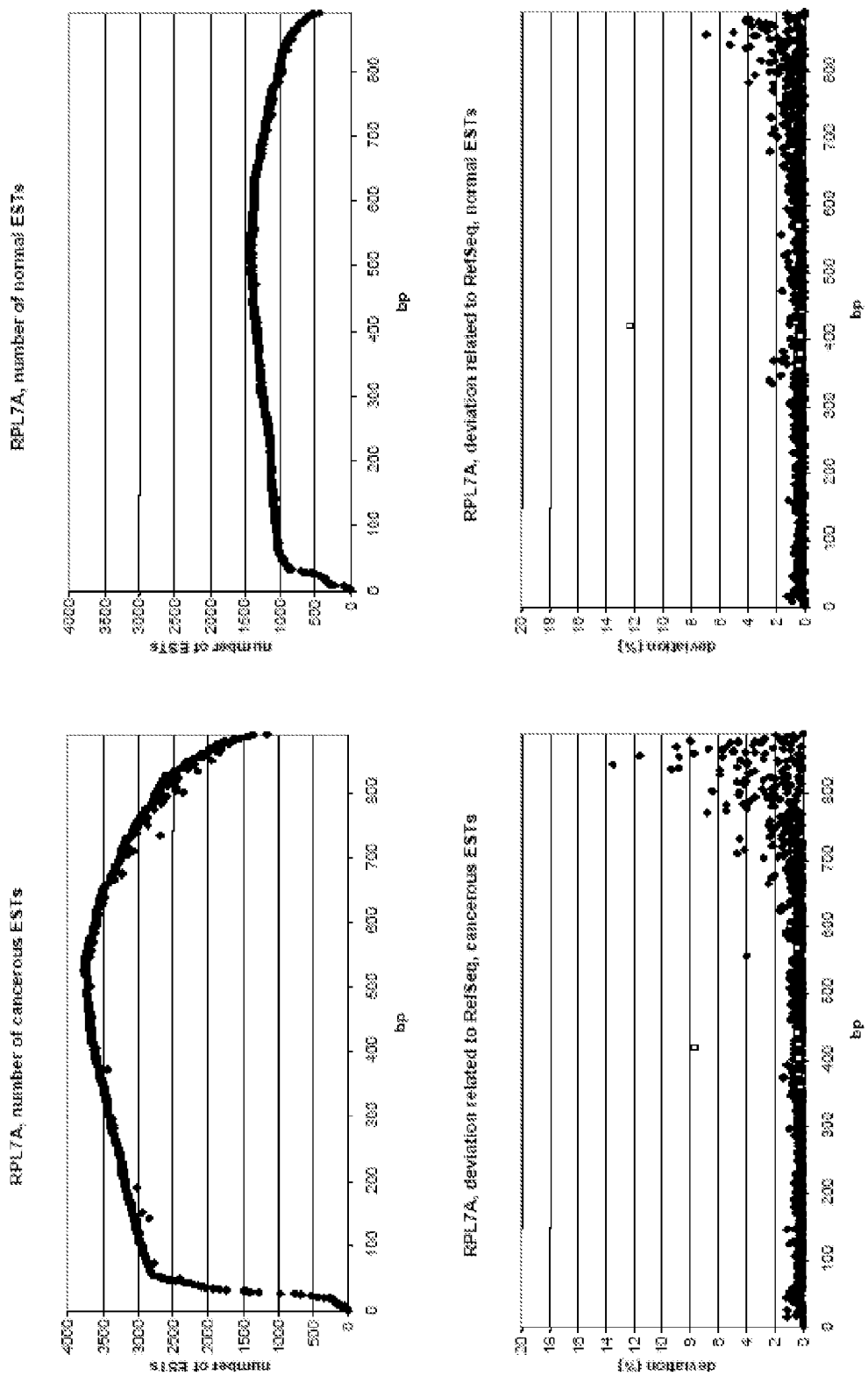
Figure 4c (following)

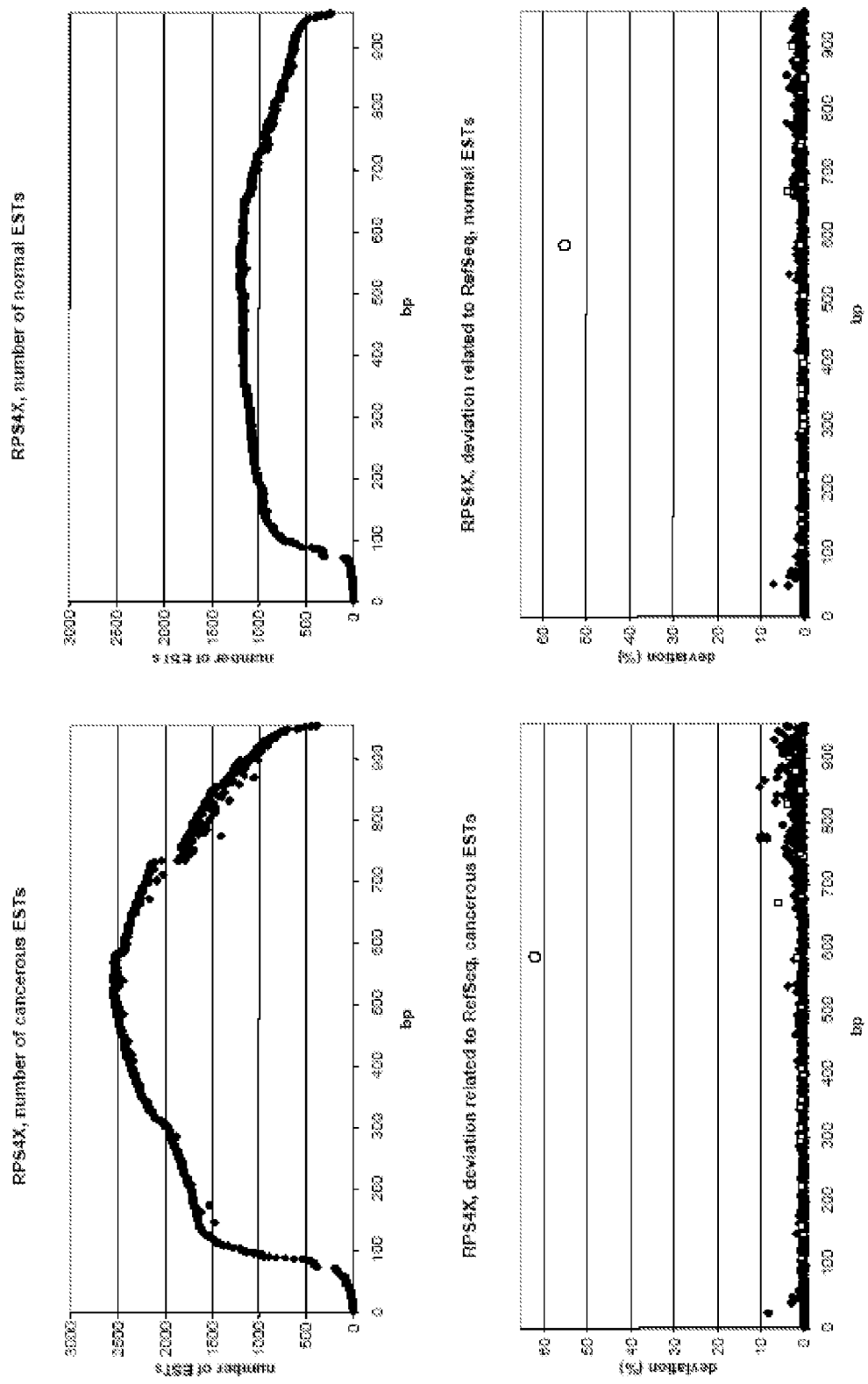
Figure 4c (following)

Figure 4D:
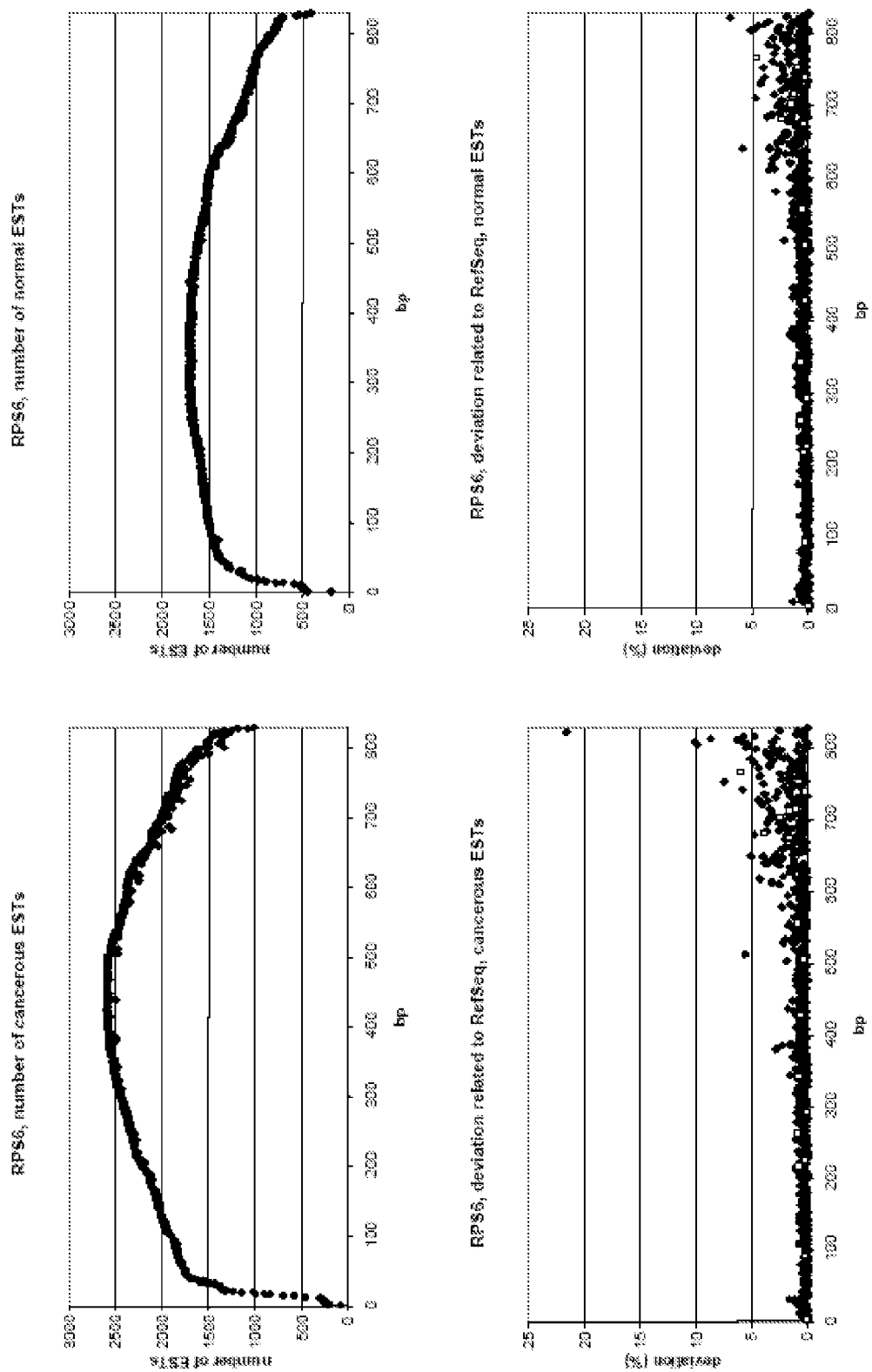

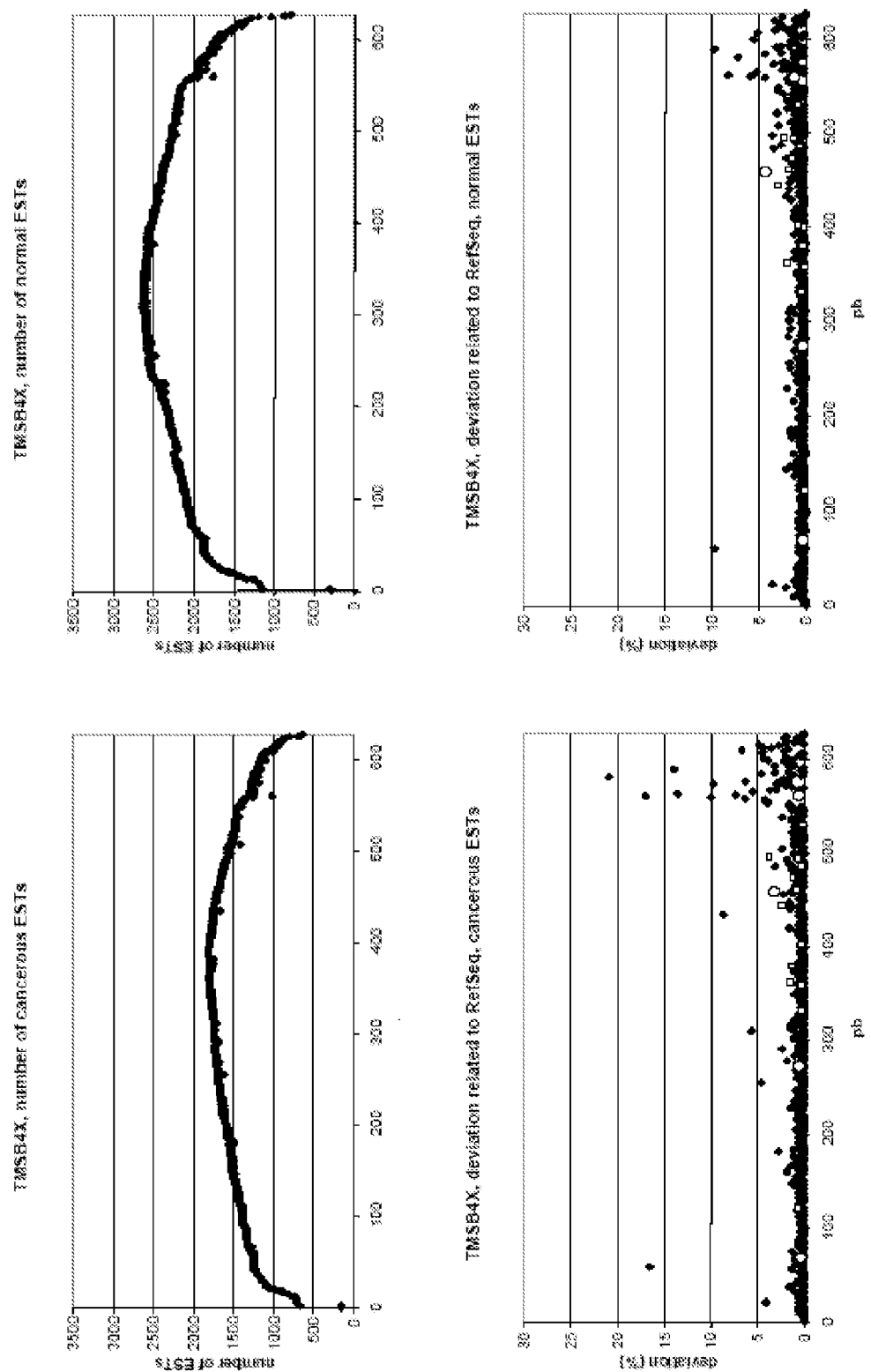
Figure 4d (following)

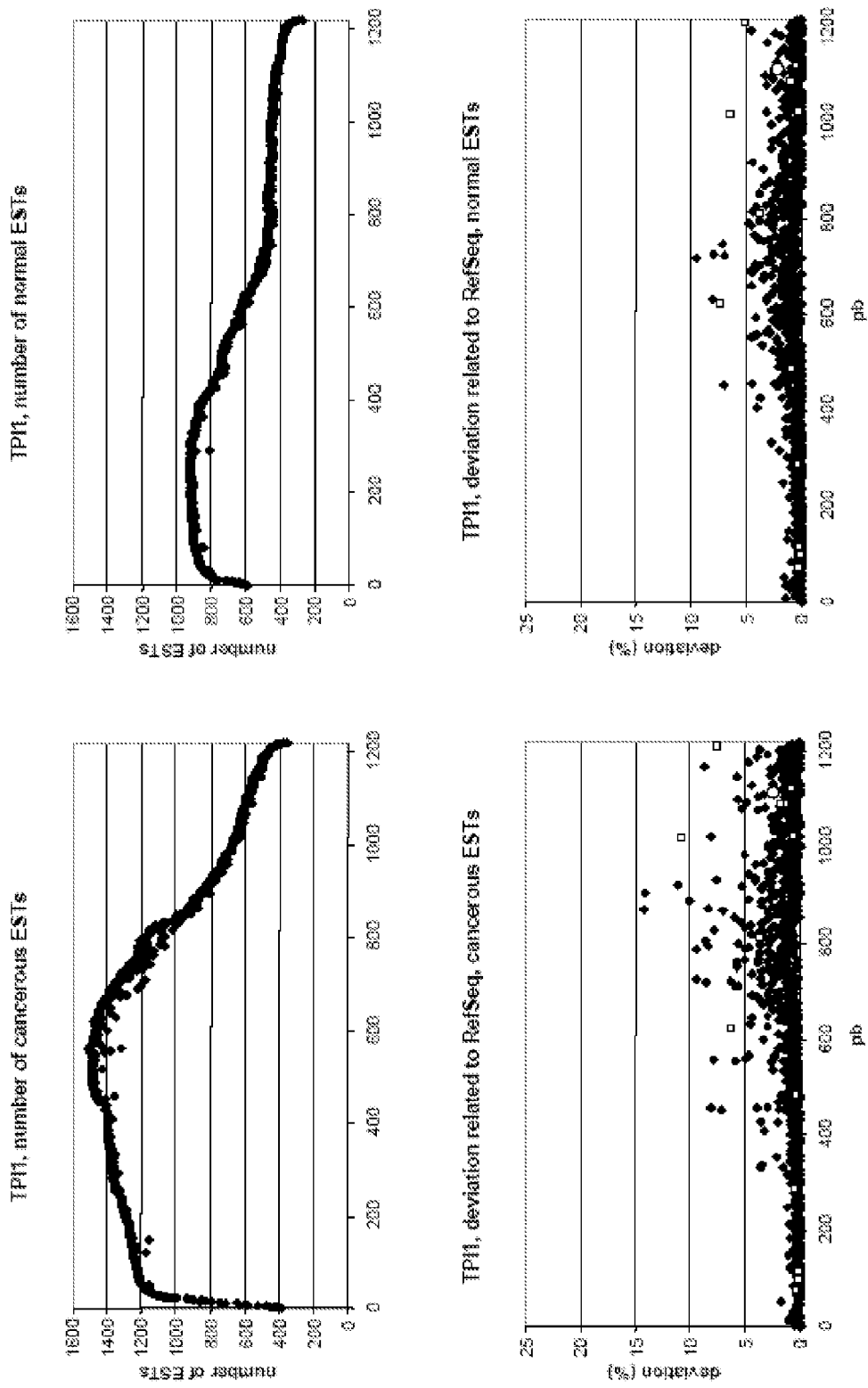
Figure 4d (following)

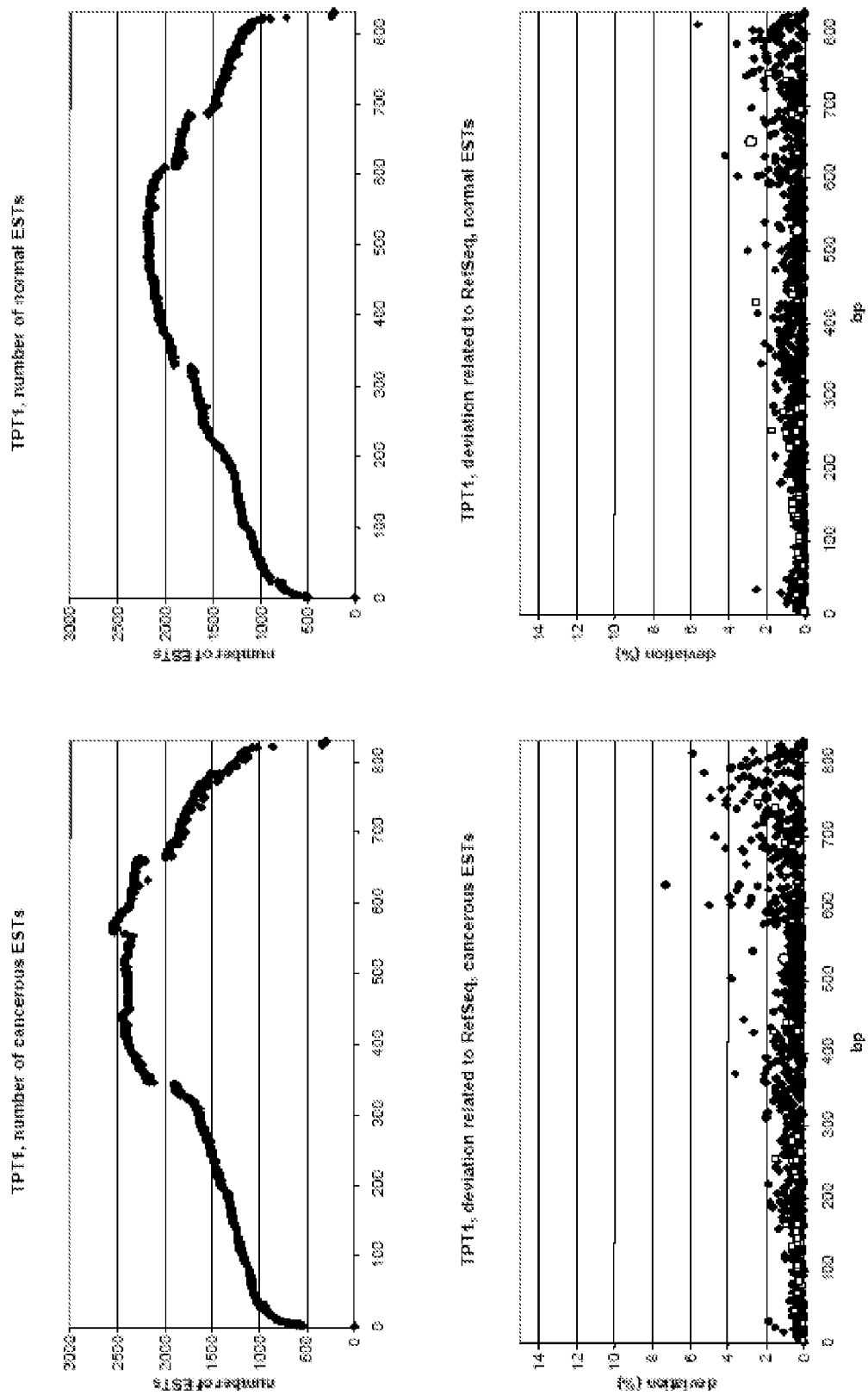
Figure 4d (following)

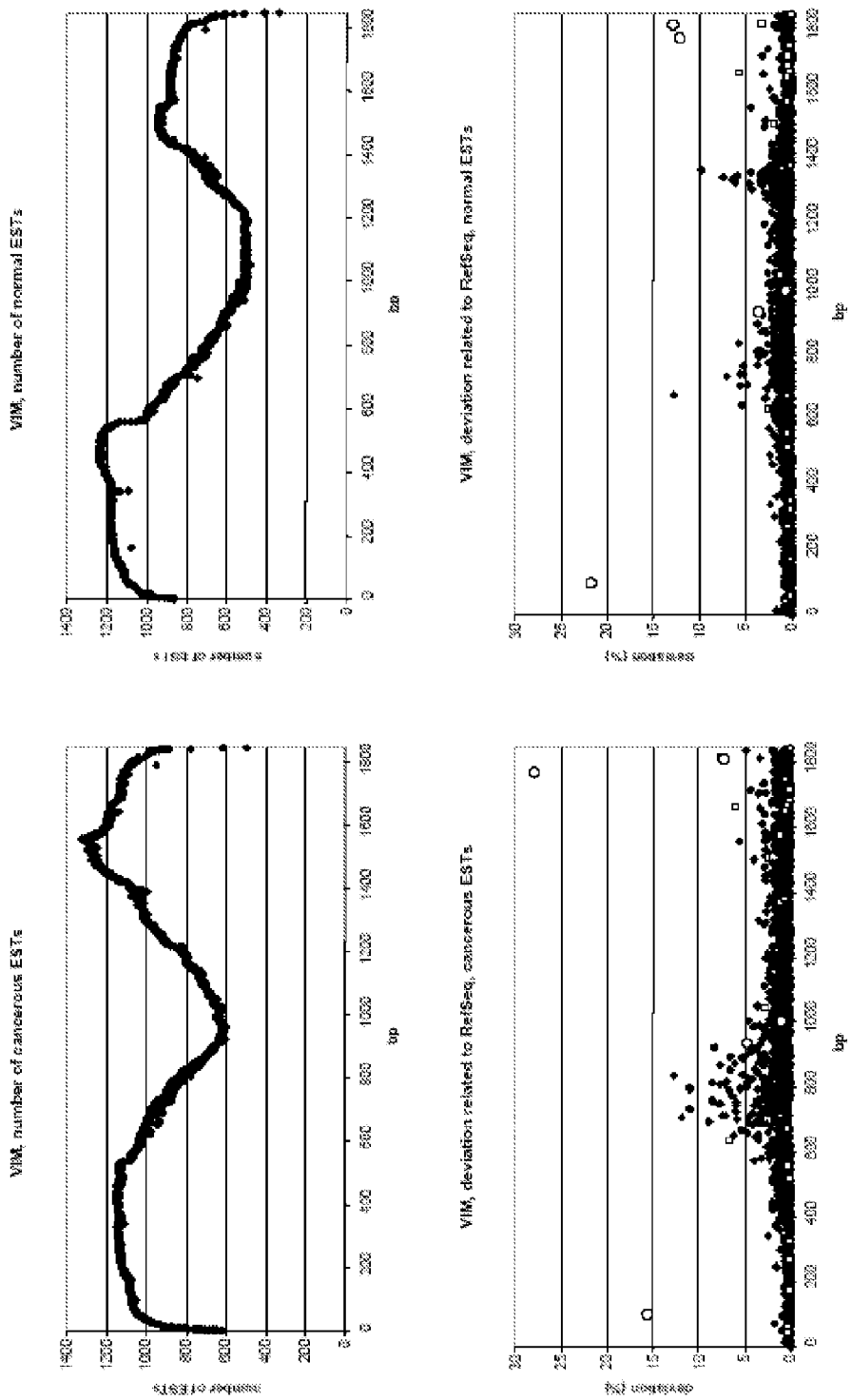
Figure 4d (following)

Proportion test analysis : results

| Gene | Number of proportion tests | % coverage | C>N | LBE | N>C | LBE |
|---|---|---|---|---|---|---|
| ALB | 194 | 9 | 38 | 10 | 56 | 8 |
| ALDOA transcript1 | 336 | 30 | 81 | 11 | 35 | 21 |
| ATP5A1 transcript1 | 238 | 38 | 123 | 3 | 6 | 20 |
| CALM2 | 374 | 23 | 69 | 16 | 40 | 21 |
| ENO1 | 614 | 27 | 186 | 18 | 31 | 42 |
| FTH1 | 592 | 71 | 226 | 20 | 57 | 38 |
| FTL | 678 | 56 | 118 | 31 | 86 | 36 |
| GAPDH | 812 | 91 | 311 | 23 | 61 | 57 |
| HSPA8 transcript1 | 513 | 59 | 163 | 13 | 18 | 37 |
| LDHA | 181 | 9 | 70 | 4 | 10 | 13 |
| RPL7A | 337 | 35 | 103 | 11 | 33 | 22 |
| RPS4X | 371 | 45 | 124 | 11 | 27 | 25 |
| RPS6 | 432 | 19 | 86 | 17 | 40 | 25 |
| TMSB4X | 352 | 19 | 70 | 18 | 74 | 17 |
| TPI1 | 379 | 31 | 99 | 14 | 47 | 23 |
| TPT1 | 489 | 26 | 145 | 15 | 26 | 33 |
| VIM | 752 | 57 | 269 | 24 | 78 | 50 |

Figure 5i

Proportion test analysis : results (deletions and insertions)

DELETIONS

| Genes | Number of proportion tests | C>N | LBE N>C | N>C | LBE | C>N / N>C |
|---|---|---|---|---|---|---|
| ALB | 17 | 1 | 1 | 10 | 0 | 0.1 |
| ALDOA | 34 | 8 | 1 | 7 | 1 | 1.1 |
| ATP5A1 | 24 | 16 | 0 | 0 | 2 | |
| CALM2 | 50 | 14 | 2 | 4 | 2 | 3.5 |
| ENO1 | 41 | 29 | 0 | 5 | 3 | 5.8 |
| FTH1 | 67 | 46 | 2 | 4 | 5 | 11.5 |
| FTL | 100 | 22 | 2 | 9 | 7 | 4.7 |
| GAPDH | 99 | 59 | 2 | 17 | 7 | 3.5 |
| HSPA8 | 30 | 27 | 0 | 0 | 2 | |
| LDHA | 14 | 6 | 0 | 3 | 0 | 2.0 |
| RPL7A | 45 | 26 | 0 | 1 | 3 | 26.0 |
| RPS4X | 35 | 29 | 0 | 1 | 3 | 29.0 |
| RPS6 | 45 | 24 | 0 | 1 | 3 | 24.0 |
| TMSB4X | 28 | 16 | 0 | 4 | 1 | 4.0 |
| TPI1 | 30 | 17 | 0 | 1 | 2 | 17.0 |
| TPT1 | 43 | 27 | 0 | 4 | 3 | 6.8 |
| VIM | 26 | 11 | 1 | 9 | 1 | 1.2 |
| Total | 728 | 398 | 9 | 83 | 45 | 4.8 |

INSERTIONS

| Genes | Number of proportion tests | C>N | LBE | N>C | LBE | C>N / N>C |
|---|---|---|---|---|---|---|
| ALB | 9 | 0 | 0 | 9 | 0 | 0.0 |
| ALDOA | 5 | 1 | 0 | 5 | 0 | 1.0 |
| ATP5A1 | 9 | 6 | 0 | 0 | 0 | |
| CALM2 | 72 | 10 | 3 | 10 | 3 | 1.0 |
| ENO1 | 40 | 14 | 0 | 2 | 3 | 7.0 |
| FTH1 | 114 | 54 | 1 | 3 | 9 | 18.0 |
| FTL | 188 | 26 | 9 | 33 | 9 | 0.8 |
| GAPDH | 137 | 46 | 4 | 18 | 9 | 2.6 |
| HSPA8 | 14 | 7 | 0 | 2 | 1 | 3.5 |
| LDHA | 2 | 0 | 0 | 0 | 0 | |
| RPL7A | 56 | 12 | 1 | 1 | 3 | 12.0 |
| RPS4X | 29 | 9 | 1 | 2 | 3 | 4.5 |
| RPS6 | 44 | 12 | 1 | 1 | 3 | 12.0 |
| TMSB4X | 22 | 5 | 1 | 6 | 0 | 0.8 |
| TPI1 | 26 | 6 | 1 | 5 | 1 | 1.2 |
| TPT1 | 41 | 7 | 1 | 4 | 2 | 1.8 |
| VIM | 27 | 10 | 1 | 3 | 1 | 3.3 |
| Total | 835 | 225 | 24 | 100 | 45 | 2.3 |

Figure 5k

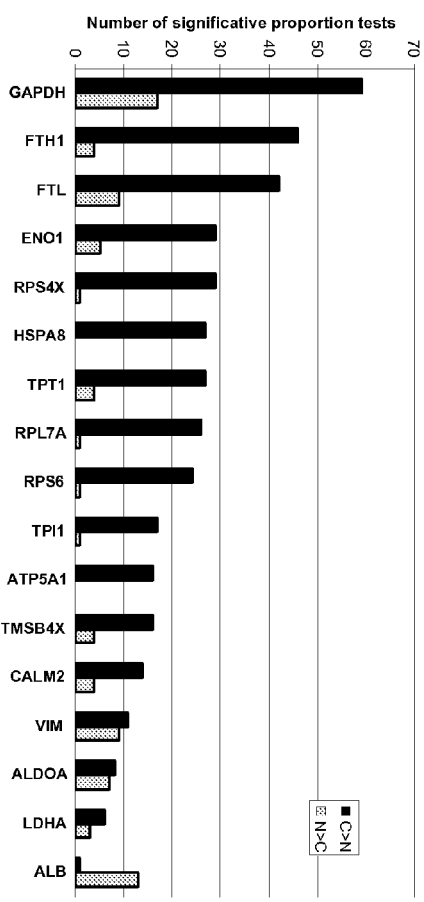 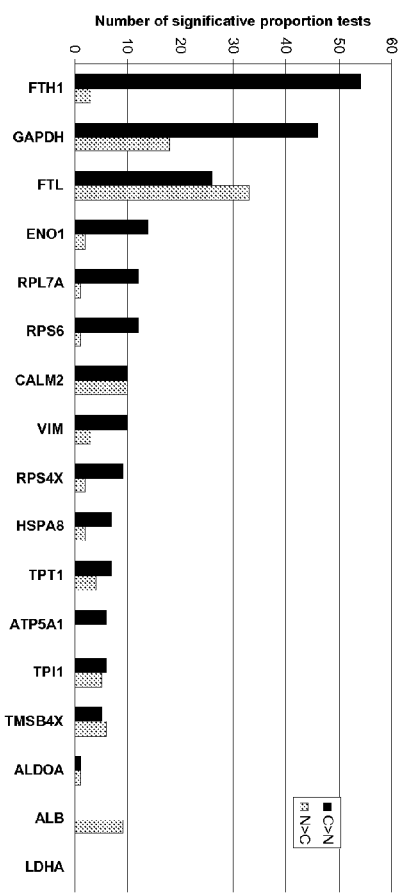
Figure 51

Figure 5m

N>C positions(83)

| Omitted base | Nb Ref | Specificity | Freq Ref | Freq EST | Singl. | Beginning 1 2 3 4 5 6 | Bipolar 1 2 3 4 5 6 7 8 | End 1 2 3 4 5 6 7 8 |
|---|---|---|---|---|---|---|---|---|
| A | 2 | 22,2% | 2,4% | 0,9% | | | | A A A A * |
| | 1 | 20,0% | 1,2% | 7,8% | | * A | | |
| | 1 | 3,6% | 1,2% | 2,6% | | | | A * |
| | 1 | 100,0% | 1,2% | 1,4% | | | A * T T | |
| | 1 | 14,3% | 1,2% | 0,6% | | | | A A A * |
| | 1 | 50,0% | 1,2% | 7,8% | | | | A A A A A A * |
| | 1 | 100,0% | 1,2% | 4,4% | | | | C C * |
| | 1 | 100,0% | 1,2% | 5,2% | | | C C C * A | |
| | 1 | 50,0% | 1,2% | 3,0% | | | | G G * |
| C | 9 | 11,5% | 10,8% | 1,6% | | | | C * |
| | 4 | 16,7% | 4,8% | 1,6% | | * C | | |
| | 3 | 50,0% | 3,6% | 1,6% | | | | C C C C * |
| | 2 | 6,5% | 2,4% | 6,2% | * | | | |
| | 2 | 33,3% | 2,4% | 4,7% | | | C C * T T | |
| | 2 | 11,1% | 2,4% | 3,1% | | | | G G * |
| | 2 | 15,4% | 2,4% | 1,1% | | | G G * C | |
| | 1 | 33,3% | 1,2% | 6,3% | | * A A | | |
| | 1 | 9,1% | 1,2% | 1,8% | | * C C | | |
| | 1 | 50,0% | 1,2% | 1,3% | | * C C C | | |
| | 1 | 100,0% | 1,2% | 1,0% | | | A A * C | |
| | 1 | 100,0% | 1,2% | 1,3% | | | A A A A * C C C | |
| | 1 | 6,7% | 1,2% | 3,0% | | | C * A A | |
| | 1 | 25,0% | 1,2% | 3,3% | | | C * A A A | |
| | 1 | 2,7% | 1,2% | 6,7% | | | | C C * |
| | 1 | 25,0% | 1,2% | 5,6% | | | C C * A A | |
| | 1 | 100,0% | 1,2% | 3,2% | | | C C * G G | |
| | 1 | 8,3% | 1,2% | 4,4% | | | | C C C C * |
| | 1 | 100,0% | 1,2% | 6,9% | | | | C C C C C * |
| | 1 | 33,3% | 1,2% | 1,6% | | | G G * C C C | |
| | 1 | 100,0% | 1,2% | 1,4% | | | G G * C C C | |
| | 1 | 100,0% | 1,2% | 2,7% | | | G G G * C C C | |
| | 1 | 50,0% | 1,2% | 11,4% | | | T T * A A | |
| G | 4 | 36,4% | 4,8% | 5,3% | | * G | | |
| | 3 | 37,5% | 3,6% | 2,8% | * | | | |
| | 3 | 16,7% | 3,6% | 3,6% | | | | G * |
| | 2 | 33,3% | 2,4% | 17,4% | | * C C | | |
| | 2 | 40,0% | 2,4% | 7,5% | | | G * C C | |
| | 1 | 10,0% | 1,2% | 8,4% | | * G G | | |
| | 1 | 20,0% | 1,2% | 10,5% | | * G G G | | |
| | 1 | 100,0% | 1,2% | 1,9% | | * G G G G G | | |
| | 1 | 50,0% | 1,2% | 2,5% | | | | A A * |
| | 1 | 100,0% | 1,2% | 4,2% | | | A A * C C | |
| | 1 | 100,0% | 1,2% | 2,6% | | | A A * C C C | |
| | 1 | 50,0% | 1,2% | 2,1% | | | A A * G G | |
| | 1 | 12,5% | 1,2% | 9,4% | | | | G G * |
| T | 2 | 9,1% | 2,4% | 2,3% | | | T T * | |
| | 1 | 20,0% | 1,2% | 1,2% | * | | | |
| | 1 | 2,2% | 1,2% | 4,1% | | * T | | |
| | 1 | 4,8% | 1,2% | 2,7% | | * T T | | |
| | 1 | 100,0% | 1,2% | 8,2% | | | C C * T T | |
| | 1 | 100,0% | 1,2% | 1,5% | | | C C C * T T T | |
| | 1 | 100,0% | 1,2% | 1,2% | | | T T * A A A | |
| | 1 | 7,1% | 1,2% | 2,5% | | | | T T T * |
| | 1 | 100,0% | 1,2% | 1,8% | | | T T T * A A | |
| | 1 | 100,0% | 1,2% | 1,3% | | | T T T T * G G | |

| | C>N-LBE | | | | | N>C-LBE | | | | |
|---|---|---|---|---|---|---|---|---|---|---|
| | F1 | F2 | F3 | F4 | F5 | F1 | F2 | F3 | F4 | F5 |
| ENO1 | 108 | 150 | 142 | 85 | 45 | 0 | 0 | 0 | 0 | 7 |
| FTH1 | 203 | 186 | 167 | 146 | 87 | 19 | 38 | 39 | 22 | 32 |
| GAPDH | 288 | 250 | 277 | 192 | 43 | 4 | 13 | 14 | 0 | 68 |
| HSPA8 | 160 | 127 | 128 | 87 | 56 | 0 | 0 | 0 | 0 | 0 |
| RPL7A | 92 | 85 | 85 | 51 | 42 | 11 | 10 | 15 | 0 | 6 |
| RPS4X | 113 | 89 | 102 | 68 | 68 | 2 | 0 | 1 | 0 | 0 |
| RPS6 | 59 | 62 | 61 | 32 | 22 | 15 | 20 | 20 | 13 | 14 |
| TPT1 | 130 | 121 | 123 | 89 | 69 | 0 | 0 | 0 | 0 | 0 |
| VIM | 245 | 209 | 216 | 140 | 140 | 23 | 32 | 6 | 1 | 1 |
| ALB | 28 | 18 | 18 | 7 | 7 | 48 | 41 | 41 | 22 | 22 |
| FTL | 57 | 92 | 92 | 65 | 34 | 50 | 58 | 57 | 32 | 50 |
| TMSB4X | 52 | 41 | 41 | 26 | 26 | 57 | 54 | 54 | 24 | 24 |
| ALDOA | 70 | 63 | 83 | 45 | 45 | 14 | 10 | 10 | 0 | 0 |
| ATP5A1 | 120 | 109 | 109 | 62 | 23 | 0 | 0 | 0 | 0 | 0 |
| CALM2 | 53 | 54 | 54 | 44 | 44 | 19 | 17 | 17 | 15 | 15 |
| LDHA | 88 | 58 | 57 | 30 | 30 | 0 | 0 | 0 | 0 | 0 |
| TPI1 | 95 | 81 | 81 | 56 | 17 | 24 | 29 | 29 | 8 | 16 |
| All genes | 2022 | 1835 | 1642 | 1168 | 793 | 281 | 326 | 303 | 147 | 257 |

[(C>N)-LBE]/[(N>C)-LBE]: F1 6.95, F2 5.59, F3 6.08, F4 7.95, F5 3.09

Figure 6c-1

| | C>N | LBE | N>C | LBE | (C>N)/(N>C) | [(C>N)-LBE]/[(N>C)-LBE] |
|---|---|---|---|---|---|---|
| F1 | 2281 | 259 | 725 | 488 | 3.15 | 6.95 |
| F2 | 2065 | 230 | 722 | 429 | 2.86 | 5.59 |
| F3 | 2065 | 223 | 694 | 428 | 2.98 | 6.08 |
| F4 | 1300 | 132 | 374 | 266 | 3.48 | 7.95 |
| F5 | 933 | 140 | 456 | 219 | 2.05 | 3.09 |

A. All deviations (n = 2281)

| affected \ replacement | A | T | C | G | % |
|---|---|---|---|---|---|
| A |  | 85 | 560 | 107 | 33 |
| T | 139 |  | 210 | 384 | 32 |
| C | 169 | 130 |  | 185 | 21 |
| G | 199 | 28 | 85 |  | 14 |
| % | 22 | 11 | 37 | 30 |  |

B. Deviations towards b-1 (n = 799)

| affected \ replacement | A | T | C | G | % |
|---|---|---|---|---|---|
| A |  | 41 | 201 | 42 | 36 |
| T | 28 |  | 56 | 83 | 21 |
| C | 77 | 41 |  | 126 | 30 |
| G | 75 | 9 | 20 |  | 13 |
| % | 23 | 11 | 35 | 31 |  |

C. Deviations towards b+1 (n = 530)

| affected \ replacement | A | T | C | G | % |
|---|---|---|---|---|---|
| A |  | 24 | 52 | 37 | 21 |
| T | 27 |  | 45 | 177 | 47 |
| C | 38 | 48 |  | 15 | 19 |
| G | 40 | 11 | 16 |  | 13 |
| % | 20 | 16 | 21 | 43 |  |

D. Deviations towards neither b-1 nor b+1 (n = 347)

| affected \ replacement | A | T | C | G | % |
|---|---|---|---|---|---|
| A |  | 7 | 148 | 8 | 47 |
| T | 42 |  | 50 | 9 | 29 |
| C | 17 | 10 |  | 23 | 14 |
| G | 7 | 2 | 24 |  | 10 |
| % | 19 | 5 | 64 | 12 |  |

E. Deviations b-1 = b+1 (n = 339)

| affected \ replacement | A | T | C | G | % |
|---|---|---|---|---|---|
| A |  | 5 | 52 | 12 | 20 |
| T | 11 |  | 12 | 95 | 35 |
| C | 25 | 30 |  | 17 | 21 |
| G | 71 | 1 | 8 |  | 24 |
| % | 31 | 11 | 21 | 37 |  |

F. Deviations within Triplet (n = 266)

| affected \ replacement | A | T | C | G | % |
|---|---|---|---|---|---|
| A |  | 8 | 107 | 8 | 46 |
| T | 31 |  | 47 | 20 | 37 |
| C | 12 | 1 |  | 4 | 6 |
| G | 6 | 5 | 17 |  | 11 |
| % | 19 | 5 | 64 | 12 |  |

| Coding Impact of the [Cancer>Normal] substitutions 17 genes study | | |
|---|---|---|
| Number of C>N substitutions | 2281 | |
| Number of C>N substitutions in CDS | 1548 | |
| Coding impact % | 67.9% | |

| CDS region study | Number of substitutions | % |
|---|---|---|
| Silencing substitutions | 369 | 23.8% |
| Coding impact (A.A. modification but same family) | 393 | 25.4% |
| Coding impact (A.A. family modification) | 744 | 48.1% |
| Non-sens substitutions | 24 | 1.6% |
| Canonical STOP codon modifications | 19 | 1.2% |

| Substitutions giving an ATG codon (MET) | 33 | 2.1% |
|---|---|---|

Figure 9

Figure 10a additional peptide of proteins whose STOP codon is affected normal proteins

Figure 10b additional peptide of proteins whose STOP codon is affected

Figure 12a

```
5' TCCCCTCGTGTCAGCTGAGG 3' 1505-1524
5' CTCATGGGTCACTGAGGTTTTAT 3' 1789-1812
Amplification product length : 308   1505-1812
GC% : 56.0%
Suggested hybridization temperature(TA) : 58.1
Primer strand + :
Primer strand - :

Primer     :     5' TCCCCTCGTGTCAGCTGAGG 3'
                    ||||||||||||||||||||
Target : 1505 :  5' TCCCCTCGTGTCAGCTGAGG 3'
Score : 174          TM : 74.4 / 52.8 / 60.

Primer     :     3' ATAAAAGCCTCAGTGACCCATGAG 5' (complement)
                    ||||||||||||||||||||||||
Target : 1789 :  5' ATAAAAGCCTCAGTGACCCATGAG 3'
Score : 181          TM : 72.5 / 50.9 / 57.
```

>gi|16507965|ref|NM_001428.2| Homo sapiens enolase 1, (alpha)(ENO1), mRNA

TAGCTAGGCAGGAAGTCGGCGGCGGCGGGGCGCGGAGCAGTTCTGTGGGTACCCGGAGCACGGAGGATCTGGAGGTCGGCGTGTCGACCTCCGCTCCCTCCCTA
GGGACGAGCAGTGCTGCCCAGTGGTGCTTCACTTGTCTGGTACGTCTATTGTCTATGACGTGCAACATCGGCCTTAGCCCATCCACTGTTGACTGTCGAAGGTCT
CTCAGGAGCTGTGCCAGTGGTGCTTCAACTGGTGCTTCAACGTGCAGAGCTCGGGACAGCTCGAGCTCCGGGACAACTTTTGACTCTCAAAGGGTGAGCACATCAA
TAAAACTATTCGGCTCAACGTCTCCGTTCCCGCTCGTTGACTAGAAACTGGTAGAAACGGAAGAACAAGGGCTCCCCTGTACCAAGTCGGATTGGCTGCAGAACTTCAGGAAGCCATGGAGGCATTGGAGCAGAGGTTTACCA
CATTCTCGGGTGTCATGGCGTTCATCATGGCGTTCTCATCAAGCTGGCCATGCAGAAGTCAAGAAGCCATGGAGGTGCAGAAACTTCAGGAAGCCATTGGAGCAGAGGTTTACCA
CAACCTGAAGGATGTCATCAAGGAATATGCGAAGATCCCAGGATCCAAGTCTCCCCAACATCCTGTGGGGAATTAAGAAGGCTGAGCTCAGACTGC
TATTGGGAAAGCTGCTACAGTAAGTGCATCGGCAGCCTTGGACTCGGGAAATATGAGCACTGGACTCTGGAGCAGCTTCAACTGTGGGGACTGGGCCAGACCAAGTA
CATCTCCCTAGACCTGGCTGCAGTCAGTGATGATCATCTACAAAGCTGTCAACGACCTGTGTCTATCAGGACTACCCCCCTTGTCATGGCCTCAGGGTCAACCAGCCAG
TGCAGGAATCAGGTAGGGGCTGAAGCTGGCTGCCGATCAGCTGTGCCCGGAGTCGTCCCAATTGGGCGTCAGCCAATTGAAGGAGGCTGAAGACTCATGGCTGCAC
GACGAGTCTTCAAGGACTCAAGAGCCCCTTGGAAGCCTGGGAGCTTCCGGGATCTTGAGCGCTTCGGAGAATTGAAGAGGCTCACAGCCAG
CCCCTTGCCAATCGCTAGCTCGGCCAAGCCCCTTCGCTGGCTGGGCTGGCCTTCGGTGACGAAGACATGAACTCACAGCGCCAAGACCATCACAACCAGCCACGGCTCTAGATCATCTAGGCCTAC
GTGACCCATGAGT

Figure 12b

Figure 12c

| | | Expasy | Plasma Proteome database | |
|---|---|---|---|---|
| | | | protein | mRNA |
| Symbol | Name | SP accession | PPD accession | PPD accession |
| A2M | alpha-2-macroglobulin | P01023 | NP_000005 | NM_000014 |
| AHSG | alpha-2-HS-glycoprotein | P02765 | NP_001613 | NM_001622 |
| ALB | albumin | P02768 | AAH39235 | BC039235 |
| APCS | amyloid P component | P02743 | NP_001630 | NM_001639 |
| APOA1 | apolipoprotein A-I | P02647 | NP_000030 | NM_000039 |
| APOA2 | apolipoprotein A-II | P02652 | NP_001634 | NM_001643 |
| APOC1 | apolipoprotein C-I | P02654 | NP_001636 | NM_001645 |
| APOC2 | apolipoprotein C-II | P02655 | NP_000483 | NM_000474 |
| APOC3 | apolipoprotein C-III | P02656 | NP_000031 | NM_000040 |
| APOD | apolipoprotein D | P05090 | NP_001638 | NM_001647 |
| APOE | apolipoprotein E | P02649 | NP_000032 | NM_000041 |
| AZGP1 | Zn-alpha2-glycoprotein | Q5XKQ4 | CAA42438 | X59766 |
| B2M | beta-2-microglobulin | P61769 | NP_004039 | NM_004048 |
| C1S | complement component 1, s subcomponent | P09871 | NP_958850 | NM_201442 |
| C3 | complement component 3 | Q6LDJ0 | NP_000055 | NM_000064 |
| C7 | complement component 7 | P10643 | NP_000578 | NM_000587 |
| CDH1 | E-cadherin | P12830 | BAA88957 | AB025106 |
| CFB | complement factor B | P00751 | NP_001701 | NM_001710 |
| CHI3L1 | chitinase 3-like 1 | P36222 | NP_001267 | NM_001276 |

Figure 13a

|  |  | Expasy | Plasma Proteome database | |
|---|---|---|---|---|
|  |  | proteins | | mRNA |
| Symbol | Name | SP accession | PPD accession | PPD accession |
| CLEC3B | C-type lectin domain family 3, member B | P05452 | NP_003269 | NM_003278 |
| CLU | clusterin | P10909 | NP_001822 | NM_001831 |
| CP | ceruloplasmin | P00450 | NP_000087 | NM_000096 |
| CRP | C-reactive protein | P02741 | AAH20766 | BC020766 |
| EDN1 | endothelin 1 | P05305 | NP_001946 | NM_001955 |
| EGFR | epidermal growth factor receptor | P00533 | NP_958441 | NM_201284 |
| F13A1 | coagulation factor XIII, A1 polypeptide | P00488 | NP_000120 | NM_000129 |
| F13B | coagulation factor XIII, B polypeptide | P05160 | NP_001985 | NM_001994 |
| FGA | fibrinogen alpha chain | P02671 | NP_000499 | NM_000508 |
| FGB | fibrinogen beta chain | Q3Q265 | NP_005132 | NM_005141 |
| FGG | fibrinogen gamma chain | P02679 | NP_068656 | NM_021870 |
| GPI | glucose phosphate isomerase | P06744 | NP_000166 | NM_000175 |
| GSTP1 | glutathione S-transferase pi | P09211 | NP_000843 | NM_000852 |
| HDLBP | cDNA FLJ45936 fis, highly similar to Vigilin | Q00341 | BAC87153 | AK127833 |
| HP | haptoglobin | P00738 | NP_005134 | NM_005143 |
| HPX | hemopexin | P02790 | NP_000604 | NM_000613 |
| HRG | histidine-rich glycoprotein | P04196 | NP_000403 | NM_000412 |
| IGFBP3 | insulin-like growth factor binding protein 3 | P17936 | NP_000589 | NM_000598 |
| IGJ | immunoglobulin J polypeptide | P01591 | NP_653247 | NM_144646 |

Figure 13b

| | | Expasy | Plasma Proteome database | |
|---|---|---|---|---|
| | | | proteins | mRNA |
| Symbol | Name | SP accession | PPD accession | PPD accession |
| INHA | inhibin, alpha | P05111 | NP_002182 | NM_002191 |
| KLK11 | kallikrein-related peptidase 11 | Q9UBX7 | NP_659196 | NM_144947 |
| LDHA | lactate dehydrogenase A | P00338 | NP_005557 | NM_005566 |
| LGALS3BP | lectin, galactoside-binding, soluble, 3 binding protein | Q08380 | NP_005558 | NM_005567 |
| LRG1 | leucine-rich alpha-2-glycoprotein 1 | P02750 | NP_443204 | NM_052972 |
| ORM1 | Homo sapiens orosomucoid 1 | P02763 | NP_000598 | NM_000607 |
| PKM2 | pyruvate kinase, muscle | P14618 | NP_872270 | NM_182470 |
| PLG | plasminogen | P00747 | NP_000292 | NM_000301 |
| PON1 | paraoxonase 1 | P27169 | NP_000437 | NM_000446 |
| PROC | protein C | P04070 | NP_000303 | NM_000312 |
| PZP | pregnancy-zone protein | P20742 | NP_002855 | NM_002864 |
| RBP4 | retinol binding protein 4 | P02753 | P02753 | BC020633 |
| SAA1 | serum amyloid A1 | P02735 | NP_000322 | NM_000331 |
| SERPINA1 | serpin peptidase inhibitor, clade A | P01009 | NP_000286 | NM_000295 |
| SERPINA3 | serpin peptidase inhibitor, clade A, member 3 | P01011 | NP_001076 | NM_001085 |
| SERPINA5 | serpin peptidase inhibitor, clade B, member 4 | P05154 | NP_003965 | NM_003974 |
| TF | transferrin | P02787 | NP_001054 | NM_001063 |
| TFRC | transferrin receptor | P02786 | NP_003225 | NM_003234 |
| TGFB1 | transforming growth factor, beta 1 | P01137 | NP_000651 | NM_000660 |

Figure 13c

| Symbol | Name | Expasy | Plasma Proteome database | |
|---|---|---|---|---|
| | | | proteins | mRNA |
| | | SP accession | PPD accession | PPD accession |
| TIMP1 | TIMP metallopeptidase inhibitor 1 | P01033 | NP_003245 | NM_003254 |
| TTR | transthyretin | P02766 | NP_000362 | NM_000371 |
| VTN | vitronectin | P04004 | NP_000629 | NM_000638 |

Figure 13d

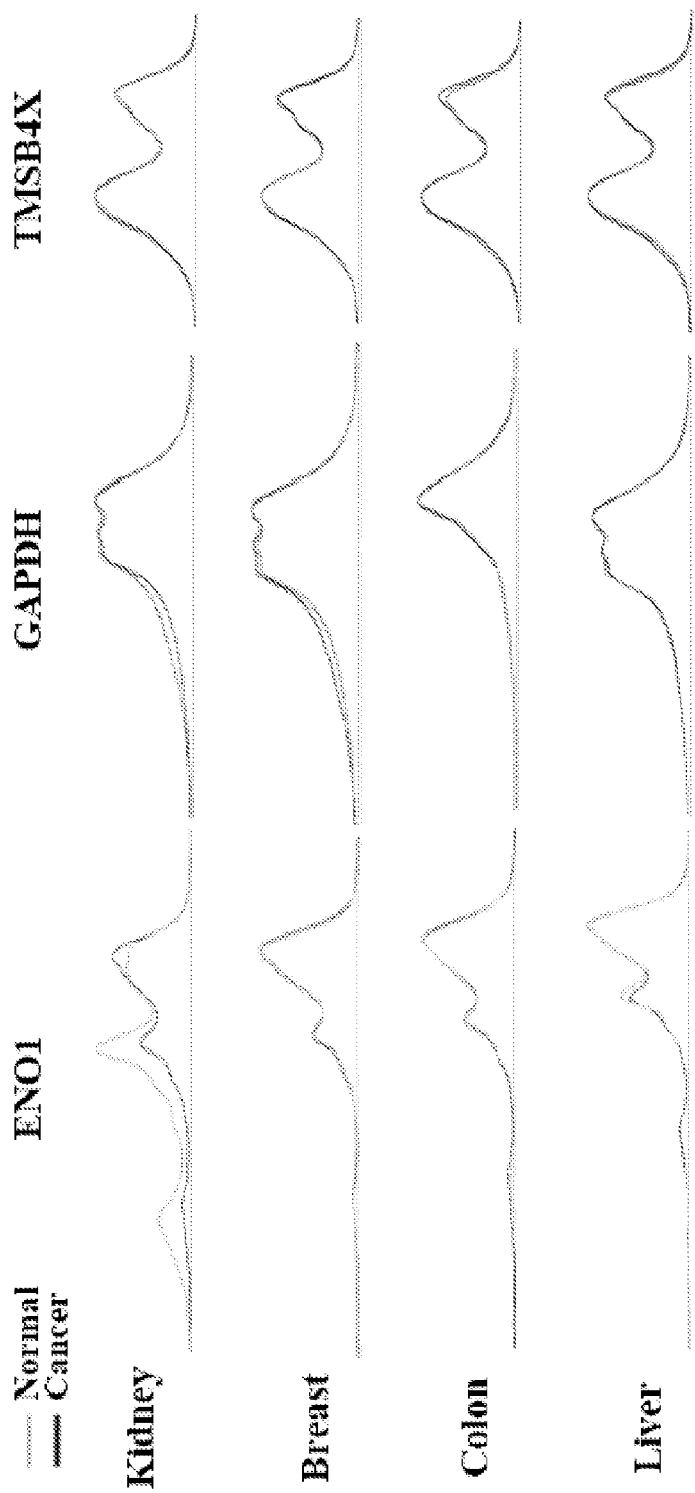

Figure 15a

DHPLC profiles of tumor tissue versus normal adjacent tissue for the ENO1, GAPDH and TMSB4X genes.

cDNA from cancerous patients (Biochain Inc.) were amplified by PCR using oligonucleotides complementary to the ENO1, GAPDH and TMSB4X genes and the *pfx* polymerase. cDNA were obtained from Kidney, Breast, colon and Liver tissues. Normal DHPLC profile is represented in Green and the cancerous profile is represented in Black. The double stranded DNA samples were injected on a DHPLC system (Transgenomic). The temperature of the oven are 62.5°C for the GAPDH gene, 61.5°C for the ENO1 gene and 55°C for the TMSB4X gene. Curves were visualized and normalized with the Navigator software (Transgenomic).

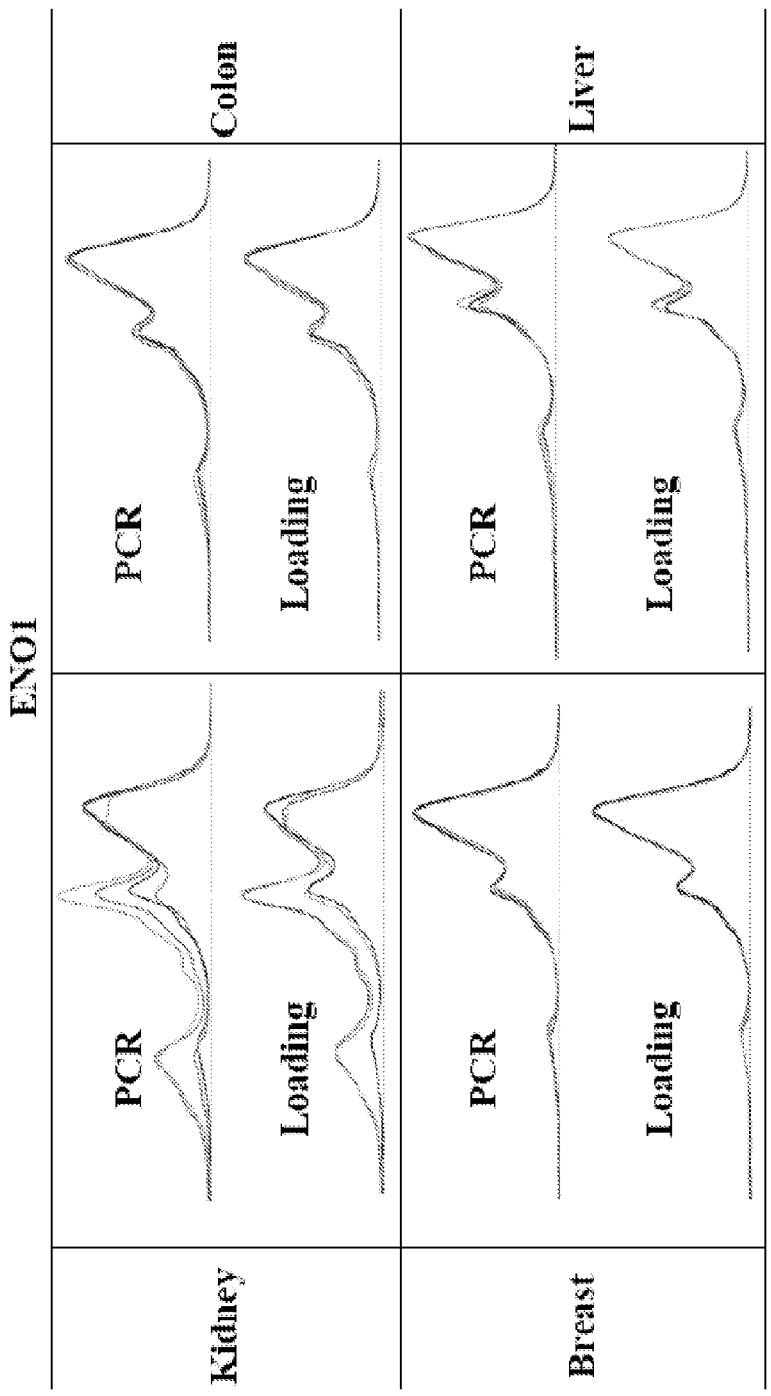

Different PCR and Loading DHPLC profiles of tumor tissue versus normal adjacent tissue for the ENO1 gene.

Two different PCR products were prepared for the 4 tissues and each PCR product was injected twice on the DHPLC system. Normal DHPLC profile is represented in Green and the cancerous profile is represented in Black. The DHPLC profile obtained for the PCR duplicate is represented in : Red for Normal and Blue for cancerous. For the loading duplicate, profiles are represented in : Purple for Normal and Light Blue for Cancerous. Curves were visualized and normalized with the Navigator software (Transgenomic).

Figure 15b

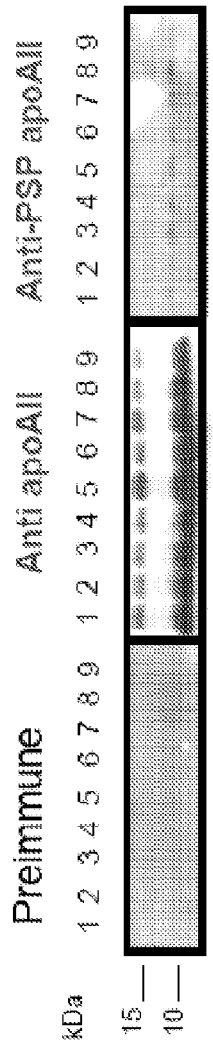

Figure 17a

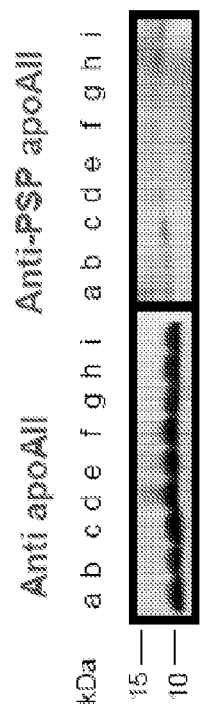

Figure 17b

Plasma from patients with prostate cancer (a) or with cancer in the metastatic phase (b) were applied to 4-12% SDS polyacrylamide gels under reducing conditions. After transfer onto PVDF membranes, and blocking in TBST containing 5% nonfat dry milk (1h, room temperature), Westerns were performed using rabbit pre-immune serum (dilution 1/100, left panel), commercially available goat anti-human apoAII antibody (1/250, middle panel), and rabbit polyclonal anti-PSP apoAII antibody (1/100, right panel). After 1 h incubation at room temperature, the membranes were washed and then incubated with the appropriate conjugated second antibody. Bands were then revealed by chemiluminescence and exposure to X-ray films.

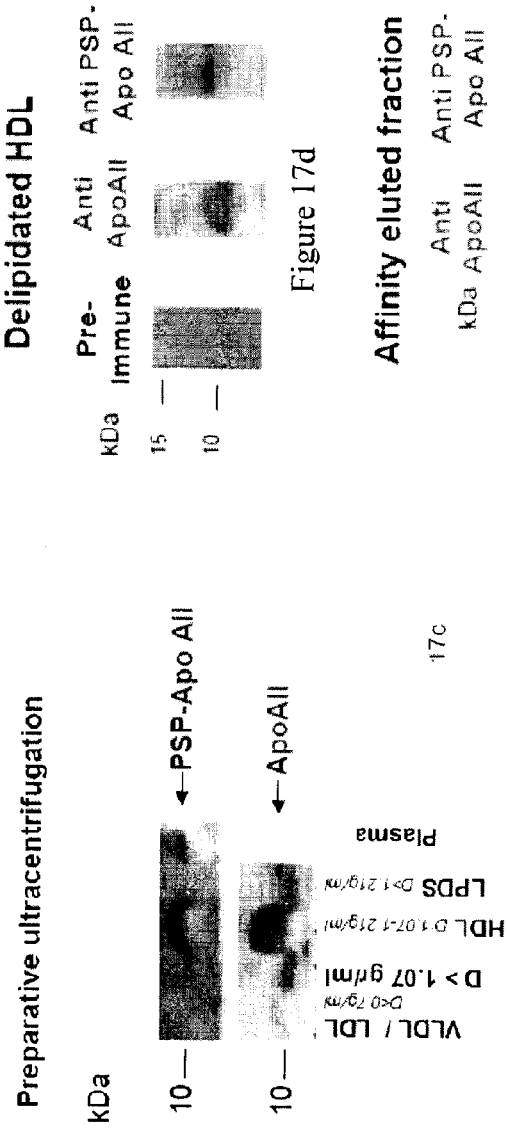

Figure 17c

Figure 17d

Figure 17e c. HDL (d1.07-1.21 g/ml) was prepared by sequential ultracentrifugation of pooled plasma from 10 cancer patients in the metastatic phase. The different fractions recovered after each step were dialyzed against 0.15 M NaCl, pH 7.4 containing 0.01% EDTA. Western blots were performed on the indicated fractions with either commercial anti-apoAII antibody (lower panel) or anti-PSP apoAII antibody (upper panel) using the same dilutions as indicated in Figures 17a et 17b. Gels were overloaded, which explains the distortion and the large bands. Western blot was also performed on the original pooled plasma or a corresponding volume of the lipoprotein-deficient serum (d>1.21 g/ml). d. Purified HDL was dialyzed against 0.01%EDTA, pH 7.4, frozen at -80°C and then lyophilized. Delipidation on the lyophilized HDL was then performed using ice-cold chloroform-methanol (2:1, v/v, 5 ml per 20 mg HDL protein). A second delipidation using diethyl ether was then followed by centrifugation (1000 rpm, 5 min, 4°C) to pellet the delipidated protein. This was repeated, and the final pellet dried under N2(g). The pellet was redissolved in 10 mM Tris containing 6 M urea, pH 8. Western blotting was performed on 10 ug delipidated HDL using preimmune serum, commercial anti-apoAII, or anti-PSP apoAII as described above. e. Affinity chromatography experiments were carried out to isolate the PSP form of apoAII using the anti-PSP antibody immobilized on matrix beads. The eluted fraction is analysed by Western blotting using both the commercial anti-apoAII and anti-PSPapoAII antibodies.

Similar experiment was performed as for Fig a, with the exception that rabbit polyclonal anti-PSP apoCII antibody was used.

| Name | mRNA id | PSP | Decision |
|---|---|---|---|
| AHSG | NM_001622.1 | ARHGRDEEVWHRKHSHHFVQAAWAWVGGLVCWPRKCHMRSTHSSLDSLLPVIPHRTEAEWVVVMF DRRH (SEQ ID NO: 101) | YES |
| ALB | BC039235 | RSKAYSSVFLFRWCKANTLSKKHKFL (SEQ ID NO: 103) | YES |
| APCS | NM_001639.2 | GLDSTRALENIMTV (SEQ ID NO: 104) | YES |
| APOA1 | NM_000039.1 | GARRRPSRCSE (SEQ ID NO: 105) | YES |
| APOA2 | NM_001643.1 | SVQTIVFQPQLASRTPTGQS (SEQ ID NO: 106) | YES |
| APOC2 | NM_000483.3 | QPDPPSVDKGRVPYSPDPPGSD (SEQ ID NO: 107) | YES |
| APOC3 | NM_000040.1 | DLNTPSPPAYPSCELLGSCNLQGCPCRLLKRDSLSALLPHLMPGPPPGMLASQ (SEQ ID NO: 108) | YES |
| APOD | NM_001647.2 | PGSTGRLHPLHVTSASLSPTPPPPHKDKPINHDKGS (SEQ ID NO: 109) | YES |
| APOE | NM_000041.2 | TPKPAAMRPHATPCLLPPRSLQRETLSPPQPSSWGGP (SEQ ID NO: 110) | YES |
| AZGP1 | X59766.1 | EARVGGNVGSQIQ (SEQ ID NO: 111) | YES |
| C3BL1 | NM_001276.1 | PSVLHTARGPRMPRPPLAPAGREPDHLPC (SEQ ID NO: 112) | YES |
| CLU | NM_001831.2 | DVDVAFAPTGASESSSPQDELQPPRESSARHQVTRPQPPGPQLRPASPRSGSCTLTLDSAAHGKNRIAP ACN (SEQ ID NO: 113) | YES |
| HRG | NM_000412.2 | NVIIPLKRKMNNTLN (SEQ ID NO: 114) | YES |
| IGFBP3 | NM_000598.4 | TPAARLMWSSNMPYFAQKTAKDMTSSWLQPRFIFLFVVN (SEQ ID NO: 115) | YES |
| INHA | NM_002191.2 | GWGVFLLNPMAGGHAPTIISWEERQSWEIDGSHSSLLSLLCLWATLPTPLLSQ (SEQ ID NO: 116) | YES |
| KLK11 | NM_144947.1 | TGPTHHSPSPSISTWCLVPVHSVNKKP (SEQ ID NO: 117) | YES |
| PKM2 | NM_182470.1 | WTPEPLLQPLSHPLPPAHPLGQQRL (SEQ ID NO: 118) | YES |
| PLG | NM_000301.1 | LDGRQSDALTHLEAGTWVGI (SEQ ID NO: 119) | YES |
| SERPINA3 | NM_001085.4 | SLPSSSGALSKELGMQAGCLGLWAQPGPCAPSGHGMCGPVCLSLEGDSDSLCSSHMHRGPWTLQSCG SWAS (SEQ ID NO: 120) | YES |
| TF | NM_001063.2 | NLRGRAATKVKMGTQMIHEFALVSLAQVVCANHVCLHSSVLPCVLNKK (SEQ ID NO: 121) | YES |
| TGFB1 | NM_000660.3 | GPAPPRPAPAGPAPPRPAPAALPMGAVFKDTRAPSPPGAPLKMERGLRISVSLGACLGSPSLTTPHSHSL SLPLCLLPVCTIPLPGIKAQGTSGEHYCS (SEQ ID NO: 122) | YES |
| TTR | NM_000371.1 | GTSPPVDLKDEGWDEM (SEQ ID NO: 123) | YES |

Figure 18a

>P02765|AHSG Alpha-2-HS-glycoprotein
MKSLVLLLCLAQLWGCHSAPHGPGLIYRQPNCDDPETEEAALVABDYINQNLPWGYKHTLNQIDEVKVWPQQPSCELFEIEIDTLETTCHVLDPTP
VARCSVRQLKEHAVEGDCDFQILKLDGKFSVVYAKCDSSPDSAEDVRKVCQDCPLLAPLNDTRVVHAAKAALAAFNAQNNGSNFQLEEISRAQL
VPLPPSTYVEFTVSGDCVAKEATEAAKCNLLAEKQYGFCKATLSEKLGGAEVAVTCTVFQTQPVTSQPQPEGANEAVPTPVVDPAPPLG
APGLPPAGSPPDSHVLLAAPPGHQLHRAHYDLRHTFMGVVSLGSPSGEVSHPRKTRTVVQPSVGAAAGPVVPPCPGRIRHFKV*

>P02768| Albumin
MKWVTFISLLFLFSSAYSRGVFRRDAHKSEVAHRFKDLGEENFKALVLIAFAQYLQQCPFEDHVKLVNEVTEFAKTCVADESAENCDKSLHTLFGD
KLCTVATLRETYGEMADCCAKQEPERNECFLQHKDDNPNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRFPKAEFAEVSKLVTDLTKVHTECCHGDLLECADDRADLA
KYICENQDSISSKLKECCEKPLLEKSHCIAEVENDEMPADLPSLAADFVESKDVCKNYAEAKDVFLGMFLYEYARRHPDYSVVLLRLAKTYETTLE
KCCAAADPHECYAKVFDEFKPLVEEPQNLIKQNCELFEQLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFHADICTLSEKERQIKKQTALVELVKHKPKATKEQLKAVM
DDFAAFVEKCCKADDKETCFAEEGKKLVAASQAALGL*

>P02743|APCS Serum amyloid P-component
MNKPLLWISVLTSLLEAFAHTDLSGKVFVFPRESVTDHVNLITPLEKPLQNFTLCFRAYSDLSRAYSLFSYNTQGRDNELLVYKERVGEYSLYIGRH
KVTSKVIEKFPAPVHICVSWESSSGIAEFWINGTPLVKKGLRQGYFVEAQPKIVLGQEQDSYGGKFDRSQSFVGEIGDLYMWDSVLPPENILSAYQ
GTPLPANILDWQALNYEIRGYVIKPLVWV*

>P02647|APOA1 Apolipoprotein A-I
MKAAVLTLAVLFLTGSQARHFWQQDEPPQSPWDRVKDLATVYVDVLKDSGRDYVSQFEGSALGKQLNLKLLDNWDSVTSTFSKLREQLGPVTQ
EFWDNLEKETEGLRQEMSKDLEEVKAKVQPYLDDFQKKWQEEMELYRQKVEPLRAELQEGARQKLHELQEKLSPLGEEMRDRARAHVDALRT
HLAPYSDELRQRLAARLEALKENGGARLAEYHAKATEHLSTLSEKAKPALEDLRQGLLPVLESFKVSFLSALEEYTKKLNTQ*

>P02652|APOA2 Apolipoprotein A-II
MKLLAATVLLLTICSLEGALVRRQAKEPCVESLVSQYFQTVTDYGKDLMEKVKSPELQAEAKSYFEKSKEQLTPLIKKAGTELVNFLSYFVELGTQP
ATQ*

>P02655|APOC2 Apolipoprotein C-II
MGTRLLPALFLVLLVLGFEVQGTQQPQQDEMPSPTFLTQVKESLSSYWESAKTAAQNLYEKTYLPAVDEKLRDLYSKSTAAMSTYTGIFTDQVLS
VLKGEE*

>P02656|APOC3 Apolipoprotein C-III
MQPRVLLVVALLALLASARASEAEDASLLSFMQGYMKHATKTAKDALSSVQESQVAQQARGWVTDGFSSLKDYWSTVKDKFSEFWDLDPEVRP
TSAVAA*

>P05090|APOD Apolipoprotein D
MVMLLLLSALAGLFGAAEGQAFHLGKCPNPPVQENFDVKKYLGRWYEIEKIPTTFENGRCIQANYSLMENGKIKVLNQELRADGTVNQIEGEATP
VNLTEPAKLEVKFSWFMPSAPYWILATDYENYALVYSCTCIIQLFHVDFAWILARNPNLPPETVDSLKNILTSNNIDVKKMTVTDQVNCPKLS*

[legend at bottom]
normal proteins | additional peptide of proteins whose STOP codon is affected

Figure 18b

>P02649|APOE Apolipoprotein E
MKVLWAALLVTFLAGCQAKVEQAVETEPEPELRQQTEWQSGQRWELALGRFWDYLRWVQTLSEQVQEELLSSQVTQELRALMDETMKELKAY
KSELEEQLTPVAEETRARLSKELQAAQARLGADMEDVCGRLVQYRGEVQAMLGQSTEELRVRLASHLRKLRKRLLRDADDLQKRLAVYQAGAR
EGAERGLSAIRERLGPLVEQGRVRAATVGSLAGQPLQERAQAWGERLRARMEEMGSRTRDRLDEVKEQVAEVRAKLEEQAQQIRLQAEAFQAR
LKSWFEPLVEDMQRQWAGLVEKVQAAVGTSAAPVPSDNH*
>Q5XKQ4|AZGP1 Alpha-2-glycoprotein 1, zinc-binding
MVRMSRMLPVLLSLLLLLGPAVPQENQDGRYSLTYIYTGLSKHVEDVPAFQALGSLNDLQFFRYNSKDRKSQPMGLWRQVEGMEDWKQDSQ
LQKAREDIFMETLKDIVEYYNDSNGSHVLQGRFGCEIENNRSSGAFWKYYYDGKDYIEFNKEIPAWVPFDPAAQITKQKWEAEPVYVQRAKAYLE
EECPATLRKYLKYSKNILDRQPPSVVVTSHQAPGEKKKLKCLAYDFYPGKIDVHWTRAGEVQEPELRGDVLHNGNGTYQSWVVVAVPPQDTAP
YSCHVQHSSLAQPLVVPWEAS*
>P36222|CHI3L1 Chitinase-3-like protein 1
MGVKASQTGFVVLVLLQCCSAYKLVCYTSWSQYREGDGSCFPDALDRFLCTHIIYSFANISNDHIIDTWEWNDVTLYGMLNTLKNRNPNLKTLLS
VGGWNFGSQRFSKIASNTQSRRTFIKSVPPFLRTHGFDGLDLAWLYPGRRDKQHFTTLIKEMKAEFIKEAQPGKKQLLLSAALSAGKVTIDSSYDIA
KISQHLDFISIIMTYDFHGAWRGTTGHHSPLFRGQEDASPDRFSNTDYAVGYMLRLGAPASKLVMGIPTFGRSFTLASSETGVGAPISGPGIPGRFT
KEAGTLAYYEICDFLRGATVHRTLGQQVPYATKGNQWVGYDDQESVKSKVQYLKDRQLAGAMVWALDLDDFQGSFCGQDLRFPLTNAIKDALA
AT*
>P10909|CLU Clusterin
MQYCSQPQRCVREQSAINATPPSAHNAASPGGARGHRVPLTEACKDSRIGGMAKTLLLFVGLLLTWESGQYLGQQTVSDMELQEMSNQGSK
YVNKEIQNAVNGVKQIKTLIEKTNEERKTLLSNLEEAKKKKEDALNETRESETKLKELPGVCNETMMALWEECKPCLSQCQNKFYARVCRSGSGL
VGRQLEEFLNQSSPFYFWMNGDRIDSLLENDRQQTHMLDVMQDHFSRASSIIDELFQDRFFTREPQDTYHYLPFSLPHRRPHFFFPKSRIVRSLM
PFSPYEYLNFHAMFQPFLEMIHEAQQAMDIHFHSPAFQHPPTEFIREGDDDRTVCREIRHNSTGCLRMKDQCDKCREILSVDCSTNNPSQAKLRR
ELDESLQVAERLTKYNELLKSYQWKMLNTSSLLEQLNEQFNWVSRLANLTQGEDQYYLRVTTVASHTSDSDVPSGVTEVVVKLFDSDPITVVP
VEVSRKNPKFMETVAEKALQEYRKKHREE*
>P04196|HRG Histidine-rich glycoprotein
MKALIAALLLITLQYSCAVSPTDCSAVEPEAEKALDLINKRRRDGYLFQLLRIADAHLDRVENTTVYYLVLDVQESDCSVLSRKYWNDCEPPDSRRP
SEIVIGQCKVIATRHSHESQDLRVIDFNCTTSSVSSALANTKDSPVLIDFFEDTERYRKQANKALEKYKEENDDFASFRVDRIERVARVRGGEGTGY
FVDFSVRNCPRHHFPRHPNVFGFCRADLFYDVEALDLESPKNLVINCEVFDPQEHENINGVPPHLGHSERSSTTKPPFKPHGSRDHHH
PHKPHEHGPPPPDERDHSHGPPLPQGPPPALPMSCSSQHATFGTNAQRSHNNNSSDLHPHKHHSHEQHPHGHHPHAHHPHEHDTHRQ
HPHGHPHGHHPHGHHPHGHHPHGHHPKGHHPHGKGPRPFHGRQIGSVYRLPPLRKGEV
LPLPEANFPSFPLPHHKHPLKPDNQFPPQSVSESCPGKFKSGFPQVSMFFTHTFPK*

Figure 18c

>P17936|IGFBP3 Insulin-like growth factor-binding protein 3
MQRARPTLWAAALTLLVLLRGPPVARAGASSAGLGPVVRCEPCDARALAQCAPPAVCAELVREPGCGCCLTCALSEGQPCGIYTERCGSGLR
CQPSPDEARPLQALLDGRGLCVNASAVSRLRAYLLPAPPAPGNASESEEDRSAGSVESPSVSSTHRVSDPKFHPLHSKIIIIKKGHAKDSQRYKVD
YESQSTDTQNFSSESKRETEYGPCRREMEDTLNHLKFLNVLSPRGVHIPNCDKKGFYKKKQCRPSKGRKRGFCWCVDKYGQPLPGYTTKGKED
VHCYSMQSK*TPNLGSKHLHPPFACKKSWLQPPSVIKP*

>P05111|INHA Inhibin alpha chain
MVLHLLLFLLLTPQGGHSCQGLELAREVLAKVRALFLDALGPPAVTREGGDPGVRRLPRRHALGGFTHRGSEPEEEDVSQAILFPATDASCED
KSAARGLAQEAEEGLFRYMFRPSQHTRSRQVTSAQLWFHTGLDRCQGTAASNSSEPLLGLLALSPGGPVAVPMSLGHAPPHWAVLHLATSALSLL
THPVLVLLLRCPLCTCSARPEATPFLVAHTRTRPPSGGERARRSTPLMSWPWSPSALRLLQRPPEEPAAHANCHRVALNISFQELGWERWIVYP
PSFIFHYCHGSGCGLHIPPNLSLPVPGAPPTPAQPYSLLPGAQPCCAALPGTMRPLHVRTTSDGGYSFKYETVPNLLTQHCACI*

>Q9UBX7|KLK11 Kallikrein-11
MQRLRWLRDWKSSGRGLTAAKEPGARSSPLQAMRILQLILLALATGLVGGETRIIKGFECKPHSQPWQAALFEKTRLLCGATLIAPRWLLTAAHCL
KPRYIVHLGQHNLQKEEGCEQTRTATESFPHPGFNNSLPNKDHRNDIMLVKMASPVSITWAVRPLTLSSRCVTAGTSCLISGWGSTSSPQLRLPH
TLRCANTIEHQKCENAYPGNITDTMVCASVQEGGKDSCQGDSGGPLVCNQSLQGIISWGQDPCAITRKPGVYTKVCKYVDWIQETMKNN*TGP >P14618|PKM2 Pyruvate kinase isozymes M1/M2
MSKPHSEAGTAFIQTQQLHAAMADTFLEHMCRLDIDSPPITARNTGIICTIGPASRSVETLKEMIKSGMNVARLNFSHGTHEYHAETIKNVRTATES
FASDPILYRPVAVALDTKGPEIRTGLIKGSGTAEVELKKGATLKITLDNAYMEKCDENILWVLDYKNICKVVEVGSKIYVDGLISLQVKQKGADFLVTE
VENGGSLGSKKGVNLPGAAVDLPAVSEKDIQDLKFGVEQDVDMVFASFIRKASDVHEVRKVLGEKGKNIKIISKIENHEGVRRFDEILEASDGIMVA
RGDLGIEIPAEKVFLAQKIMIGRCNRAGKPVICATQMLESMIKKPRPTRAEGSDVANAVLDGADCIMLSGETAKGDYPLEAVRMQHLIAREAEAA
MFHRKLFEELVRASSHSTDLMEAMAMGSVEASYKCLAAALIVLTESGRSAHQVARYRPRAPIIAVTRNPQTARQAHLYRGIFPVLCKDPVQEAWA
EDVDLRVNFAMNVGKARGFFKKGDVVIVLTGWRPGSGFTNTMRVVPVPVITEELDPSHIPGILLLKSP*

>P00747|PLG Plasminogen
MEHKEVVLLLFLFLKSQGEPLDDYVNTQGASLFSVTKKQLGAGSIEECAAKCEEDEEFTCRAFQYHSKEQQCVMAENRKSSIIIRMRDVVLFEK
KVYLSECKTGNGKNYRGTMSKTKNGITCQKWSSTSPHRPRFSPATHPSEGLEENYCRNPDNDPQGPWCYTTDPEKRYDYCDILECEEECMHC
SGENYDGKISKTMSGLECQAWDSQSPHAHGYIPSKFPNKNLKKNYCRNPDRELRPWCFTTDPNKRWELCDIRCTTPPPSSGPTYQCLKGTGE
NYRGNVAVTVSGHTCQHWSAQTPHTHNRTPENFPCKNLDENYCRNPDGKRAPWCHTTNSQVRWEYCKIPSCDSSPVSTEQLAPTAPPELTPV
VQDCYHGDGQSYRGTSSTTTTGKKCQQSWSSMIPHRHQKTPENYPNAGLTMNYCRNPDADKGPWCFTTDPSVRWEYCNLKKCSGTEASVVAP
PPVVLLPDVETPSEEDCMFGNGKGYRGKRATTVTGTPCQDWAAQEPHRHSIFTPETNPRAGLEKNYCRNPDGDVGGPWCYTTNPRKLYDYCD
VPQCAAPSFDCGKPQVEPKKCPGRVVGGCVAHPHSWPWQVSLRTRFGMHFCGGTLISPEWVLTAAHCLEKSPRPSSYKVILGAHQEVNLEPHV
QEIEVSRLFLEPTRKDIALLKLSSPAVITDKVIPACLPSPNYVVADRTECFITGWGETQGTFGAGLLKEAQLPVIENKVCNRYEFLNGRVQSTELCAG
HLAGGTDSCQGDSGGPLVCFEKDKYILQGVTSWGLGCARPNKPGVYVRVSRFVTWIEGVMRNN*DGKAAAPTWKGP*

Figure 18d

>P01011|SERPINA3 Alpha-1-antichymotrypsin
MERMLPLLALGLLAAGFCPAVLCHPNSPLDEENLTQENQDRGTHVDLGLASANWDFAFSLYKQLVLKAPDKNVIFSPLSISTALAFLSLGAHNTTLT
EILKGLKFNLTETSEAEIHQSFQHLLRTLNQSSDELQLSMGNAMFVKEQLSLLDRFTEDAKRLYGSEAFATDFQDSAAAKKLINDYVKNGTRGKITD
LIKDLDSQTMMVLVNYIFFKAKWEMPFDPQDTHQSRFYLSKKKWVMVPMMSLHHLTIPYFRDEELSCTVVELKYTGNASALFILPDQDKMEEVEA
MLLPETLKRWRDSLEFREIGELYLPKFSISREYELYLDILQLGIEEAFTSKADLSGITGARNLAVSQVVHKAVLDVFEEGTEASAATAVKITLLSALVE
TRTIVRFNRPFLMIIVPTDTQNIFFMSKVTNPKQA...

>P02787|TF Serotransferrin
MRLAVGALLVCAVLGLCLAVPDKTVRWCAVSEHEATKCQSFRDHMKSVIPSDGPSVACVKKASYLDCIRAIAANEADAVTLDAGLVYDAYLAPNN
LKPVVAEFYGSKEDPQTFYYAVAVVKKDSGFQMNQLRGKKSCHTGLGRSAGWNIPIGLLYCDLPEPRKPLEKAVANFFSGSCAPCADGTDFPQL
CQLCPGCGCSTLNQYFGYSGAFKCLKDGAGDVAFVKHSTIFENLANKADRDQYELLCLDNTRKPVDEYKDCHLAQVPSHTVVARSMGGKEDLIW
ELLNQAQEHFGKDKSKEFQLFSSPHGKDLLFKDSAHGFLKVPPRMDAKMYLGYEYVTAIRNLREGTCPEAPTDECKPVKWCALSHHERLKCDE
WSVNSVGKIECVSAETTEDCIAKIMNGEADAMSLDGGFVYIAGKCGLVPVLAENYNKSDNCEDTPEAGYFAVAVVKKSASDLTWDNLKGKKSCH
TAVGRTAGWNIPMGLLYNKINHCRFDEFFSEGCAPGSKKDSSLCKLCMGSGLNLCEPNNKEGYYGYTGAFRCLVEKGDVAFVKHQTVPQNTGG
KNPDPWAKNLNEKDYELLCLDGTRKPVEEYANCHLARAPAHAVVTRDDKEACVHKILRQQQHLFGSNVTDCSGNFCLFRSETKDLLFRDDTVCL
AKLHDRNTYEKYLGEEYVKAVGNLRKCSTSSLLEACTFRRP...

>P01137|TGFB1 Transforming growth factor beta-1
MPPSGLRLLLLLLPLLWLVLTPGRPAAGLSTCKTIDMELVKRKRIEAIRGQILSKLRLASPPSQGEVPPGPLPEAVLALYNSTRDRVAGESAEPEP
EPEADYYAKEVTRVLMVETHNEIYDKFKQSTHSIYMFFNTSELREAVPEPVLLSRAELRLLRLKLKVEQHVELYQKYSNNSWRYLSNRLLAPSDSP
EWLSFDVTGVVRQWLSRGGEIEGFRLSAHCSCDSRDNTLQVDINGFTTGRRGDLATIHGMNRPFLLLMATPLERAQHLQSSRHRRALDTNYCFS
STEKNCCVRQLYIDFRKDLGWKWIHEPKGYHANFCLGPCPYIWSLDTQYSKVLALYNQHNPGASAAPCCVPQALEPLPIVYYVGRKPKVEQLSN
MIVRSCKCS...

>P02766|TTR Transthyretin
MASHRLLLLCLAGLVFVSEAGPTGTGESKCPLMVKVLDAVRGSPAINVAVHVFRKAADDTWEPFASGKTSESGELHGLTTEEEFVEGIYKVEIDTK
SYWKALGISPFHEHAEVVFTANDSGPRRYTIAALLSPYSYSTTAVVTNPKE...

Figure 18e

|  | Predictions | | | |
|---|---|---|---|---|
|  | M | nM | Total | |
| M | 315 | 132 | 447 | 70.47% |
| nM | 705 | 1725 | 2428 | 71.05% |
| Total | 1020 | 1855 | 2875 | |
|  | TP 30.88% | TN 92.99% | | 70.88% |

Observations (row labels on left)

*TP : True Positives ; TN : True Negatives*

Figure 19

TRANSCRIPTION INFIDELITY, DETECTION AND USES THEREOF

CROSS-REFERENCE TO RELATED APPLICATION

This application is the U.S. national stage application of International Patent Application No. PCT/EP2007/057541, filed Jul. 20, 2007, the disclosure of which is hereby incorporated by reference in its entirety, including all figures, tables and amino acid or nucleic acid sequences.

The Sequence Listing for this application is labeled "SeqList-replace.txt" which was created on Apr. 10, 2012 and is 180 KB. The entire contents of the sequence listing is incorporated herein by reference in its entirety.

The present invention relates to the identification of a novel mechanism of transcription infidelity in cells. The invention provides compositions and methods to detect the level of transcription infidelity in a sample, as well as the use thereof, e.g., for therapeutic, diagnostic, pharmacogenomic or drug design. As will be disclosed, the invention is particularly suited for detecting, monitoring or treating disorders (such as for example, proliferative cell disorders), for the design and/or screening of drugs, for patient or disease profiling, prediction of disease severity and evaluation of drug efficacy.

INTRODUCTION TO THE INVENTION

Nucleic acid DNA and RNA are macro-molecules that serve to store genomic information in the cell nucleus (DNA) and to transfer genomic information into the cytoplasm after a process called transcription that generates messenger RNA in order to produce protein. Both are linear polymers composed of monomers called nucleotides. DNA and RNA each represent combinations of four types of nucleotides. All nucleotides have a common structure: a phosphate group linked by a phosphodiester bond to pentose that in turn is linked to an organic base: adenine, cytosine, thymine and guanine (A, C, T, G) for DNA and adenine, cytosine, uracil and guanine (A, C, U, G) for RNA. In RNA, the pentose is ribose and in DNA, it is deoxyribose. The DNA molecule is organized as a double strand of ordered nucleotides arranged as a double helix. RNA molecules are single strand polynucleotides that mainly yield 4 types of molecules: 1) messenger RNA (mRNA), which are single strand nucleotides that are transcribed from DNA and translated into proteins in the cytoplasm, 2) transfer RNA (tRNA), which adopt a well defined 3 dimensional structure and bind specific amino acids (AA) that are transferred to polypeptide chains to form protein with specific AA sequences in a process called translation, 3) ribosomal RNA (rRNA), which are larger molecules that together with specific proteins constitute the ribosome, a structure that allows the assembly of AA into protein following the information provided by the sequence specified by codons (one codon=3 nucleotides) present in a given order on the mRNA and 4) short regulating RNA referred to as noncoding RNA (ncRNA).

The sequence of mRNA is then transformed into a different language, i.e., the AA language by a process referred to as translation.

Here, we demonstrate for the first time that the fidelity of transcription, i.e., the transfer of DNA information into mRNA, is dramatically reduced in pathological cells, particularly in cancer cells. This lack of transcription fidelity in cancer cells is a general phenomenon that affects all cancers and most of the genes tested in the reported examples as well as the majority of transcript present in available databases and that has several immediate and important implications. In particular, the discovery of transcription infidelity allows the improvement of currently used proteomic and transcriptomic approaches for the investigation of pathological conditions. The discovery of transcription infidelity also allows a better classification of diseases with respect to their severity, and improves the prediction of therapeutic effect and design novel methods to screen the efficacy of drugs on the basis of their ability to correct a lack or modification of transcription fidelity. The present invention has thus major implications and utilities in diagnostic and in the development of drugs, as well as in the treatment, detection and monitoring of patients and drug efficacy.

In order to understand the impact of the discovery described below, it is important to recognize that it is currently believed that absolute fidelity in the transcription of DNA to RNA is needed for normal cell function. However, a currently important but unresolved issue persists. Indeed, sequencing and annotation of the human genome led to the notion that 30-40 thousand genes are encoded. This estimate remains far below the current number of proteins that can be identified by proteomic methods: up to 300 thousand proteins have been identified. To reconcile these differences, it is proposed that a single gene can produce several different mRNA encoding different proteins through a process called alternative splicing. Alternative splicing removes different parts of pre-messenger RNA (pmRNA), thereby leading to removal of different elements corresponding to specific introns, and produces different mature mRNA. Analysis of RefSeq database indicate it contains 11259 transcripts corresponding to 6946 genes. Thus, alternative splicing can increase transcripts heterogeneity by 76%. The mechanism that we describe here is different from alternative splicing and induced a far greater protein heterogeneity. Indeed, we demonstrate the occurrence of non-random modifications of mRNA sequence that result in changes in encoded AA, introduction of premature stop codons that yield shorter protein isoforms, alterations of natural stop codons implying introduction of novel coding sequences that yield elongated protein isoforms. Introduction of gap and insertion thereby modify mRNA reading frame and thereby create unsuspected protein sequences. The data described in this invention show that this phenomenon of transcription infidelity is present in normal cells but dramatically enhanced in pathological cells, such as cancer-derived cells. It is thus proposed that transcription infidelity (TI) contributes to diversification of the information transferred from DNA to RNA. Our results further establish that transcription infidelity does not occur randomly but follows specific rules in which the context surrounding b0, bases affected by TI event, is important.

Another mechanism could be envisioned to explain that RNA heterogeneity does not occur at the genomic but at the RNA level: RNA editing. However, RNA editing cannot explain two types of TI event, introduction of gap and insertion. RNA editing is characterized by a post-transcriptional base changes in mRNA and tRNA in eukaryotes. The vast majority of the known substitution editing events consists of C to U or A to I (read as G) conversions (Gott, J. M. & Emeson, R. B. (2000) *Annu Rev Genet* 34, 499-531—Maas, S. & Rich, A. (2000) *Bioessays* 22, 790-802.—Niswender, C. M. (1998) *Cell Mol Life Sci* 54, 946-64). Different works have shown that these conversions arise via deamination mechanisms, catalyzed by adenosine and cytidine deaminases. One other substitution editing event is the "U to C" conversion. While the theory of microscopic reversibility dictates that the cytidine deaminase reaction could go backward to generate this conversion, it has also been proposed that a CTP synthetase-type activity could be responsible. It has been shown in several examples that RNA editing can be specific to cancer cells versus normal cells. Moreover, the rate of this phenomenon can be affected in cancer conditions.

In the cancer set, we observed at the cDNA level 5.7% C→T, 9.2% T→C and 4.7% A→G changes. Thus, mRNA editing cannot account for more than 20% of single base substitutions described here. Indeed, the most common base substitutions: A→C (24.6%) and T→G (16.8%) represent base family changes that are currently not explained by known human enzymatic RNA editing processes.

Furthermore, transcription infidelity is expected to cause base deletions and/or insertions through a mechanism (or mechanisms) different from mRNA editing.

Moreover, a recent study shows that number of dbSNP records (Single Nucleotide Polymorphism database) are in fact editing sites (Eisenberg, E. et al. (2005) *Nucleic Acids Res.* 33 (14), 4612-7). In our approach all SNPs from dbSNP are not considered, therefore known SNPs or false SNPs corresponding to editing sites are excluded.

The mechanism to explain the observed cancer mRNA heterogeneity is therefore transcription infidelity.

SUMMARY OF THE PRESENT INVENTION

The present invention relates to compositions and methods of using, detecting or altering transcription infidelity in cells, particularly in mammalian cells. The invention is particularly suited for therapeutic and diagnostic purposes, e.g., to detect and/or treat diseases caused by or associated with an increased or reduced level of transcription infidelity.

A particular object of this invention relates to a method of detecting the presence or stage of a disease in a subject, the method comprising assessing (in vitro or ex vivo) the presence or rate of transcription infidelity in a sample from said subject, said presence or rate being an indication of the presence or stage of a disease in said subject.

A further object of this invention resides in a method of screening, identifying or optimising a drug, the method comprising a step of assessing whether said drug alters (e.g., reduces or increases) the rate of transcription infidelity of a gene.

A further object of this invention is a method of treating a subject in need thereof, the method comprising administering to said subject an effective amount of a compound that alters (e.g., reduces or increases) the rate of transcription infidelity of a mammalian gene.

A further object of this invention relates to the use of a compound that alters (e.g., reduces or increases) the rate of transcription infidelity of a mammalian gene for the manufacture of a pharmaceutical composition for use in a method of treatment of a human or animal, particularly for treating diseases such as proliferative cell disorders including without limitation, cancers, immune diseases, inflammatory diseases or aging.

A further object of this invention resides in a method of assessing the efficacy of a drug or candidate drug, the method comprising a step of assessing whether said drug alters (e.g., reduces or increases) the rate of transcription infidelity of a mammalian gene, such an alteration being an indication of drug efficacy.

The invention further relates to methods and products (such as probes, primers, antibodies or derivatives thereof), for detecting or measuring (the level of) transcription infidelity in a sample, as well as to corresponding kits.

The invention also relates to methods of identifying transcription infidelity sequences in proteins or nucleic acids, as well as to their use e.g., as markers, immunogens and/or to generate specific ligands thereof.

In this respect, the invention relates to a method of identifying and/or producing biomarkers, the method comprising identifying, in a sample from a subject, the presence of transcription infidelity site(s) in a target protein or nucleic acid and, optionally, determining the sequence of said transcription infidelity site(s). In a particular and preferred embodiment, the target protein is a cell surface protein or a secreted protein, particularly a cell surface protein or a plasma protein.

A further object of the invention relates to a method of identifying and/or producing a ligand specific for a trait or pathological condition, the method comprising identifying, in a sample from a subject having said trait or pathological condition, the presence of at least one transcription infidelity site in one or several target proteins or nucleic acid optionally determining the sequence of said at least one transcription infidelity site, and producing a ligand that specifically binds to said at least one protein (or domain) or nucleic acid created by transcription infidelity.

The invention is particularly suited for identifying biomarkers of cell proliferative disorders, such as cancers, immune diseases, inflammatory diseases or aging. It is particularly useful for producing ligands that are specific for such disorders in mammalian subjects, in particular ligands that can detect the presence or severity of a cell proliferative disorder in a subject.

A further object of this invention resides in a ligand that specifically binds a protein (or domain) or nucleic acid created by transcription infidelity. The ligand may be an antibody (or any fragment such as Fab, Fab', CDR, etc.) or derivative thereof, as described later), that specifically binds a protein (or domain) created by transcription infidelity. The ligand may also be a nucleic acid that specifically binds a nucleic acid created by transcription infidelity (e.g., probe, primer, RNAi (interference RNA), etc.).

A further aspect of this invention relates to a peptide comprising a domain of a protein created by transcription infidelity, particularly of a mammalian protein, more preferably of a human protein. The peptide is typically a synthetic peptide, i.e., a peptide that has been prepared artificially, e.g., by chemical synthesis, amino acid synthesis and/or extension, protein digestion, peptide assembling, recombinant expression, etc. The peptide typically comprises the sequence of a C-terminal fragment of said protein. The peptide preferably comprises less than 100, 80, 75, 70, 65, 60, 50, 45, 40, 35, 30, 25 or even 20 amino acids (although, in other embodiments, the peptide length can be higher). The protein may be a cell surface protein (e.g., a receptor etc.), a secreted protein (e.g., a plasma protein etc.), or an intracellular protein.

A further aspect of this invention resides in the use of a peptide created by transcription infidelity as defined above, as an immunogen. The invention also relates to a vaccine composition comprising a peptide comprising a part of a protein created by transcription infidelity, as defined above, and optionally a suitable carrier, excipient and/or adjuvant.

A further aspect of this invention relates to a method of producing an antibody, the method comprising immunizing a non-human mammal with a peptide created by transcription infidelity, as defined above, and recovering antibodies that bind said peptide, or corresponding antibody-producing cells. Optionally, derivatives of the antibody may be produced.

In a particular embodiment, the invention relates to a method of producing an antibody, the method comprising (i) identifying a domain of a protein created by transcription infidelity and (ii) producing an antibody that specifically binds said domain. Optionally, derivatives of the antibody may be produced.

A further aspect of this invention resides in an antibody that specifically binds a part of a protein created by transcription infidelity, or a derivative of such an antibody having substantially the same antigen specificity. The antibody may be polyclonal or monoclonal. The term derivative includes any fragment (such as Fab, Fab', CDR, etc.) or other derivatives such as single chain antibodies, bi-functional antibodies, humanized antibodies, human antibodies, chimeric antibodies, etc.

A further aspect of this invention relates to an antibody or derivative thereof, as defined above, that is conjugated to a molecule. The molecule may be a drug, a label, a toxic molecule, a radioisotope, etc.

The invention also relates to the use of an antibody or derivative thereof as defined above, for detecting or quantifying (e.g., in vitro) transcription infidelity of a gene.

The invention also relates to the use of a conjugated antibody or derivative thereof as defined above, as a medicament or diagnostic reagent.

The invention also relates to a device or product comprising, immobilized on a support, a reagent that specifically binds a protein or nucleic acid created by transcription infidelity. The reagent may be e.g., a probe or an antibody or derivative thereof.

A further aspect of this invention relates to a method of causing or inducing or stimulating transcription infidelity in a cell or tissue or organism. Such a method may comprise, typically, the introduction of a transcription infidelity site into normal genomic sequences, e.g., by means of a gene therapy vector. Such a modification can result in a destruction of a cell or tissue. In particular, it is possible to create an open reading frame in any gene sequence that results in the production of cell toxic proteins or compounds. It is also possible to cause expression, in a diseased (or target) cell, of a specific biomarker that can be targeted using toxic or therapeutic molecules. Using this approach, it is therefore possible to cause cell death or therapy when transcription infidelity occurs or exceeds a certain rate.

In this regard, a further object of this invention is a method of treating a subject in need thereof, the method comprising introducing into cells of said subject a nucleic acid that contains transcription infidelity site(s), whereby expression of said nucleic acid results in the treatment of said subject.

A further object of this invention is a method of causing or stimulating or controlling transcription infidelity in a subject in need thereof, the method comprising introducing into cells of said subject a nucleic acid that contains transcription infidelity site(s).

A further object of this invention relates to the use of a nucleic acid that contains transcription infidelity site(s) for the manufacture of a pharmaceutical composition for use in a method of treatment of a human or animal. The gene may be any gene, including a mammalian gene or a gene from a pathogenic agent, such as a viral gene, a bacterial gene, etc. In this regard, the invention relates to a method of treating a disease caused by a pathogen, the method comprising causing or stimulating transcription infidelity of a gene encoded by said pathogen.

The invention also relates to methods of producing recombinant polypeptides in vitro with reduced transcription infidelity. Such methods allow a reduction in microheterogeneity in recombinant polypeptides. The method comprises using host cells comprising a recombinant nucleic acid with adapted codon usage, to reduce the occurrence of transcription infidelity. The method may also include the use of any compound or treatment which reduces the occurrence of transcription infidelity. The method may be used in prokaryotic or eukaryotic hosts cells, e.g., in E. coli or CHO strains.

The invention may be used in any mammalian subject, particularly any human subject, to detect, monitor or treat a variety of pathological conditions associated with an increased or reduced transcription infidelity rate, such as e.g., cell proliferative disorders (e.g., cancers), immune diseases (e.g., auto-immune diseases (multiple sclerosis, Amyotrophic Lateral Sclerosis (ALS)), graft rejection), aging, inflammatory diseases, diabetes, etc., and/or to produce, design or screen therapeutically active drugs. The invention may also be used to detect, monitor, modulate or target transcription infidelity in any other tissues or cell types, such as prokaryotic cells, lower eukaryotes (e.g., yeasts), insect cells, plant cells, fungi, etc.

LEGEND TO THE FIGURES

FIG. 1: Principle of cDNA library construction and sequencing.

Figure 2A:
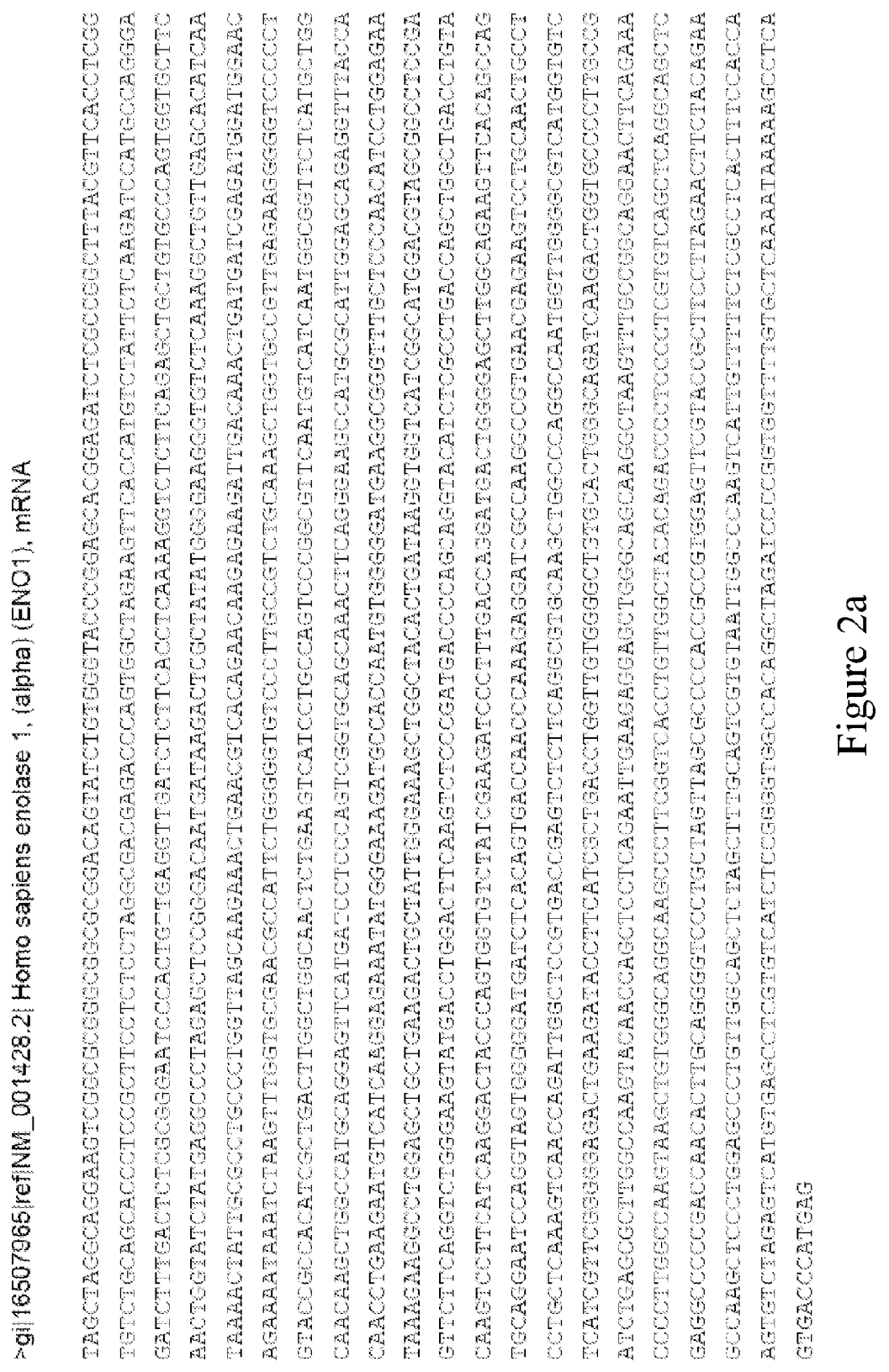
Figure 2K:
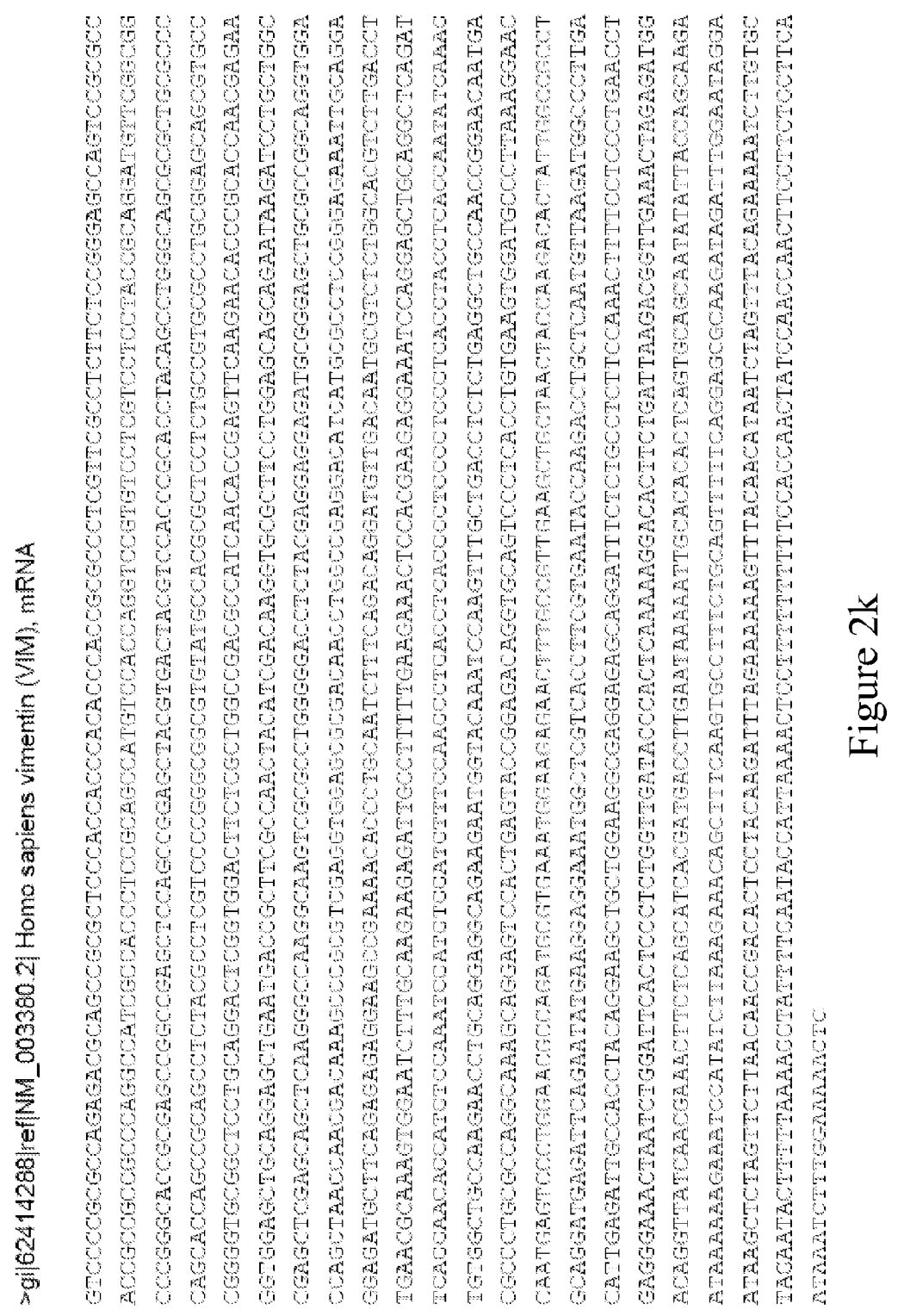

FIG. 2: (a-q, SEQ ID NOs: 33-49, respectively) mRNA reference sequences used for the analysis. In order to avoid distorting the blast, the polyA tail of mRNA reference sequences were systematically removed. FIG. 2r provides a list of tested genes.

Figure 3H:
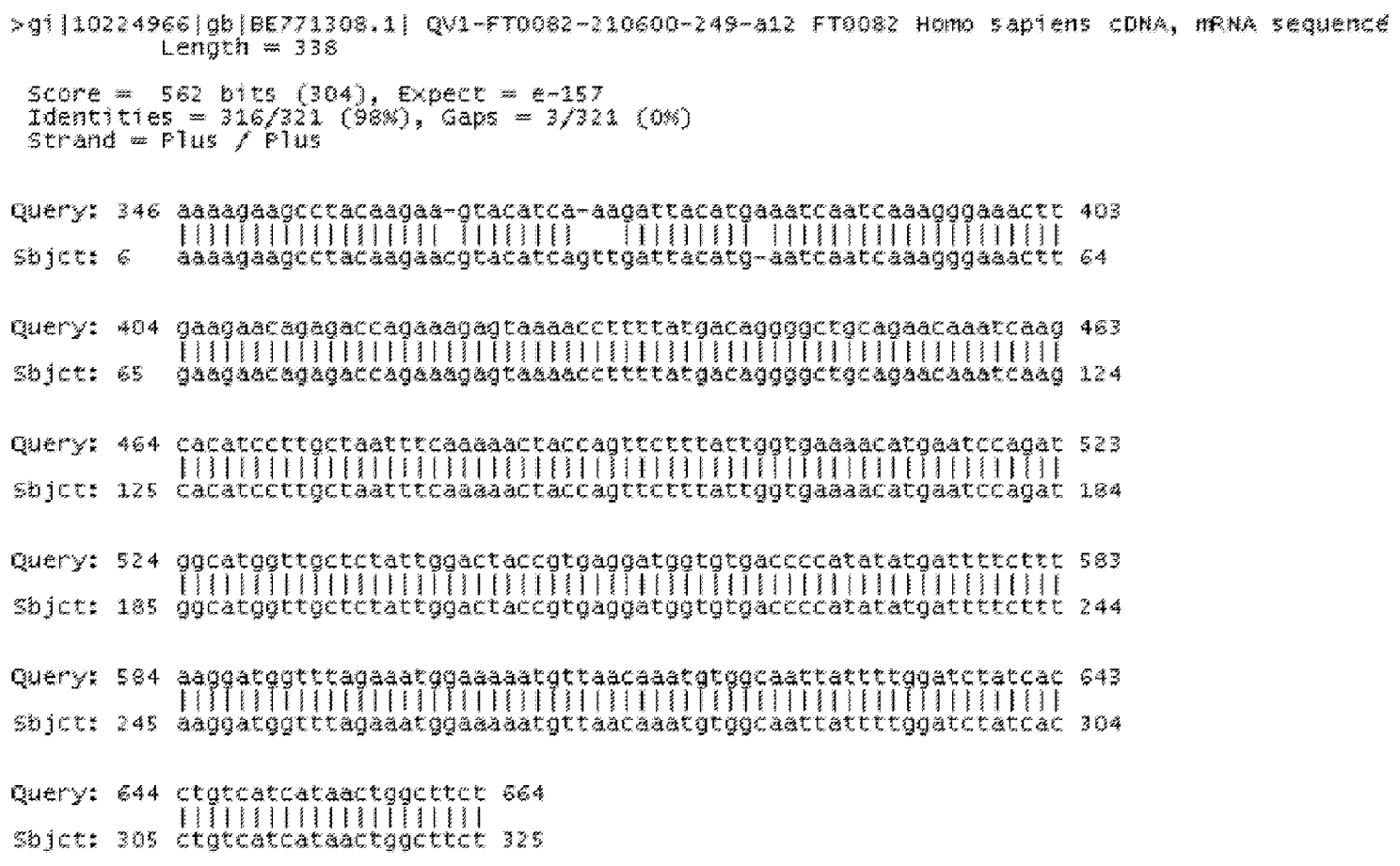

FIG. 3: Typical MegaBLAST output files (FIG. 3a-i). The sequence alignment for the Query and subject sequences in FIGS. 3a-3b (SEQ ID NO: 50) are identical. The sequence alignment for the Query and subject sequences in FIGS. 3c-3d (SEQ ID NO: 51) are identical. FIGS. 3e-3f show an alignment between a non-identical Query sequence (SEQ ID NO: 52) and a subject sequence (SEQ ID NO: 53). FIG. 3g shows an alignment between a non-identical Query sequence (SEQ ID NO: 54) and a subject sequence (SEQ ID NO: 55). FIG. 3h shows an alignment between a non-identical Query sequence (SEQ ID NO: 56) and a subject sequence (SEQ ID NO: 57). The sequence alignment for the Query and subject sequences in FIG. 3i (SEQ ID NO: 58) are identical.

FIG. 4: FIGS. 4a-4d provide a graphical representation of variations occurring in normal and cancer sets for the 17 identified in FIG. 2r, including the percentage of nucleotide sequence deviation at any position for each studied genes.

FIG. 5: FIGS. 5a-5p illustrate the results of EST and proportion test analyses for TPT1 and VIM. SEQ ID NO: 59 is shown in the "Ref" of the "Deletion" and the "EST" in the "Insertion" of FIG. 5j. SEQ ID NO: 60 is shown in the "EST" of the Deletion and the "Ref" in the "Insertion" of FIG. 5j.

FIG. 6: Variations in ESTs before and after sequential application of electronic filters (FIGS. 6a-e). Clip 400 and cell lines removal effects.

FIG. 7: DNA context: a) Effect of pmRNA base composition on base b0 heterogeneity. b) Composition of replacement base for each substituted base. c) Repartition of affected and replacement bases within statistically significant C>N tests. d) Effect of pmRNA base composition on substitution base corresponding to repetition of b−1 or b+1 (FIGS. 7a-7g).

FIG. 8: Virtual variant mRNA and protein for VIM. FIG. 8a: vim nat is SEQ ID NO: 61; vim variant is SEQ ID NO: 62. The top rows (vim mute) of the sequence alignment (SEQ ID NO: 62) and the bottom rows (vim) of the sequence alignment (SEQ ID NO: 61) are shown in FIGS. 8b-8c. FIG. 8d, VIM 1 and vim, bottom rows of the sequence alignment, is SEQ ID NO: 63; VIM variant 1 and vim mute, top rows of the sequence alignment, is SEQ ID NO: 64.

FIG. 9: Coding impact

FIG. 10: Proteins of interest=amino acid sequences when the stop codon is statistically affected. FIG. 10a: tumor protein, translationally controlled 1, SEQ ID NO: 65; vimentin, SEQ ID NO: 66; ribosomal protein S6, SEQ ID NO: 67; ribosomal protein L7a, SEQ ID NO: 68; ribosomal protein S4, SEQ ID NO: 69. FIG. 10b: ferritin, heavy polypeptide 1, SEQ ID NO: 70; ferritin, light polypeptide, SEQ ID NO: 71;

glyceraldehyde-3-phosphate dehydrogenase, SEQ ID NO: 72; triosephosphate isomerase 1, SEQ ID NO: 73.

FIG. 11: Denaturing High Performance Liquid Chromatography (DHPLC)=principle and limits of detection (FIGS. 11a-d).

Figure 12A:
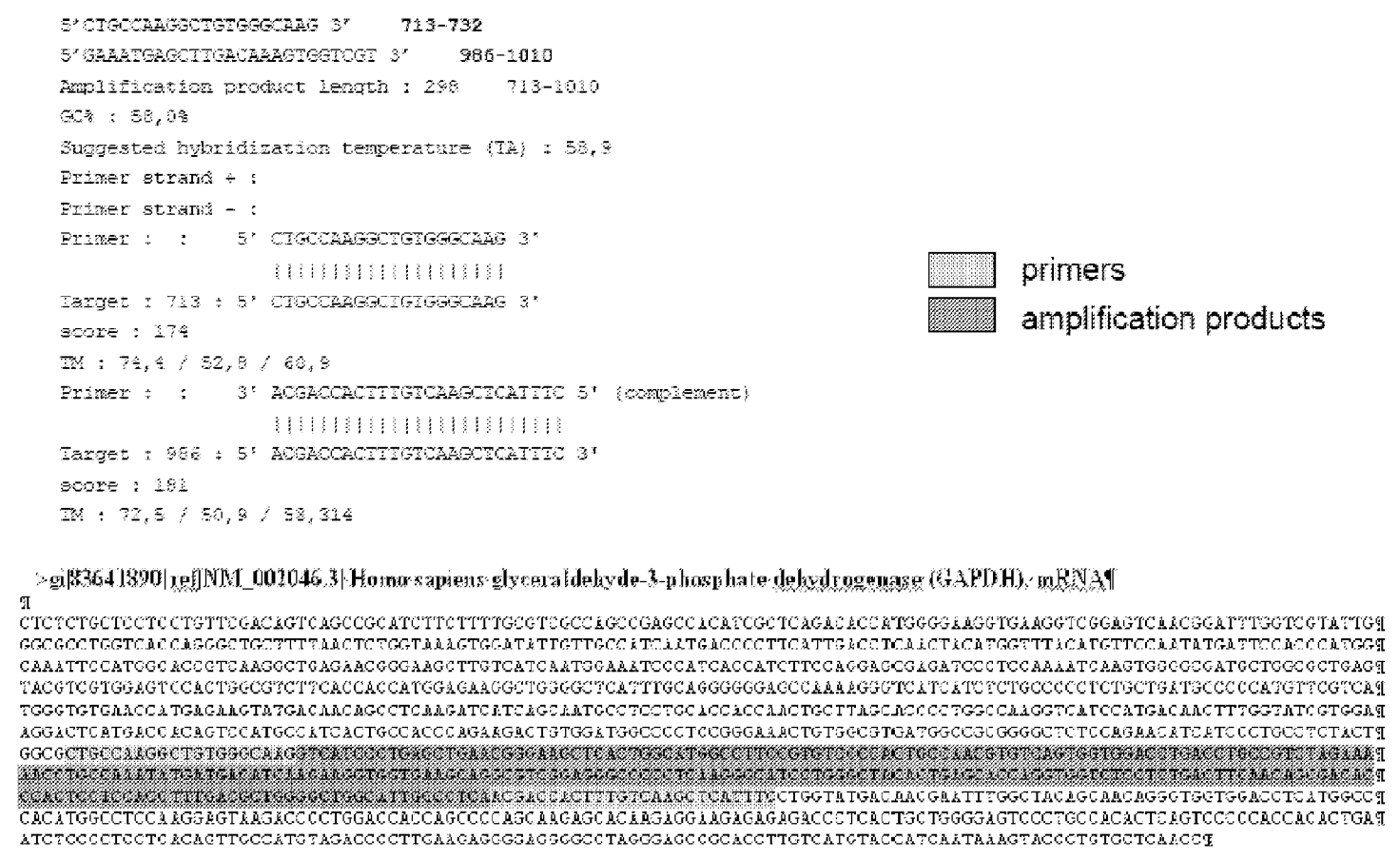

FIG. 12: Denaturing High Performance Liquid Chromatography (DHPLC)=primers and expected PCR products (FIGS. 12a-c). FIG. 12a, SEQ ID NO: 74 is a sequence encoding GAPDH. Primers corresponding to nucleotides 713-732 and the complement of nucleotides 986-1010 of SEQ ID NO: 74 (SEQ ID NO: 124) are also provided; FIG. 12b, SEQ ID NO: 75 is a sequence encoding ENO1. Primers corresponding to nucleotides 1505-1524 of SEQ NO: 75 and the complement of nucleotides 1788-1812 of SEQ ID NO: 75 (SEQ ID NO: 125) are also provided; FIG. 12c, SEQ ID NO: 76 is a sequence encoding thyomysin beta 4. Primers corresponding to nucleotides 311-335 of SEQ ID NO: 75 and the complement of nucleotides 590-614 of SEQ ID NO: 76 (SEQ ID NO: 126) are also provided.

FIG. 13: List of 60 studied proteins (FIGS. 13a-d).

Figure 14:
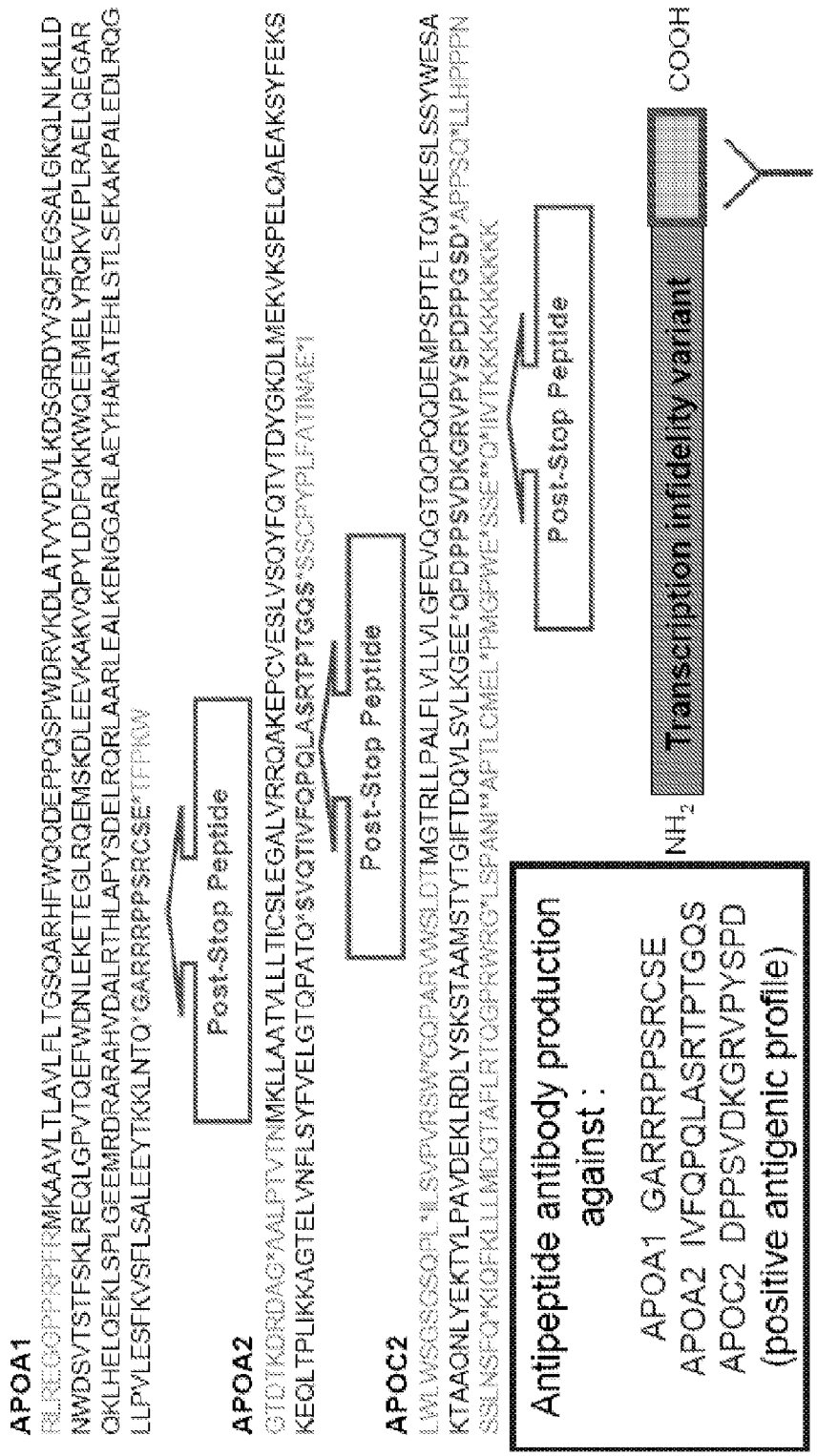

FIG. 14: Antibody production. Selection of 3 plasma proteins: APOA1, SEQ ID NO: 77; APOA2, SEQ ID NO: 78; APOC2, SEQ ID NO: 79. Antipeptide antibody production against: APOA1, SEQ ID NO: 12; APOA2, SEQ ID NO: 14; APOC2, SEQ ID NO: 16.

Figure 15C:
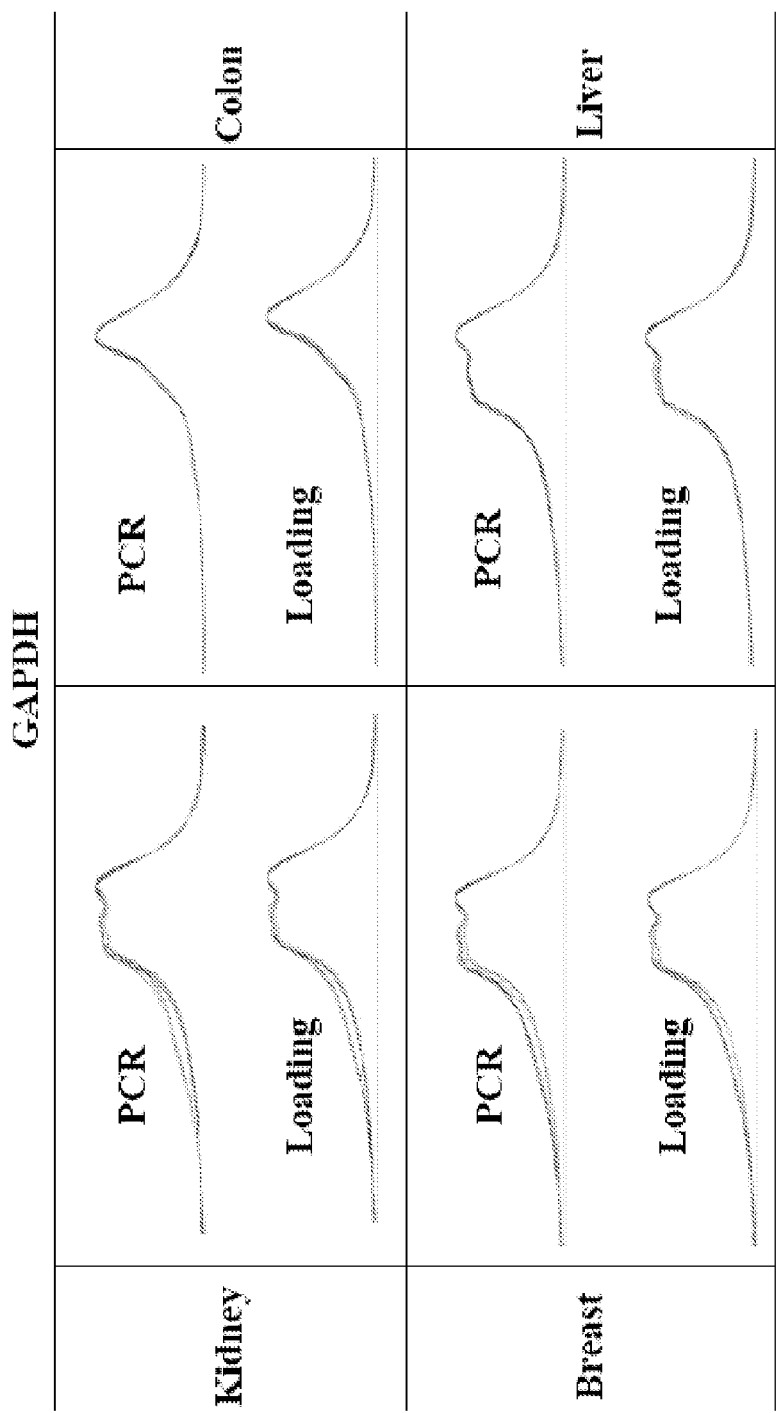

FIG. 15: Denaturing High Performance Liquid Chromatography (DHPLC) results (FIGS. 15a-c).

Figure 16:
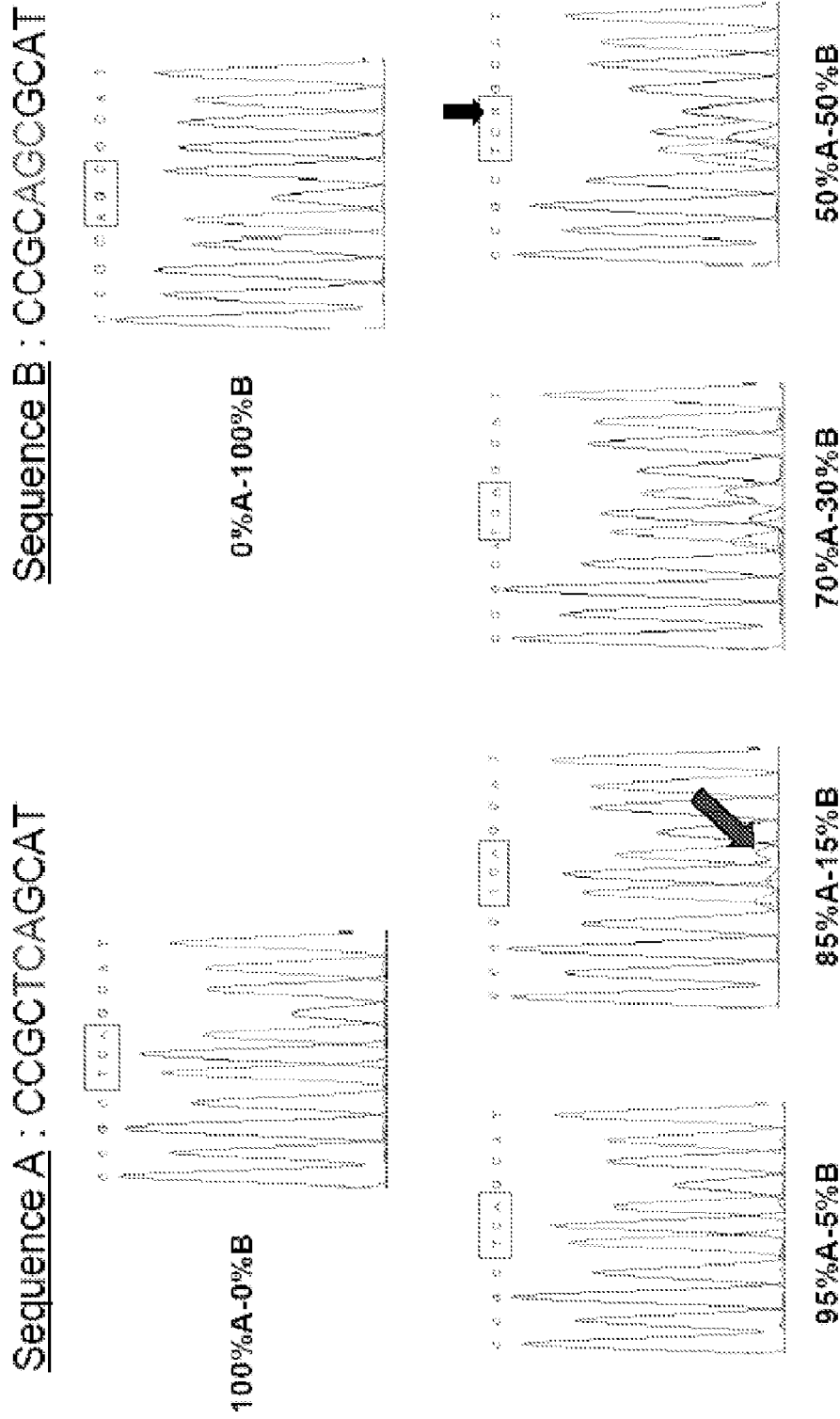

FIG. 16: Sanger sensibility. Classical Sanger sequencing of reverse transcribed PCR amplified mRNA does not detect sequence variants occurring at rates lower than 15-30% at a specific position.

Figure 17F:
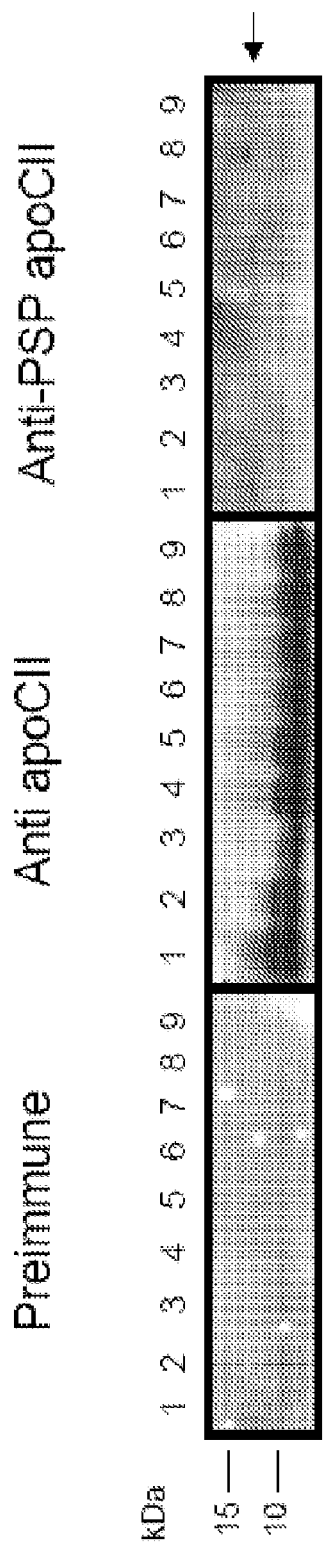

FIG. 17: Detection of APOAII and APOCII post stop peptides (PSP) in cancerous-patient plasma (FIGS. 17a-f).

FIG. 18: Potential PSP on plasma proteins (FIGS. 18a-e). FIG. 18b: AHSG Alpha-2-HS-glycoprotein, SEQ ID NO: 80; Albumin, SEQ ID NO: 81; APCS serum anyloid P-component, SEQ ID NO: 82; APOA1 Apolipoprotein A-I SEQ ID NO: 83. APOA2 Apolipoprotein A-II, SEQ ID NO: 84; APOC2 Apolipoprotein C-II, SEQ ID NO: 85; APOC3 Apolipoprotein C-III, SEQ ID NO: 86; APOD Apolipoprotein D. SEQ ID NO: 87. FIG. 18c: APOE Apolipoprotein E, SEQ ID NO: 88; AZGP1 Alpha-2-glycoprotein 1, zinc-binding, SEQ ID NO: 89; CH13L1 Chitinase-3-like protein 1, SEQ ID NO: 90; CLU Clusterin, SEQ ID NO: 91; HRG Histidine-rich glycoprotein, SEQ ID NO: 92. FIG. 18d: IGFBP3 Insulin-like growth factor binding 3, SEQ ID NO: 93; INHA Inhibin alpha chain, SEQ ID NO: 94; KLK11 Kallikrein-11, SEQ ID NO: 95; PKM2 Pyruvate kinase isozymes M1/M2, SEQ ID NO: 96; PLG Plasminogen, SEQ ID NO: 97. FIG. 18e: SERPINA3 Alpha-1-antichymotrypsin, SEQ ID NO: 98; TF Serotransferrin, SEQ ID NO: 99; TGFB1 Transforming growth factor beta-1, SEQ ID NO: 100; TTR Transthyretin, SEQ ID NO: 101.

FIG. 19: Evaluation of mRNA sequence substitutions predictions

DETAILED DESCRIPTION OF THE INVENTION

Definitions

Transcription Infidelity

The term transcription infidelity designates a novel mechanism by which several distinct RNA molecules are produced in a cell from a single gene sequence. This newly identified mechanism potentially affects any gene, is non-random, and follows particular rules, as will be disclosed below. As shown in the examples, transcription infidelity can introduce substitutions, deletions and insertions in RNA molecules, thereby creating a diversity of proteins from a single gene. Transcription infidelity can also affect non coding RNA sequences, thereby modulating their functions. Measuring, modulating or targeting transcription infidelity therefore represents a novel approach for detecting or treating disorders, as well as for drug development.

Transcription Infidelity Site

Within the context of the present invention, the term Transcription Infidelity Site designates a sequence and/or position affected by transcription infidelity. This can be a nucleic acid or amino acid domain that contains at least one modification generated as a result of transcription infidelity. Such a modification can result e.g., from a switch in the coding frame (insertion and/or deletion), from the introduction or suppression of stop codons, from the introduction of a new start codon, from nucleotide(s) substitution(s) (implying or not change of AA), etc. A transcription infidelity site may comprise one or several sequence variations resulting from transcription infidelity. A transcription infidelity site can comprise from e.g., 1 modified nucleotide or amino acid residue to e.g., 150 modified nucleotides or amino acid residues, or even more. The transcription infidelity site typically differs from the sequence resulting from faithful transcription by at least one nucleotide or amino acid modification (e.g., substitution, deletion, insertion, inversion, etc.). A protein or a domain created by transcription infidelity (TI-protein) typically comprises from 1 to 50 amino acids (or even more), with at least one modified amino acid residue. A nucleic acid transcription infidelity sequence typically comprises from 1 to 150 nucleotides (or even more), with at least one modified nucleotide residue.

Transcription Infidelity Rules and Identification

Based on specific techniques of detection and/or particular rules of transcription infidelity as defined in the present application, it is now possible to predict and identify, for any gene or protein, Transcription Infidelity Sites. These sites can also be obtained by aligning sequences available for given RNA and identifying base substitutions. They can ultimately be validated by various techniques, e.g. by using ligands specific for a predicted TI-protein.

A particular method for identifying a transcription infidelity site comprises:
  providing the sequence of a given gene, RNA or cDNA molecule, or a portion thereof, and
  identifying, within said sequence, the presence of a nucleotide change (e.g., substitution, deletion, insertion, inversion) resulting from transcription infidelity, following the transcription infidelity rules, e.g., as discussed in (iii) below.

A further particular method for identifying a transcription infidelity site comprises:
  providing the sequence of a given protein or a portion thereof, and
  identifying, within said sequence, the presence of an amino acid change (e.g., substitution, deletion, insertion, inversion) resulting from transcription infidelity, following the transcription infidelity rules, e.g., as discussed in (iii) below.

The presence of a change resulting from transcription infidelity in a molecule can be identified in a three step process, comprising:
  (i) identification of transcription infidelity sites with a learning machine relying on quadratic discrimination on Multiple Correspondence Factorial Analysis (MCFA) factors (ii) identification of the category of the transcription infidelity sites (b−1 or b+1 or else) with the same method, and (iii) predicting the replacement base using the following transcription infidelity rules:

For any base present as singleton, i.e., any base that is not preceded or followed by itself, then the substituted base is most likely identical to the base preceding the one that is substituted (in case of b−1 category) or identical to the base following the one that is substituted (in case of b+1 category). For example CAT will become CCT (b−1 rule); ATG will become AGG (b+1 rule);

When substitutions occur within three consecutive A, substitution of second A goes preferentially to C;

When substitutions occur within three consecutive T, substitution of second T goes preferentially to C, then A, then G;

Stretches of C and G are rarely substituted on the second, but if any, substitution of second C goes preferentially to A and substitution of second G goes preferentially to C;

For other cases, replacement base is preferentially C.

Further methods to identify transcription infidelity sites within the sequence of any target protein or nucleic acid comprise e.g., comparison of existing expressed sequence tag (ESTs), direct amplification of identified sequences and sequencing of amplification products with specific sequencing method (Sanger, chemical, Pyro-sequencing). Such an approach yields variant sequences that involve AA changes, modifications of protein length, etc. Oligonucleotide selectively matching mRNA or cDNA bearing transcription infidelity sites can then be designed, allowing selective amplification of nucleotide with transcription infidelity sites from a pool of sequences. Antibodies targeting TI-protein can also be produced.

Alternatively, it is possible to identify a transcription infidelity site by means of sequence analysis or bioinformatics rules. The resulting sequence may be cloned in any transfection vector. It is also possible to design a construct comprising such transcription infidelity sequence in frame with a reporter gene, that will be transcribed and translated only if transcription infidelity occurs. The reporter gene may be an enzyme or fluorescent protein or any gene that will make the target cell sensitive, or resistant to exposure to a toxin.

A detailed method that allows the identification of transcription infidelity sites (or substitutions) includes the TDG method as disclosed below:

A technique described by Pan and Weissman and Liu et al. (PNAS, 2002, 99(14), 9346-9351 and Anal Biochem. 2006 Sep. 1; 356(1):117-24) can be adapted for detecting transcription infidelity site(s) in RNA. This technique is based on the use of an enzyme, Thymine DNA glycosylase (TDG) that is capable of separately enriching mismatch-containing DNA duplexes from complex mixtures. These enzymes specifically recognize nucleotide mismatches and generate abasic sites (the bond between the deoxyribose and one of the bases of DNA is cleaved). Then, TDG can reversibly bind these abasic sites and thus can be used for affinity purification of mismatch-containing DNA fragments. In a typical experiment, RNA are extracted from 2 cell types (normal and cancerous) and reverse transcribed to make double-stranded cDNA. After heat denaturation and slow renaturation of each sample, cDNA with mismatche(s) are generated and can be separated from perfect duplexes. These cDNA can then be analysed either by direct sequencing or compared by DHPLC (see later).

Further techniques that may be adapted to identify transcription infidelity sites or mutations are disclosed, e.g., in U.S. Pat. No. 6,329,147; U.S. Pat. No. 4,979,330; WO02/077286 or U.S. Pat. No. 6,120,992.

Typically, the methods of identifying transcription infidelity sites further comprise a step of validating the sequence of the transcription infidelity site by producing a molecule comprising the identified sequence, generating a ligand that specifically binds to said molecule and verifying, in a biological sample, the presence of an antigen specifically recognized by said ligand.

A typical transcription infidelity sequence of a nucleic acid is a sequence of between 1 and 150 nucleotides in length comprising at least one base substitution, deletion or insertion caused by transcription infidelity, preferably following a rule as disclosed in Example 5. The transcription infidelity sequence could be higher.

A typical domain of a TI-protein is an amino acid sequence of between 1 and 50 amino acids in length comprising at least one amino acid substitution (or more changes due to modification in the coding frame resulting from base deletion or insertion) caused by transcription infidelity, preferably following a rule as disclosed in Example 5. The domain of a TI-protein could be higher. Examples of domains of TI-proteins are provided in the experimental section, e.g. in FIGS. 13 and 14.

Detecting or Measuring Transcription Infidelity

This invention is based on the unexpected discovery of a high rate of natural sequence abnormalities occurring during or shortly after transcription of DNA to RNA. The process may be present in normal cells but greatly increases in pathological cells, e.g., cancer cells. The discovery that DNA transcription into RNA is introducing sequence variations following rules that are different from those defined by one to one base complementarities allows the rational design of novel reagents (e.g., probes, primers, antibodies, aptamers etc.) that are specific for nucleic acid or protein created by transcription infidelity. Such reagents can therefore allow to detect or measure transcription infidelity, and to discriminate between normal or diseased conditions, as well as to target molecules to cells exhibiting transcription infidelity.

Furthermore, the invention also allows the rational design of reagents (e.g., probes, primers, antibodies, aptamers) that are predictive of disease (e.g., cancer) severity. Indeed, a greater rate of transcription infidelity is expected to correlate with the severity of the disease and this rate is increasing progressively as more and more gene products are affected. The direct measure of transcription (in)fidelity in diseased cell(s) using the methods described herein or any other technology allows to detect cells at different stages of disease progression in any given tissue. Accurately measuring these variations in gene expression (transcripts and proteins) also improves the capacity to evaluate drug efficacy with respect to disease severity. Currently, various microarray techniques allow measurement of changes in gene expression. However, the reliability and, most importantly, the reproducibility of these data are currently not sufficient. We can now postulate that a great deal of variability of these transcriptomic experiments is caused in part by transcription infidelity as discovered by the inventors. Thus, the discovery of this common phenomenon allows the design of gene expression reagents that either are minimally affected by transcription infidelity or that directly reflect transcription infidelity occurring in specific sequences following the rules described in the present application.

It is also possible and even likely that transcription infidelity is modulated by the transcription rate. We speculate that increase expression of a given gene in pathological condition will increase TI and thereby increase protein heterogeneity.

Transcription infidelity can be detected or measured using a number of techniques known per se in the art, which can be adapted to the present invention. In particular, transcription infidelity can be measured using reagents specific for nucleic acid or protein created by transcription infidelity, such as specific probes, primers or antibodies, by electrophoresis, gel migration analysis, spectrometry, etc., that allow the detection between various forms of a protein or nucleic acid. The rate of transcription infidelity can be determined by assessing the number of genes in a cell that are subject to transcription infidelity, and/or the number of transcription infidelity sites generated for a given gene. Such a rate can be determined by comparing the level of nucleic acid or protein created by transcription infidelity in a test sample to that obtained in a reference sample.

Detection of Transcription Infidelity at the Level of Nucleic Acids

As discussed above, transcription infidelity introduces sequence variation(s) in RNA molecules. Detecting or measuring transcription infidelity can thus be accomplished by detecting the presence or (absolute or relative) amount of such sequence variation(s) in RNAs encoded by one or several genes, or in a whole cell or tissue or sample. The detection of transcription infidelity in nucleic acids can be performed by various techniques such as hybridization, amplification, heteroduplex formation, etc.

Virtually all technologies used for identification of nucleotides present in diverse tissue types rely on a process called hybridization. Hybridization is critical for technologies such as microarrays used to identify polymorphisms and search for variation in gene expression. This technique is applied to measure the level of gene expression. Hybridization of oligonucleotide probes is also used to subtract sequences of gene abundantly expressed in order to allow better study of low abundance messages—this procedure is called subtractive hybridization. Hybridization is also the first step of gene amplification reaction commonly used in PCR experiments either under the direct form or after application of reverse transcriptase to convert message sequence from RNA type into DNA type sequence.

The basic mechanism underlying hybridization is that single strand nucleotide(s) sequences can bind to one another provided that their respective sequences are complementary. Both the length and the specific ordering of each of the 4 bases define the efficacy of hybridization and specificity of the sequence. This implies that each specific base binds in a non-covalent manner to its complementary base: A to T and C to G and vice versa. This non-covalent binding in a sequence match is conditioned by the ordering of the base. Thus, in general practice, a defined sequence of bases binds to a single complementary sequence. This specific binding reaction provides the basis for hybridization that allows identification of any complementary sequence in any given mixture of nucleotides. The efficacy of hybridization is determined by the number of bases that, in the appropriate order, match to one another (some degree of mismatches are tolerated) and determined by the conditions of the experiment such as the stringency of the binding buffer, the relative content of CG versus TA—CG and TA are linked by 3 and 2 hydrogen bonds, respectively—and by the melting temperature, i.e. the temperature that is needed to allow dissociation of 50% of double-stranded DNA.

Detecting transcription infidelity using hybridization typically comprises placing a sample in contact with a nucleic acid probe that is specific for a transcription infidelity sequence, and detecting the presence (or amount) of hybrids formed, said presence or amount being a direct indication of the presence or rate of transcription infidelity. In a preferred embodiment, the method uses a set of nucleic acid probes that are specific for distinct transcription infidelity sequences of one or several genes, respectively. Nucleic acid probes specific for a transcription infidelity sequence can be prepared for any gene using the sequence information and nucleotide substitution, insertion or deletion rules as disclosed in the present application (see e.g., Example 5).

Within the context of this invention, a nucleic acid "probe" refers to a nucleic acid or oligonucleotide having a polynucleotide sequence which is capable of selective hybridization with a transcription infidelity sequence or a complement thereof, and which is suitable for detecting the presence (or amount thereof) in a sample containing said sequence or complement. Probes are preferably perfectly complementary to a transcription infidelity sequence however, some mismatch may be tolerated. Probes typically comprise single-stranded nucleic acids of between 8 to 1500 nucleotides in length, for instance between 10 and 1000, more preferably between 10 and 800, typically between 20 and 700. It should be understood that longer probes may be used as well. A preferred probe of this invention is a single stranded nucleic acid molecule of between 8 to 400 nucleotides in length, which can specifically hybridize to a transcription infidelity sequence.

A specific embodiment of this invention is a nucleic acid probe that selectively hybridizes to a region of a nucleic acid molecule that does not contain a transcription infidelity sequence.

Selectivity, when used to denote nucleic acid hybridization, indicates that hybridization of the probe to the target sequence is distinct from hybridization of said probe to another sequence. In this regard, although perfect complementarity between the probe and the target sequence is not required, it shall be sufficiently high to allow selective hybridization.

Preferred probes of this invention comprise a sequence which is complementary to a transcription infidelity sequence in a RNA molecule (or corresponding cDNA molecule) that encodes a cell surface protein or a secreted protein. Specific examples of probes of this invention have a sequence complementary to a transcription infidelity sequence or encoding a peptide sequence of any one of SEQ ID Nos: 1 to 32.

The sequence of the probes can be modified, e.g., chemically, in order e.g., to increase the stability of hybrids (e.g., intercalating groups or modified nucleotides, such as 2' alkoxyribonucleotides) or to label the probe. Typical examples of labels include, without limitation, radioactivity, fluorescence, luminescence, enzymatic labelling, and the like. The probe may be hybridized to the target nucleic acid in solution, suspension, or attached to a solid support, such as, without limitation, a bead, column, plate, a substrate (to produce nucleic acid arrays or chips), etc.

According to another embodiment (which may be used in combination with hybridization probes), transcription infidelity is detected or measured by selective amplification using specific primers. Detecting transcription infidelity by selective amplification typically comprises placing a sample in contact with a nucleic acid primer that specifically amplifies a transcription infidelity sequence, and detecting the presence (or amount) of amplification products formed, said presence or amount being a direct indication of the presence or rate of transcription infidelity. In a preferred embodiment, the method uses a set of nucleic acid primers that allow specific amplification of distinct transcription infidelity sequence of one or several genes, respectively. Amplification may be performed according to various techniques known per se in the art, such as, without limitation, by polymerase chain reaction (PCR), ligase chain reaction (LCR), transcription-mediated amplification (TMA), strand displacement amplification (SDA) and nucleic acid sequence based amplification (NASBA).

Nucleic acid primers specific for a transcription infidelity sequence can be prepared for any gene using the sequence information and nucleotide substitution, insertion or deletion rules as disclosed in the present application (see e.g., Example 5).

The term "primer" designates a nucleic acid or oligonucleotide having a polynucleotide sequence which is capable of selective hybridization with a transcription infidelity sequence or a complement thereof, or with a region of a nucleic acid that flanks a transcription infidelity site, and which is suitable for amplifying all or a portion of said transcription infidelity site in a sample containing said sequence or complement. Typical primers of this invention are single-stranded nucleic acid molecules of about 5 to 60 nucleotides in length, more preferably of about 8 to about 50 nucleotides in length, further preferably of about 10 to 40, 35, 30 or 25 nucleotides in length. Perfect complementarity is preferred, to ensure high specificity. However, certain mismatch may be tolerated, as discussed above for probes.

The term "flanks" indicates that the region should be located at a distance of the transcription infidelity site that is compatible with conventional polymerase activities, e.g., not above 250 bp, preferably not exceeding 200, 150, 100 or, further preferably, 50 bp upstream from said site.

A further aspect of this invention also includes at least one pair of nucleic acid primers, wherein said pair of primers comprises a sense and a reverse primer, and wherein said sense and reverse primers allow selective amplification of a transcription infidelity sequence, or of the exactly complementary sequence. Specific examples of primers of this invention are disclosed e.g., in FIG. 12.

According to a further embodiment of this invention, transcription infidelity is measured by Denaturing High Performance Liquid Chromatography (DHPLC). The principle of this method is disclosed e.g., in FIG. 11. Basically, amplification products are denatured and re-annealed. During re-annealing, both homoduplexes and heteroduplexes are formed, as a result of the presence of transcription infidelity sequences. The mixture is then analyzed by DHPLC. Since heteroduplexes and homoduplexes DNA structures are different at the analysis temperature, they are eluted differently and their (relative) amount can be assessed.

As a verification of transcription infidelity sequences existing in cancer cells with greater frequency than in normal cells, predicted transcription infidelity of selected genes (ENO1, GAPDH, TMSB4X) were amplified by RT-PCR using the indicated oligonucleotides (see Example 6). Variations of homo- and heteroduplexes were verified (FIG. 15).

Any other technique suitable for detecting nucleic acids can be used or adapted for use in the present invention, to detect, quantify or monitor transcription infidelity.

Detection of Transcription Infidelity at the Level of Proteins

Because transcription infidelity leads to changes in protein sequence, the presence or level of transcription infidelity can also be measured by detecting the presence or amount of TI-proteins.

Various techniques known per se in the art can be used and/or adapted to measure transcription infidelity in proteins. In particular, since transcription infidelity causes modifications of proteins leading to direct changes in their behavior, these changes can be detected by e.g., 2-dimensional gel electrophoresis and mass spectrometry or by surface enhanced laser desorption ionization. As a verification that TI protein are present in human plasma, we show the mass spectrometry profile of a peptide located after the canonical STOP of ApoAII. Mass spectrometry data shows that arginine is substituted to canonical STOP. Furthermore, since transcription infidelity causes the occurrence of longer and shorter (cellular and plasma) protein isoforms (as a result of premature stop codon due to base substitution, or a switch in open reading frame in case of deletions or insertions), such isoforms may be detected or quantified using specific ligands thereof and/or protein sequencing strategies. In this regard, we demonstrate that changes in protein length and AA primary sequence predominantly occur on the carboxy-terminal domain of the protein. Accordingly, sequencing strategies shall be directed mainly towards the C-terminal end of proteins, a previously unsuspected region (indeed, direct protein sequencing methods presently used can only be achieved starting at the $NH_2$ terminal AA).

Detecting transcription infidelity using specific ligands typically comprises placing a sample in contact with a ligand that is specific for a domain of a TI-protein, and detecting the presence (or amount) of complex formed, said presence or amount being a direct indication of the presence or rate of transcription infidelity. In a preferred embodiment, the method uses a set of ligands that are specific for distinct domains of one or several TI-proteins, respectively. Ligands specific for these domains can be prepared for any protein using the sequence information and amino acid substitution rules as disclosed in the present application (see e.g., Example 5). The ligand may be used in soluble form, or coated on a surface or support.

In this respect, the invention also relates to any ligand that selectively binds a domain of a TI-protein. Different types of ligands may be contemplated, such as specific antibodies, synthetic molecules, aptamers, peptides, and the like.

In a specific embodiment, the ligand is an antibody, or a fragment or derivative thereof. Accordingly, a particular aspect of this invention resides in an antibody that specifically binds a domain of a TI-protein.

Within the context of this invention, an antibody designates a polyclonal antibody, a monoclonal antibody, as well as fragments or derivatives thereof having substantially the same antigen specificity. Fragments include e.g., Fab, Fab'2, CDR regions, etc. Derivatives include single-chain antibodies, humanized antibodies, human antibodies, poly-functional antibodies, etc.

Antibodies against domains of TI-proteins may be produced by procedures generally known in the art. For example, polyclonal antibodies may be produced by injecting the domain of the TI-protein (e.g., as a protein or peptide) alone or coupled to a suitable protein into a non-human animal. After an appropriate period, the animal is bled, sera recovered and purified by techniques known in the art (Paul, W. E. "Fundamental Immunology" Second Ed. Raven Press, NY, p. 176, 1989; Harlow et al. "Antibodies: A laboratory Manual", CSH Press, 1988; Ward et al (Nature 341 (1989) 544).

Peptides with the same sequence as TI-proteins may be produced by procedures generally known in the art. Such peptides can be coupled to a suitable support and used for the detection of auto-antibodies present in biological samples (for example body fluids).

Monoclonal antibodies against domains of TI-proteins may be prepared, for example, by the Kohler-Millstein (2) technique (Kohler-Millstein, Galfre, G., and Milstein, C, Methods Enz. 73 p. 1 (1981)) involving fusion of an immune B-lymphocyte to myeloma cells. For example, an immunogen as described above can be injected into a non-human mammal as described. Subsequently, the spleen is removed and fusion with myeloma conducted according to a variety of methods. The resulting hybridoma cells can then be tested for the secretion of antibodies against domains of TI-proteins.

An antibody "selective" for a particular domain of TI-proteins designates an antibody whose binding to said domain (or an epitope-containing fragment thereof) can be reliably discriminated from non-specific binding (i.e., from binding to another antigen, particularly to the native protein not containing said domain). Antibodies selective for domains of TI-proteins allow the detection of the presence of proteins containing such domains in a sample.

Diagnostics

The present invention allows the performance of detection or diagnostic assays that can be used, among other things, to detect the presence, absence, predisposition, risk or severity of a disease from a sample derived from a subject. The term "diagnostics" shall be construed as including methods of pharmacogenomics, prognostic, and so forth.

In a particular aspect, the invention relates to a method of detecting in vitro or ex vivo the presence, absence, predisposition, risk or severity of diseases in a biological sample, preferably, a human biological sample, comprising placing said sample in contact with a ligand that specifically binds a transcription infidelity site and determining the formation of a complex.

A particular object of this invention resides in a method of detecting the presence, absence, predisposition, risk or severity of cancers in a subject, the method comprising placing in vitro or ex vivo a sample from the subject in contact with a ligand that specifically binds a transcription infidelity site expressed by cancer cells, and determining the formation of a complex.

Another embodiment of this invention is directed to a method of assessing the response or responsiveness of a subject to a treatment of a cancer, the method comprising detecting the presence or rate of transcription infidelity in a sample from the subject at different times before and during the course of treatment.

This invention also relates to a method of determining the efficacy of a treatment of a cancer disease, the method comprising (i) providing a tissue sample from the subject during or after said treatment, (ii) determining the presence and/or rate of transcription infidelity in said sample and (iii) comparing said presence and/or rate to the amount of transcription infidelity in a reference sample from said subject taken prior to or at an earlier stage of the treatment.

The presence (or increase) in transcription infidelity in a sample is indicative of the presence, predisposition or stage of progression of a cancer disease. Therefore, the invention allows the design of appropriate therapeutic intervention, which is more effective and customized. Also, this determination at the pre-symptomatic level allows a preventive regimen to be applied.

The diagnostic methods of the present invention can be performed in vitro, ex vivo or in vivo, preferably in vitro or ex vivo. The sample may be any biological sample derived from a subject, which contains nucleic acids or polypeptides, as appropriate. Examples of such samples include body fluids, tissues, cell samples, organs, biopsies, etc. Most preferred samples are blood, plasma, serum, saliva, urine, seminal fluid, and the like. The sample may be treated prior to performing the method, in order to render or improve availability of nucleic acids or polypeptides for testing. Treatments may include, for instance one or more of the following: cell lysis (e.g., mechanical, physical, chemical, etc.), centrifugation, extraction, column chromatography, and the like.

A method of the present invention consist at determining the presence in human samples of antibodies directed against novel peptides produced by transcription infidelity and generating immune stimulation leading to antibody production. A second method of this invention is directed at detecting cells bearing immunological structure directed against transcription infidelity peptides.

Drug Design and Therapy

As discussed above, the invention allows the design (or screening) of novel drugs by assessing the ability of a candidate molecule to modulate transcription infidelity. Such methods include binding assays and/or functional (activity) assays, and may be performed in vitro (e.g., in cell systems or in non cellular assays), in animals, etc.

A particular object of this invention resides in a method of selecting, characterizing, screening or optimizing a biologically active compound, said method comprising determining in vitro whether a test compound modulates transcription infidelity. Modulation of transcription infidelity can be assessed with respect to a particular gene or protein, or with respect to a pre-defined set of genes or proteins, or globally.

A further embodiment of the present invention resides in a method of selecting, characterizing, screening or optimizing a biologically active compound, said method comprising placing in vitro a test compound in contact with a gene and determining the ability of said test compound to modulate the production, from said gene, of RNA molecules containing transcription infidelity sites.

A further embodiment of this invention resides in a method of selecting, characterizing, screening and/or optimizing a biologically active compound, said method comprising contacting a test compound with a cell and determining, in said cell, whether the test compound modulates transcription infidelity.

The above screening assays may be performed in any suitable device, such as plates, tubes, dishes, flasks, etc. Typically, the assay is performed in multi-well microtiter dishes. Using the present invention, several test compounds can be assayed in parallel. Furthermore, the test compound may be of various origin, nature and composition. It may be any organic or inorganic substance, such as a lipid, peptide, polypeptide, nucleic acid, small molecule, in isolated or in mixture with other substances. The compounds may be all or part of a combinatorial library of compounds, for instance.

Compounds that modulate transcription infidelity of the present invention have many utilities, such as therapeutic utilities, to reduce or increase transcription infidelity in a cell. Such compounds may be used to treat (or prevent) diseases caused by or associated with abnormal transcription infidelity, such as proliferative disorders (e.g., cancers), immune diseases, aging, inflammatory diseases, etc.

Other compounds of the present invention are compounds that target transcription infidelity, i.e., compounds that selectively bind transcription infidelity sites. Such compounds (e.g., antibodies, RNAi, etc.), may be used as diagnostic reagents, or as therapeutic agents, either alone or conjugated to a label.

Compounds that modulate or target transcription infidelity of the present invention can be administered by any suitable route, including orally, or by systemic delivery, intravenous, intra-arterial, intra-cerebral or intrathecal injections. The dosage can vary within wide limits and will have to be adjusted to the individual requirements in each particular case, depending upon several factors known to those of ordinary skill in the art. Any pharmaceutically acceptable dosage form known in the art may be used, such as any solution, suspension, powder, gel, etc., including isotonic solution, buffered and saline solutions, etc. The compounds can be administered alone, but are generally administered with a pharmaceutical carrier, with respect to standard pharmaceutical practice (such as described in Remington's Pharmaceutical Sciences, Mack Publishing). Antibodies may be administered according to methods and protocols known per se in the art, which are presently used in human trials and therapies.

Effect of Transcription Infidelity on Normal Cell Function

It is generally accepted that proteins are responsible for most cell functions. However, it is also clear that RNA, known as non-coding RNA, are therefore also functional molecules by themselves. These transcripts, whose importance was previously underestimated, would be present in many organisms and regulating a lot of cellular functions. Among them, one finds rRNA, tRNA, tmRNA (transmessenger RNA), but also other non-coding RNA (snoRNA, snRNA etc.) intervening in post-transcriptional modifications of RNA, in splicing or another cellular functions. The functions of both RNA and protein can be affected by a lack of transcription fidelity described in this application. The sequence of DNA is transcribed into mRNA in the nucleus by the action of a protein called RNA polymerase II that recognizes the sequence of the DNA molecule and synthesizes a single strand polymer of nucleotides that is complementary to the mother DNA template. The order and type of RNA base at any given position is determined by the order and type of base present on the DNA strand that serves as template. The 5' end of the transcribed RNA, which corresponds to the first base of mRNA, is linked to 7-methylguanylate attached to the initial nucleotide thereby constituting the 5' CAP that protects RNA from degradation. This modification occurs before transcription is completed. Processing at the 3' end of the primary transcript involves cleavage by an endonuclease to yield a free 3'-hydroxyl group to which a string of adenine residues is added by an enzyme called poly(A) polymerase. The resulting poly(A) tail contains between 100-250 nucleotides. The final step of the processing is splicing, which consists of the cleavage from the primary transcript of the element corresponding to intronic sequences followed by ligation of the exons. This process is controlled by numerous proteins and ncRNA, some of which bind to RNA. It is possible that this binding is one step that can be affected by lack of transcription fidelity. Indeed, all of these proteins are themselves encoded by specific RNA; the function of these proteins is therefore potentially affected by a lack of transcription fidelity. The highly complex process of RNA maturation leads to production of mRNA that will be exported from the nucleus in order for translation to occur. It is important to recognize that, at this stage, not all nucleotide triplets that are present on mature mRNA will be translated into AA. Mature messenger RNA contain non-coding regions referred to as the 5' and 3' untranslated regions that bear functional significance in determining the overall stability of mRNA and other roles in translation. In order to effectively convey the information contained in the DNA into the proper protein AA sequence, absolute fidelity of transcription is required. Indeed, any error occurring either during the transcription or during the maturation processes will potentially result in the introduction of changes in mRNA stability and ultimately in a variation in protein AA primary sequence. These variations in protein sequence might then exacerbate the phenomenon of transcription infidelity by alteration of the sequence of protein involved in initiation of transcription, transcription itself, 5' capping of RNA, 3' polyadenylation, RNA splicing and/or the export of RNA. Thus, the demonstration in this invention of transcription infidelity affecting a great number of genes isolated from cancer cells opens the possibility that the phenomenon might exacerbate itself thereby leading to progressive increase in disease severity. Variation in RNA sequences introduced by infidelity of transcription may have immediate consequences on cell function. Indeed, introduction of bases into the RNA primary transcript that are not complementary to that of the DNA template has immediate potential consequences on the resulting protein AA primary sequence. Where the change affects the first 2 bases of the codon, it typically exerts a direct impact on the AA sequence. Variations affecting the third base of the codon will have a lower impact on protein AA sequence because the genetic code is degenerated. Thus, the changes of the base located on the third position of the codon may not directly influence the AA sequence of the protein. On the basis of the data described below, we believe that infidelity of transcription is a phenomenon that affects all bases irrespective of their position on the codon, and therefore impacts on protein AA primary sequence. The changes in protein can be either neutral or cause a modification of protein function, whether it be an increase or loss of activity. The phenomenon of transcription infidelity is predominantly observed after encoding at least the first 400-500 bases of mature mRNA is completed; the 5' end of the mRNA are relatively less affected. It is believed that shorter as well as longer fragments of protein will be present in cancer cells as well as in plasma from cancer patients. These shorter and longer isoforms can be directly deduced from transcription infidelity rules described below. This allows the production of rationally designed methods for identification of specific markers of cancer or of immunological disease severity. Because the transcription rate of most genes is controlled to adapt to cellular needs, it is proposed that transcription infidelity causes changes in gene expression directly due to either excessive or lack of protein function. Thus, the phenomenon of transcription infidelity exerts a profound effect on the cell capacity to perform its task. The identification of this defect as being a common feature of most genes isolated from all types of cancer cells therefore provides a rationale to seek new methods allowing quantitative measurement of the rate of transcription infidelity in any given cell. This screening assay allows testing of novel drugs capable of limiting transcription infidelity, thereby preventing progression of the disease and restoring normal cell function.

Transcription Infidelity and Pathology

The present invention shows that transcription infidelity leads to important changes in protein sequence. The function of any given protein is determined by its 3-D structure that is directly dependent on its AA sequence. Proteins with a variant AA, protein truncation or protein elongation might result in either a profound modification of protein activity or remain neutral. Examples of modified proteins that significantly inhibit the function of their normal homologs have been described. Transcription infidelity is a phenomenon that affects a great number of genes, hence yielding a large number of proteins. Because several of these proteins participate in maintaining stable DNA structure and participate in DNA repair, defective function of these proteins may result in defective DNA repair and result in a significantly decreased capacity of the cells to successfully repair any damaged DNA. Because transcription fidelity in normal cells is due to the activity of several protein complexes that control transcription, it is quite possible that initial small alterations of these proteins might progressively exacerbate the phenomenon. This will ultimately result in a greater rate of transcription infidelity that will consequently suppress cell differentiation status and lead to increasingly severe forms of the disease. The demonstration that transcription infidelity actually occurs in cancer cells and leads to wide diversification of proteins encoded by any given gene opens a novel area to screen for novel diagnostic probes and design novel therapeutic targets.

The present invention describes a novel phenomenon that contributes to diversification of the information present on DNA and that follows specific rules. This process of non-random transcription infidelity is greatly exacerbated in cancer cells but also occurs in normal cells following the same rules. This mechanism introduces novel bases in mRNA thereby causing profound changes in the message that will be translated at the ribosome level. The phenomenon is likely to be quite general because it is present in most tested genes. The immediate consequence of transcription infidelity is that a single gene can produce many more proteins than suspected. Thus, our discovery has the potential to explain in part the relative discrepancy between the limited number of genes present on the genome and the large number of proteins present in biological samples. We have shown that transcription infidelity is a non-random process and is governed by specific rules, some of which have already been described here. Some will be revealed by further characterization of the process using bioinformatics and biological methods. We have focused here on the implication of transcription infidelity in cancer. However, we believe that the process is general and that this can contribute to generate diversity of proteins. This diversification of proteins might exert a significant influence on the capacity of the immune system to recognize a specific protein pattern. In this regard, it is believed that transcription infidelity plays a role in the pathogenesis of immune diseases. We have considered here the events of transcription infidelity that lead to the substitution of single base. We have focused on single base substitutions because this mechanism is unlikely to cause significant destabilization of mRNA structure. Thus, single base substitutions should not interfere with translation, but be recognized as a bona-fide novel message. We will see further that transcription infidelity is also expected to cause base deletions and/or insertions. The same method described above will detect alternate mechanisms of transcription infidelity.

The novel process described in this application has several immediate practical applications.

Optimization of Proteomic Experiments to Identify Novel Disease-Specific Biomarkers and Design Novel Antibodies that Will be Targeted Towards Specific Disease Proteins.

Based on the teaching of the present application, it is now possible to predict the changes that can occur in any protein sequence as a result of transcription infidelity, and therefore to predict changes in physico-chemical properties such as apparent molecular masses and isoelectric points. This can yield modified protein patterns in 2-D gels and mass spectrometry. Because transcription infidelity affects most genes, it is now possible to focus on a limited set of proteins and characterize their changes in order to identify disease (e.g. cancer) specific biomarkers. Transcription infidelity algorithms can speed up the biomarkers discovery process. Alternatively, it is possible to design specific antibodies directed toward domains of TI-proteins, i.e., the protein domains that contain modified AA, as well as additional new AA which extend the native protein generated by transcription infidelity. Antibodies directed against these domains will be specific for the protein variant and therefore targeted toward disease (e.g., cancer)-specific proteins present in body fluid, at the cell surface, or inside cancer cells. These antibodies will be used to detect proteins characteristic of a pathological condition in body fluids, to detect diseased cells circulating in plasma, to identify diseased cells in histological samples, to evaluate disease severity, and also to target medications toward specific diseased cells. This can be achieved by gene transfer of transcription infidelity-prone sequence by means of gene therapy vector e.g. adenoviruses, liposomes, etc.

Alternatively, we designed specific peptides having the same sequence as a domain that result from TI. They can be used to detect specific and natural auto-antibodies directed toward domains of TI-proteins present for example in body fluids.

Transcription infidelity occurs non-randomly and frequently affects mRNA stop codons in a great proportion of tested genes. Further, because one can estimate that up to 6% of any given population of mRNA contain these additional sequences, one can therefore detect in a given cancer cell a specific population of protein that exhibits a novel sequence in the carboxy-terminal end. Targeting of these sequences was thus far not conceivable because no process reported, except for rare genetic diseases affecting DNA, was capable of introducing in-frame reading of sequences that immediately follow canonical stop codons. The existence of these hidden sequences was not previously suspected. The discovery of transcription infidelity leading to single base substitution occurring on canonical stop codons reveals the existence of such coding sequences and further show that their presence is increased in cancer cells because of enhanced transcription infidelity in these cells. Thus, it is possible to identify and target these normally hidden sequences to design novel cancer-specific drugs.

TI concerning single base deletion or insertion occurring on the coding sequence leads to a switch in the coding frame. As a convergence, the sequences in the corresponding protein are modified (change in the AA sequence and in protein length). One can therefore detect in a given cancer cell a specific population of protein that exhibits a novel sequence. Thus, it is possible to identify and target these normally hidden sequences to design novel cancer-specific drugs.

Because of the existence of novel or modified protein sequences, and considering that these alterations are present on the protein present on the cell surface, it is proposed to use these sequences in order to vaccinate against disease-specific sequences. These vaccinations will be used to trigger immune responses in patients diagnosed with any given form of disease (e.g., of cancer) or to initiate preventive immune responses in patients with increased risk for developing specific diseases (e.g., cancer) because of genetic predisposition or because of increased exposure to an environmental toxin or risk.

A particular object of this invention thus relates to a method of detecting the presence or stage of a disease in a subject, the method comprising assessing (in vitro or ex vivo) the presence or rate of transcription infidelity in a sample from said subject, said presence or rate being an indication of the presence or stage of a disease in said subject. The sample may be any tissue, cell, fluid, biopsy, etc., containing nucleic acids and/or proteins. The sample may be treated prior to the reaction, i.e., by dilution, concentration, lysis, etc. The method typically comprises assessing transcription infidelity of a number of distinct genes or proteins, such as plasma proteins, cell surface proteins, etc.

A further object of this invention is a method of treating a subject in need thereof, the method comprising administering to said subject an effective amount of a compound that alters (e.g., reduces or increases) the rate of transcription infidelity of a mammalian gene.

A further object of this invention relates to the use of a compound that alters (e.g., reduces or increases) the rate of transcription infidelity of a mammalian gene for the manufacture of a pharmaceutical composition for use in a method of treatment of a human or animal, particularly for treating a proliferative cell disorder, such as cancers and immune diseases.

A further object of this invention resides in a method of assessing the efficacy of a drug or candidate drug, the method comprising a step of assessing whether said drug alters the rate of transcription infidelity of a mammalian gene, such an alteration being an indication of drug efficacy.

The invention further relates to methods and products (such as probes, primers, antibodies or derivatives thereof), for detecting or measuring (the level of) transcription infidelity in a sample, as well as to corresponding kits.

The invention also relates to a method of identifying and/or producing biomarkers, the method comprising identifying, in a sample from a subject, the presence of transcription infidelity site(s) in a target protein, RNA or gene and, optionally, determining the sequence of said transcription infidelity site(s). In a particular and preferred embodiment, the target protein is a cell surface protein or a secreted protein, particularly a cell surface protein or a plasma protein.

A further object of the invention relates to a method of producing or identifying ligands specific for a trait or pathological condition, the method involving identifying, in a sample from a subject having said trait or pathological condition, the presence of transcription infidelity site(s) in one or several target proteins, RNA or gene, optionally determining the sequence of said transcription infidelity site(s), and producing (a) ligand(s) that specifically bind(s) to said transcription infidelity site(s).

The invention is particularly suited for identifying biomarkers of cell proliferative disorders, such as cancers, immune diseases, inflammation or aging. It is particularly useful for producing ligands that are specific for such disorders in mammalian subjects, in particular ligands that can detect the presence or severity of a cell proliferative disorder in a subject.

A further aspect of this invention relates to a (synthetic) peptide comprising a transcription infidelity site of a protein, particularly of a mammalian protein, more preferably of a human protein. The peptide typically comprises an internal fragment of protein, or the sequence of a C-terminal fragment of said protein. The peptide preferably comprises less than 100, 80, 75, 70, 65, 60, 50, 45, 40, 35, 30, 25 or even 20 amino acids. The protein may be a cell surface protein (e.g., a receptor, etc.), a secreted protein (e.g., a plasma protein), or an intracellular protein. Examples of such plasma proteins are provided e.g., in FIG. 13, and include apolipoproteins (e.g., AI, AII, CI, CII, CIII, D, E), complement components (e.g., C1s, C3, C7), C-reactive protein, serpin peptidase inhibitors, fibrinogen (e.g., FGA1, FGA2), plasminogen, transferrin, transthyretin, etc. Examples of cell surface receptors include e.g., cytokine receptors and hormone receptors, etc. In a specific embodiment, the invention relates to a synthetic peptide comprising a transcription infidelity site of an abundant human plasma protein or cell surface receptor as listed above.

Specific examples of such peptides are disclosed in FIGS. 10, 14 and 18. More specifically, examples of synthetic peptides of the present invention comprise all or a fragment of the following amino acid sequences:

```
                                              (SEQ ID No; 1)
QMWQLFWIYHLSS (TPT1)

(SEQ ID NO: 2)
KLHTLSAAIYYQQE (VIM)

(SEQ ID NO: 3)
DFLSKN (RPS6)

(SEQ ID NO: 4)
MYTVEFSVHKNN (RPL7A)

(SEQ ID NO: 5)
NGSLGDMSDLCT (RPS4X)

(SEQ ID NO: 6)
ASG (FTH1)

(SEQ ID NO: 7)
EPSEPSDF (FTL)

(SEQ ID NO: 8)
APSIFPTLPAKPGTKQPRSPVTALSLHMLLMVSSAPSCGLIQTVSSFTVY
IFTL (TPI1)

(SEQ ID NO: 9)
ARHGRDEEVWHRKHSHHFVQAWAWVGGLCVWPRKCHMRSTLISSLDSLLP
VIPHRTEAEWVVVMFDRRH (AHSG)

(SEQ ID NO: 10)
RSKAYSSVFLFRWCKANTLSKKHKFL (ALB)

(SEQ ID NO: 11)
GLDSTRALENEMTV (APCS)

(SEQ ID NO: 12)
GARRRPPSRCSE (APOA1)

(SEQ ID NO: 13)
SVQTIVFQPQLASRTPTGQS (APOA2)

(SEQ ID NO: 14)
IVFQPQLASRTPTGQS (APOA2)

(SEQ ID NO: 15)
QPDPPSVDKGRVPYSPDPPGSD (APOC2)

(SEQ ID NO: 16)
DPPSVDKGRVPYSPD (APOCII)

(SEQ ID NO: 17)
DLNTPSPPAYPSCELLGSCNLQGCPCRLLKRDSILSALLPHLMPGPPPGM
LASQ (APOC3)

(SEQ ID NO: 18)
PGSTGRLHPLHVTSASLSPTPPPPHKDKPINHDKGS (APOD)

(SEQ ID NO: 19)
TPKPAAMRPHATPCLLPPRSLQRETLSPPQPSSWGGP (APOE)

(SEQ ID NO: 20)
EARVGGNVGSQTQ (AZGP1)

(SEQ ID NO: 21)
PSVLHTARGPRMPRPPLAPAGREPDHLPC (CHI3L1)

(SEQ ID NO: 22)
DVDVAFAPTGASESSSPQDELQPPRESSARHQVTRPQPPGPQLRPASPRS
GSCTLTLDSAAHGKNRIAPACN (CLU)

(SEQ ID NO: 23)
NVIPLKRKMNNTLN (HRG)

(SEQ ID NO: 24)
TPAARLMWSSNMPYFAQKTAKDMTSSWLQPRFIFLFVVN (IGFBP3)

(SEQ ID NO: 25)
GWGVFLLNPMAGGHAPTIISWEERQSWEIDGSHSSLLSLLCLWATLPTPL
LSQ (INHA)
```

```
                                                          (SEQ ID NO: 26)
TGPTHHSPSPSISTWCLVPVHSVNKKP (KLK11)

(SEQ ID NO: 27)
WTPEPLLQPLSHPLPPAHPLGQQRL (RKM2)

(SEQ ID NO: 28)
LDGRQSDALTHLEAGTWVGI (PLG)

(SEQ ID NO: 29)
SLPSSSGALSKELGMQAGCLGLWAQPGPCAPSGHGMCGPVCLSLEGDSDS
LCSSHMHRGPWTLQSGGSWAS (SERPINA3)

(SEQ ID NO: 30)
NLRGRAATKVKMGTQMIHEFALVSLAQVVCANHVCLHSSVLPCVLNKK
(TF)

(SEQ ID NO: 31)
GPAPPRPAPAGPAPPRPAPAALPMGAVFKDTRAPSPPGAPLKMERGLRIS
VSLGACLGSPSLTFPHSHSLSLPLCLLLPVCTIPLPGIKAQGTSGEHYCS
(TGFB1)

(SEQ ID NO: 32)
GTSPPVDLKDEGWDFM (TTR)
```

A further aspect of this invention resides in the use of a peptide comprising a transcription infidelity site, as defined above, as an immunogen. The invention also relates to a vaccine composition comprising a peptide comprising a transcription infidelity site, as defined above, and optionally a suitable carrier, excipient and/or adjuvant.

The invention also relates to a device or product comprising, immobilized on a support, a reagent that specifically binds a transcription infidelity site. The reagent may be e.g., a probe or an antibody or derivative thereof.

The invention may be used in any mammalian subject, particularly any human subject, to detect, monitor or treat a variety of pathological condition associated with an increased or reduced transcription infidelity rate, such as e.g., cell proliferative disorders (e.g., cancers), immune diseases (e.g., auto-immune diseases (multiple sclerosis, ALS), graft rejection), aging, inflammatory diseases, diabetes, etc., and/or to produce, design or screen therapeutically active drugs. The invention may also be used to detect, monitor, modulate or target transcription infidelity in any other cell type, such as prokaryotic cells, lower eukaryotes (e.g., yeasts), insect cells, plant cells, fungi, etc.

Producing and Using Agents that Target Transcription Infidelity Sites

Using the teaching of the present invention, it is possible to produce agents that can target transcription infidelity sites, e.g., that bind to proteins or nucleic acids containing a transcription infidelity site, or to cells or tissues containing or expressing such proteins or nucleic acids. The targeting agent may be an antibody (or a derivative thereof), a probe, a primer, an aptamer, etc., as disclosed above.

Such targeting agents may be used e.g., as diagnostic agents, to detect, monitor, etc. transcription infidelity in a sample, tissue, subject, etc. For that purpose, the agent may be coupled to a labeling moiety, such as a radiolabel, an enzyme, a fluorescent label, a luminescent dye, etc.

The targeting agents may also be used as a therapeutic molecule, e.g., to treat a cell or tissue or organism exhibiting abnormal transcription infidelity. The agent may be used as such or, preferably, coupled to an active molecule, such as a toxic molecule, a drug, etc.

A particular embodiment of this invention thus resides in a method of producing an agent that targets transcription infidelity, the method comprising (i) identifying a transcription infidelity site of a protein or nucleic acid and (ii) producing an agent that selectively binds said site. The transcription infidelity site may be identified e.g., by alignment of sequences available for a given RNA molecule and identification of sequence variations, particularly at the 3' end. Transcription infidelity sites may also be identified by applying the transcription infidelity rules, as described in the present application (see e.g., Example 5) or new rules later described, to any gene sequence. The peptide or nucleic acid molecule comprising said identified site may then be produced using conventional methods. In a preferred embodiment, step (i) of the method comprises identifying a transcription infidelity site of a secreted or cell surface protein (e.g., a receptor, etc.), or of a nucleic acid. Indeed, secreted proteins and cell surface proteins can be easily targeted using a targeting agent that is contacted to a cell or administered to a subject. Examples of domains of such TI-proteins are disclosed in the examples.

Producing and Using a Vaccine that Causes or Stimulates or Inhibits an Immune Response Against a Domain of a TI-Protein Using the teaching of the present invention, it is possible to produce a vaccine composition that causes or inhibits an immune response against TI-proteins, or against cells or tissues containing or expressing such TI-proteins or corresponding nucleic acids.

Typically, the vaccine composition comprises, as an immunogen, a molecule comprising the sequence of a transcription infidelity site. The vaccine composition may comprise any pharmaceutically acceptable carrier, excipient or adjuvant. The vaccine composition can be used to generate an immune response against a diseased cell or tissue expressing TI-proteins, which results in a destruction of said cell or tissue by the immune system. Alternatively, the vaccine composition may be used to induce a tolerance against transcription infidelity sites involved in auto-immune diseases.

A particular embodiment of this invention thus resides in a method of producing an immunogen that causes, stimulates or inhibits an immune response against a domain of TI-proteins, or against a cell or tissue expressing such a protein, the method comprising (i) identifying a transcription infidelity site of a protein or nucleic acid and (ii) producing a peptide comprising such a site or a variant thereof. The transcription infidelity site may be identified e.g., by alignment of sequences available for a given RNA molecule and identification of sequence variations, particularly at the 3' end. Transcription infidelity site may also be identified by applying the transcription infidelity rules, as described in the present application (see e.g., Example 5) or new rules later described, to any gene sequence. The peptide molecule comprising said identified site may then be produced using conventional methods. In a preferred embodiment, step (i) of the method comprises identifying a transcription infidelity site of a secreted or cell surface protein (e.g., a receptor, etc.), or of a nucleic acid. Indeed, secreted proteins and cell surface proteins are more subject to a response by the immune system. Examples of domains of such TI-proteins are disclosed in the examples.

Reducing Transcription Infidelity in Recombinant Protein Production Systems

A particular object of this invention resides in a method of preventing or reducing transcription infidelity that can occur in recombinant production systems, particularly in therapeutic proteins production systems. Indeed, such a transcription infidelity may either decrease the yield of production of the system, or result in the production of mixtures on uncharacterized proteins which may exhibit various activity profiles. It is therefore recommended and highly valuable to be able to reduce the occurrence or rate of transcription infidelity in recombinant production systems, such as bacterial production systems (if transcription infidelity rules are the same for prokaryotic systems), as eukaryotic production systems (e.g., yeasts, mammalian cells, etc). Such a reduction may be accomplished e.g., by adapting the sequence of the coding nucleic acid molecule, and/or by inhibiting RNA molecules generated through transcription infidelity. Alternatively, proteins containing transcription infidelity sites may be removed from the medium.

Reducing the Sensibility to Transcription Infidelity for a Gene

A particular object of this invention resides in a method of preventing or reducing TI that can occur in a gene. Indeed, such TI may affect either the expression or the activity of a protein, or result in the production of mixtures of uncharacterized proteins which may exhibit various activity profiles. It is therefore recommended and highly valuable to be able to reduce the occurrence or rate of TI for said gene. Such a reduction may be accomplished e.g., by modifying the sequence of the gene (gene therapy), and/or by inhibiting RNA molecules generated through transcription infidelity. Alternatively, proteins containing TI sites may be specifically degraded (e.g. specifically targeted for degradation).

Measuring Transcription Infidelity at the RNA Level.

Transcriptomics is the science that measures variation in RNA (preferentially mRNA) levels occurring in a variety of pathological conditions, of which cancer is the most frequent. Transcriptomics relies on hybridization of cDNA with a specific set of oligonucleotides that identify predefined subsets of genes. Hybridization efficacy is dependent on specific sequences of any given RNA that will be reverse transcribed in cDNA. Introduction of unsuspected sequence variation in a given RNA will decrease the efficacy of hybridization and hence cause variation in the signal perceived by transcriptomic chips. The discovery that transcription infidelity causes alterations of RNA base sequence has two immediate consequences: first, it allows optimization of transcriptomic chips in order to minimize the consequence of base mismatch due to transcription infidelity and thereby improve the accuracy of the transcriptomic experiment. Indeed, the current limitation of transcriptomic experiments is their lack of reproducibility between studies. We currently believe that a major part of said variability is caused by transcription infidelity. Understanding the rules of transcription infidelity as described above now allows the design of microarray chips that specifically measure the rate of transcription infidelity in any given mixture of cDNA obtained from normal or diseased cells. Monitoring of transcription infidelity rate at the RNA level allows high-throughput screening of the relative rate of transcription infidelity occurring in a given cell. This provides essential information to determine disease severity, define the therapeutic strategies and classify diseased cells according to their pharmacological sensitization profile. The same screen also allows testing for the efficacy of novel drugs, e.g., in cancer therapy.

Further Applications of Transcription Infidelity

Transcription infidelity is a newly discovered natural mechanism that adds diversification to the well-established genetic code. We have observed that transcription infidelity occurs, albeit at low rates, even in normal tissues. We propose that transcription infidelity contributes to explain the relative low abundance of genes identified on the genome and the much greater diversity of proteins present in living cells of biological fluids and tissues.

We propose that transcription infidelity serves a specific function at the immunological level. We further propose that the immune system relies at least in part on a given rate of transcription infidelity affecting preferentially specific genes in order to identify self. Thus, abnormalities in the rate of transcription infidelity occurring for yet unknown reasons might contribute to trigger specific immune response and contribute to the pathogenesis of auto-immune and allergic diseases. Inter-individual differences in transcription infidelity might also be conditioned by polymorphisms of genes of the immune system, hence determining the rate of transcription infidelity occurring in circulating cells of the immune system, e.g., T or B lymphocytes, and might also contribute in the evaluation of the suitability of donor and acceptor of grafts and in determining the severity of graft versus host severity of diseases.

We also postulate that transcription infidelity occurs at greater rate during the normal aging process. This would create conditions of progressive reduction of performance affecting all enzymes generally and most specifically those proteins that are involved in cell replication, DNA repair and maintenance of normal rate of transcription fidelity. The concept described above might therefore redirect research onto the mechanisms of aging. Biochemical, proteomic, transcriptomic and other methods that allow screening for mRNA and cDNA sequences and fidelity to that specified by DNA might therefore be used to quantify the rate of transcription infidelity occurring in a given individual. Testing of novel molecules reducing the rate of transcription infidelity will therefore be amenable to biological screening and lead to development of drugs reducing the aging rate.

Further aspects and advantages of the invention will be disclosed in the following experimental section, which illustrates the invention and does not limit the scope of the present application.

EXPERIMENTAL SECTION

Example 1

Principle of Typical cDNA Library Construction and Sequencing (see FIG. 1)

The first step in preparing a complementary DNA (cDNA) library is to isolate the mature mRNA from the cell or tissue type of interest. Because of their poly(A) tail, it is straightforward to obtain a mixture of all cell mRNA by hybridization with complementary oligo dT linked covalently to a matrix. The bound mRNA is then eluted with a low salt buffer. The poly(A) tail of mRNA is then allowed to hybridize with oligo dT in the presence of a reverse transcriptase, an enzyme that synthesizes a complementary DNA strand from the mRNA template. This yields double strand nucleotides containing the original mRNA template and its complementary DNA sequence. Single strand DNA is next obtained by removing the RNA strand by alkali treatment or by the action of RNase H. A series of dG is then added to the 3' end of single strand DNA by the action of an enzyme called terminal transferase, a DNA polymerase that does not require a template but adds deoxyoligonucleotide to the free 3' end of each cDNA strand. The oligo dG is allowed to hybridize with oligo dC, which acts as a primer to synthesize, by the DNA polymerase, a DNA strand complementary to the original cDNA strand. These reactions produce a complete double strand DNA molecule corresponding to the mRNA molecules found in the original preparation. Each of these double strand DNA molecules are commonly referred to as cDNA, each containing an oligo dC-oligo dG double strand on one end and an oligo dT-oligo dA double strand region on the other end. This DNA is then protected by methylation at restriction sites. Short restriction linkers are then ligated to both ends. These are double strand synthetic DNA segments that contain the recognition site for a particular restriction enzyme. The ligation is carried out by DNA ligase from bacteriophage T4 which can join "blunt ended" double strand DNA molecules. The resulting double strand blunt ended DNA with a restriction site at each extremity is then treated with restriction enzyme that creates a sticky end. The final step in construction of cDNA libraries is ligation of the restriction cleaved double strand with a specific plasmid that is transfected into a bacterium. Recombinant bacteria are then grown to produce a library of plasmids—in the presence of antibiotics corresponding to the specific antibiotic resistance of the plasmid. Each clone carries a cDNA derived from a single part of mRNA. Each of these clones is then isolated and sequenced using classical sequencing methods. A typical run of sequencing starts at the insertion site and yields 400 to 800 base pair sequences for each clone. This sequence serves as a template to start the second run of sequencing. This forward progression leads to progressive sequencing of the entire plasmid insert. The results of sequencing of numerous cDNA designated ESTs have been deposited in several public databases.

Example 2

Database Annotation

EST databases contain sequence information that correspond to the cDNA sequence obtained from cDNA libraries and therefore correspond essentially to the sequence of individual mRNA present at any given time in the tissue that was used to produce these libraries. The quality of these sequences has been called into question for several reasons. First, as discussed above, the process of producing cDNA libraries initially relied heavily on the presence of a poly(A) tail at the 3' end of eukaryotic mRNA. Second, mRNA are quite fragile molecules that are easily digested by high abundance nucleases called RNases. Third, while building and sequencing these libraries, little attention was paid to the quality of the original material used and its storage. Because of this, EST sequences have been used to annotate genomic information i.e., to determine whether an identified and fully sequenced segment of genomic DNA encodes any specific mRNA. In this context, EST sequences were useful in order to identify coding genomic sequence. However, little attention has been paid to the information borne by the EST sequence itself. Indeed, DNA genomic sequence is considered as much more reliable with strong technical arguments in support of this position. We speculate that diversity included in EST sequences might contain biologically, analytically or clinically relevant information. Indeed, EST databases were produced by a number of investigators that all used various methods: this led us to speculate that each methodological bias must contribute to a background noise level with a certain number of errors. However, if differences in errors were to exist due to the source of material used to generate the library, then the difference in error rate would be directly related to the underlying source.

In order to test this, we retrieved est_human database available at the NCBI ftp site. We selected these databases because these sequences were not annotated or cured by human or bioinformatic tools.

We used a library identification system in order to determine whether an EST was obtained from a cancerous tissue or a normal one. Each library has been labeled normal or cancerous. By matching the accession number of each EST with the identifier of the corresponding library, we classified 2.6 millions ESTs as those obtained from cancerous tissues and 2.8 millions ESTs as those obtained from normal tissues.

In order to obtain EST alignments, we used publicly available megaBLAST 2.2.13 software (*Basic Local Alignment Search Tool, Zheng Zhang, A greedy algorithm for nucleotide sequence alignment search, J Comput Biol,* 2000) and specified the following selection parameters:
d est_human: database to search against (all human ESTs from dbEST),
i sequences.fasta: FASTA file format containing the reference sequence corresponding to abundantly expressed genes (FIG. 2) in,
D 2: traditional blast output,
q −2: Score of −2 for a nucleotide mismatch,
r 1: Score of 1 for single nucleotide match,
b 100000: maximal number of sequences for which the alignment is reported,
p 90: minimal percent identity between EST and the reference sequence,
S 3: takes into account ESTs that match reference sequence,
W 16: length of best perfect match to start with alignment extension
e 10: Expectation value (E-value), number of alignments expected to be found merely by chance for a given sequence and a given database, according to the stochastic model of Karlin and Altschul (1990),
F F: none filtering the reference sequence.
o NonFiltre_test_90.out: megaBLAST report outfile
v 0: maximal number of sequences to show one line description for,
R T: (T for True): report the log information at the end of the megaBLAST output,
I T: show GI's in defines [T/F]
The command line for the blast is:
megablast-d est_human-i C:\SeqRef\TPT1\sequences.fasta
o C:\blast\NonFiltre_test_90.out-R T-D 2-I T-q-2-r1-v0-b 100000-p 90.00-S 3-W 16-e 10.0-F F FIG. 2(*a-q*) shows the 17 sequences used for the analysis; in order to avoid distorting the blast, the polyA tail of mRNA reference sequences were systematically removed. FIG. 2*r* provides a list of genes that were used to test the occurrence of sequence variations.

Example 3

Identification of Sequence Variations Between ESTs from Normal and Cancer Origins 17 genes are selected on the basis of their large representation in the database. Each EST sequence was then aligned against its curated mRNA reference sequence (RefSeq) from NCBI using the MegaBLAST. This creates a matrix in which any given base is defined by the number of ESTs matching to this position. We then measured the proportion of ESTs deviating from RefSeq at any given position. Comparison of aligned EST sequences according to the tissue origin led us to identify sequence variations occurring at each base position in either the cancer or the normal group. FIG. 4 provides a graphical representation of these variations occurring in the normal and cancer sets for the 17 selected genes. Visual examination of the data revealed that sequence variation occurred most frequently in the cancer set, and further that the phenomenon appeared most predominant in specific mRNA sites. The majority of the observations are located at least 400-500 bases after beginning of the mRNA sequence hence predominantly in the 3' part of the gene. The very high number of variations could not be explained by SNPs. Putative SNPs (□) and biologically validated SNPs (○) are shown on the graph; these SNPs were obtained from the NCBI database (dbSNP, build 126, September 2006) (Sherry, S. T., et al. (2001) Nucleic Acids Res 29, 308-11). Both putative and biologically validated SNPs leading to EST variations (n=442) were excluded from further analysis (therefore RNA editing sites (false SNPs) were also excluded).

The next step of this analysis was to test the statistical significance of the differences in sequence variation occurring between cancer and normal ESTs. For each position, we compared the proportion of the RefSeq base to that of the three other bases between normal and cancer groups using a two-sided proportion test. This test was systematically applied provided that the following conditions were met: n>70 and $(n_i*n_j)/n$>5 i=1, 2; j=1, 2 (where n=the number of cancer and normal ESTs for a gene, $n_1$=the number of cancer ESTs, $n_2$=the number of normal ESTs, $n_1$=the number of ESTs having the RefSeq, $n_2$=the number of ESTs having a substitution). A statistical test is said to be positive at the threshold level of 5% whenever corresponding P-value is lower than 0.05; in this case, the null hypothesis (i.e. both proportions are the same) is rejected.

Moreover the two following one-sided proportion tests were considered in order to precise in which set the variability was bigger. The first one allowed to conclude that variabilities were different in both groups when statistical test is positive, then it measured in this case whether variability was statistically greater in the cancer set. On the contrary the second test verified the hypothesis that variability was significantly higher in the normal set. Both one-sided tests were performed whenever the same conditions than two-sided test ones were met.

Figure 5A:
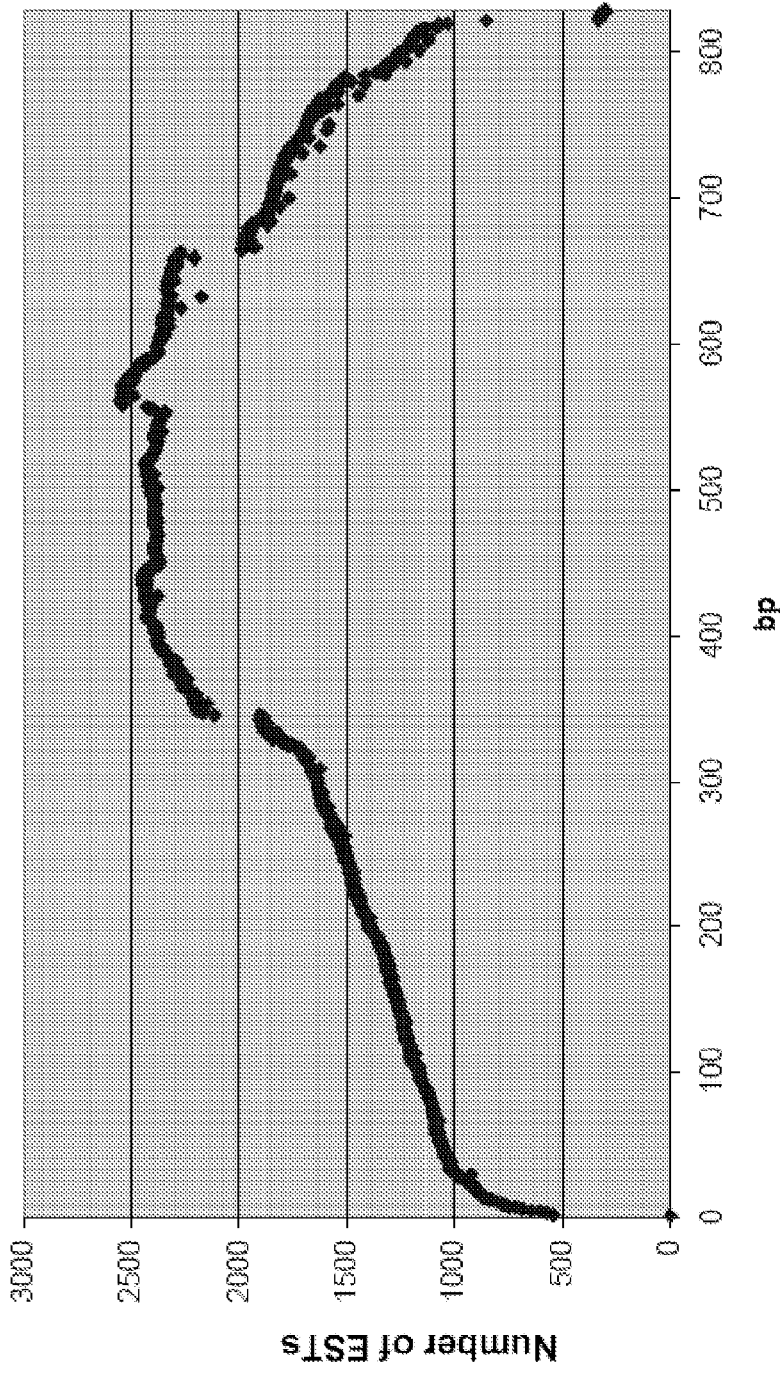
Figure 5B:
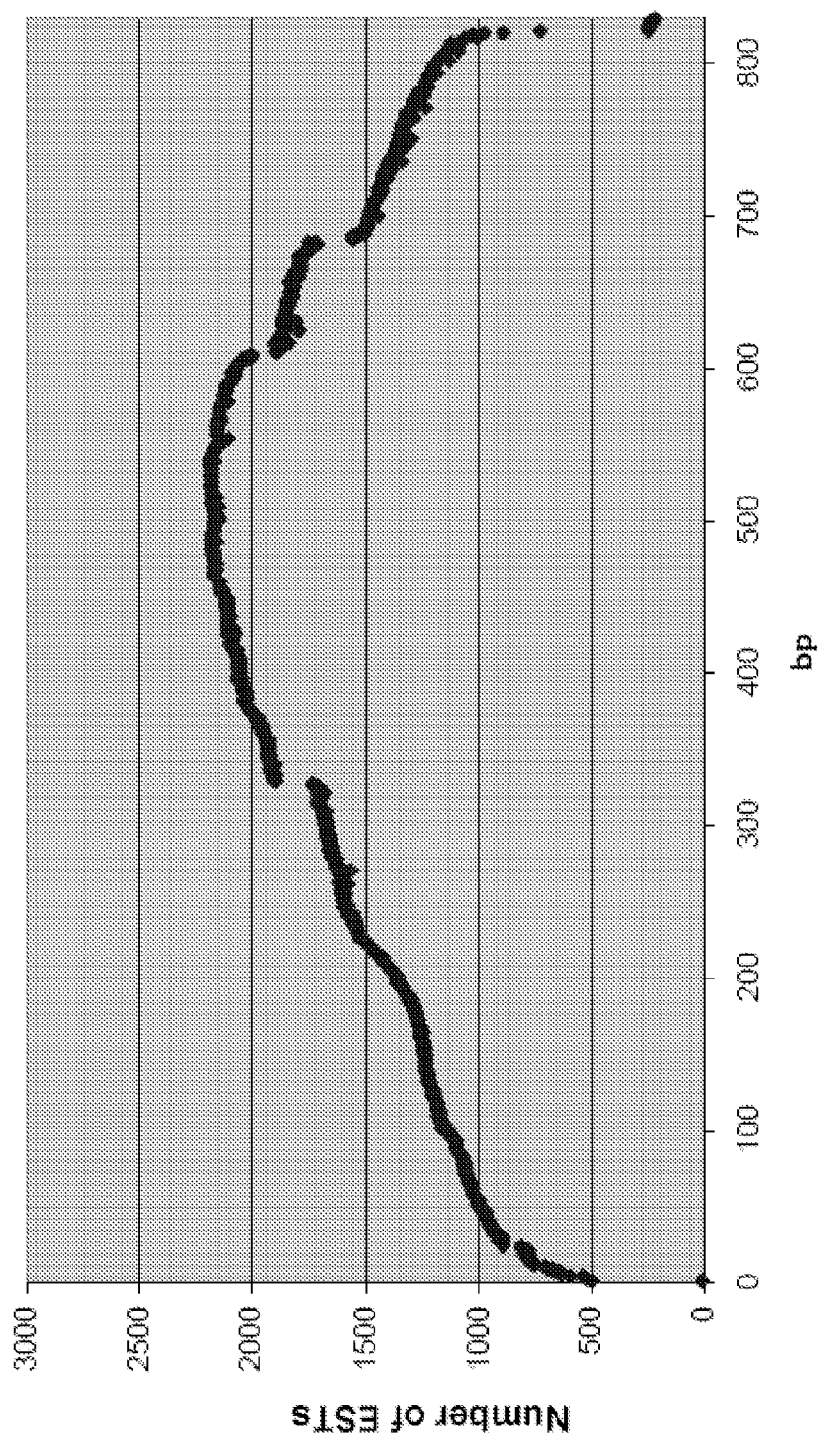
Figure 5C:
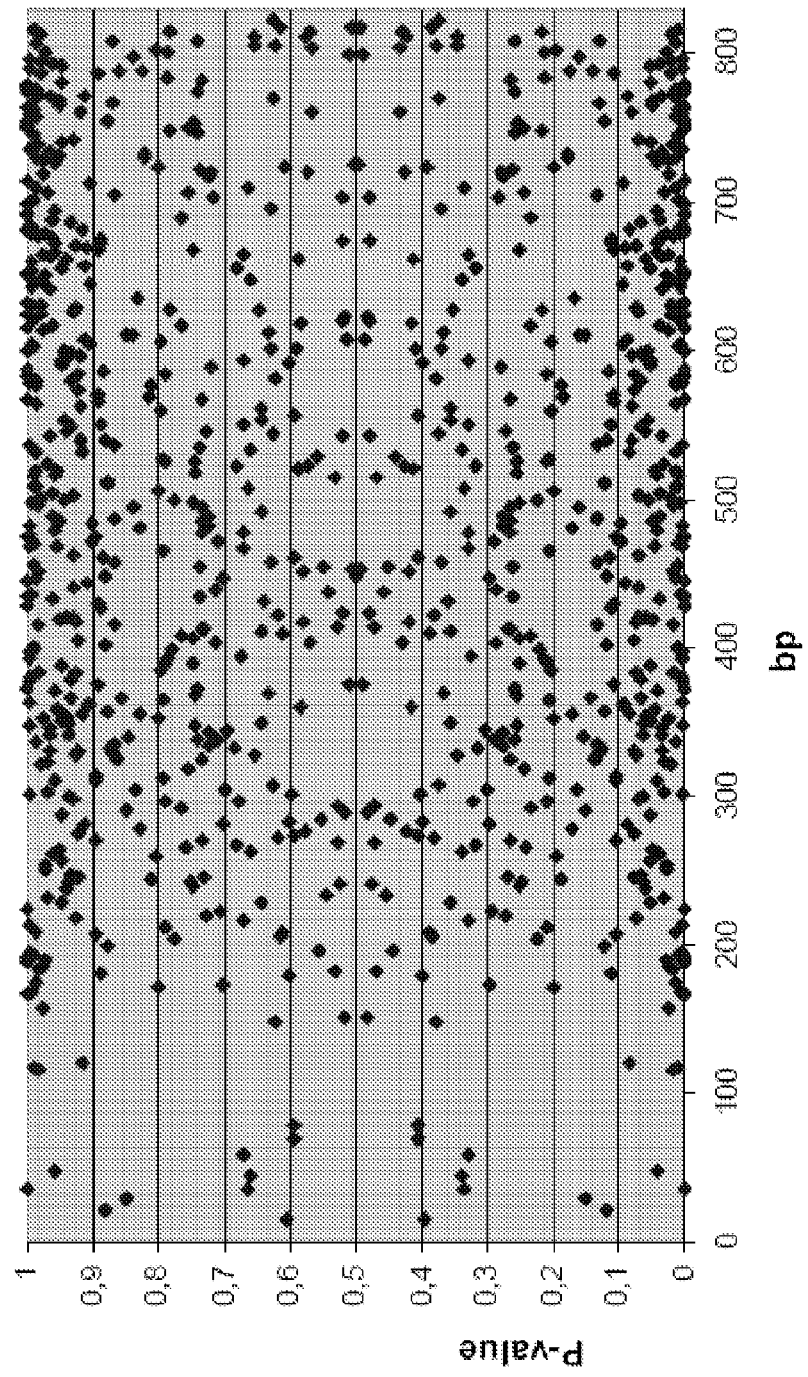
Figure 5D:
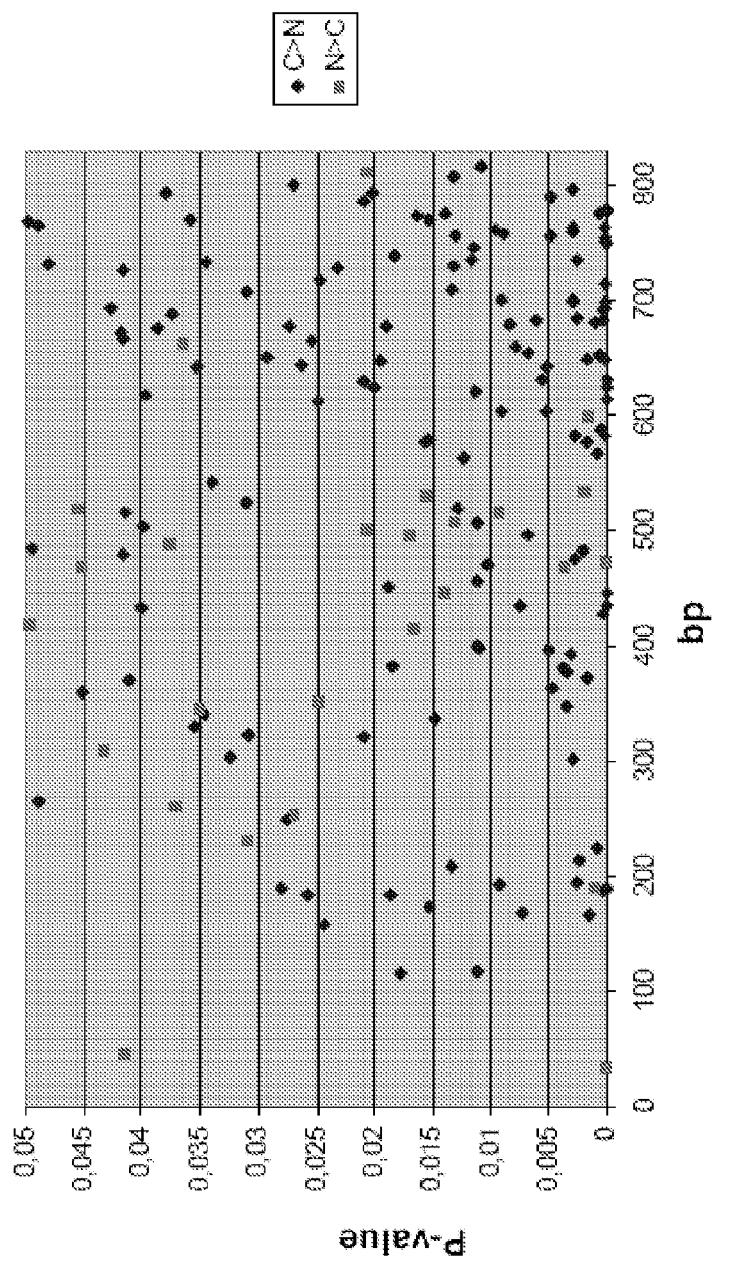
Figure 5E:
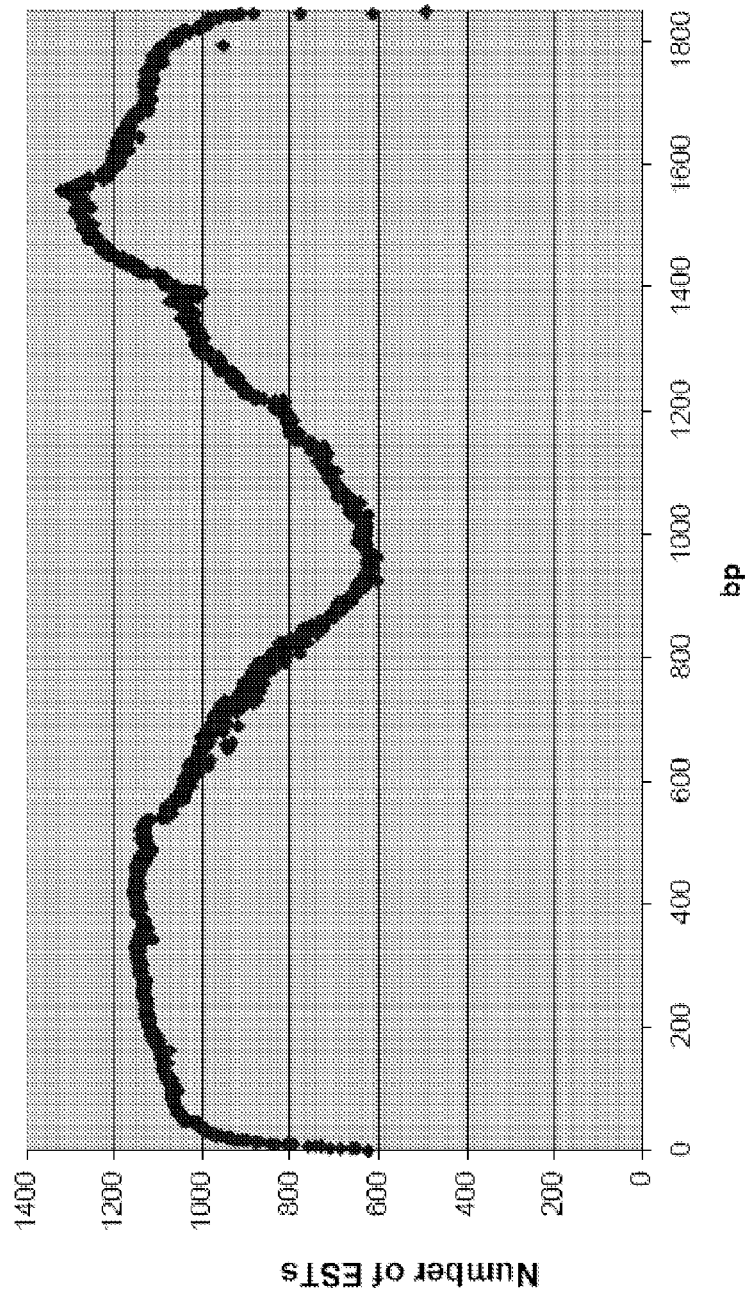
Figure 5F:
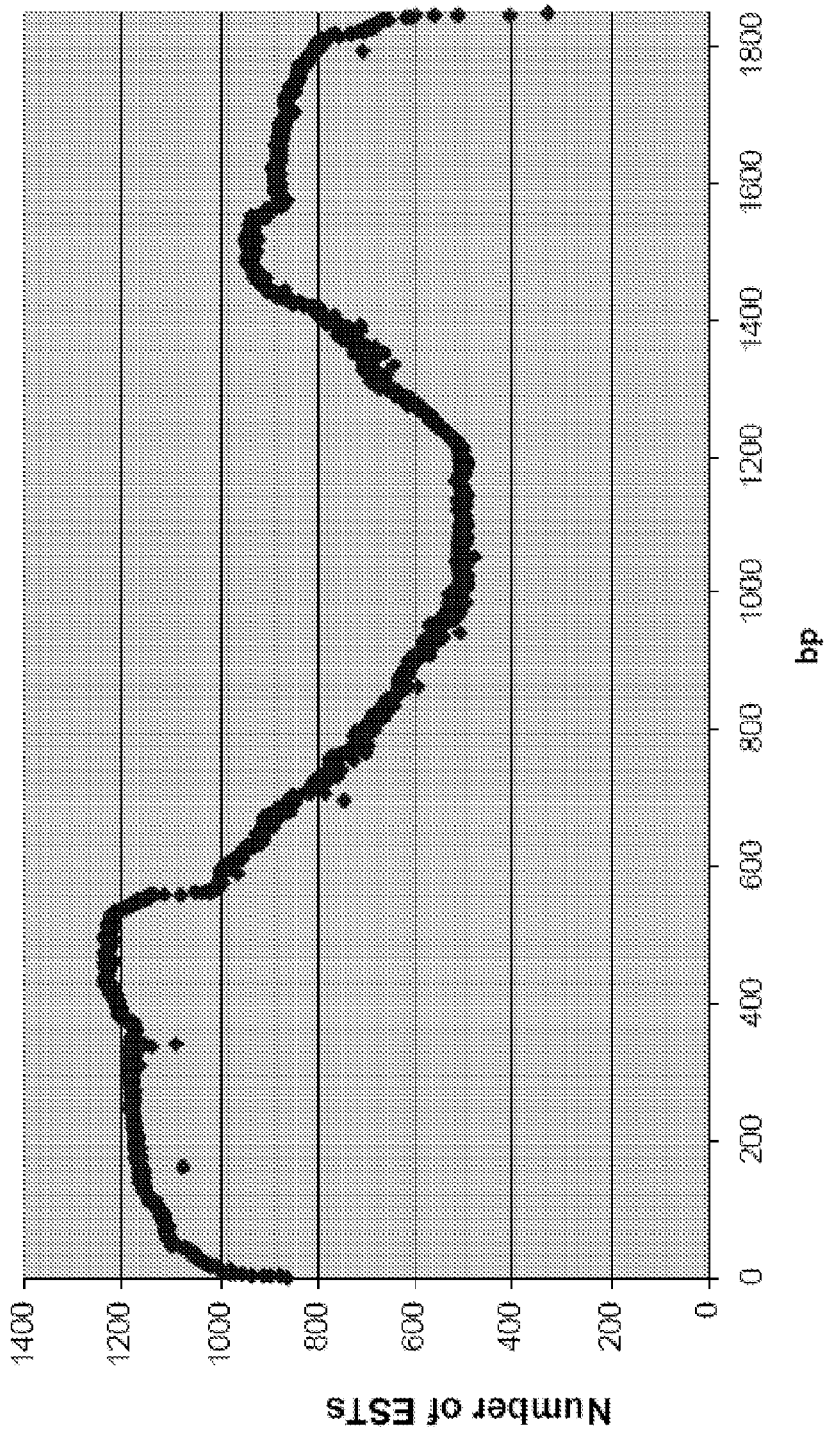
Figure 5G:
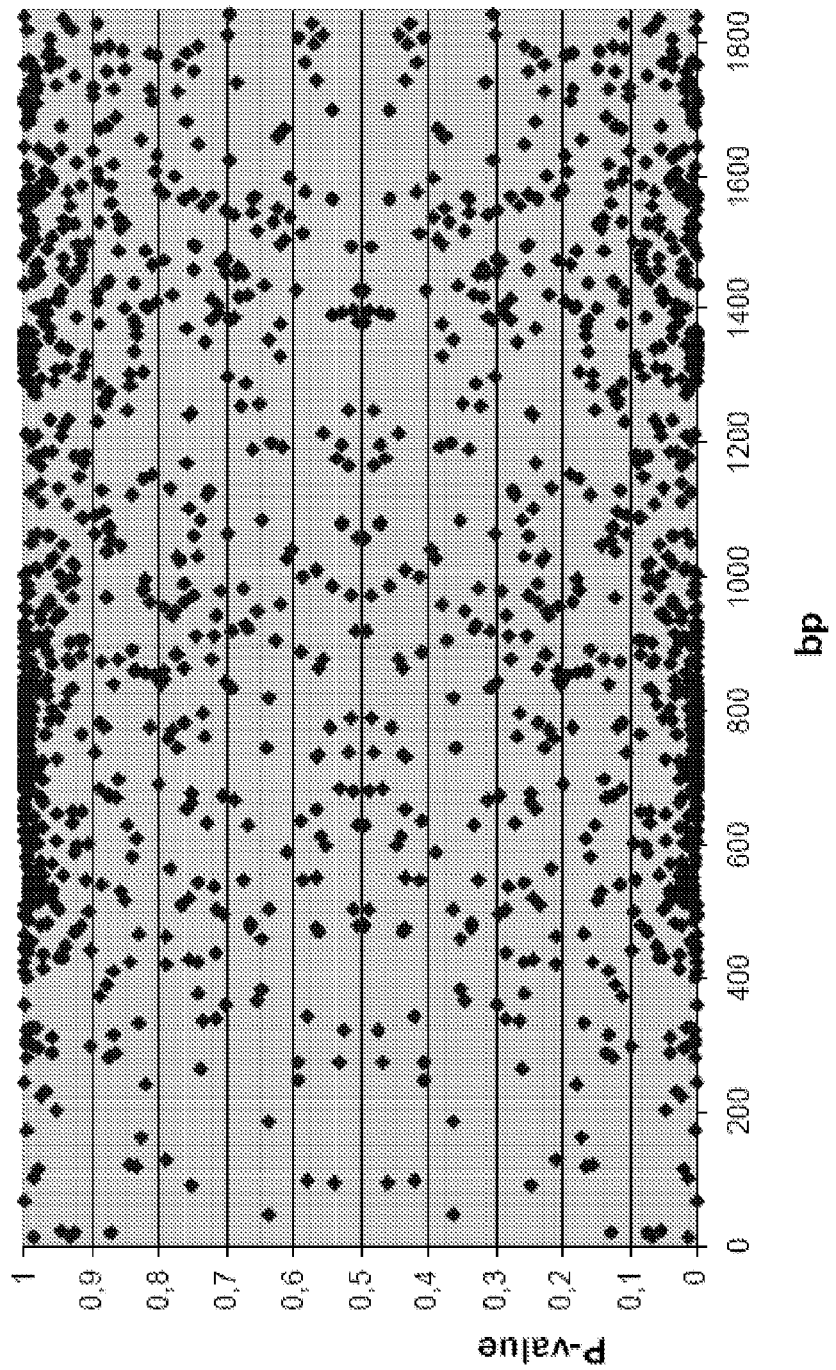
Figure 5H:
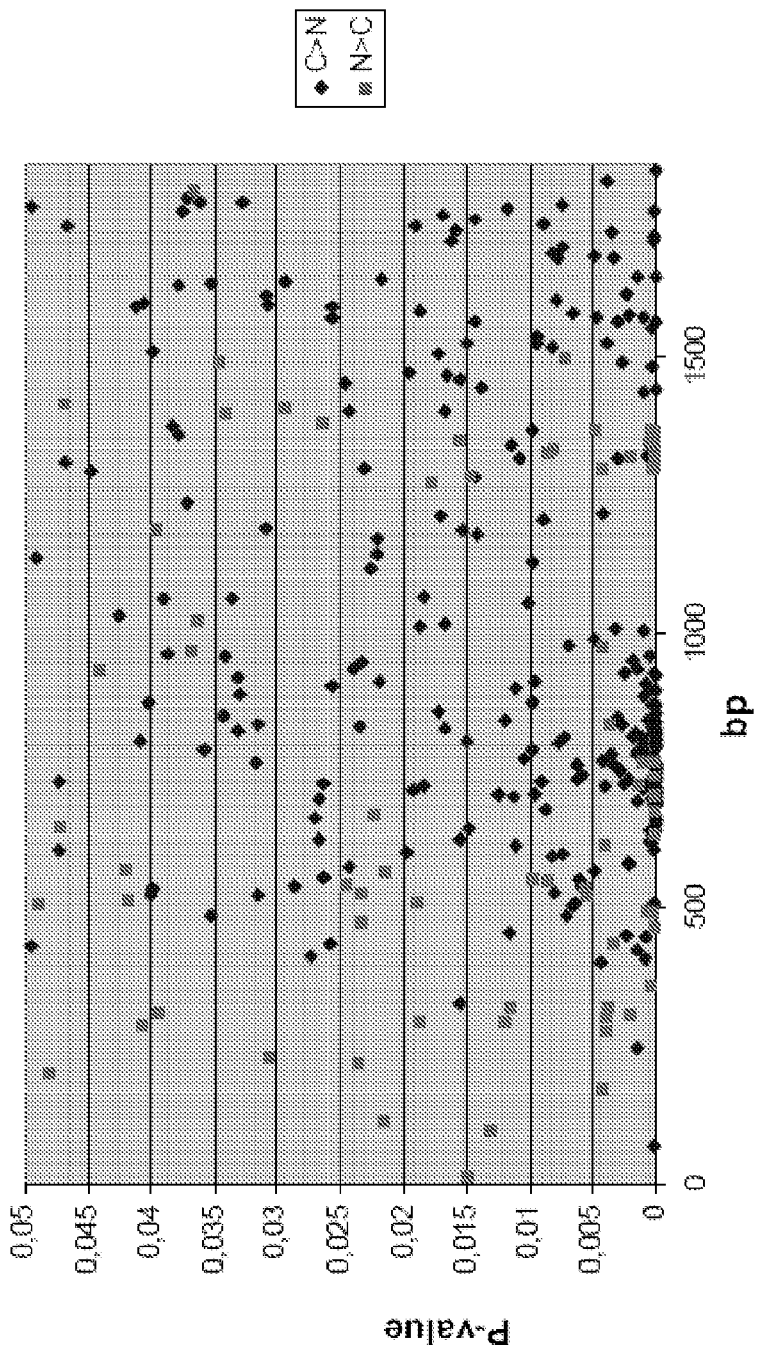
Figure 5J:
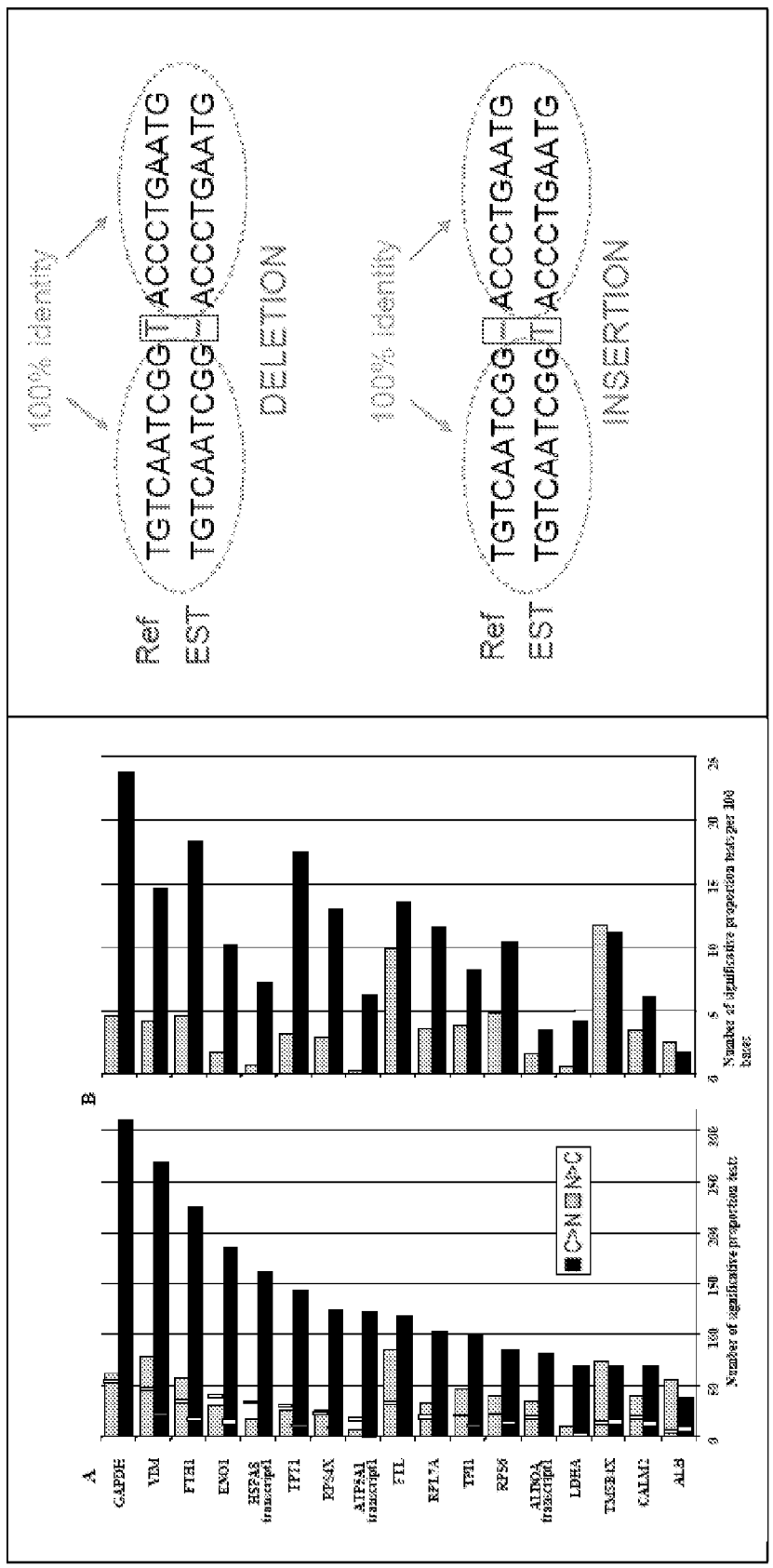
Figure 5M:
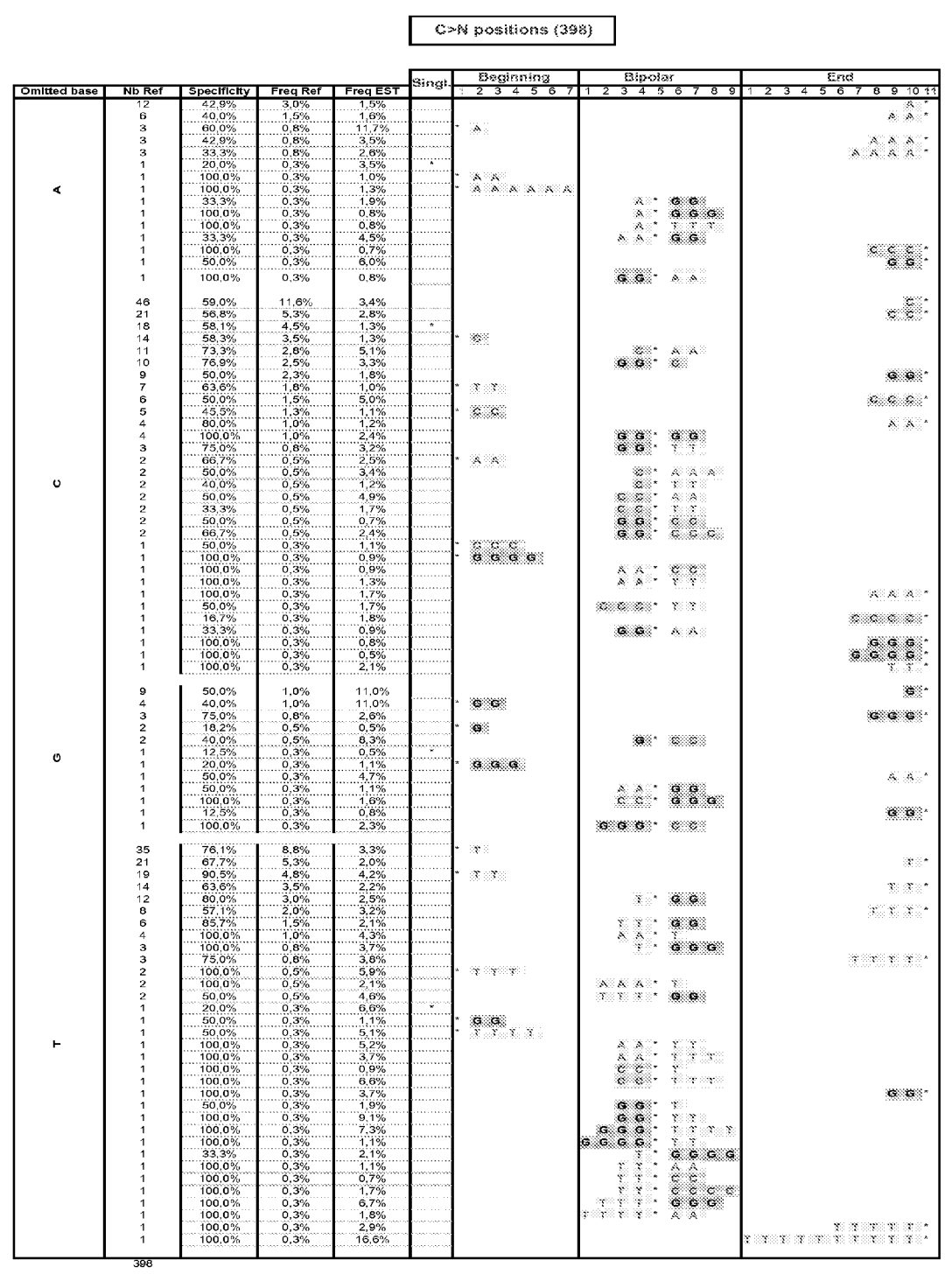

FIG. 3 provides a description of typical blast results. As shown in FIGS. 5a and 5b, for representative gene TPT1, the number of ESTs at any given position on the gene is similar in both cancer and normal groups. FIG. 5c shows that 489 out of 830 possible proportion tests meet the assigned criteria. Proportion tests that were statistically significant at the level of 5% are shown in FIG. 5d. An estimated error resulting from multiple testing, defined by the Location Based Estimator (C. Dalmasso, P. Broet (2005) Journal de la Société Française de Statistique, tome 146, n1-2, 2005) can be calculated. 26 proportion tests positives are due to base substitutions occurring in the normal tissue (N>C) in FIG. 5d (n=26; LBE=33). This contrasts with the accumulation of statistically significant proportion tests occurring because of sequence variations in the cancer group (C>N), (n=145; LBE=15). A similar analysis was conducted for a second gene VIM (FIG. 5e-5h). Again the number of ESTs at any given gene position is superimposable in cancer and normal groups. 752 out of 1847 proportion tests matched the criteria. Again, we observed a large difference in the number of positive proportion tests: n=78 variations are due to the normal group (LBE=50) and n=269 variations are due to the cancer group (LBE=24). We repeated the same analysis on 17 genes that are abundantly present in the EST database. FIG. 5i is a summary of the statistical results obtained. Out of 17 tested genes, 15 exhibit greater sequence variations in ESTs obtained from cancer tissues (FIG. 5j). At this stage, statistical analysis covered only 9 to 91% of the positions of each gene (an average of 32%) due to constraints of the statistical test.

The conclusion of this first round of analysis is that ESTs of the same gene were different when compared according to the source of tissue (normal versus cancer) from which mRNA was extracted. Assuming that the rate of technical errors that yield the EST sequence variation was not different according to the normal or cancerous origins of tissue and considering the fact that 15 out of 17 tested genes showed sequence variations due to the source of tissue, we propose that these differences directly result from the status—normal versus cancerous—of the cells from which the ESTs were produced.

Similar experiments are performed to study insertions and deletions. Results are obtained after applying the F3 filter (see Example 4). A more stringent condition was used to avoid non biological events (sequencing errors, Megablast misalignment . . . ): a gap or an insertion was only considered if no other modifications were present in a -10/+10 window. For each position, we compared the proportion of windows with deletion (or insertion) to other windows between normal and cancer groups using a two-sided proportion test as described above. FIG. 5k is a summary of the statistical results obtained. Out of 17 tested genes, 14 (or 10 for insertion) exhibit greater sequence variations (deletions and insertions) in ESTs obtained from cancer tissues (FIG. 5l).

Example 4

Verification of the Variation Excess in Cancer Set C>N Versus Normal Set N>C

Libraries originating from cancer or from normal samples are processed essentially in the same manner. Therefore, random errors resulting from library construction or clone sequencing are expected to occur at the same rates in both sets and cannot account for the observed differences between the normal and cancer EST groups. Mathematical analysis is consistent with this interpretation (Brulliard M., et al PNAS May 1, 2007 vol. 104 no. 18 7522-7527—see Supplementary material FIG. 7).

Figure 6A:
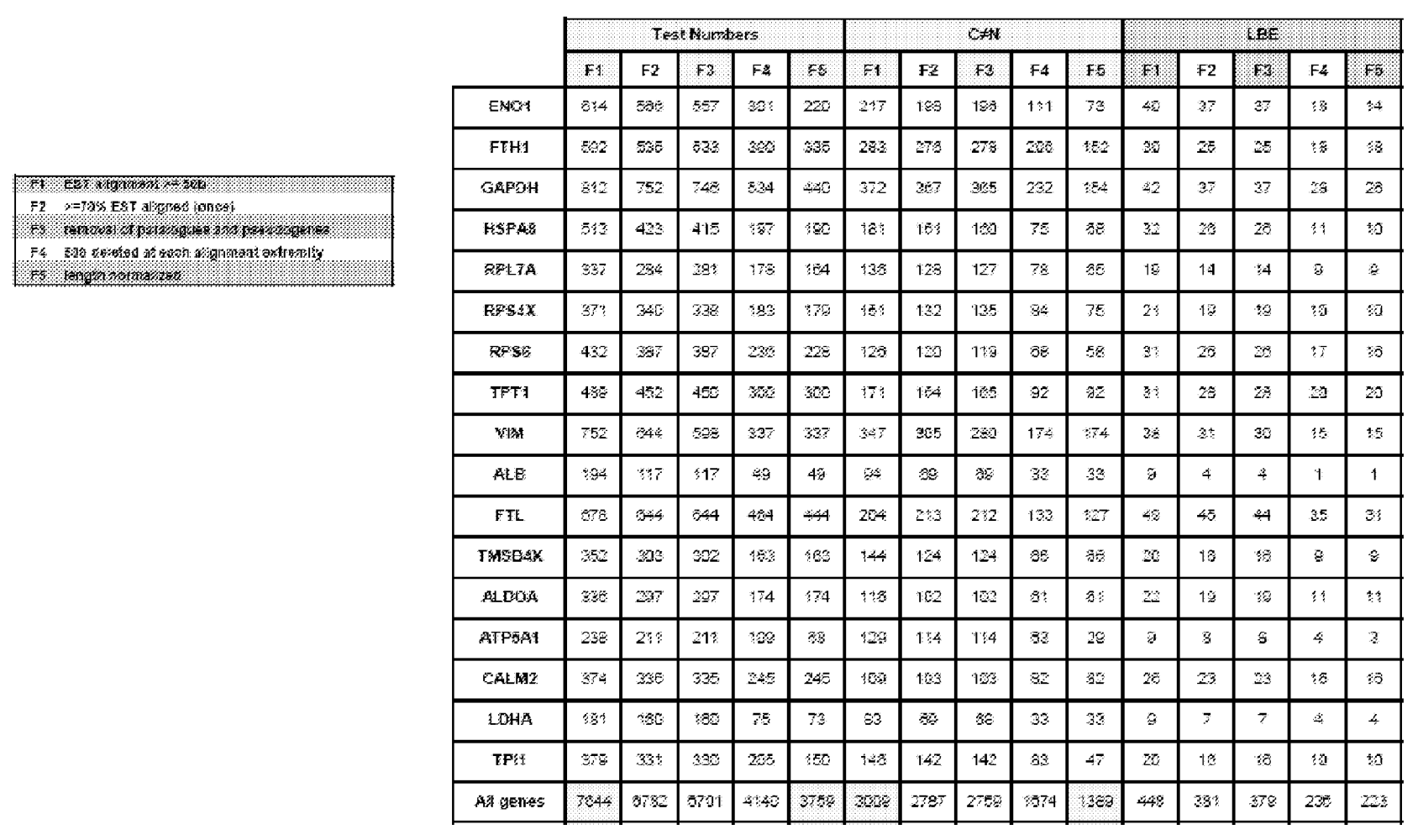
Figure 6B:
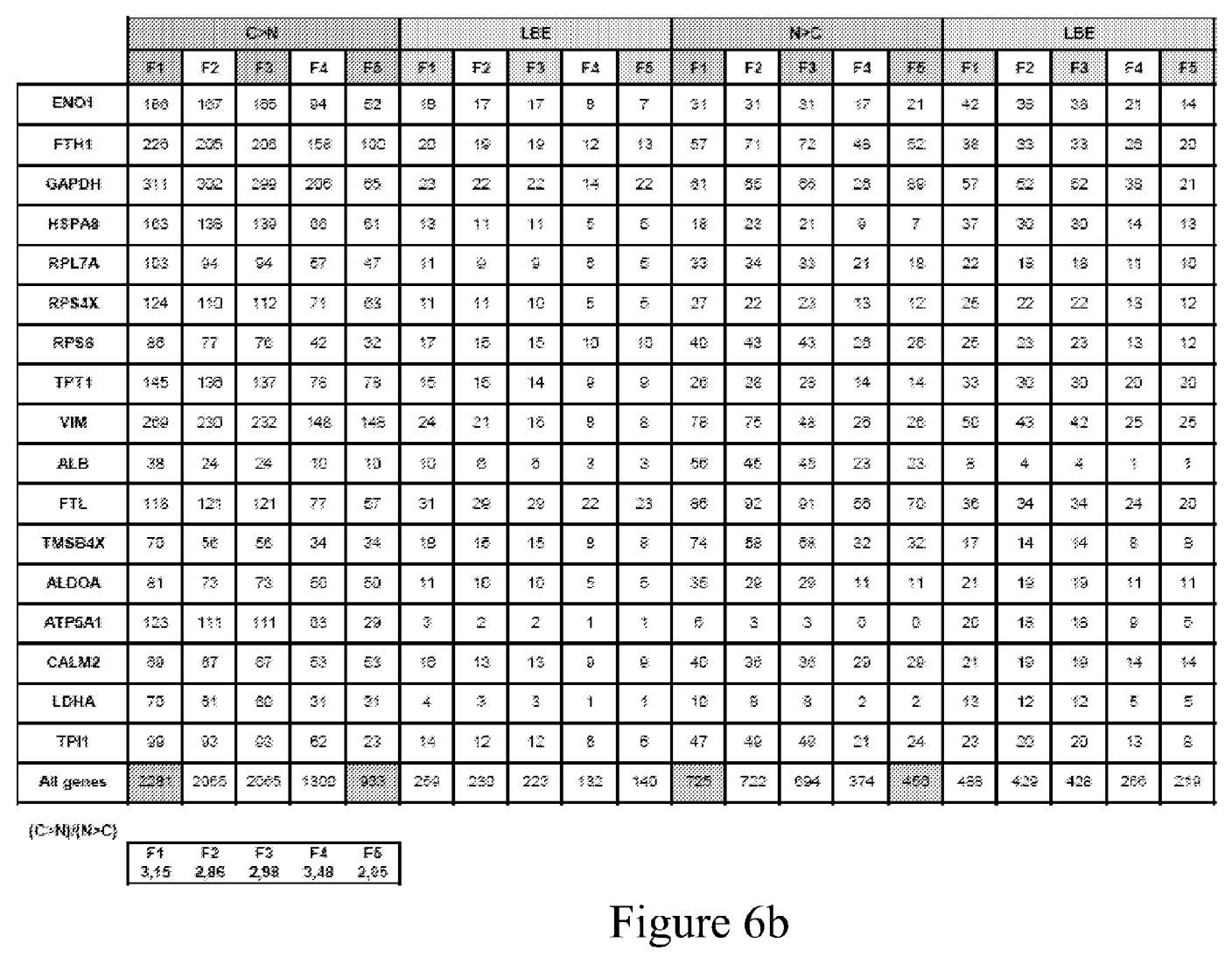

We next searched to eliminate other sources of EST heterogeneity by sequentially applying filtering procedures based on the following rationale. Our initial requirements were that EST aligned to RefSeq with 100% identity on at least 16 consecutive bases, and with ≧90% identity on at least 50 bases. As shown in FIG. 6b, this yields, when comparing cancer and normal sets for all 17 genes, 2281 and 725 statistically significant differences C>N and N>C respectively (column F1), and distinct from putative or biologically validated SNPs. The second filter (F2) required that each EST aligned to RefSeq continuously on more than 70% of its length. The third filter (F3) removed ESTs with sequence more closely related to paralogues and pseudogenes than to the bona fide RefSeq. The fourth filter (F4) deleted from analysis the first and last 50 bases of each EST alignment. We used this filter in order to remove mismatches at the 3' and 5' borders of EST that can be created by the MegaBLAST program to further optimize alignments and/or resulting from error accumulation at aligned EST extremities. The last filter (F5) normalized EST sequence lengths for each gene in order to remove any difference in length between normal and cancer sets. Indeed, we noticed after applying the first 4 filters, the average cancer EST length was greater than that of normal ESTs (640±248 and 554±229 bases, respectively). However, we also observed significantly greater cancer EST heterogeneity in 5 genes where the average EST length was not different between the normal and cancer sets (TPT1, VIM, HSPA8, LDHA, CALM2).

The number of statistically significant C>N tests remained greater than the number of N>C tests, but the ratio C/N decreased from 3.15 (F1) to 2.05 (F5) (FIG. 6c).

Figure 6D:
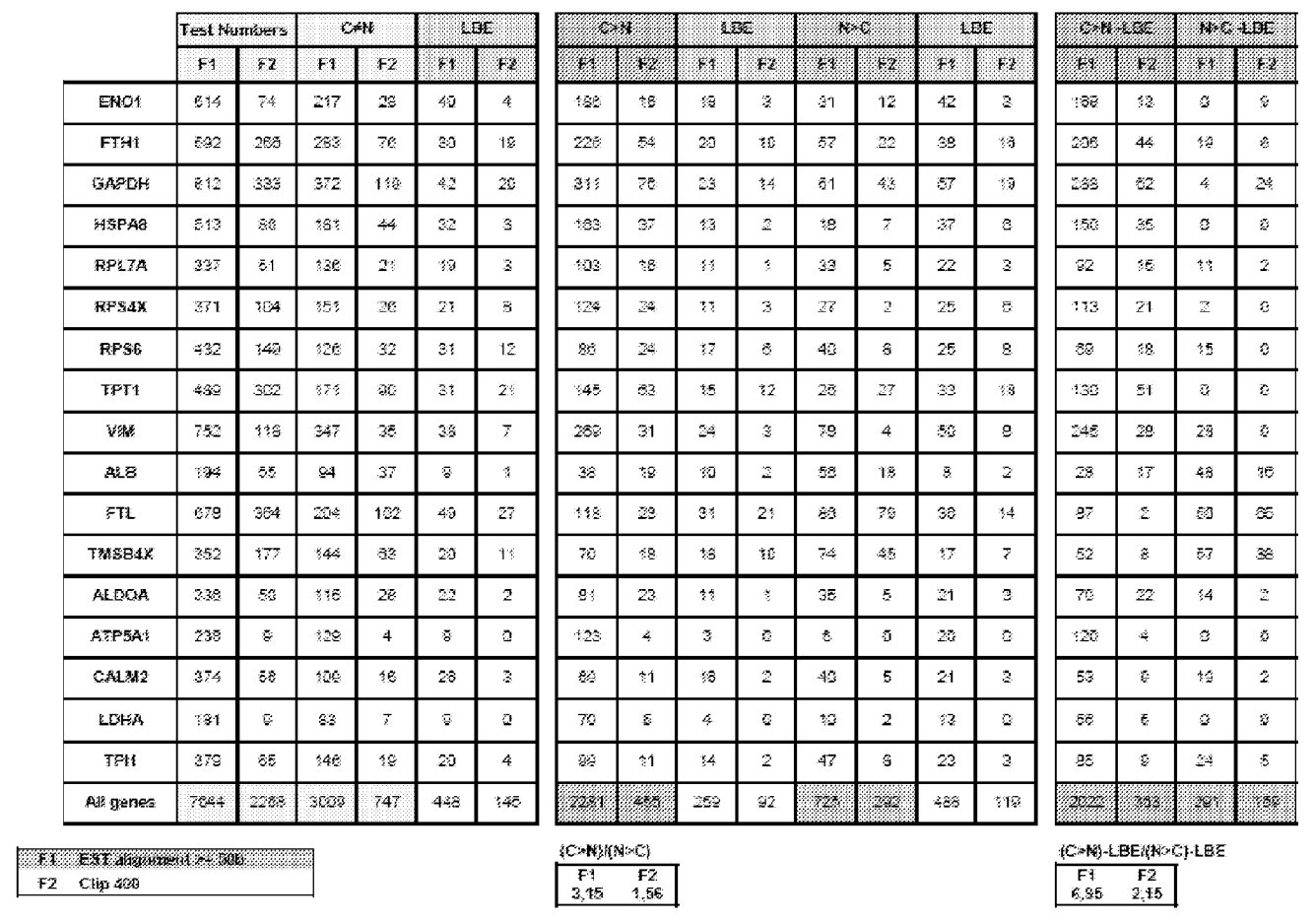

To further ascertain that cancer EST heterogeneity was not due to accumulation of errors at the end of sequencing runs, we took into account only the information provided after the first 50 bases and no longer than 450 bases of any sequencing run. After this drastic filtering, statistically significant C>N tests were 455 (LBE=92) and N>C tests were 292 (LBE=119) for all 17 genes. It can therefore reasonably be assumed that sequence variations causing increased EST heterogeneity in the cancer set are a direct reflection of cancer cell mRNA heterogeneity (FIG. 6d).

Figure 6E:
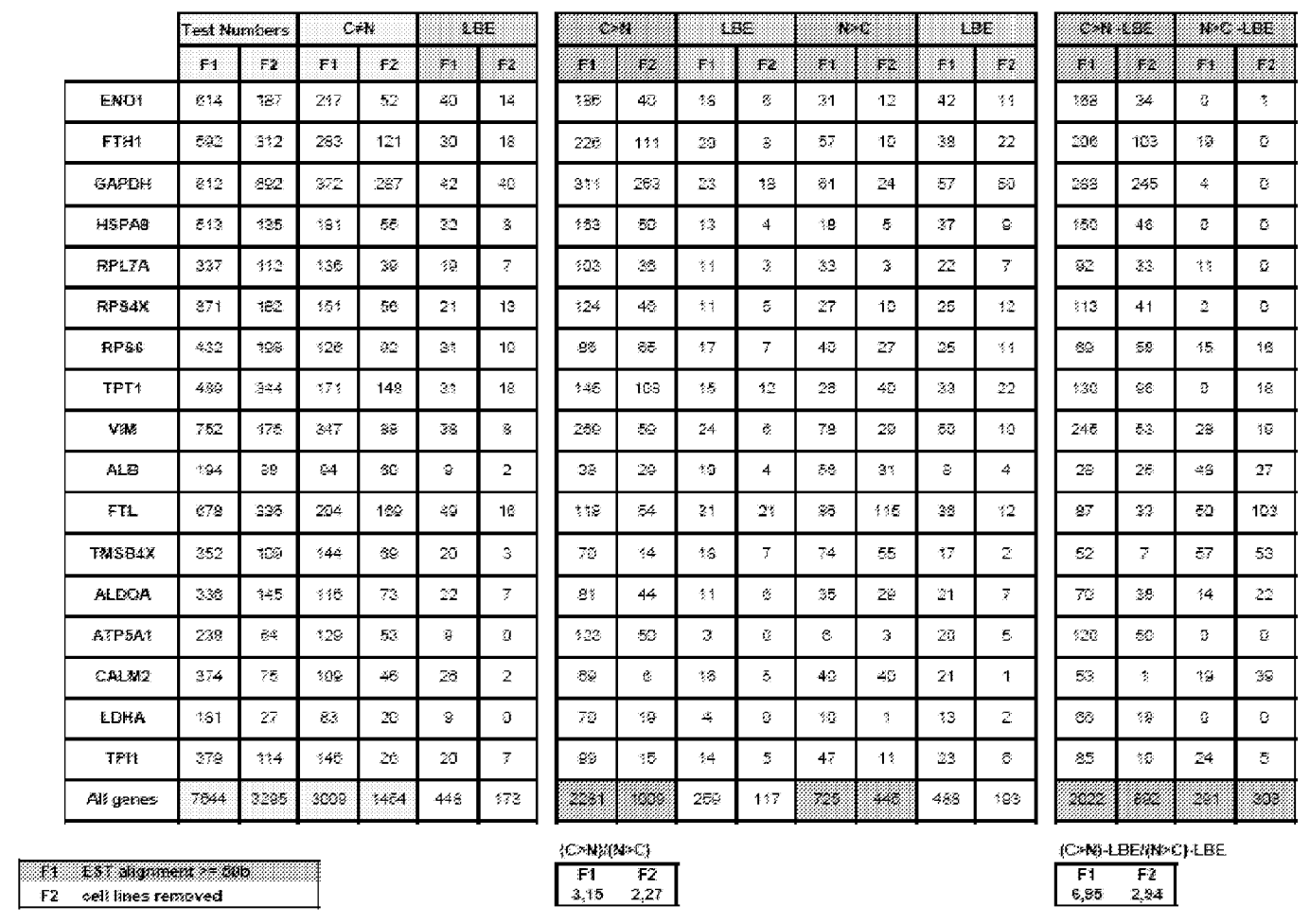

We next independently verified that a greater statistically significant EST heterogeneity persisted in the cancer set after removing ESTs produced from cultured cancer cells. After this filtering, statistically significant C>N tests were 1009 (LBE=117) and N>C tests were 445 (LBE=193) for all 17 genes (FIG. 6e).

Example 5

Figure 7A:
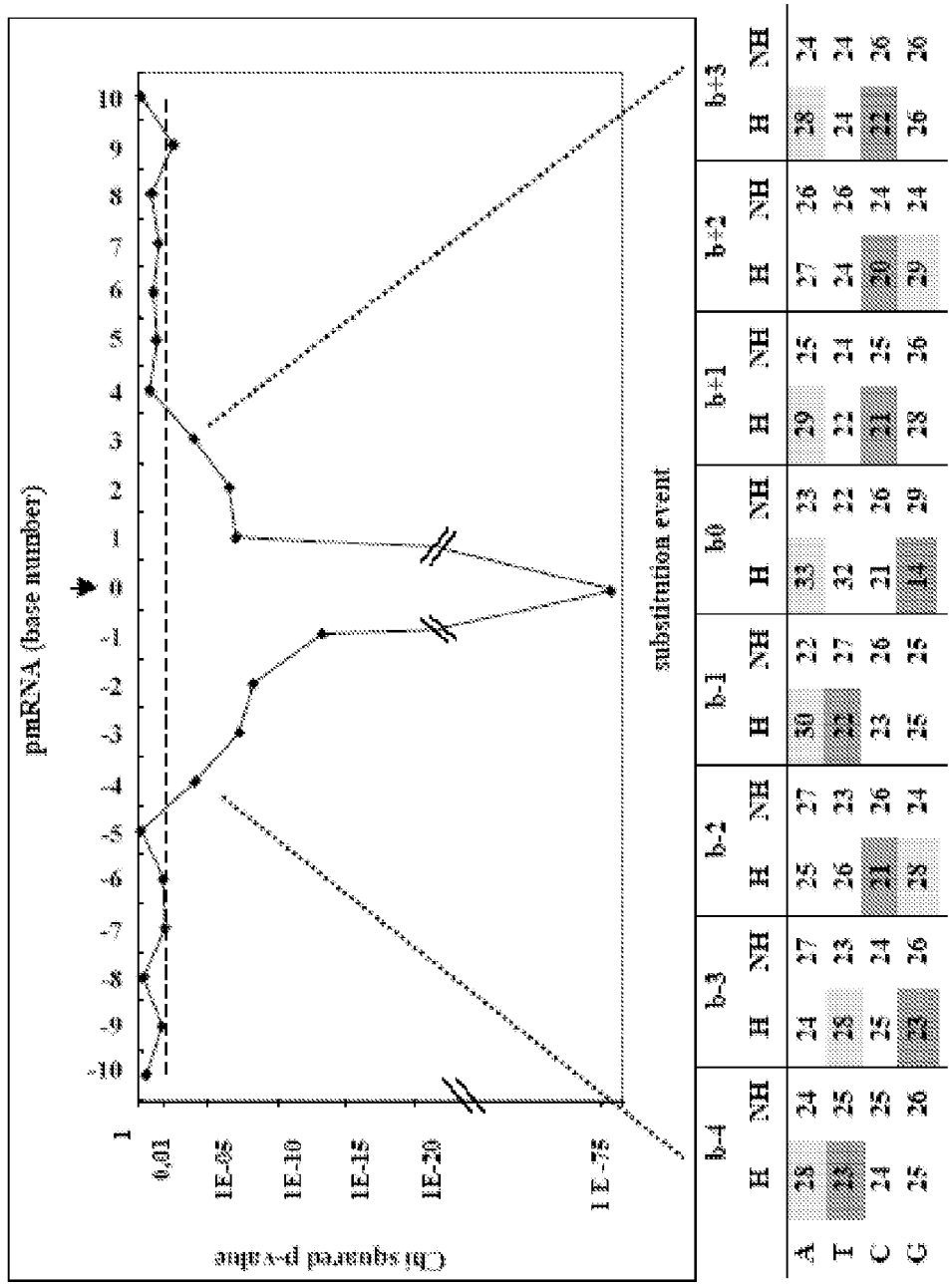
Figure 7B:
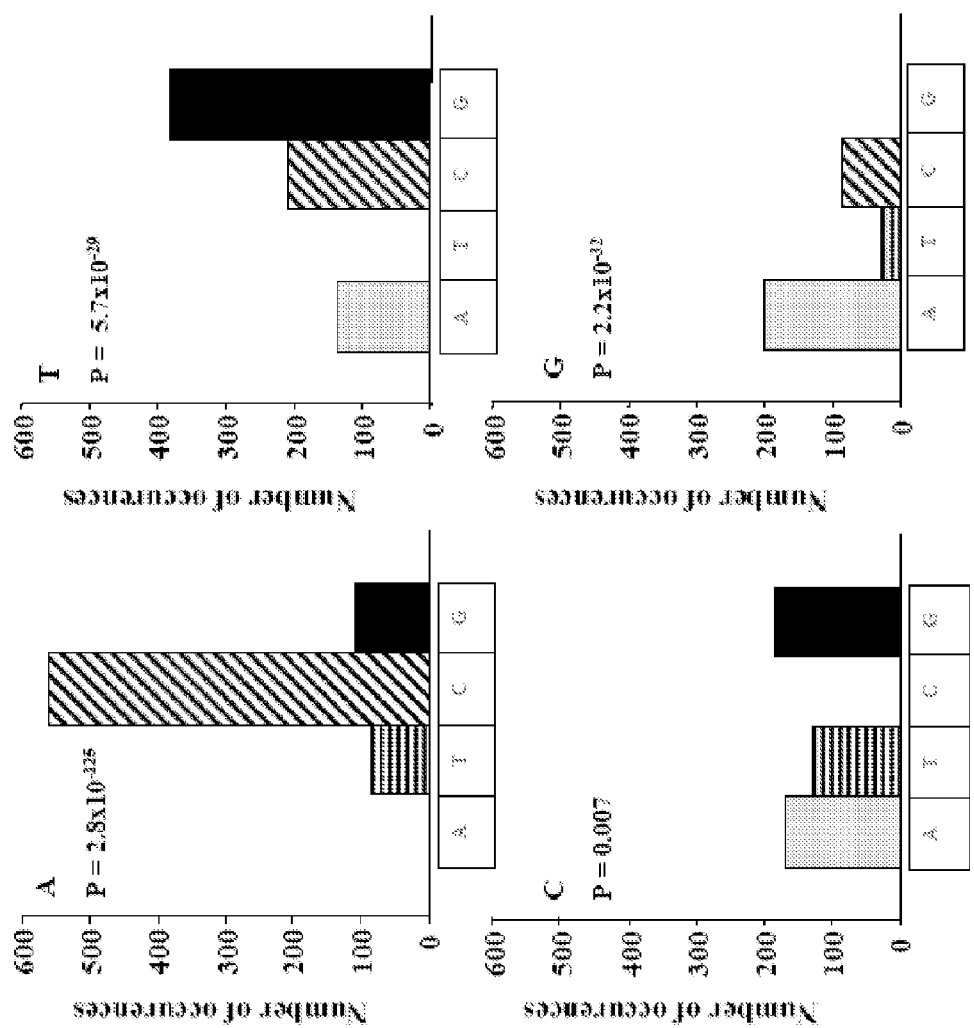

Breaking the Code of Base Substitution Occurring Because of Transcription Infidelity in Cancer Cells Our next goal was to determine whether the described phenomenon of base substitution due to transcription infidelity is a random phenomenon or follows specific rules. To achieve this, we focused on EST variations where C>N was statistically significant. To avoid bias that might be introduced by the filtering procedures, we used all available non-filtered data. The first indication that transcription infidelity is not a random process was that base substitutions rarely occurred in the 5' region of the tested genes. For all tested genes, we very rarely observed the phenomenon of base substitution occurring in the first 400-500 bases of the mature mRNA. The second observation indicating that transcription infidelity is not random stems from the observation that there is a difference in base composition on genomic DNA template observed when comparing sequences upstream and downstream of substitution events (heterogeneous, H, n=2281) with those where no substitution event was detected (non heterogeneous, NH, n=12273). The criteria for NH sites were cancer set variations lower than 0.5% and not statistically different from normal set variations (FIG. 7a). In this analysis, we refer to the base undergoing substitution as b0, bases located on pmRNA 5' end are referred to as b−n, and bases located on 3' end as b+n. For the sake of clarity, we refer in this analysis to the base composition of pmRNA: this corresponds on the DNA to the non-template strand (the strand not transcribed by RNAP). The data show first that not all 4 bases were equally susceptible to variation: b0=A (33%) ≈T (32%)>>C (21%)>>G (14%). Further, the compositions of the 4 bases upstream and 3 bases downstream of the site of event were statistically different (results of Chi-squared analysis) from those of the sites without significant EST variation (FIG. 7a, the base composition is expressed in % and Gray shading show enriched bases; darker gray show paucity bases). Specifically, sites where variations occur were more frequently preceded and followed by A≧G>T≈C.

Thus, the occurrence of cancer EST heterogeneity is not random, but determined first by the nature of the base undergoing substitution and second by the nature of the bases that immediately precede and follow the event.

We next questioned whether the replacement base was selected randomly. It is clear from FIG. 7b that it is not the case. Statistical significance of difference in proportions was calculated with the null hypothesis that replacement base is selected randomly (adjustment test of all three replacement bases to uniform distribution). A was preferentially replaced by C ($p=2.8\times10^{-125}$), T by G ($p=5.7\times10^{-29}$) and G by A ($p=2.2\times10^{-32}$). Substitution of C showed a more even distribution, with a slight paucity of T (p=0.007).

We then sought for the causes underlying preferential base replacement. To achieve this, we distinguished two sets of informative and non-informative events.

Figure 7D:
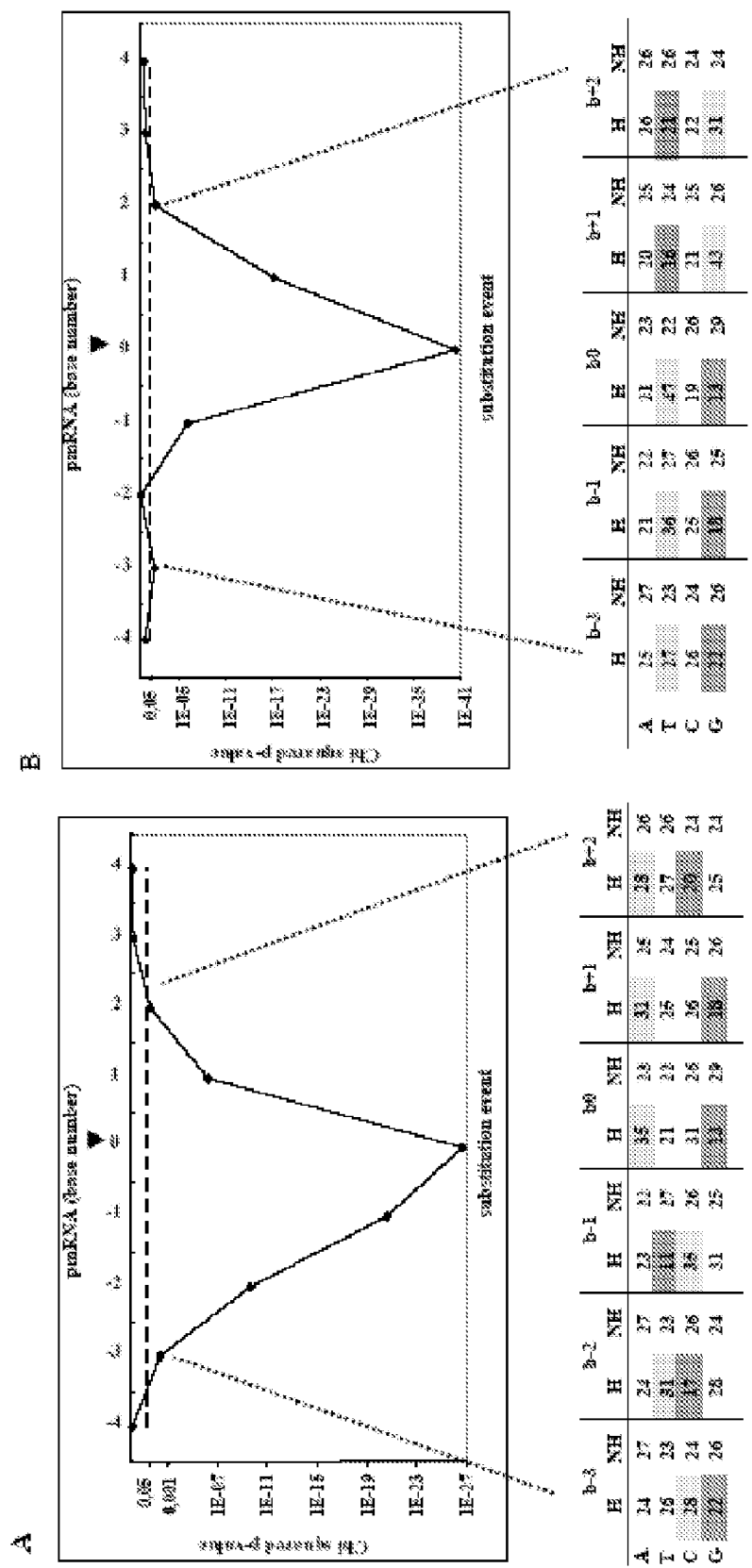

Informative events were situations where the substituted base was different from either preceding base (b−1) or following base (b+1) (n=1676) (FIG. 7c). Non-informative events were situations not matching these criteria. When informative events were analysed, two cases were encountered: substituted base was replaced by b−1 or b+1 (79%) or by another base, different from b−1 and b+1 (21%). 1) In the first subset, replacement base was identical to b−1 (n=799; FIG. 7c panel B) or b+1 (n=530; FIG. 7c panel C). When replacement base was b−1, then b0=A (36%)>C (30%)>>T (21%)>>G (13%) (FIG. 7d panel A). A was preferentially replaced by C (71% of the cases). When replacement base was b+1, then b0=T (47%)>>A (21%)>C (19%)>>G (13%) (FIG. 7a panel B). T was preferentially replaced by G (71%). Interestingly, the statistical importance of the surrounding bases was also different (FIG. 7d panel A and 7d panel B). For b−1 substitutions, the pattern of relative influence of base composition was b0>b−1>b−2>b+1>b−3>b+2. For b+1 substitutions, the relative influence of surrounding base followed a pattern of b0>b+1>b−1>b+2>b−3>b−2. 2) In the second subset of informative events, the replacement base did not correspond to either b−1 or b+1 (n=347; FIG. 7c panel D). Affected bases were in the following order: A (47%)>T (29%)>C (14%)>G (10%). A was most commonly replaced by C (91% of the cases), T by C (50%) and A (42%), C by G (46%) and G by C (73%). Thus, when replacement base does not correspond to b−1 or b+1, the replacement base is not randomly selected but C is in large excess.

We next considered the set of non-informative events, i.e., situations where 1) b−1=b+1 and where 2) b−1=b0=b+1 (FIG. 7c). When b−1 and b+1 were identical but different from b0 (n=339; FIG. 7c panel E), substituted bases were in the following order: T (34.8%)>G (23.6%)>C (21.2%)>A (20.4%) and followed the same pattern of preference as in FIG. 7b: T→G, G→A, A→C. Substitutions occurring on the central base of repeat of three identical bases (n=266; FIG. 7c panel F) were observed in the following order: A (46.2%)>T (36.9%)>G (10.5%)>C (6.4%). In this case, most common substitution events were: A→C and T→C and A. Rare GGG substitutions were most commonly replaced by GCG and CCC by CAC (FIG. 7c).

Thus, when substitutions occur within three consecutive identical bases and when substitutions do not correspond to either b−1 or b+1, then C is the most common replacement base (FIG. 7c). When the replacement base corresponds to b−1, most common substitution is A→C; when the replacement base corresponds to b+1, most common substitution is T→G.

It can therefore be concluded that neither the base undergoing substitution nor the replacement base are selected randomly. Both phenomena follow predictable patterns defined by the composition of the base undergoing substitution and that of bases located upstream and downstream of this event.

Specific algorithms can be defined to identify precisely the motif composition that determines the occurrence of base substitution in any given sequence.

We next separated the set C>N in two sets where N is stable (no deviation observed at the same position in the Normal set) or not. Deviation is considered only if it exceeds a certain threshold defined as the average percentage of deviation in the Normal set.

Figure 7E:
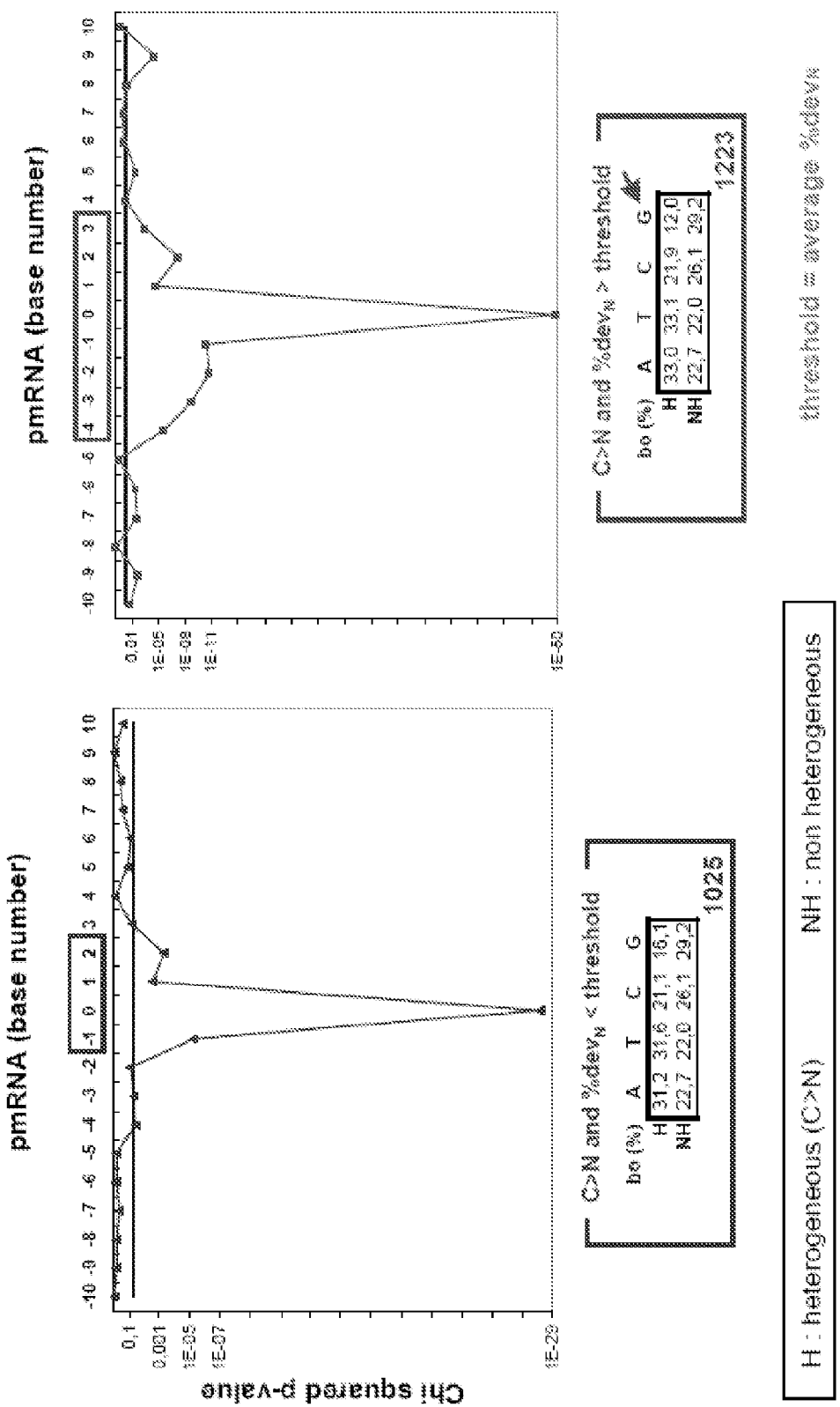
Figure 7F:
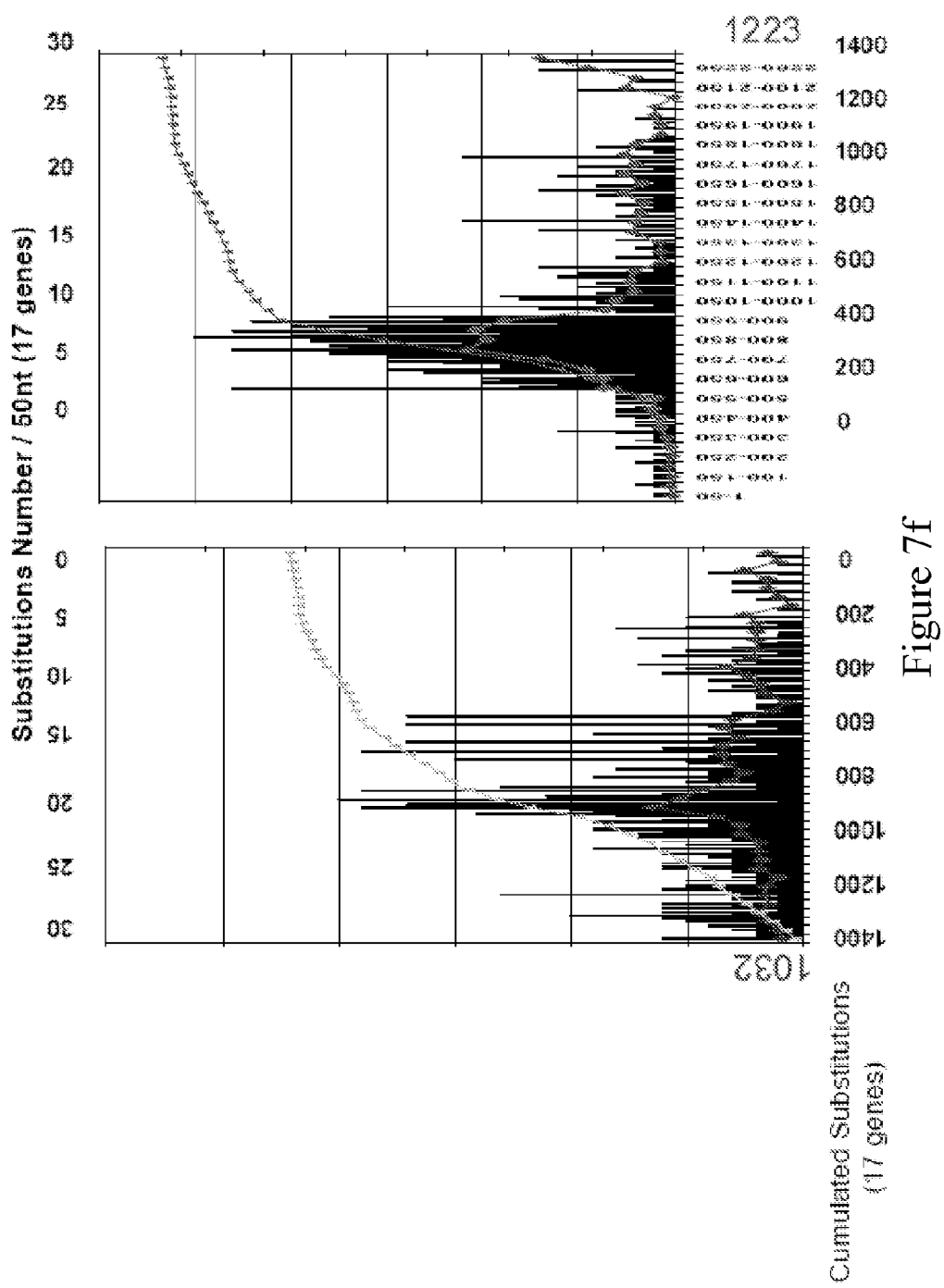
Figure 7G:
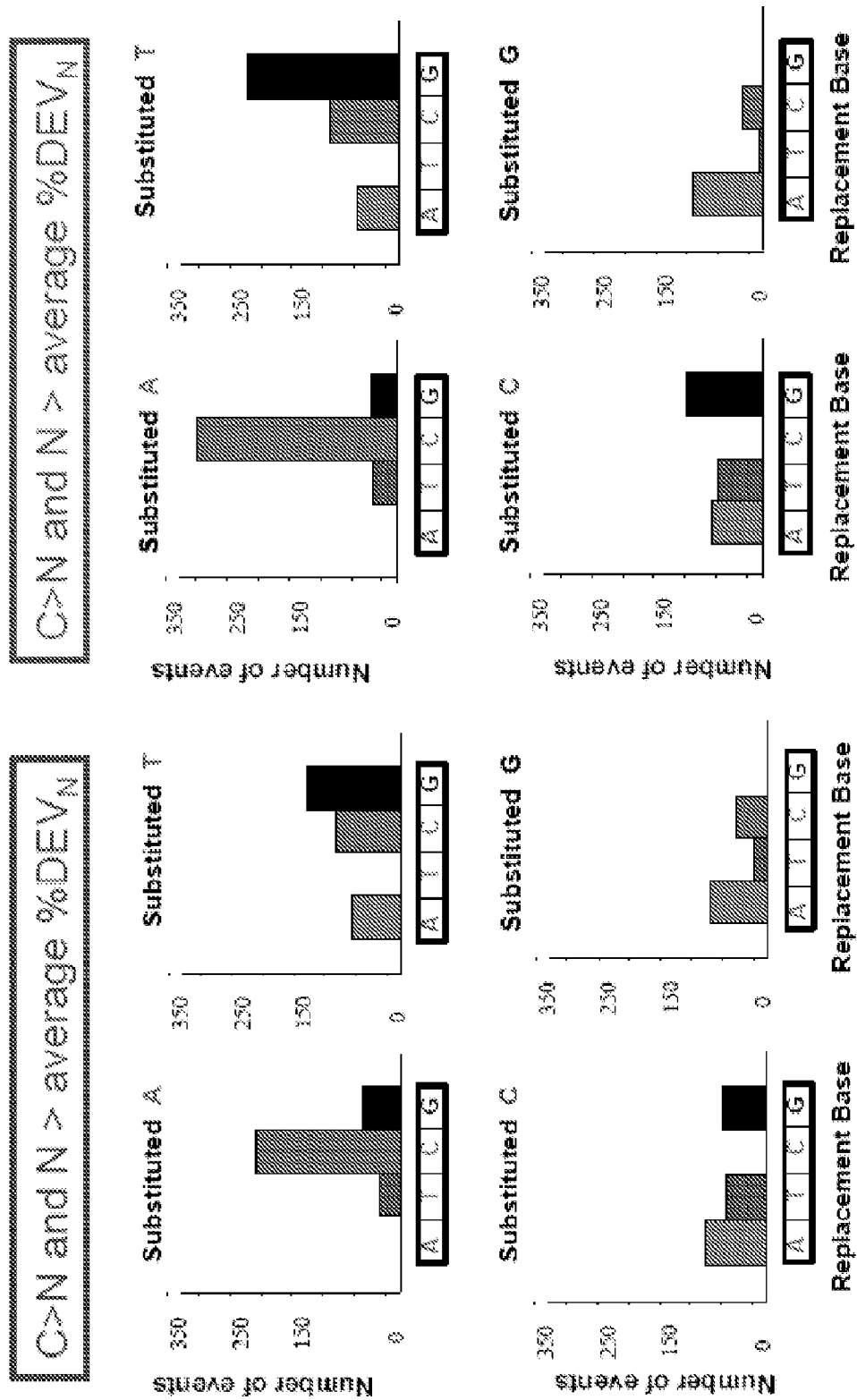

FIG. 7e shows that the −4/+3 signature is carried by the C>N set where N deviates. Context length is less important in the other set. FIG. 7f shows an accumulation in the 500-1000 interval that is more important in the C>N set where N deviates than in C>N set where N is stable. In the latter, it seems that earlier events (0-500 interval) appeared. Replacement bases for C>N sites were similar between the two sets (FIG. 7g).

Figure 5O:
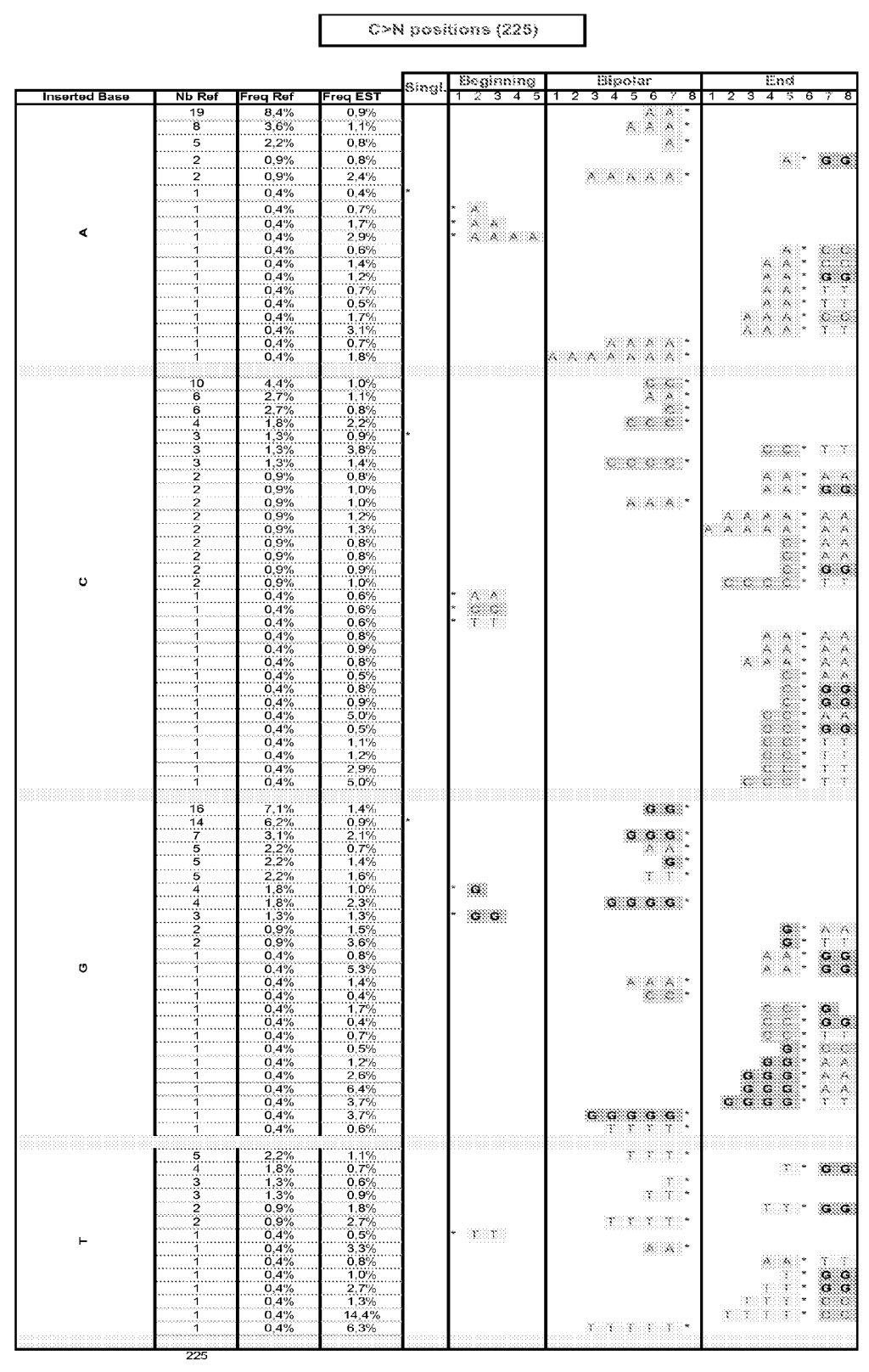
Figure 5P:
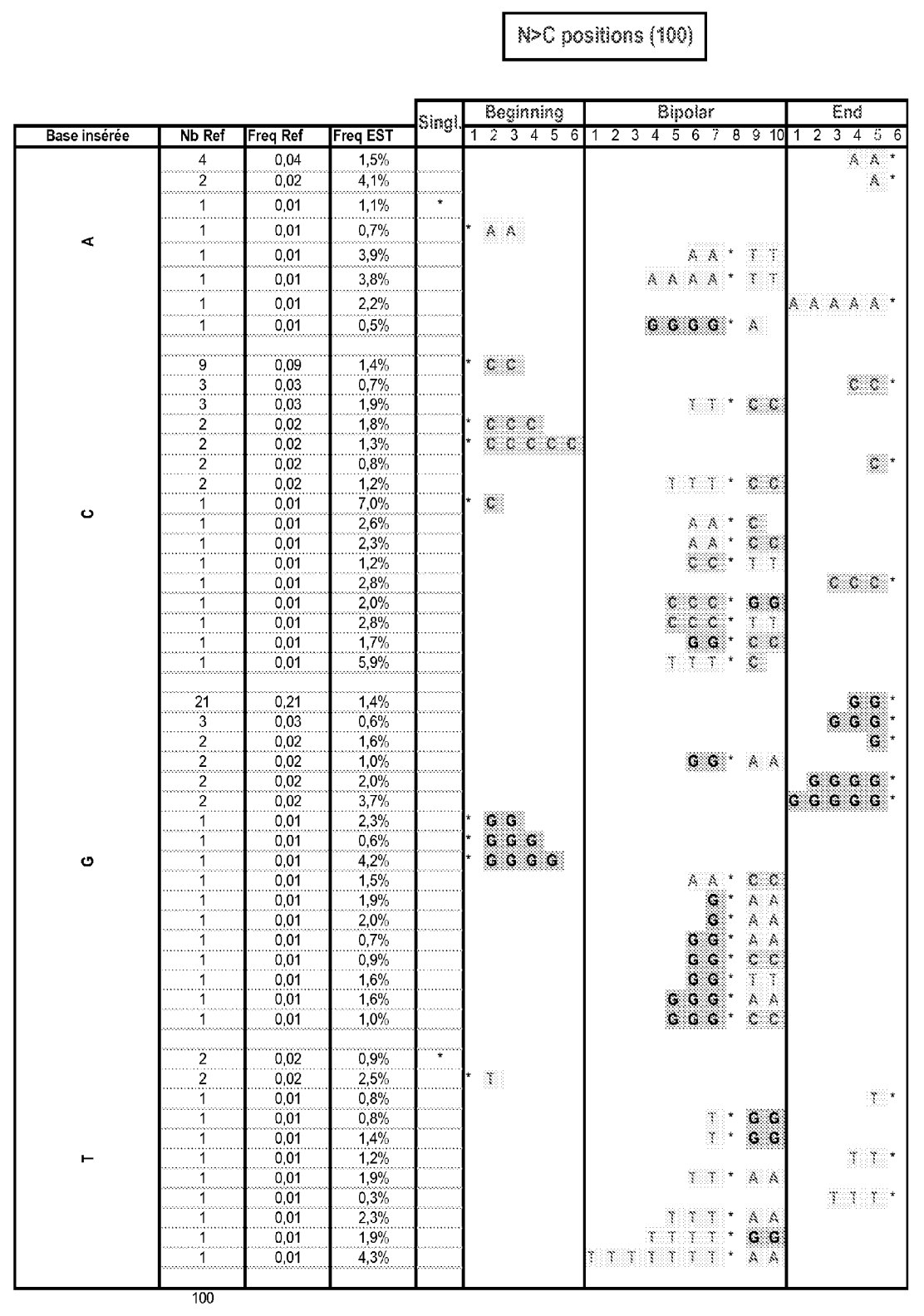

In case of deletion or insertion, results show that omitted bases (398 C>N cases) were in the following order: C (46.0%) >T (37.9%)>>A (9.3%)>G (6.8%) (FIG. 5m), and that inserted bases (225 C>N cases) were in the following order: G (36.0%)>C (30.2%)>A (21.8%)>T (12.0%) (FIG. 5o). We observed that deletion or insertion events often occur in conserved identical bases. A specific program designed to analyze such events shows effectively that 94.7% of deletions and 81% of insertions occur in stretches of variables length. Stretches can be bipolar and symmetrical (e.g. AAATAA) or not (e.g. CCCGG) or single nucleotides repeats (e.g. AAA) (see motifs on FIG. 5m-5p). In the deletion case, omitted bases are identical to the b−1 or b+1 base (stretch) in 84% of cases. Most motifs are doublet or triplet of C>T>A~G. Similar results are observed in the case of insertion. In fact, stretch motifs did not appear to be different between C>N and N>C. C>N or N>C specificity would come from other information around the stretches. Additional analyzes on more genes will confirm these observations.

Figure 8A:
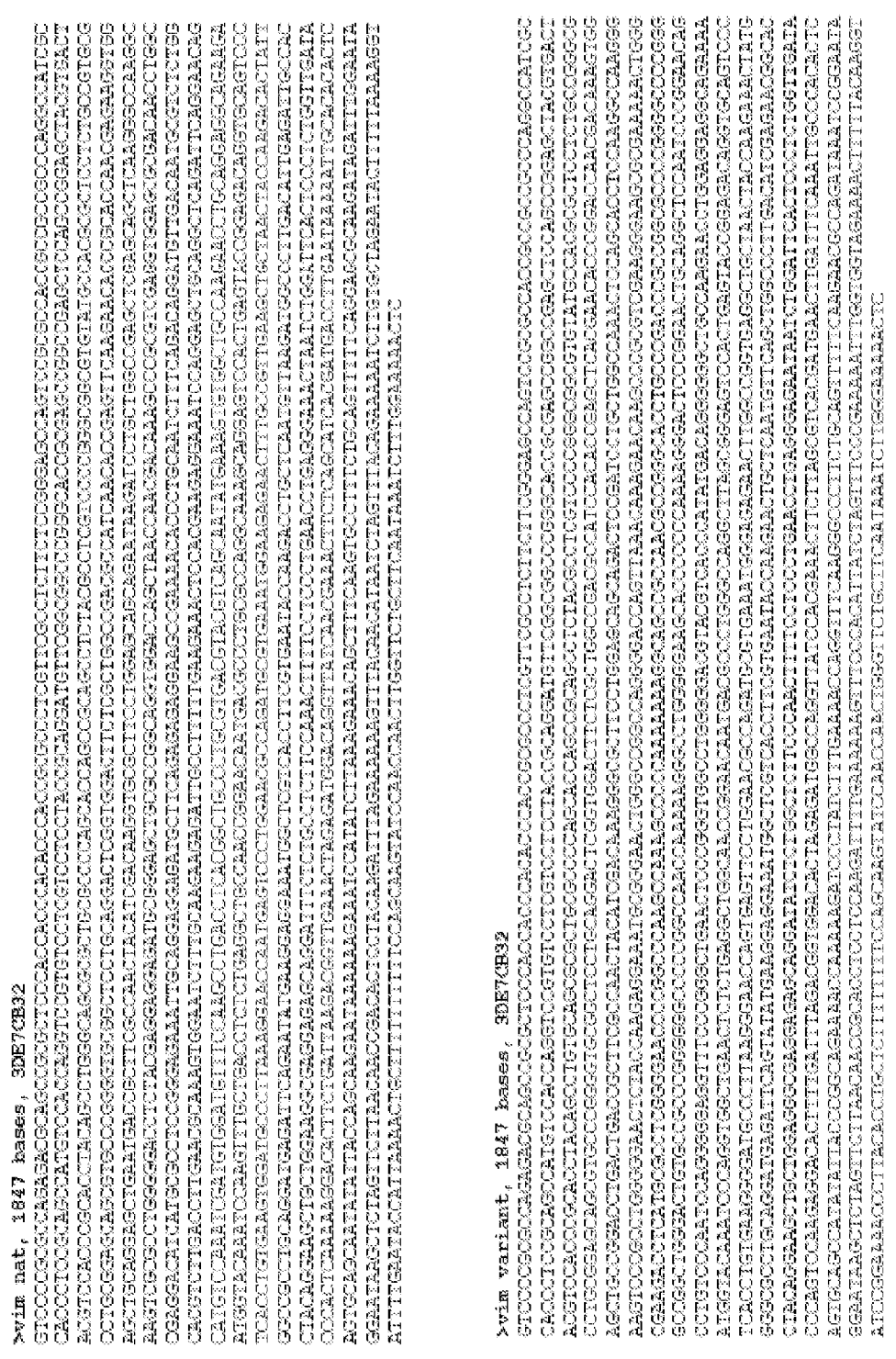
Figure 8B:
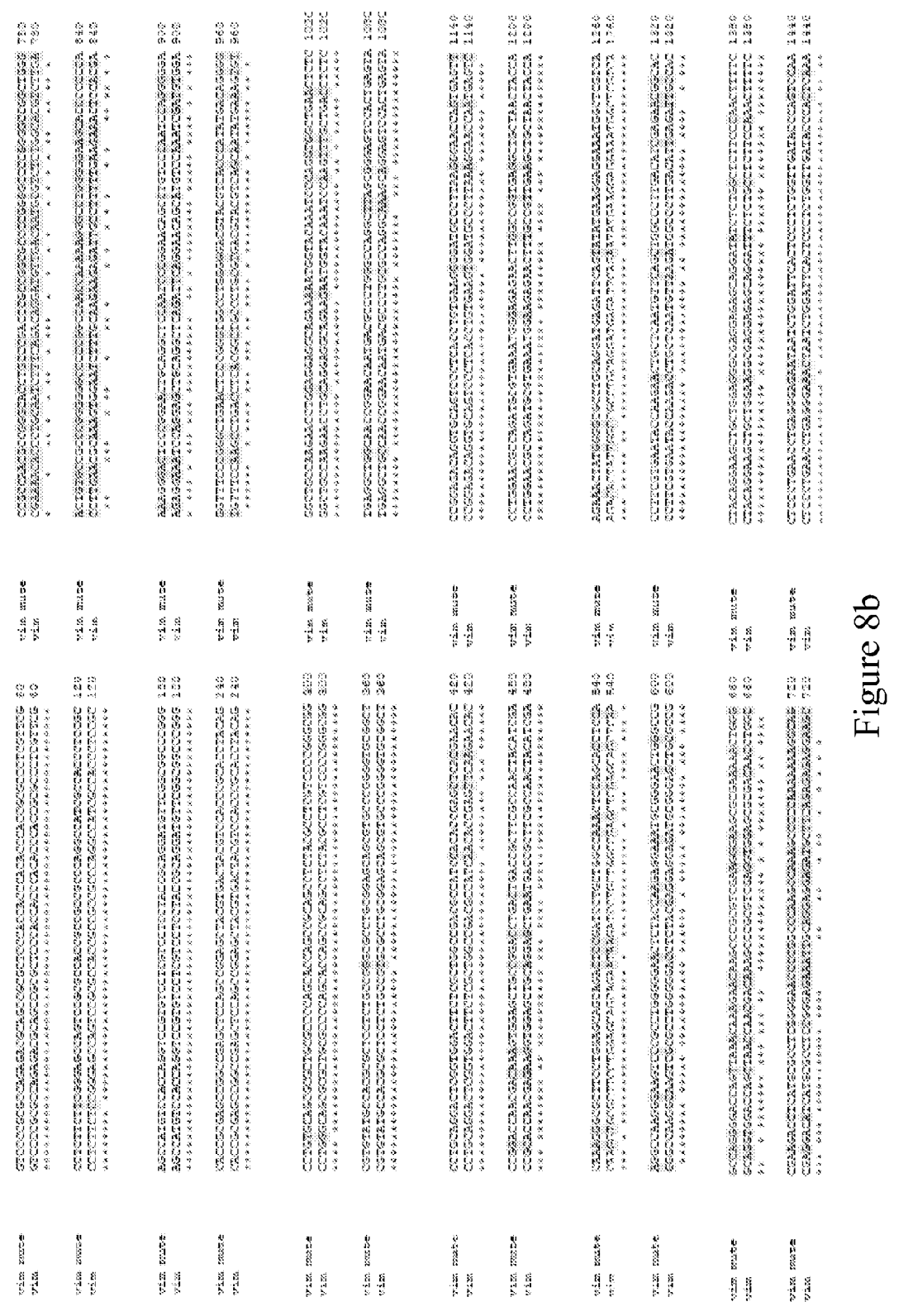
Figure 8C:
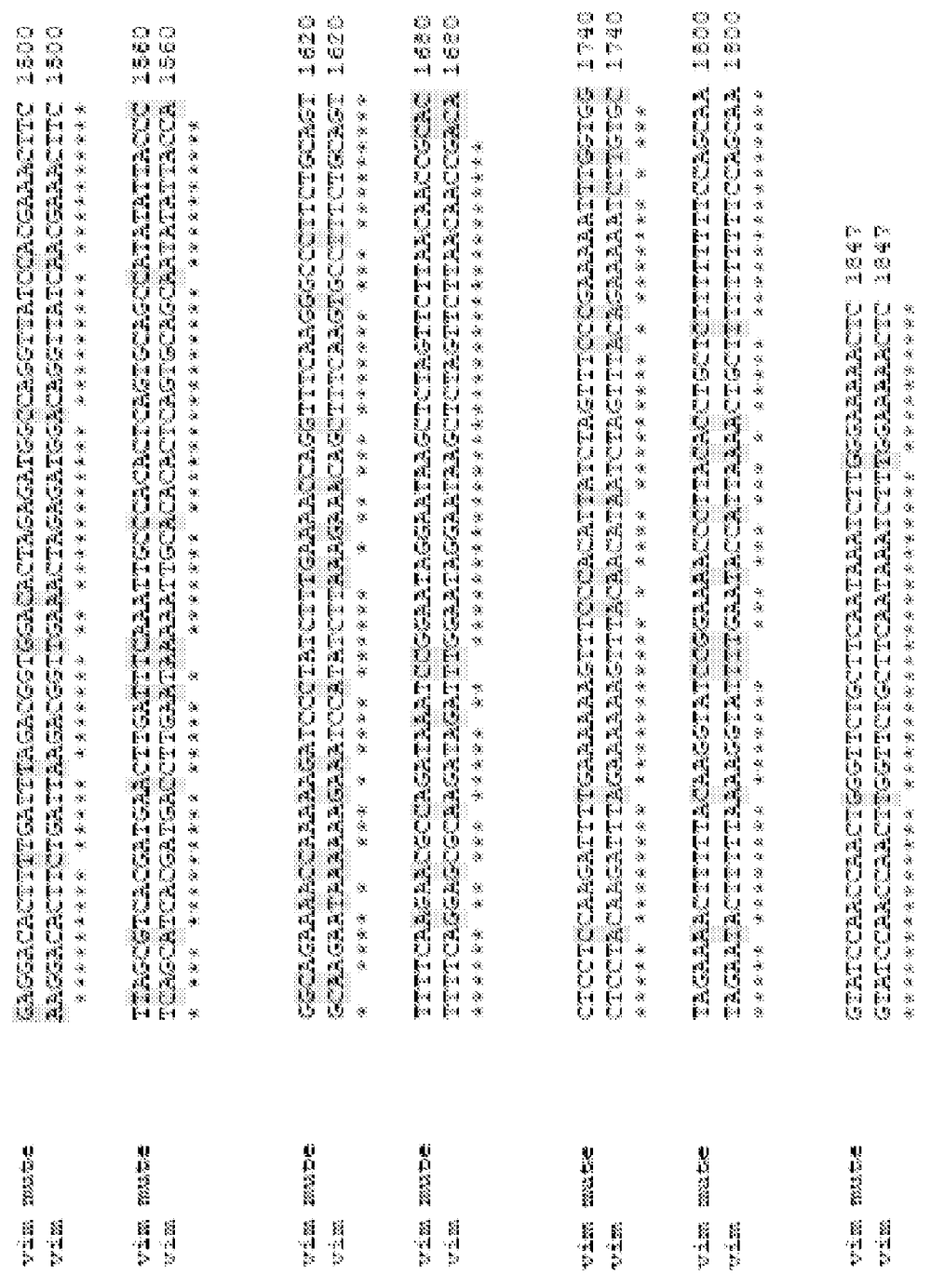
Figure 8D:
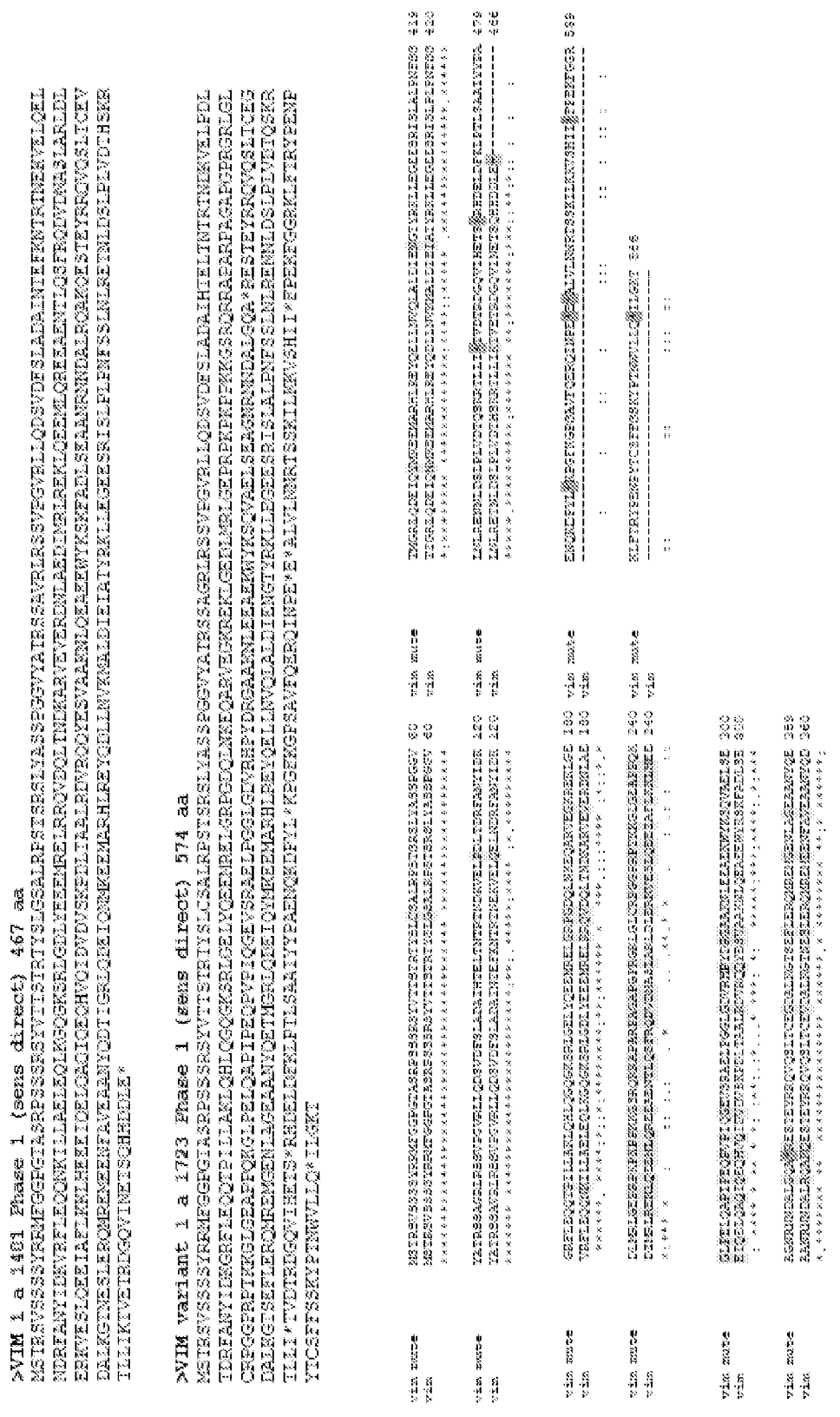

Taking into account all 17 genes, we observed EST heterogeneity at the rate of 10 per 100 bases (FIG. 5j and FIG. 8a-c). This rate is in excess of any described rate of mutation occurring in genomic DNA. As a reference, one can estimate that single nucleotide polymorphisms occur randomly in the genome once every 300 bases. The rate of single nucleotide polymorphisms affecting transcribed DNA is much lower: it is estimated to occur once every 3000 bases. It is clear that DNA mutations occur more frequently in cancer. However, in depth efforts of breast and colon cancer DNA sequencing that included 14 out of 17 genes used in our study led to an estimated somatic mutation rate of 3.1 mutations per $10^6$ bases (Sjoblom, T., et al. (2006) Science 314, 268-74). Therefore, transcription infidelity that is described in this invention occurs at a rate far greater than that of mutations affecting DNA. More importantly, most base substitutions on DNA have limited consequences at the protein level because less than 10% of genomic DNA is transcribed to mRNA. In contrast, base substitution due to transcription infidelity often has direct consequences on protein function. Indeed, 1179 out of 2281 substitutions described here (1548 CDS—369 silent substitutions) led to base substitutions with immediate impact on protein AA primary sequence (FIG. 8d). Most importantly, significant base substitutions affecting the stop codon were observed in 9 out of 17 tested genes. Before the concept of transcription infidelity, it had not, however, been proposed that human proteins would contain additional coding sequences encoded by RNA sequences considered thus far as "untranslated regions". We now show that base substitution occurring in natural stop codons because of transcription infidelity reveals novel coding regions that encode specific AA. This novel coding region is in phase with the native open reading frame. The natural stop codon is transformed into a coding codon. The next triplet of base is then read as an AA and the translation proceeds with a novel coding region until a new stop codon is reached. We have verified that this is indeed the case in 8 of 17 genes that demonstrated transcription infidelity. All 8 contain alternative stop codons in frame with the corresponding RefSeq (GAPDH does not contain an alternative STOP codon). This has immediate consequence because in each case, it created novel coding sequences of 14, 7, 13, 15, 13, 4, 9, 55 AA in TPT1, RPS6, RPL7A, VIM, RPS4X, FTH1, FTL and TPI1 respectively (FIG. 10). The addition of these AA has the potential to create motifs that will be greatly enhanced in cancer; these motifs will or will not result in novel function of the proteins. Predicting this occurrence leads to possible development of useful tools that could be use in diagnostic, therapeutic or other goals. Predicting this occurrence leads also to possible development of specific antibodies that will recognize cancer specific sequences in the carboxy-terminal end of the protein. No analytical method is currently capable of direct protein sequencing at the carboxy-terminal end. It is, however, possible to cleave proteins enzymatically and sequence cleavage products from their $NH_2$ terminal end. It is also possible to analyze the AA content of peptides generated by proteolysis using mass spectrometry. We further show that these alternative stop codons are also affected by transcription infidelity (7/9 genes have the second alternative STOP codon affected). The same phenomenon described above can further expand the reading to a novel set of sequences. Annotation of all protein sequences using our method will reveal several unsuspected coding mRNA sequences that will be more or less effectively transcribed depending on codon usage as well as the ability of translation machinery to or not to correctly translate the base substitution. In fact, base substitutions can lead to mRNA structure changes, which can modify ribosomal reading rate. Nevertheless, we assume that base substitutions don't involve RNA structure changes. On the basis of the occurrence of stop codon alterations, we estimate in affected genes that up to 4% of mRNA in cancer tissues contain these additional coding regions.

A specific program based on several filters can be used to annotate all protein sequences for the presence of a putative Post STOP Peptide (PSP). After retrieving nucleic sequence corresponding to the studied proteins, the program searches the presence or not of an in phase nucleic sequence after the canonical STOP, with another STOP in phase (the possibility to bypass one or more STOP in case of transcription infidelity affecting these alternative STOP codons can be take into account). A minimal length can be fixed (e.g. only sequences coding more than 12 amino acids, but eventually, the peptide length could be smaller) according to minimal criterion for a potential antigenic pattern prediction. Antigenic PSP are then stored (FIG. 18). An additional step is used to validate the candidates with the annotation by training learning machine of the canonical STOP: indeed the probability that one or more bases of the STOP codon could be substituted by transcription infidelity can be determined. It is also possible to analyze the AA content of peptides generated by proteolysis using mass spectrometry.

We have also shown that besides creating conditions allowing translation of novel protein sequences, transcription infidelity can introduce premature stops in mRNA. Twenty-four novel stop codons occurring within the canonical open reading frame were identified within 13 out of 17 genes. This indicated that transcription infidelity could yield the production of shorter proteins that are lacking specific domains. These truncated proteins might result in an increase or loss of function. The 3-D structure of the protein is likely to be affected and would thus create novel entities that might be recognized by the immune system.

Finally, transcription infidelity in the 17 tested genes revealed that 50% of all identified C>N substitutions lead to AA changes. 17% correspond to replacement of AA by another from the same family, and 33% correspond to substitutions of AA from a different class of AA. Thus, transcription infidelity is capable of generating proteins with novel AA sequences with potentially modified functions or activity. Predicting transcription infidelity using the rules described above will allow the rational prediction of changes in protein behavior and the outcome of proteomic experiments.

Example 6

Biological Validations

Biological validations are performed at two levels: mRNA and proteins.

Figure 11A:
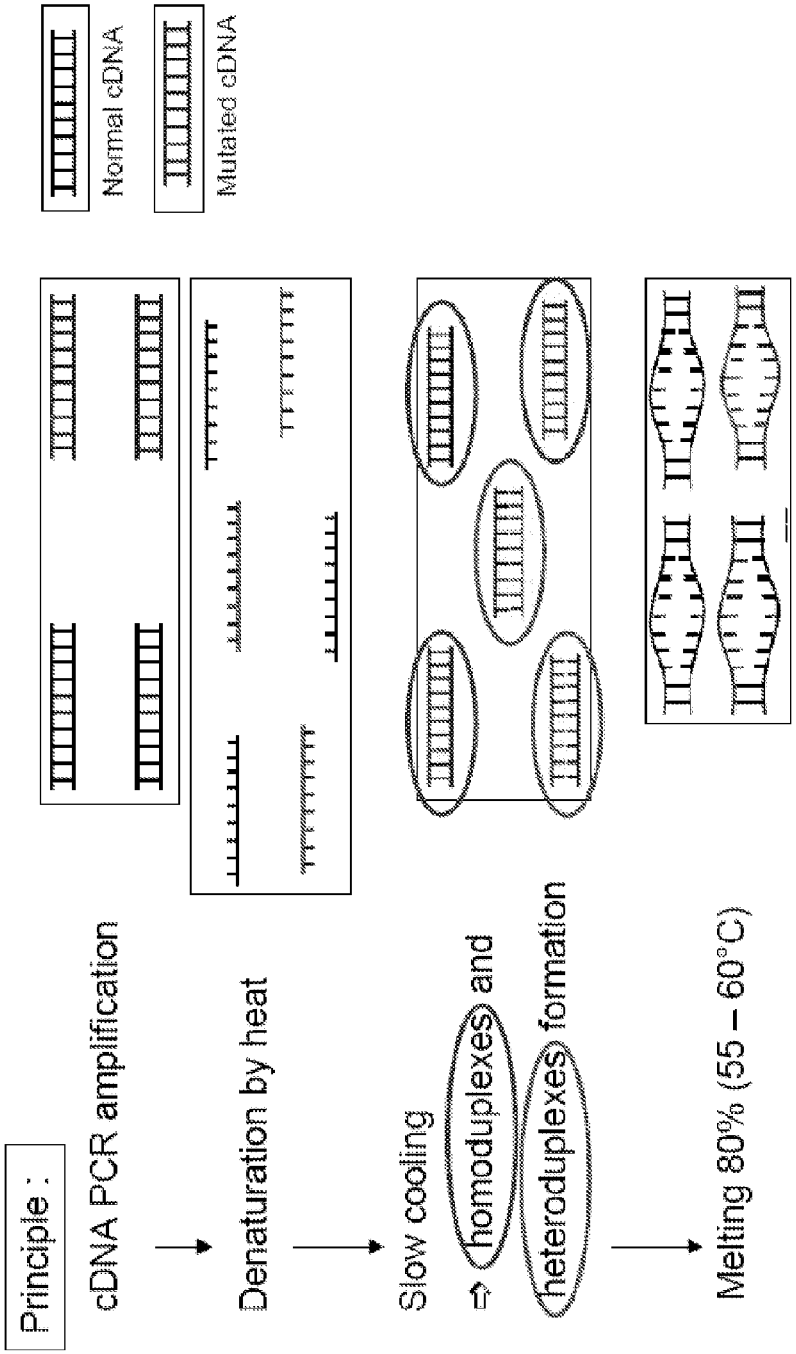
Figure 11B:
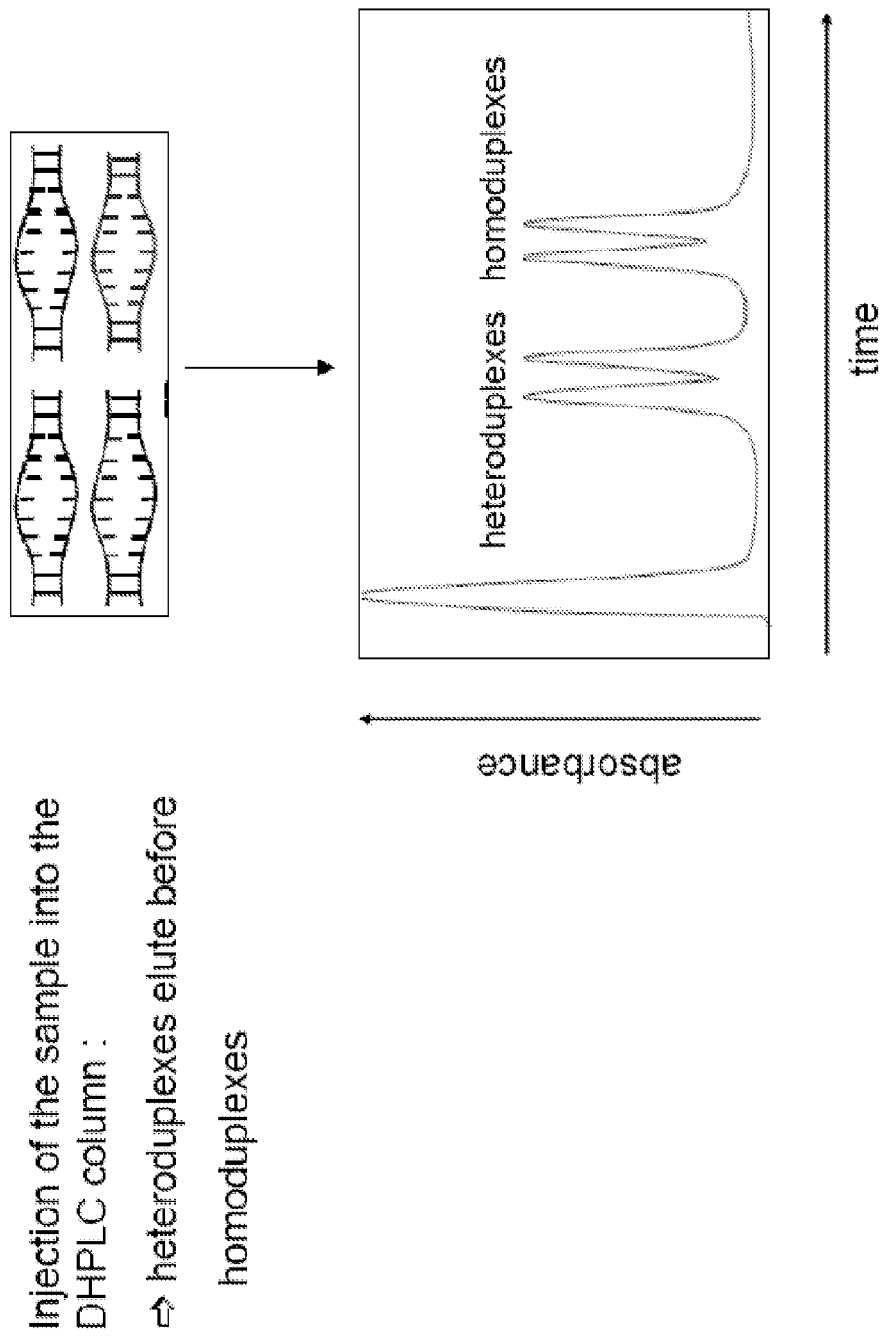
Figure 11C:
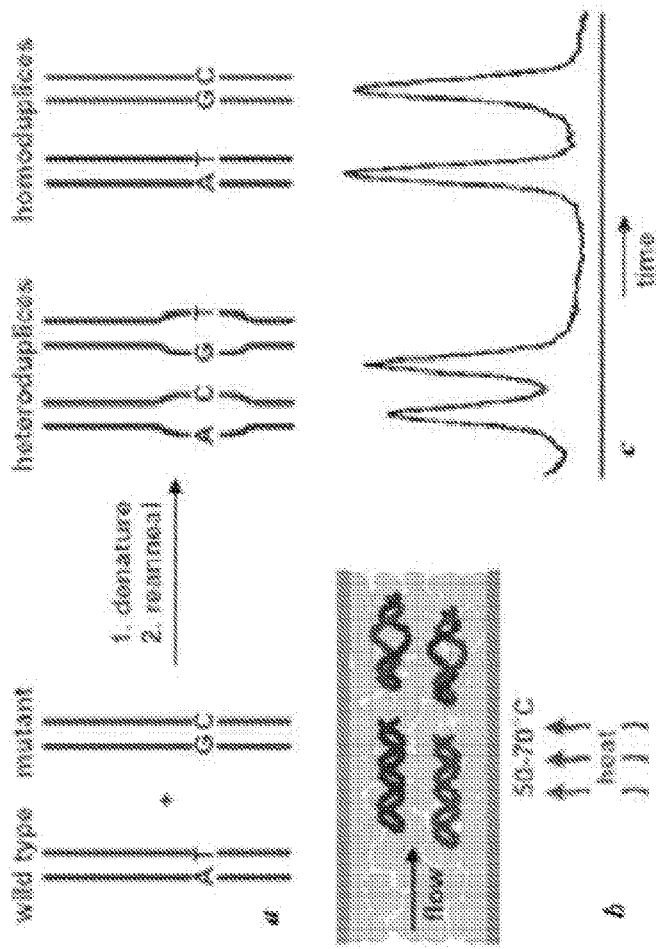
Figure 11D:
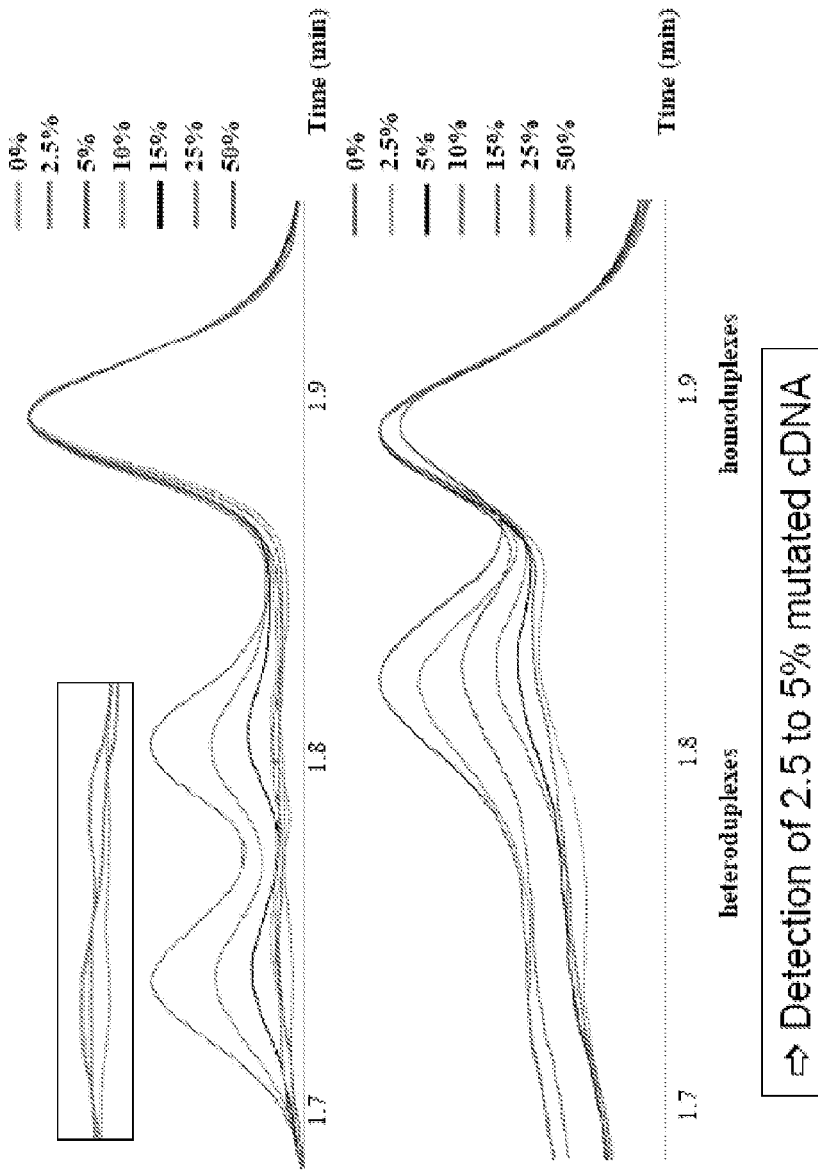

First, mRNA substitutions of the 17 genes of interest will be detected in human cancerous tissues. We used DHPLC (Denaturing High Performance Liquid Chromatography), which is a large scale chromatographic method to detect sequence mutations. The principle of the experiment is described in FIG. 11a-c. First, we have developed a method to test the Transgenomic DHPLC threshold in order to estimate the percentage of mutated DNA in the sample which is sufficient to allow heteroduplex formation and detection. Indeed, 300 bp PCR fragments with 1 and 3 bases substitutions were used. Different ratios of these fragments were prepared: 0%, 2.5%, 5%, 7.5%, 10%, 20% or 50%. The DHPLC allowed us to distinguish [normal] and [normal plus mutated] DNA as soon as the sample contained 2.5 to 5% mutated DNA (FIG. 11d).

These results indicate that we are able to distinguish mRNA from normal and cancerous tissues for the genes of interest. mRNA extracted from normal and cancerous adjacent tissues (Biochain Inc) were used to test three genes: GAPDH, ENO1 and TMSB4X. As DHPLC works on DNA, mRNA samples are converted into cDNA using reverse transcriptase. We chose regions that exhibit far more significant substitutions in ESTs coming from cancer tissues than in ESTs coming from normal tissues. Primers used for amplification are shown in FIG. 12.

In a first set of experiment, several cDNA from cancerous and adjacent normal tissue (liver, kidney, breast and colon) were amplified by PCR with said primers and injected on the DHPLC system. The temperature of the oven was selected with the Navigator software (Transgenomic). Profiles were obtained for the genes described above and a representative experiment is presented in FIG. 15 for the ENO1, the GAPDH and the TMSB4X genes. As shown in FIG. 15a to 15c, cancer profiles are clearly different from normal profiles for GAPDH and ENO1 genes. No differences were observed for the TMSB4X gene as we expected (far less transcription infidelity sites). The injections of the same PCR product and of 2 other PCR products were done in triplicate (FIG. 15b and 15c) and the profiles are very reproducible in the same experiment. However, the nature of the difference cannot be deduced from this experiment.

Consequently, the continuation of this biological validation based on mRNA is performed. In fact, sequencing of PCR products issued from cancerous tissues can allow to precisely detect most abundant mutations.

Classical Sanger sequencing method of reverse transcribed PCR amplified mRNA does not detect sequence variants occurring at rates lower than 15-30% at a specific position (FIG. 16). Indeed, mutated base calling obtained by sequencing amplification products mixes from mutated and non mutated known sequences is obtained for 50-50% mixes and minor peaks are detected from 15%. Pyrosequencing and Emulsion PCR are more sensitive methods allowing the detection of cDNA heterogeneity, thereby analysis of RT-PCR products obtained from cancer and normal cells is possible (Thomas, R. K, et al. (2006) *Nat Med* 12, 852-5).

A gene affected by transcription infidelity is cloned either entirely or a fragment comprising and not comprising its transcription infidelity site. The construct with and without canonical stop codon is ligated in frame with the gene encoding neomycin resistance. Cancer and normal cells are transfected with this chimeric construct first transiently then stably. We predict that transcription infidelity leads to change the canonical stop codon, thereby allowing translation of neomycin gene and creating neomycin resistant cell. We predict that the cancer cells that are neomycin resistant will grow more rapidly and that the shape of these cells will differ significantly from that of normal cells. Moreover, we predict that these cells are more invasive and can be compared to cells at a later stage of cancer progression. Therefore, this technique may be used to determine cancerous phase of different cells from an individual patient.

The final proof that neomycin resistance occurs as a result of transcription infidelity will be obtain by sequencing the inserted construct amplified from genomic DNA and showing that genomic information remains unchanged. We will also verify that mRNA from neomycin resistant cell contain a mutated stop codon due to transcription infidelity.

One technique that permits the detection of transcription infidelity sites is the construction of cDNA libraries that consists in cloning cDNA reverse-transcribed from RNA extracted from cancerous and normal patient tissues. Each cDNA amplified or not from a specific gene are cloned in separate plasmids that are transformed in *Escherichia coli*. Different *E. coli* colonies are picked and the plasmids are sequenced. The number of clones needed to be sequenced depends on the percentage of substitutions in the cloned cDNA fragment. A statistical analysis will give us the sequence variation in transcription infidelity sites. This technique can be ameliorated. Indeed, after reverse transcription and amplification with specific primers, cDNA can be cloned in a plasmid that carries a reporter gene e.g. lacZ gene. The cDNA and the reporter gene are cloned in phase. When a substitution appears in the STOP codon sequence of the mRNA, the reporter gene is expressed. When *E. coli* cells are transformed with this construction, colonies that carry the plasmid where the cDNA is mutated in the stop codon are selected with the expression of the reporter gene. After that, plasmid can be sequenced in order to verify if the substitution of the stop codon is present.

Another technique based on real-time PCR with specific primers is used to detect transcription infidelity sites. These primers are designed to match cDNA with sequence variation(s) based on statistical analysis. A second primer is designed to match the cDNA without the sequence variation (reference). The number of variation(s) in the primer sequence is very important and we have determined in a test experiment on known sequence variation that 2 mutations outside of the position that is studied are necessary to obtain a specific fluorescence signal. When the primer is complementary to the cDNA without a sequence substitution (reference), the fluorescence signal is detected at a specific number of amplification cycles. The same cDNA amplified with the primer that bears the sequence substitution leads to a fluorescence signal that appears with a greater number of amplification cycles. The difference between the numbers of amplification cycle with the 2 primers is a direct estimation of the presence of a cDNA with a sequence substitution. Moreover, we verified that the method is sensitive enough to detect 1% of mutated sequence in a mix of known sequences.

In a typical experiment, RNA extracted from cancerous and normal patient tissues are reverse transcribed and amplified with each of said specific primers. The difference between amplification cycle with both primers is then measured.

Finally, we can focus on novel proteins induced when the natural stop codon is affected. We showed that stop codon is significantly affected for 9 of our 17 genes of interest. That leads to distinct specific populations of proteins with a novel sequence in the carboxy-terminal end. We estimate that cancerous tissues for affected genes contain 4% proteins that are longer than normal ones.

In view of this hypothesis, we analysed 60 abundant plasma proteins (FIG. 13) and searched for possible PSP. We found 22 genes for which a PSP was long enough and antigenic (FIG. 18). We then searched for putative longer protein sequences induced (FIG. 18b-c). We then searched for putative new peptides in plasma obtained from normal and cancerous individuals (FIG. 18). We selected 3 out of these 22 interesting proteins: APOAI, APOAII and APOCII. Based on the above analysis, we expect to find longer proteins in cancerous-patient plasma (13, 16 and 17 AA longer). These transcription infidelity peptide sequences are predicted to be immunogenic, and antibodies directed against these novel sequences represent specific ligands to measure transcription infidelity (FIG. 14). Since Kyte-Doolittle analysis indicates that these sequences are not hydrophobic, we expect these three novel proteins to be secreted into the circulation (see below).

Identification of Post Stop Peptide (PSP) of ApoAII and ApoCII Due to Substitution in Canonical Stop Codon PSPs that result from base substitutions in the canonical stop codon can be identified and characterized in the following manner. Rabbit polyclonal antibodies are prepared that recognize an immunogenic portion(s) of the PSP in question. These anti-peptide antibodies can be checked by dot blot using the purified peptide to verify that they indeed recognize the PSP. Western blots can then be performed on plasma samples obtained from cancer patients using the antibodies directed against the PSP. FIG. 17a (right panel) shows that the anti-PSP ApoAII antibody recognizes a band in Western blots performed on plasma samples obtained from prostate cancer patients, that is not observed when using rabbit pre-immune serum as a negative control (FIG. 17a, left panel). The PSP ApoAII band is also observed in cancer patients in the metastatic phase (FIG. 17b, right panel). This band has a slightly greater molecular mass (11.4 kDa) as compared to that of the native monomer form of ApoAII (FIG. 17a, middle panel, 17b, left panel). This molecular mass corresponds to that predicted based on the additional peptide sequence. Two-dimensional gels can also be performed in order to further characterize this band.

Affinity chromatography experiments can be carried out to isolate the PSP form of ApoAII using the anti-PSP antibody (FIG. 17e). The anti-PSP antibody is immobilized on matrix beads and the following column is incubated in presence of plasma or delipidated HDL then sequentially washed to remove aspecifically bound proteins and finally eluted with detergent or chaotropic reagents. The eluted fraction is analysed by Western blotting using both the anti-PSP and the commercial anti-ApoAII antibodies. Two bands at 9 kDa and 11.4 kDa are recognized by the commercial anti-apoAII antibody whereas only the 11.4 kDa band is recognized by the anti-PSP antibody. Therefore, the 9 kDa band corresponds to the native ApoAII form and the 11.4 kDa one corresponds to the PSP form of ApoAII. The presence of native ApoAII in the eluted fraction suggests that the PSP ApoAII protein can form dimers with the native ApoAII protein under native non-reducing conditions. Indeed, ApoAII exists normally in plasma as a dimer of 2 monomers linked by a single disulfide bridge.

ApoAII is located primarily on the HDL fraction in plasma, which can be isolated by sequential ultracentrifugation. Western blotting shows that the PSP ApoAII is not detected in the d<1.07 g/ml fraction containing VLDL and LDL, but rather in the d>1.07 g/ml fraction containing HDL and plasma proteins (FIG. 17c). After further ultracentrifugation steps to purify and wash HDL (d1.07-1.21 g/ml), Western blotting reveals that the PSP ApoAII remains associated with the HDL fraction rather than the d>1.21 g/ml fraction, also referred to as lipoprotein deficient serum (LPDS). A corresponding amount of plasma is shown on the Western blot to demonstrate that this is not due to a dilution of the d>1.21 g/ml fraction during the purification steps. The separation of lipoproteins from plasma by gel filtration using Superose 6B (Amersham, GE Healthcare) also demonstrates that the PSP ApoAII elutes in a similar manner to that of ApoAII associated with HDL.

PSP ApoAII association with HDL allowed the purification of the PSP form of ApoAII in a manner similar to that of ApoAII. HDL is first delipidated to remove all lipids. The resulting lipid-free protein pellet is then resuspended in a 10 mM Tris buffer containing urea or guanidine in presence or absence of reducing agent, and applied to a gel filtration column (example, Superdex 200, Amersham-GE Healthcare). Western blotting (FIG. 17d) shows that the PSP form of ApoAII is still present in the delipidated HDL. Further purification was achieved by preparative electrophoresis (example: DE52). The PSP form of ApoAII was tracked by Western blotting. The purified PSP form of ApoAII was then cleaved enzymatically (trypsin) and the resulting peptides are analyzed on MS-MS for full AA sequencing. Results show that canonical STOP is replaced preferentially by Arginine with either (U to C) or (U to A) substitution followed by Serine, Valine, Glutamic acid, Threonine, Isoleucine, Valine, Phenylalanine, Glutamic acid, Proline, Glutamic acid, Leucine, Alanine, Serine, Arginine. This is the exact sequence of amino acid predicted to occur following bypass of ApoAII canonical STOP. Thus canonical UGA STOP of ApoAII is substituted to AGA or CGA leading to Arginine. A yet unexplored hypothesis is that UGA is converted to GGA leading to Glycine. But detection of this variant by mass spectrometry is currently beyond technological limits.

Another example is illustrated by the PSP of ApoCII. FIG. 17f shows a similar experiment to that of FIG. 17a, with the exception that Westerns were performed with commercially available anti-ApoCII or anti PSP ApoCII antibodies. A procedure similar to that for the PSP of ApoAII can be followed for ApoCII. However, ApoCII is less abundant in the plasma. A much larger quantity of plasma that contains the PSP ApoCII is therefore required in order to obtain sufficient amounts for analysis on MS-MS.

CONCLUSIONS

We describe here a novel mechanism leading to base substitutions occurring mostly in the 3' end of coding sequence and untranslated region of mRNA. These base substitutions lead to changes in protein AA sequences due to changes of AA identity, introduction of premature stop codons as well as the modification of naturally-occurring stop codons resulting in the introduction of novel coding regions. This phenomenon of transcription infidelity could also affect the ncRNA world and disturb the regulation mediated by these RNA. It occurs in most genes at a rate that exceeds any described phenomenon leading to DNA mutation. Transcription infidelity is greatly increased in cancer cells. Transcription infidelity provides a novel paradigm to understand cancer pathology, disease severity and disease progression. It has important implications not only for the design of novel transcriptomic and proteomic experiments, but also for the development of specific diagnostics and therapeutics.

The invention claimed is:

1. A method to diagnose the presence of a cancer in a subject, the method comprising the following steps:
   (a) detecting in vitro or ex vivo the presence or rate of transcription infidelity in a sample from said subject, wherein said transcription infidelity introduces sequence variations into an RNA primary transcript during transcription of DNA to RNA, and
   (b) diagnosing the presence of cancer in said subject, said presence or rate of transcription infidelity is an indication of the presence of a cancer in said subject.

2. The method of claim 1, wherein transcription infidelity is detected using at least one ligand specific for a transcription infidelity site of a protein or nucleic acid.

3. The method of claim 1, wherein transcription infidelity is detected by hybridization of the nucleic acid in the sample with a nucleic acid probe specific for a transcription infidelity domain.

4. The method of claim 3, wherein the transcription infidelity domain comprises at least one modification encoded by a nucleic acid alteration according to the following rules:
   A is substituted when A is preceded or followed by C,
   T is substituted when T is preceded or followed by G,
   C is substituted when C is preceded or followed by G or A, and
   G is substituted when G is preceded or followed by A.

5. The method of claim 1, wherein transcription infidelity is detected by amplification of the nucleic acid in the sample with a nucleic acid primer specific for a transcription infidelity domain.

6. The method of claim 5, wherein the transcription infidelity domain comprises at least one modification encoded by a nucleic acid alteration according to the following rules:
   A is substituted when A is preceded or followed by C,
   T is substituted when T is preceded or followed by G,
   C is substituted when C is preceded or followed by G or A, and
   G is substituted when G is preceded or followed by A.

7. The method of claim 1, wherein transcription infidelity is detected in a nucleic acid encoding a cell surface protein or a secreted protein.

8. The method of claim 7, wherein the nucleic acid encodes a plasma protein or a receptor.

9. The method of claim 1, which comprises detecting in vitro or ex vivo the presence or rate of one or more sequence variations in nucleotide molecules in a sample from said subject, said variation(s) being selected from nucleotide base deletions, insertions or base family changes.

10. The method of claim 9, wherein the base family change(s) is/are selected from A→C, T→G, G→T, A→T, A→U, G→C, G→U, T→A, C→A, or C→G.

11. The method of claim 10, wherein the base family change(s) is A→C.

12. The method of claim 10, wherein the base family change(s) is T→G.

13. The method of claim 1, wherein the cancer is breast cancer or colon cancer.

14. The method of claim 1, wherein said transcription infidelity does not arise from a post-transcriptional base change in a mRNA molecule.

15. The method of claim 1, which comprises detecting in vitro or ex vivo the presence or rate of:
   a) one or more sequence variations in nucleotide molecules in a sample from said subject, said variation(s) being selected from A→C or T→G nucleotide base changes; and/or
   b) one or more protein modifications resulting from sequence variations of step a);
   wherein said sequence variations are introduced into the RNA primary transcript during transcription of DNA to RNA by transcription infidelity (TI) and said presence or rate of sequence variations and/or protein modifications is an indication of the presence of a cancer in said subject.

* * * * *

UNITED STATES PATENT AND TRADEMARK OFFICE
CERTIFICATE OF CORRECTION

PATENT NO. : 8,288,091 B2  Page 1 of 1
APPLICATION NO. : 12/374431
DATED : October 16, 2012
INVENTOR(S) : Bernard Bihain It is certified that error appears in the above-identified patent and that said Letters Patent is hereby corrected as shown below:

In the Specification

Column 22,
Line 7, "DFLSKN" should read --DFLSNK--.
Line 23, "ARHGRDEEVWHRKHSHHFVQAWAWVGGLCVCWPRKCHMRSTLISSLDSLLPVIPHRT EAEWVVVMFDRRH (AHSG)" should read --ARHGRDEEVWHRKHSHHFVQAWAWVGGLVCCWPRKCHMRSTLISSLDSLLPVIPHRT EAEWVVVMFDRRH (AHSG)--.

Column 23,
Line 5, "(RKM2)" should read --(PKM2)--.

Signed and Sealed this
Nineteenth Day of November, 2013

Teresa Stanek Rea
*Deputy Director of the United States Patent and Trademark Office*

SEQUENCE LISTING

<160> NUMBER OF SEQ ID NOS: 126

<210> SEQ ID NO 1
<211> LENGTH: 13
<212> TYPE: PRT
<213> ORGANISM: Homo sapiens

<400> SEQUENCE: 1

Gln Met Trp Gln Leu Phe Trp Ile Tyr His Leu Ser Ser
1               5                   10

<210> SEQ ID NO 2
<211> LENGTH: 14
<212> TYPE: PRT
<213> ORGANISM: Homo sapiens

<400> SEQUENCE: 2

Lys Leu His Thr Leu Ser Ala Ala Ile Tyr Tyr Gln Gln Glu
1               5                   10

<210> SEQ ID NO 3
<211> LENGTH: 6
<212> TYPE: PRT
<213> ORGANISM: Homo sapiens

<400> SEQUENCE: 3

Asp Phe Leu Ser Asn Lys
1               5

<210> SEQ ID NO 4
<211> LENGTH: 12
<212> TYPE: PRT
<213> ORGANISM: Homo sapiens

<400> SEQUENCE: 4

Met Tyr Thr Val Glu Phe Ser Val His Lys Asn Asn
1               5                   10

<210> SEQ ID NO 5
<211> LENGTH: 12
<212> TYPE: PRT
<213> ORGANISM: Homo sapiens

<400> SEQUENCE: 5

Asn Gly Ser Leu Gly Asp Met Ser Asp Leu Cys Thr
1               5                   10

<210> SEQ ID NO 6
<211> LENGTH: 3
<212> TYPE: PRT
<213> ORGANISM: Homo sapiens

<400> SEQUENCE: 6

Ala Ser Gly
1

<210> SEQ ID NO 7
<211> LENGTH: 8
<212> TYPE: PRT
<213> ORGANISM: Homo sapiens

<400> SEQUENCE: 7

Glu Pro Ser Glu Pro Ser Asp Phe
1               5

```
<210> SEQ ID NO 8
<211> LENGTH: 54
<212> TYPE: PRT
<213> ORGANISM: Homo sapiens

<400> SEQUENCE: 8

Ala Pro Ser Ile Phe Pro Thr Leu Pro Ala Lys Pro Gly Thr Lys Gln
1               5                   10                  15

Pro Arg Ser Pro Val Thr Ala Leu Ser Leu His Met Leu Leu Met Val
            20                  25                  30

Ser Ser Ala Pro Ser Cys Gly Leu Ile Gln Thr Val Ser Ser Phe Thr
        35                  40                  45

Val Tyr Ile Phe Thr Leu
    50

<210> SEQ ID NO 9
<211> LENGTH: 69
<212> TYPE: PRT
<213> ORGANISM: Homo sapiens

<400> SEQUENCE: 9

Ala Arg His Gly Arg Asp Glu Glu Val Trp His Arg Lys His Ser His
1               5                   10                  15

His Phe Val Gln Ala Trp Ala Trp Val Gly Gly Leu Val Cys Trp Pro
            20                  25                  30

Arg Lys Cys His Met Arg Ser Thr Leu Ile Ser Ser Leu Asp Ser Leu
        35                  40                  45

Leu Pro Val Ile Pro His Arg Thr Glu Ala Glu Trp Val Val Val Met
    50                  55                  60

Phe Asp Arg Arg His
65

<210> SEQ ID NO 10
<211> LENGTH: 26
<212> TYPE: PRT
<213> ORGANISM: Homo sapiens

<400> SEQUENCE: 10

Arg Ser Lys Ala Tyr Ser Ser Val Phe Leu Phe Arg Trp Cys Lys Ala
1               5                   10                  15

Asn Thr Leu Ser Lys Lys His Lys Phe Leu
            20                  25

<210> SEQ ID NO 11
<211> LENGTH: 14
<212> TYPE: PRT
<213> ORGANISM: Homo sapiens

<400> SEQUENCE: 11

Gly Leu Asp Ser Thr Arg Ala Leu Glu Asn Glu Met Thr Val
1               5                   10

<210> SEQ ID NO 12
<211> LENGTH: 12
<212> TYPE: PRT
<213> ORGANISM: Homo sapiens

<400> SEQUENCE: 12

Gly Ala Arg Arg Arg Pro Pro Ser Arg Cys Ser Glu
1               5                   10
```

```
<210> SEQ ID NO 13
<211> LENGTH: 20
<212> TYPE: PRT
<213> ORGANISM: Homo sapiens

<400> SEQUENCE: 13

Ser Val Gln Thr Ile Val Phe Gln Pro Gln Leu Ala Ser Arg Thr Pro
1               5                   10                  15
Thr Gly Gln Ser
            20

<210> SEQ ID NO 14
<211> LENGTH: 16
<212> TYPE: PRT
<213> ORGANISM: Homo sapiens

<400> SEQUENCE: 14

Ile Val Phe Gln Pro Gln Leu Ala Ser Arg Thr Pro Thr Gly Gln Ser
1               5                   10                  15

<210> SEQ ID NO 15
<211> LENGTH: 22
<212> TYPE: PRT
<213> ORGANISM: Homo sapiens

<400> SEQUENCE: 15

Gln Pro Asp Pro Pro Ser Val Asp Lys Gly Arg Val Pro Tyr Ser Pro
1               5                   10                  15
Asp Pro Pro Gly Ser Asp
            20

<210> SEQ ID NO 16
<211> LENGTH: 15
<212> TYPE: PRT
<213> ORGANISM: Homo sapiens

<400> SEQUENCE: 16

Asp Pro Pro Ser Val Asp Lys Gly Arg Val Pro Tyr Ser Pro Asp
1               5                   10                  15

<210> SEQ ID NO 17
<211> LENGTH: 54
<212> TYPE: PRT
<213> ORGANISM: Homo sapiens

<400> SEQUENCE: 17

Asp Leu Asn Thr Pro Ser Pro Pro Ala Tyr Pro Ser Cys Glu Leu Leu
1               5                   10                  15
Gly Ser Cys Asn Leu Gln Gly Cys Pro Cys Arg Leu Leu Lys Arg Asp
            20                  25                  30
Ser Ile Leu Ser Ala Leu Leu Pro His Leu Met Pro Gly Pro Pro Pro
        35                  40                  45
Gly Met Leu Ala Ser Gln
    50

<210> SEQ ID NO 18
<211> LENGTH: 36
<212> TYPE: PRT
<213> ORGANISM: Homo sapiens

<400> SEQUENCE: 18

Pro Gly Ser Thr Gly Arg Leu His Pro Leu His Val Thr Ser Ala Ser
1               5                   10                  15
```

-continued

```
Leu Ser Pro Thr Pro Pro Pro His Lys Asp Lys Pro Ile Asn His
            20                  25                  30
Asp Lys Gly Ser
        35

<210> SEQ ID NO 19
<211> LENGTH: 37
<212> TYPE: PRT
<213> ORGANISM: Homo sapiens

<400> SEQUENCE: 19

Thr Pro Lys Pro Ala Ala Met Arg Pro His Ala Thr Pro Cys Leu Leu
1               5                   10                  15

Pro Pro Arg Ser Leu Gln Arg Glu Thr Leu Ser Pro Pro Gln Pro Ser
            20                  25                  30

Ser Trp Gly Gly Pro
        35

<210> SEQ ID NO 20
<211> LENGTH: 13
<212> TYPE: PRT
<213> ORGANISM: Homo sapiens

<400> SEQUENCE: 20

Glu Ala Arg Val Gly Gly Asn Val Gly Ser Gln Thr Gln
1               5                   10

<210> SEQ ID NO 21
<211> LENGTH: 29
<212> TYPE: PRT
<213> ORGANISM: Homo sapiens

<400> SEQUENCE: 21

Pro Ser Val Leu His Thr Ala Arg Gly Pro Arg Met Pro Arg Pro Pro
1               5                   10                  15

Leu Ala Pro Ala Gly Arg Glu Pro Asp His Leu Pro Cys
            20                  25

<210> SEQ ID NO 22
<211> LENGTH: 72
<212> TYPE: PRT
<213> ORGANISM: Homo sapiens

<400> SEQUENCE: 22

Asp Val Asp Val Ala Phe Ala Pro Thr Gly Ala Ser Glu Ser Ser Ser
1               5                   10                  15

Pro Gln Asp Glu Leu Gln Pro Pro Arg Glu Ser Ser Ala Arg His Gln
            20                  25                  30

Val Thr Arg Pro Gln Pro Pro Gly Pro Gln Leu Arg Pro Ala Ser Pro
        35                  40                  45

Arg Ser Gly Ser Cys Thr Leu Thr Leu Asp Ser Ala Ala His Gly Lys
    50                  55                  60

Asn Arg Ile Ala Pro Ala Cys Asn
65                  70

<210> SEQ ID NO 23
<211> LENGTH: 14
<212> TYPE: PRT
<213> ORGANISM: Homo sapiens

<400> SEQUENCE: 23

Asn Val Ile Pro Leu Lys Arg Lys Met Asn Asn Thr Leu Asn
```

```
<210> SEQ ID NO 24
<211> LENGTH: 39
<212> TYPE: PRT
<213> ORGANISM: Homo sapiens

<400> SEQUENCE: 24

Thr Pro Ala Ala Arg Leu Met Trp Ser Ser Asn Met Pro Tyr Phe Ala
1               5                   10                  15

Gln Lys Thr Ala Lys Asp Met Thr Ser Ser Trp Leu Gln Pro Arg Phe
            20                  25                  30

Ile Phe Leu Phe Val Val Asn
            35

<210> SEQ ID NO 25
<211> LENGTH: 53
<212> TYPE: PRT
<213> ORGANISM: Homo sapiens

<400> SEQUENCE: 25

Gly Trp Gly Val Phe Leu Leu Asn Pro Met Ala Gly Gly His Ala Pro
1               5                   10                  15

Thr Ile Ile Ser Trp Glu Glu Arg Gln Ser Trp Glu Ile Asp Gly Ser
            20                  25                  30

His Ser Ser Leu Leu Ser Leu Leu Cys Leu Trp Ala Thr Leu Pro Thr
        35                  40                  45

Pro Leu Leu Ser Gln
        50

<210> SEQ ID NO 26
<211> LENGTH: 27
<212> TYPE: PRT
<213> ORGANISM: Homo sapiens

<400> SEQUENCE: 26

Thr Gly Pro Thr His His Ser Pro Ser Pro Ser Ile Ser Thr Trp Cys
1               5                   10                  15

Leu Val Pro Val His Ser Val Asn Lys Lys Pro
            20                  25

<210> SEQ ID NO 27
<211> LENGTH: 25
<212> TYPE: PRT
<213> ORGANISM: Homo sapiens

<400> SEQUENCE: 27

Trp Thr Pro Glu Pro Leu Leu Gln Pro Leu Ser His Pro Leu Pro Pro
1               5                   10                  15

Ala His Pro Leu Gly Gln Gln Arg Leu
            20                  25

<210> SEQ ID NO 28
<211> LENGTH: 20
<212> TYPE: PRT
<213> ORGANISM: Homo sapiens

<400> SEQUENCE: 28

Leu Asp Gly Arg Gln Ser Asp Ala Leu Thr His Leu Glu Ala Gly Thr
1               5                   10                  15

Trp Val Gly Ile
            20
```

<210> SEQ ID NO 29
<211> LENGTH: 71
<212> TYPE: PRT
<213> ORGANISM: Homo sapiens

<400> SEQUENCE: 29

Ser Leu Pro Ser Ser Gly Ala Leu Ser Lys Glu Leu Gly Met Gln
1               5                   10                  15

Ala Gly Cys Leu Gly Leu Trp Ala Gln Pro Gly Pro Cys Ala Pro Ser
                20                  25                  30

Gly His Gly Met Cys Gly Pro Val Cys Leu Ser Leu Glu Gly Asp Ser
                35                  40                  45

Asp Ser Leu Cys Ser Ser His Met His Arg Gly Pro Trp Thr Leu Gln
    50                  55                  60

Ser Gly Gly Ser Trp Ala Ser
65                  70

<210> SEQ ID NO 30
<211> LENGTH: 48
<212> TYPE: PRT
<213> ORGANISM: Homo sapiens

<400> SEQUENCE: 30

Asn Leu Arg Gly Arg Ala Ala Thr Lys Val Lys Met Gly Thr Gln Met
1               5                   10                  15

Ile His Glu Phe Ala Leu Val Ser Leu Ala Gln Val Val Cys Ala Asn
                20                  25                  30

His Val Cys Leu His Ser Ser Val Leu Pro Cys Val Leu Asn Lys Lys
                35                  40                  45

<210> SEQ ID NO 31
<211> LENGTH: 100
<212> TYPE: PRT
<213> ORGANISM: Homo sapiens

<400> SEQUENCE: 31

Gly Pro Ala Pro Pro Arg Pro Ala Pro Ala Gly Pro Ala Pro Pro Arg
1               5                   10                  15

Pro Ala Pro Ala Ala Leu Pro Met Gly Ala Val Phe Lys Asp Thr Arg
                20                  25                  30

Ala Pro Ser Pro Pro Gly Ala Pro Leu Lys Met Glu Arg Gly Leu Arg
                35                  40                  45

Ile Ser Val Ser Leu Gly Ala Cys Leu Gly Ser Pro Ser Leu Thr Phe
    50                  55                  60

Pro His Ser His Ser Leu Ser Leu Pro Leu Cys Leu Leu Leu Pro Val
65                  70                  75                  80

Cys Thr Ile Pro Leu Pro Gly Ile Lys Ala Gln Gly Thr Ser Gly Glu
                85                  90                  95

His Tyr Cys Ser
            100

<210> SEQ ID NO 32
<211> LENGTH: 16
<212> TYPE: PRT
<213> ORGANISM: Homo sapiens

<400> SEQUENCE: 32

Gly Thr Ser Pro Pro Val Asp Leu Lys Asp Glu Gly Trp Asp Phe Met
1               5                   10                  15

<210> SEQ ID NO 33
<211> LENGTH: 1812
<212> TYPE: DNA
<213> ORGANISM: Homo sapiens

<400> SEQUENCE: 33

```
tagctaggca ggaagtcggc gcgggcggcg cggacagtat ctgtgggtac ccggagcacg      60
gagatctcgc cggctttacg ttcacctcgg tgtctgcagc accctccgct tcctctccta     120
ggcgacgaga cccagtggct agaagttcac catgtctatt ctcaagatcc atgccaggga     180
gatctttgac tctcgcggga atcccactgt tgaggttgat ctcttcacct caaaaggtct     240
cttcagagct gctgtgccca gtggtgcttc aactggtatc tatgaggccc tagagctccg     300
ggacaatgat aagactcgct atatggggaa gggtgtctca aaggctgttg agcacatcaa     360
taaaactatt gcgcctgccc tggttagcaa gaaactgaac gtcacagaac aagaagat       420
tgacaaactg atgatcgaga tggatggaac agaaaataaa tctaagtttg gtgcgaacgc     480
cattctgggg gtgtcccttg ccgtctgcaa agctggtgcc gttgagaagg gggtccccct     540
gtaccgccac atcgctgact ggctggcaa ctctgaagtc atcctgccag tcccggcgtt      600
caatgtcatc aatggcggtt ctcatgctgg caacaagctg ccatgcagg agttcatgat      660
cctcccagtc ggtgcagcaa acttcaggga agccatgcgc attggagcag aggtttacca    720
caacctgaag aatgtcatca aggagaaata tgggaaagat gccaccaatg tggggatga     780
aggcgggttt gctcccaaca tcctggagaa taagaaggc ctggagctgc tgaagactgc      840
tattgggaaa gctggctaca ctgataaggt ggtcatcggc atggacgtag cggcctccga    900
gttcttcagg tctgggaagt atgacctgga cttcaagtct cccgatgacc cagcaggta     960
catctcgcct gaccagctgg ctgacctgta caagtccttc atcaaggact acccagtggt    1020
gtctatcgaa gatcccttg accaggatga ctggggagct tggcagaagt tcacagccag    1080
tgcaggaatc caggtagtgg gggatgatct cacagtgacc aacccaaaga ggatcgccaa    1140
ggccgtgaac gagaagtcct gcaactgcct cctgctcaaa gtcaaccaga ttggctccgt    1200
gaccgagtct cttcaggcgt gcaagctggc ccaggccaat ggttggggcg tcatggtgtc    1260
tcatcgttcg ggggagactg aagatacctt catcgctgac ctggttgtgg ggctgtgcac    1320
tgggcagatc aagactggtg ccccttgccg atctgagcgc ttggccaagt acaaccagct    1380
cctcagaatt gaagaggagc tgggcagcaa ggctaagttt gccggcagga acttcagaaa    1440
cccccttggcc aagtaagctg tgggcaggca agcccttcgg tcacctgttg gctacacaga   1500
ccccctcccct cgtgtcagct caggcagctc gaggccccg accaacactt gcagggtcc     1560
ctgctagtta gcgccccacc gccgtggagt tcgtaccgct tccttagaac ttctacagaa    1620
gccaagctcc ctggagccct gttggcagct ctagctttgc agtcgtgtaa ttggcccaag    1680
tcattgtttt tctcgcctca cttttccacca agtgtctaga gtcatgtgag cctcgtgtca    1740
tctccggggt ggccacaggc tagatccccg gtggttttgt gctcaaaata aaaagcctca    1800
gtgacccatg ag                                                        1812
```

<210> SEQ ID NO 34
<211> LENGTH: 1228
<212> TYPE: DNA
<213> ORGANISM: Homo sapiens

<400> SEQUENCE: 34

```
ataagagacc acaagcgacc cgcagggcca gacgttcttc gccgagagtc gtcggggttt      60
```

```
cctgcttcaa cagtgcttgg acggaacccg gcgctcgttc cccacccegg ccggccgccc    120 atagccagcc ctccgtcacc tcttcaccgc accctcggac tgccccaagg ccccegccgc    180 cgctccagcg ccgcgcagcc accgccgccg ccgccgcctc ccttagtcg ccgccatgac      240 gaccgcgtcc acctcgcagg tgcgccagaa ctaccaccag gactcagagg ccgccatcaa    300
ccgccagatc aacctggagc tctacgcctc ctacgtttac ctgtccatgt cttactactt    360
tgaccgcgat gatgtggctt tgaagaactt tgccaaatac tttcttcacc aatctcatga    420
ggagagggaa catgctgaga aactgatgaa gctgcagaac caacgaggtg ccgaatctt     480 ccttcaggat atcaagaaac cagactgtga tgactgggag agcgggctga atgcaatgga    540
gtgtgcatta catttgggaa aaaatgtgaa tcagtcacta ctggaactgc acaaactggc    600
cactgacaaa aatgaccccc atttgtgtga cttcattgag acacattacc tgaatgagca    660
ggtgaaagcc atcaaagaat tgggtgacca cgtgaccaac ttgcgcaaga tgggagcgcc    720
cgaatctggc ttggcggaat atctctttga caagcacacc ctgggagaca gtgataatga    780
aagctaagcc tcgggctaat ttccccatag ccgtggggtg acttccctgg tcaccaaggc    840
agtgcatgca tgttggggtt tccttacct tttctataag ttgtaccaaa acatccactt     900
aagttctttg atttgtacca ttccttcaaa taaagaaatt tggtacccag gtgttgtctt    960
tgaggtcttg ggatgaatca gaaatctatc caggctatct tccagattcc ttaagtgccg   1020
ttgttcagtt ctaatcacac taatcaaaaa gaaacgagta tttgtattta ttaaactcat    1080
tagtttgggc agtatactaa ggtgtggctg tcttggattc agatagaact aagggttccc    1140
gactctgaat ccagagtctg agttaaatgt ttccaatggt tcagtctagc tttcacagtt    1200
tttatgaata aaaggcatta aaggctga                                       1228
```

<210> SEQ ID NO 35
<211> LENGTH: 870
<212> TYPE: DNA
<213> ORGANISM: Homo sapiens

<400> SEQUENCE: 35

```
gcagttcggc ggtcccgcgg gtctgtctct tgcttcaaca gtgtttggac ggaacagatc      60
cggggactct cttccagcct ccgaccgccc tccgatttcc tctccgcttg caacctccgg    120
gaccatcttc tcggccatct cctgcttctg ggacctgcca gcaccgtttt tgtggttagc    180
tccttcttgc caaccaacca tgagctccca gattcgtcag aattattcca ccgacgtgga    240
ggcagccgtc aacagcctgg tcaatttgta cctgcaggcc tcctacacct acctctctct    300
gggcttctat ttcgaccgcg atgatgtggc tctggaaggc gtgagccact tcttccgcga    360
attggccgag gagaagcgcg agggctacga gcgtctcctg aagatgcaaa accagcgtgg    420
cggccgcgct ctcttccagg acatcaagaa gccagctgaa gatgagtggg gtaaaacccc    480
agacgccatg aaagctgcca tggccctgga gaaaaagctg aaccaggccc ttttggatct    540
tcatgccctg ggttctgccc gcacggaccc ccatctctgt gacttcctgg agactcactt    600
cctagatgag gaagtgaagc ttatcaagaa gatgggtgac cacctgacca acctccacag    660
gctgggtggc ccggaggctg ggctgggcga gtatctcttc gaaaggctca ctctcaagca    720
cgactaagag ccttctgagc ccagcgactt ctgaagggcc ccttgcaaag taatagggct    780
tctgcctaag cctctcccte cagccaatag gcagctttct taactatcct aacaagcctt    840
ggaccaaatg gaaataaagc tttttgatgc                                      870
```

```
<210> SEQ ID NO 36
<211> LENGTH: 1310
<212> TYPE: DNA
<213> ORGANISM: Homo sapiens

<400> SEQUENCE: 36
aaattgagcc cgcagcctcc cgcttcgctc tctgctcctc ctgttcgaca gtcagccgca      60
tcttcttttg cgtcgccagc cgagccacat cgctcagaca ccatggggaa ggtgaaggtc     120
ggagtcaacg gatttggtcg tattgggcgc ctggtcacca gggctgcttt taactctggt     180
aaagtggata ttgttgccat caatgacccc ttcattgacc tcaactacat ggtttacatg     240
ttccaatatg attccaccca tggcaaattc catggcaccg tcaaggctga aacgggaag     300 cttgtcatca atggaaatcc catcaccatc ttccaggagc gagatccctc caaaatcaag     360
tggggcgatg ctggcgctga gtacgtcgtg gagtccactg gcgtcttcac caccatggag     420
aaggctgggg ctcatttgca gggggagcc aaaagggtca tcatctctgc ccctctgct     480 gatgccccca tgttcgtcat gggtgtgaac catgagaagt atgacaacag cctcaagatc     540
atcagcaatg cctcctgcac caccaactgc ttagcacccc tggccaaggt catccatgac     600
aactttggta tcgtggaagg actcatgacc acagtccatg ccatcactgc cacccagaag     660
actgtggatg gcccctccgg gaaactgtgg cgtgatggcc gcgggctct ccagaacatc     720 atccctgcct ctactggcgc tgccaaggct gtgggcaagg tcatccctga ctgaacggg     780 aagctcactg gcatggcctt ccgtgtcccc actgccaacg tgtcagtggt ggacctgacc     840
tgccgtctag aaaaacctgc caaatatgat gacatcaaga aggtggtgaa gcaggcgtcg     900
gagggccccc tcaagggcat cctgggctac actgagcacc aggtggtctc ctctgacttc     960
aacagcgaca cccactcctc cacctttgac gctggggctg gcattgccct caacgaccac    1020
tttgtcaagc tcatttcctg gtatgacaac gaatttggct acagcaacag ggtggtggac    1080
ctcatggccc acatggcctc caaggagtaa gaccccctgga ccaccagccc cagcaagagc    1140
acaagaggaa gagagagacc ctcactgctg gggagtccct gccacactca gtccccccacc    1200 acactgaatc tcccctcctc acagttgcca tgtagacccc ttgaagaggg gaggggccta    1260
gggagccgca ccttgtcatg taccatcaat aaagtaccct gtgctcaacc                1310

<210> SEQ ID NO 37
<211> LENGTH: 2260
<212> TYPE: DNA
<213> ORGANISM: Homo sapiens

<400> SEQUENCE: 37
ctcattgaac tcgcctgcag ctcttgggtt ttttgtggct tccttcgtta ttggagccag      60
gcctacaccc cagcaaccat gtccaaggga cctgcagttg gtattgatct ggcaccacc     120 tactcttgtg tgggtgtttt ccagcacgga aaagtcgaga taattgccaa tgatcaggga     180
aaccgaacca ctccaagcta tgtcgccttt acggacactg aacggttgat cggtgatgcc     240
gcaaagaatc aagttgcaat gaaccccacc aacacagttt ttgatgccaa acgtctgatt     300
ggacgcagat ttgatgatgc tgttgtccag tctgatatga aacattggcc ctttatggtg     360
gtgaatgatg ctggcaggcc caaggtccaa gtagaataca agggagagac caaaagcttc     420
tatccagagg aggtgtcttc tatggttctg acaaagatga aggaaattgc agaagcctac     480
cttgggaaga ctgttaccaa tgctgtggtc acagtgccag cttactttaa tgactctcag     540
cgtcaggcta ccaaagatgc tggaactatt gctggtctca atgtacttag aattattaat     600
gagccaactg ctgctgctat tgcttacggc ttagacaaaa aggttggagc agaaagaaac     660
```

```
gtgctcatct tgacctggg aggtggcact tttgatgtgt caatcctcac tattgaggat      720
ggaatctttg aggtcaagtc tacagctgga gacacccact tgggtggaga agattttgac    780
aaccgaatgg tcaaccattt tattgctgag tttaagcgca agcataagaa ggacatcagt    840
gagaacaaga gagctgtaag acgcctccgt actgcttgtg aacgtgctaa gcgtaccctc    900
tcttccagca cccaggccag tattgagatc gattctctct atgaaggaat cgacttctat    960
acctccatta cccgtgcccg atttgaagaa ctgaatgctg acctgttccg tggcaccctg   1020
gacccagtag agaaagccct tcgagatgcc aaactagaca agtcacagat tcatgatatt   1080
gtcctggttg gtggttctac tcgtatcccc aagattcaga agcttctcca agacttcttc   1140
aatggaaaag aactgaataa gagcatcaac cctgatgaag ctgttgctta tggtgcagct   1200
gtccaggcag ccatcttgtc tggagacaag tctgagaatg ttcaagattt gctgctcttg   1260
gatgtcactc ctcttttccct tggtattgaa actgctggtg gagtcatgac tgtcctcatc   1320
aagcgtaata ccaccattcc taccaagcag acacagacct tcactaccta ttctgacaac   1380
cagcctggtg tgcttattca ggtttatgaa ggcgagcgtg ccatgacaaa ggataacaac   1440
ctgcttggca agtttgaact cacaggcata cctcctgcac cccgaggtgt tcctcagatt   1500
gaagtcactt ttgacattga tgccaatggt atactcaatg tctctgctgt ggacaagagt   1560
acgggaaaag agaacaagat tactatcact aatgacaagg gccgtttgag caaggaagac   1620
attgaacgta tggtccagga agctgagaag tacaaagctg aagatgagaa gcagagggac   1680
aaggtgtcat ccaagaattc acttgagtcc tatgccttca acatgaaagc aactgttgaa   1740
gatgagaaac ttcaaggcaa gattaacgat gaggacaaac agaagattct ggacaagtgt   1800
aatgaaatta tcaactggct tgataagaat cagactgctg agaaggaaga atttgaacat   1860
caacagaaag agctggagaa agtttgcaac cccatcatca ccaagctgta ccagagtgca   1920
ggaggcatgc caggaggaat gcctggggga tttcctggtg gtggagctcc tccctctggt   1980
ggtgcttcct cagggcccac cattgaagag gttgattaag ccaaccaagt gtagatgtag   2040
cattgttcca cacattttaaa acatttgaag gacctaaatt cgtagcaaat tctgtggcag   2100
ttttaaaaag ttaagctgct atagtaagtt actgggcatt ctcaatactt gaatatggaa   2160
catatgcaca ggggaaggaa ataacattgc actttataaa cactgtattg taagtggaaa   2220
atgcaatgtc ttaaataaaa ctatttaaaa ttggcaccat                          2260
```

<210> SEQ ID NO 38
<211> LENGTH: 890
<212> TYPE: DNA
<213> ORGANISM: Homo sapiens

<400> SEQUENCE: 38

```
tttcctttct ctctcctccc gccgcccaag atgccgaaag gaagaaggc caagggaaag       60 aaggtggctc cggccccagc tgtcgtgaag aagcaggagg ctaagaaagt ggtgaatccc    120
ctgtttgaga aaaggcctaa gaattttggc attggacagg acatccagcc caaaagagac    180
ctcacccgct ttgtgaaatg gccccgctat atcaggttgc agcggcagag agccatcctc    240
tataagcggc tgaaagtgcc tcctgcgatt aaccagttca cccaggccct ggaccgccaa    300
acagctactc agctgcttaa gctggcccac aagtacagac cagagacaaa gcaagagaag    360
aagcagagac tgttggcccg ggccgagaag aaggctgctg caaagggga cgtcccaacg    420 aagagaccac ctgtccttcg agcaggagtt aacaccgtca ccaccttggt ggagaacaag    480
aaagctcagc tggtggtgat tgcacacgac gtggatccca tcgagctggt tgtcttcttg    540
```

```
cctgccctgt gtcgtaaaat gggggtccct tactgcatta tcaagggaaa ggcaagactg      600
ggacgtctag tccacaggaa gacctgcacc actgtcgcct tcacacaggt gaactcggaa      660
gacaaaggcg cttttggctaa gctggtggaa gctatcagga ccaattacaa tgacagatac     720
gatgagatcc gccgtcactg gggtggcaat gtcctgggtc ctaagtctgt ggctcgtatc      780
gccaagctcg aaaaggcaaa ggctaaagaa cttgccacta aactgggtta aatgtacact      840
gttgagtttt ctgtacataa aaataattga ataatacaa  attttccttc                 890

<210> SEQ ID NO 39
<211> LENGTH: 955
<212> TYPE: DNA
<213> ORGANISM: Homo sapiens

<400> SEQUENCE: 39
gggcggagca gctgaaaatc cggcgcgcgc agtctccagc cccaatttct acgcgcaccg       60
gaagacggag gtcctctttc cttgcctaac gcagccatgg ctcgtggtcc caagaagcat      120
ctgaagcggg tggcagctcc aaagcattgg atgctggata aattgaccgg tgtgtttgct      180
cctcgtccat ccaccggtcc ccacaagttg agagagtgtc tcccctcat  cattttcctg      240 aggaacagac ttaagtatgc cctgacagga gatgaagtaa agaagatttg catgcagcgg      300
ttcattaaaa tcgatggcaa ggtccgaact gatataacct accctgctgg attcatggat      360
gtcatcagca ttgacaagac gggagagaat ttccgtctga tctatgacac caagggtcgc      420
tttgctgtac atcgtattac acctgaggag gccaagtaca agttgtgcaa agtgagaaag      480
atctttgtgg gcacaaaagg aatccctcat ctggtgactc atgatgcccg caccatccgc      540
taccccgatc ccctcatcaa ggtgaatgat accattcaga ttgatttgga gactggcaag      600
attactgatt tcatcaagtt cgacactggt aacctgtgta tggtgactgg aggtgctaac      660
ctaggaagaa ttggtgtgat caccaacaga gagaggcacc ctggatcttt tgacgtggtt      720
cacgtgaaag atgccaatgg caacagcttt gccactcgac tttccaacat ttttgttatt      780
ggcaagggca acaaaccatg gatttctctt ccccgaggaa agggtatccg cctcaccatt      840
gctgaagaga gagacaaaag actggcggcc aaacagagca gtgggtgaaa tgggtccctg      900
ggtgacatgt cagatctttg tacgtaatta aaaatattgt ggcaggatta atagc          955

<210> SEQ ID NO 40
<211> LENGTH: 829
<212> TYPE: DNA
<213> ORGANISM: Homo sapiens

<400> SEQUENCE: 40
cctcttttcc gtggcgcctc ggaggcgttc agctgcttca agatgaagct gaacatctcc       60
ttcccagcca ctggctgcca gaaactcatt gaagtggacg atgaacgcaa acttcgtact      120
ttctatgaga agcgtatggc cacagaagtt gctgctgacg ctctgggtga agaatggaag      180
ggttatgtgg tccgaatcag tggtgggaac gacaaacaag gtttccccat gaagcagggt      240
gtcttgaccc atggccgtgt ccgcctgcta ctgagtaagg ggcattcctg ttacagacca      300
aggagaactg gagaaagaaa gagaaaatca gttcgtggtt gcattgtgga tgcaaatctg      360
agcgttctca acttggttat tgtaaaaaaa ggagagaagg atattcctgg actgactgat      420
actacagtgc ctcgccgcct gggccccaaa gagctagca  gaatccgcaa actttttcaat     480 ctctctaaag aagatgatgt ccgccagtat gttgtaagaa agcccttaaa taagaaaggt      540
aagaaaccta ggaccaaagc acccaagatt cagcgtcttg ttactccacg tgtcctgcag      600
```

```
cacaaacggc ggcgtattgc tctgaagaag cagcgtacca agaaaaataa agaagaggct    660
gcagaatatg ctaaactttt ggccaagaga atgaaggagg ctaaggagaa gcgccaggaa    720
caaattgcga agagacgcag actttcctct ctgcgagctt ctacttctaa gtctgaatcc    780
agtcagaaat aagattttt gagtaacaaa taaataagat cagactctg              829
```

<210> SEQ ID NO 41
<211> LENGTH: 627
<212> TYPE: DNA
<213> ORGANISM: Homo sapiens

<400> SEQUENCE: 41

```
acaactcggt ggtggccact gcgcagacca gacttcgctc gtactcgtgc gcctcgcttc     60
gcttttcctc cgcaaccatg tctgacaaac ccgatatggc tgagatcgag aaattcgata    120
agtcgaaact gaagaagaca gagacgcaag agaaaaatcc actgccttcc aaagaaacga    180
ttgaacagga gaagcaagca ggcgaatcgt aatgaggcgt gcgccgccaa tatgcactgt    240
acattccaca agcattgcct tcttatttta cttctttag ctgtttaact ttgtaagatg    300
caaagaggtt ggatcaagtt taaatgactg tgctgcccct ttcacatcaa agaactactg    360
acaacgaagg ccgcgcctgc ctttcccatc tgtctatcta tctggctggc agggaaggaa    420
agaacttgca tgttggtgaa ggaagaagtg gggtggaaga agtggggtgg acgacagtg    480 aaatctagag taaaaccaag ctggcccaag gtgtcctgca ggctgtaatg cagtttaatc    540
agagtgccat tttttttttt gttcaaatga ttttaattat tggaatgcac aatttttta    600 atatgcaaat aaaagtttta aaaactt                                       627
```

<210> SEQ ID NO 42
<211> LENGTH: 830
<212> TYPE: DNA
<213> ORGANISM: Homo sapiens

<400> SEQUENCE: 42

```
ccccccgag cgccgctccg gctgcaccgc gctcgctccg agtttcaggc tcgtgctaag     60
ctagcgccgt cgtcgtctcc cttcagtcgc catcatgatt atctaccggg acctcatcag    120
ccacgatgag atgttctccg acatctacaa gatccgggag atcgcggacg ggttgtgcct    180
ggaggtggag gggaagatgg tcagtaggac agaaggtaac attgatgact cgctcattgg    240
tggaaatgcc tccgctgaag gccccgaggg cgaaggtacc gaaagcacag taatcactgg    300
tgtcgatatt gtcatgaacc atcacctgca ggaaacaagt ttcacaaaag aagcctacaa    360
gaagtacatc aaagattaca tgaaatcaat caagggaaa cttgaagaac agagaccaga    420
aagagtaaaa ccttttatga caggggctgc agaacaaatc aagcacatcc ttgctaattt    480
caaaaactac cagttcttta ttggtgaaaa catgaatcca gatggcatgg ttgctctatt    540
ggactaccgt gaggatggtg tgaccccata tatgattttc tttaaggatg gtttagaaat    600 ggaaaatgt taacaaatgt ggcaattatt ttgatctat cacctgtcat cataactggc    660
ttctgcttgt catccacaca acaccaggac ttaagacaaa tgggactgat gtcatcttga    720
gctcttcatt tattttgact gtgattatt tggagtggag gcattgtttt taagaaaaac    780
atgtcatgta ggttgtctaa aaataaaatg catttaaact catttgagag              830
```

<210> SEQ ID NO 43
<211> LENGTH: 1847
<212> TYPE: DNA
<213> ORGANISM: Homo sapiens

<400> SEQUENCE: 43

```
gtccccgcgc cagagacgca gccgcgctcc caccacccac acccaccgcg ccctcgttcg      60
cctcttctcc gggagccagt ccgcgccacc gccgccgccc aggccatcgc caccctccgc     120
agccatgtcc accaggtccg tgtcctcgtc ctcctaccgc aggatgttcg gcggcccggg     180
caccgcgagc cggccgagct ccagccggag ctacgtgact acgtccaccc gcacctacag     240
cctgggcagc gcgctgcgcc ccagcaccag ccgcagcctc tacgcctcgt ccccgggcgg     300
cgtgtatgcc acgcgctcct ctgccgtgcg cctgcggagc agcgtgcccg gggtgcggct     360
cctgcaggac tcggtggact ctcgctggcc gacgccatc  aacaccgagt tcaagaacac     420
ccgcaccaac gagaaggtgg agctgcagga gctgaatgac cgcttcgcca actacatcga     480
caaggtgcgc ttcctggagc agcagaataa gatcctgctg gccgagctcg agcagctcaa     540
gggccaaggc aagtcgcgcc tggggggacct ctacgaggag gagatgcggg agctgcgccg     600
gcaggtggac cagctaacca acgacaaagc ccgcgtcgag gtggagcgcg acaacctggc     660
cgaggacatc atgcgcctcc gggagaaatt gcaggaggag atgcttcaga gagaggaagc     720
cgaaaacacc ctgcaatctt tcagacagga tgttgacaat gcgtctctgg cacgtcttga     780
ccttgaacgc aaagtggaat cttttgcaaga agagattgcc ttttttgaaga aactccacga     840
agaggaaatc caggagctgc aggctcagat tcaggaacag catgtccaaa tcgatgtgga     900
tgtttccaag cctgacctca cggctgccct gcgtgacgta cgtcagcaat atgaaagtgt     960
ggctgccaag aacctgcagg aggcagaaga atggtacaaa tccaagtttg ctgacctctc    1020
tgaggctgcc aaccggaaca atgacgccct gcgccaggca aagcaggagt ccactgagta    1080
ccggagacag gtgcagtccc tcacctgtga agtggatgcc cttaaaggaa ccaatgagtc    1140
cctggaacgc cagatgcgtg aaatggaaga gaactttgcc gttgaagctg ctaactacca    1200
agacactatt ggccgcctgc aggatgagat tcagaatatg aaggaggaaa tggctcgtca    1260
ccttcgtgaa taccaagacc tgctcaatgt taagatggcc cttgacattg agattgccac    1320
ctacaggaag ctgctggaag gcgaggagag caggatttct ctgcctcttc caaactttc    1380
ctccctgaac ctgagggaaa ctaatctgga ttcactccct ctggttgata cccactcaaa    1440
aaggacactt ctgattaaga cggttgaaac tagagatgga caggttatca acgaaacttc    1500
tcagcatcac gatgaccttg aataaaaatt gcacacactc agtgcagcaa tatattacca    1560
gcaagaataa aaagaaatc catatcttaa agaaacagct tcaagtgcc tttctgcagt     1620
ttttcaggag cgcaagatag atttggaata ggaataagct ctagttctta acaaccgaca    1680
ctcctacaag atttagaaaa aagtttacaa cataatctag tttacagaaa atcttgtgc     1740
tagaatactt tttaaaaggt attttgaata ccattaaaac tgcttttttt tttccagcaa    1800
gtatccaacc aacttggttc tgcttcaata aatctttgga aaaactc                   1847
```

<210> SEQ ID NO 44
<211> LENGTH: 2215
<212> TYPE: DNA
<213> ORGANISM: Homo sapiens

<400> SEQUENCE: 44

```
agcttttctc ttctgtcaac cccacacgcc tttggcacaa tgaagtgggt aacctttatt      60
tccccttcttt ttctctttag ctcggcttat tccaggggtg tgtttcgtcg agatgcacac    120
aagagtgagg ttgctcatcg gtttaaagat ttgggagaag aaaatttcaa agccttggtg    180
ttgattgcct ttgctcagta tcttcagcag tgtccatttg aagatcatgt aaaattagtg    240
```

```
aatgaagtaa ctgaatttgc aaaaacatgt gttgctgatg agtcagctga aaattgtgac    300
aaatcacttc ataccctttt tggagacaaa ttatgcacag ttgcaactct tcgtgaaacc    360
tatggtgaaa tggctgactg ctgtgcaaaa caagaacctg agagaaatga atgcttcttg    420
caacacaaag atgacaaccc aaacctcccc cgattggtga gaccagaggt tgatgtgatg    480
tgcactgctt ttcatgacaa tgaagagaca tttttgaaaa aatacttata tgaaattgcc    540
agaagacatc cttactttta tgccccggaa ctccttttct ttgctaaaag gtataaagct    600
gcttttacag aatgttgcca agctgctgat aaagctgcct gcctgttgcc aaagctcgat    660
gaacttcggg atgaagggaa ggcttcgtct gccaaacaga gactcaagtg tgccagtctc    720
caaaaatttg agaaagagc tttcaaagca tgggcagtag ctcgcctgag ccagagattt    780
cccaaagctg agtttgcaga gtttccaag ttagtgacag atcttaccaa agtccacacg    840
gaatgctgcc atggagatct gcttgaatgt gctgatgaca gggcggacct tgccaagtat    900
atctgtgaaa atcaagattc gatctccagt aaactgaagg aatgctgtga aaaacctctg    960
ttggaaaaat cccactgcat tgccgaagtg gaaaatgatg agatgcctgc tgacttgcct    1020
tcattagctg ctgattttgt tgaaagtaag gatgtttgca aaaactatgc tgaggcaaag    1080
gatgtcttcc tgggcatgtt tttgtatgaa tatgcaagaa ggcatcctga ttactctgtc    1140
gtgctgctgc tgagacttgc caagacatat gaaaccactc tagagaagtg ctgtgccgct    1200
gcagatcctc atgaatgcta tgccaaagtg ttcgatgaat ttaaacctct tgtggaagag    1260
cctcagaatt taatcaaaca aaattgtgag cttttgagc agcttggaga gtacaaattc    1320
cagaatgcgc tattagttcg ttacaccaag aaagtacccc aagtgtcaac tccaactctt    1380
gtagaggtct caagaaacct aggaaaagtg ggcagcaaat gttgtaaaca tcctgaagca    1440
aaaagaatgc cctgtgcaga agactatcta tccgtggtcc tgaaccagtt atgtgtgttg    1500
catgagaaaa cgccagtaag tgacagagtc accaaatgct gcacagaatc cttggtgaac    1560
aggcgaccat gcttttcagc tctggaagtc gatgaaacat acgttcccaa agagtttaat    1620
gctgaaacat tcaccttcca tgcagatata tgcacacttt ctgagaagga gagacaaatc    1680
aagaaacaaa ctgcacttgt tgagctcgtg aaacacaagc ccaaggcaac aaaagagcaa    1740
ctgaaagctg ttatggatga tttcgcagct tttgtagaga agtgctgcaa ggctgacgat    1800
aaggagacct gctttgccga ggagggtaaa aaacttgttg ctgcaagtca agctgcctta    1860
ggcttataac atctacattt aaaagcatct cagcctacca tgagaataag agaaagaaaa    1920
tgaagatcaa aagcttattc atctgttttc tttttcgttg gtgtaaagcc aacaccctgt    1980
ctaaaaaaca taaatttctt taatcatttt gcctcttttc tctgtgcttc aattaataaa    2040
aaatggaaag aatctaatag agtggtacag cactgttatt tttcaaagat gtgttgctat    2100
cctgaaaatt ctgtaggttc tgtggaagtt ccagtgttct ctcttattcc acttcggtag    2160
aggatttcta gtttctgtgg gctaattaaa taaatcacta atactcttct aagtt         2215
```

<210> SEQ ID NO 45
<211> LENGTH: 2303
<212> TYPE: DNA
<213> ORGANISM: Homo sapiens

<400> SEQUENCE: 45

```
cctagcttgg cgcggaatcc gtgaattgcc cgcggcccga gggtgcagct cccggactga     60
ctggctctgc ccttccccat ggacgcctcc tctagcccgt ggaatccaac cccggctcct    120
gtcagcagcc ctcccctgct gctccccatc cctgccatcg tcttcatcgc tgtgggcatc    180
```

```
tatttgttgc tgctgggtct agtcctgctg actaggaact gcctgctggc ccagggctgc    240
tgcgcggacg gtagctcccc ctgcaggaag caaggttcct ccgggccccc agactgctgc    300
tggacctgtg cagaagcctg caactttcct ctgcctagcc cggcccactt cctggatgct    360
tgctgccccc agcccaccag agctgactgg gcacctcgct gccccgctg ctgcccactc     420 tgcgactgtg cctgtacgtg ccagctcccc gactgccaga gctcaactg tctctgcttc     480 gagatcaagc tccgatgagg acccagggcc cctgccctct ggggagcggc cagcccccag    540
ggcccatgtg ccctcctccc tgaagagcct ttccccacgc cactggaacc acagatggcc    600
tgccgagcac ccaggcctgg gaactggaag tggcagcgca gggcctggct ccctgcaggg    660
caggactctt ggccggctgg acggcagctc tctggaggg ccagaaaaga gaggggctag     720
tgctcgggca ggtgccctgg cttcccttcc cctccacacg tcaacgattc tatttgaagt    780 tggggcagggg ggtggcgctg ctcaccacac acaagtgtta taggaggagt ctggcccttg    840
agtaccgggt acgcaggggt gcctcaacca cactccgtcc acggactctc cgttatttta    900
ggaggtccct ggccaaagat ttatttctct tgacaaccaa gggcctccgt ctggatttcc    960
aaggaagaat ttcctctgaa gcaccggaac ttgctactac cagcaccatg ccctaccaat    1020
atccagcact gaccccggag cagaagaagg agctgtctga catcgctcac cgcatcgtgg    1080
cacctggcaa gggcatcctg gctgcagatg agtccactgg gagcattgcc aagcggctgc    1140
agtccattgg caccgagaac accgaggaga accggcgctt ctaccgccag ctgctgctga    1200
cagctgacga ccgcgtgaac ccctgcattg ggggtgtcat cctcttccat gagacactct    1260
accagaaggc ggatgatggg cgtcccttcc cccaagttat caaatccaag ggcggtgttg    1320
tgggcatcaa ggtagacaag ggcgtggtcc ccctggcagg acaaatggc gagactacca    1380 cccaagggtt ggatgggctg tctgagcgct gtgcccagta caagaaggac ggagctgact    1440
tcgccaagtg gcgttgtgtg ctgaagattg ggaacacac cccctcagcc ctcgccatca    1500
tggaaaatgc caatgttctg gcccgttatg ccagtatctg ccagcagaat ggcattgtgc    1560
ccatcgtgga gcctgagatc ctccctgatg gggaccatga cttgaagcgc tgccagtatg    1620
tgaccgagaa ggtgctggct gctgtctaca aggctctgag tgaccaccac atctacctgg    1680
aaggcacctt gctgaagccc aacatggtca ccccaggcca tgcttgcact cagaagtttt    1740
ctcatgagga gattgccatg gcgaccgtca cagcgctgcg ccgcacagtg ccccccgctg    1800
tcactgggat caccttcctg tctggaggcc agagtgagga ggaggcgtcc atcaacctca    1860
atgccattaa caagtgcccc ctgctgaagc cctgggccct gaccttctcc tacggccgag    1920
ccctgcaggc ctctgccctg aaggcctggg gcgggaagaa ggagaacctg aaggctgcgc    1980
aggaggagta tgtcaagcga gccctggcca acagccttgc ctgtcaagga agtacactc    2040 cgagcggtca ggctggggct gctgccagcg agtccctctt cgtctctaac cacgcctatt    2100
aagcggaggt gttcccaggc tgcccccaac actccaggcc ctgcccctc ccactcttga    2160 agaggaggcc gcctcctcgg ggctccaggc tggcttgccc gcgctctttc ttccctcgtg    2220
acagtggtgt gtggtgtcgt ctgtgaatgc taagtccatc acccttccg gcacactgcc    2280 aaataaacag ctatttaagg ggg                                           2303
```

<210> SEQ ID NO 46
<211> LENGTH: 1945
<212> TYPE: DNA
<213> ORGANISM: Homo sapiens

<400> SEQUENCE: 46

```
tctggcattg caagcctcgc ttcgttgcca cttcccagct cttcccgcct tccgcggtat      60
aatcaacact acgagagata gagccgccta gaaccagtcc ggaggctgcg gctgcagaag     120
taccgcctgc ggagtaactg caaagatgct gtccgtgcgc gttgctgcgg ccgtggtccg     180
cgcccttcct cggcgggccg gactggtctc cagaaatgct ttgggttcat ctttcattgc     240
tgcaaggaac ttccatgcct ctaacactca tcttcaaaag actgggactg ctagatgtc      300
ctctattctt gaagagcgta ttcttggagc tgatacctct gttgatcttg aagaaactgg     360
gcgtgtctta agtattggtg atggtattgc ccgcgtacat gggctgagga atgttcaagc     420
agaagaaatg gtagagtttt cttcaggctt aaagggtatg tccttgaact tggaacctga     480
caatgttggt gttgtcgtgt ttggaaatga taaactaatt aaggaaggag atatagtgaa     540
gaggacagga gccattgtgg acgttccagt tggtgaggag ctgttgggtc gtgtagttga     600
tgcccttggt aatgctattg atggaaaggg tccaattggt tccaagacgc gtaggcgagt     660
tggtctgaaa gcccccggta tcattcctcg aatttcagtg cgggaaccaa tgcagactgg     720
cattaaggct gtggatagct tggtgccaat tggtcgtggt cagcgtgaac tgattattgg     780
tgaccgacag actgggaaaa cctcaattgc tattgacaca atcattaacc agaaacgttt     840
caatgatgga tctgatgaaa agaagaagct gtactgtatt tatgttgcta ttggtcaaaa     900
gagatccact gttgcccagt tggtgaagag acttacagat gcagatgcca tgaagtacac     960
cattgtggtg tcggctacgg cctcgatgc tgccccactt cagtacctgg ctccttactc    1020
tggctgttcc atgggagagt attttagaga caatggcaaa catgctttga tcatctatga    1080
cgacttatcc aaacaggctg ttgcttaccg tcagatgtct ctgttgctcc gccgacccc     1140
tggtcgtgag gcctatcctg tgatgtgtt ctacctacac tcccggttgc tggagagagc    1200
agccaaaatg aacgatgctt ttggtggtgg ctccttgact gctttgccag tcatagaaac    1260
acaggctggt gatgtgtctg cttacattcc aacaaatgtc atttccatca ctgacggaca    1320
gatcttcttg gaaacagaat tgttctacaa aggtatccgc cctgcaatta acgttggtct    1380
gtctgtatct cgtgtcggat ccgctgccca aaccagggct atgaagcagg tagcaggtac    1440
catgaagctg gaattggctc agtatcgtga ggttgctgct tttgcccagt tcggttctga    1500
cctcgatgct gccactcaac aacttttgag tcgtggcgtg cgtctaactg agttgctgaa    1560
gcaaggacag tattctccca tggctattga agaacaagtg gctgttatct atgcgggtgt    1620
aaggggatat cttgataaac tggagcccag caagattaca aagtttgaga atgctttctt    1680
gtctcatgtc gtcagccagc accaagcctt gttgggcact atcagggctg atggaaagat    1740
ctcagaacaa tcagatgcaa agctgaaaga gattgtaaca aatttcttgg ctggatttga    1800
agcttaaaact cctgtggatt cacatcaaat accagttcag ttttgtcatt gttctagtaa    1860
attagttcca tttgtaaaag ggttactctc atactcctta tgtacagaaa tcacatgaaa    1920
aataaaggtt ccataatgca tagtt                                          1945
```

<210> SEQ ID NO 47
<211> LENGTH: 1128
<212> TYPE: DNA
<213> ORGANISM: Homo sapiens

<400> SEQUENCE: 47

```
agtccgagtg gagagagcga gctgagtggt tgtgtggtcg cgtctcggaa accggtagcg      60
cttgcagcat ggctgaccaa ctgactgaag agcagattgc agaattcaaa gaagcttttt     120
cactatttga caaagatggt gatggaacta taacaacaaa ggaattggga actgtaatga     180
```

```
gatctcttgg gcagaatccc acagaagcag agttacagga catgattaat gaagtagatg      240
ctgatggtaa tggcacaatt gacttccctg aatttctgac aatgatggca agaaaaatga      300 aagcacacaga cagtgaagaa gaaattagag aagcattccg tgtgtttgat aaggatggca     360
atggctatat tagtgctgca gaacttcgcc atgtgatgac aaaccttgga gagaagttaa      420
cagatgaaga agttgatgaa atgatcaggg aagcagatat tgatggtgat ggtcaagtaa      480
actatgaaga gtttgtacaa atgatgacag caaagtgaag accttgtaca gaatgtgtta      540
aatttcttgt acaaaattgt ttatttgcct tttctttgtt tgtaacttat ctgtaaaagg      600
tttctcccta ctgtcaaaaa aatatgcatg tatagtaatt aggacttcat tcctccatgt      660
tttcttccct tatcttactg tcattgtcct aaaaccttat tttagaaaat tgatcaagta      720
acatgttgca tgtggcttac tctggatata tctaagccct tctgcacatc taaacttaga      780 tggagtggt caaatgaggg aacatctggg ttatgccttt tttaaagtag ttttctttag       840
gaactgtcag catgttgttg ttgaagtgtg gagttgtaac tctgcgtgga ctatggacag      900
tcaacaatat gtacttaaaa gttgcactat tgcaaaacgg gtgtattatc caggtactcg      960
tacactattt ttttgtactg ctggtcctgt accagaaaca ttttctttta ttgttacttg     1020
ctttttaaac tttgtttagc cacttaaaat ctgcttatgg cacaatttgc ctcaaaatcc     1080
attccaagtt gtatatttgt tttccaataa aaaaattaca atttaccc                  1128

<210> SEQ ID NO 48
<211> LENGTH: 1661
<212> TYPE: DNA
<213> ORGANISM: Homo sapiens

<400> SEQUENCE: 48
tgctgcagcc gctgccgccg attccggatc tcattgccac gcgccccga cgaccgcccg        60 acgtgcattc ccgattcctt ttggttccaa gtccaatatg gcaactctaa aggatcagct     120
gatttataat cttctaaagg aagaacagac cccccagaat aagattacag ttgttggggt     180
tggtgctgtt ggcatggcct gtgccatcag tatcttaatg aaggacttgg cagatgaact     240
tgctcttgtt gatgtcatcg aagacaaatt gaagggagag atgatggatc tccaacatgg     300
cagccttttc cttagaacac caaagattgt ctctggcaaa gactataatg taactgcaaa     360
ctccaagctg gtcattatca cggctggggc acgtcagcaa gagggagaaa gccgtcttaa     420
tttggtccag cgtaacgtga acatatttaa attcatcatt cctaatgttg taaaatacag     480
cccgaactgc aagttgctta tgtttcaaa tccagtggat atcttgacct acgtggcttg     540
gaagataagt ggttttccca aaaccgtgt tattggaagt ggttgcaatc tggattcagc     600
ccgattccgt tacctgatgg gggaaaggct gggagttcac ccattaagct gtcatgggtg     660
ggtccttggg gaacatggag attccagtgt gcctgtatgg agtggaatga atgttgctgg     720
tgtctctctg aagactctgc acccagattt agggactgat aaagataagg aacagtggaa     780
agaggttcac aagcaggtgg ttgagagtgc ttatgaggtg atcaaactca aaggctacac     840
atcctgggct attggactct ctgtagcaga tttggcagag agtataatga agaatcttag     900
gcgggtgcac ccagttttcca ccatgattaa gggtctttac ggaataaagg atgatgtctt     960
ccttagtgtt ccttgcattt tgggacagaa tggaatctca gaccttgtga aggtgactct    1020
gacttctgag gaagaggccc gtttgaagaa gagtgcagat acactttggg ggatccaaaa    1080
ggagctgcaa ttttaaagtc ttctgatgtc atatcatttc actgtctagg ctacaacagg    1140
attctaggtg gaggttgtgc atgttgtcct ttttatctga tctgtgatta aagcagtaat    1200
```

| | | |
|---|---|---|
| attttaagat ggactgggaa aaacatcaac tcctgaagtt agaaataaga atggtttgta | 1260 | |
| aaatccacag ctatatcctg atgctggatg gtattaatct tgtgtagtct tcaactggtt | 1320 | |
| agtgtgaaat agttctgcca cctctgacgc accactgcca atgctgtacg tactgcattt | 1380 | |
| gccccttgag ccaggtggat gtttaccgtg tgttatataa cttcctggct ccttcactga | 1440 | |
| acatgcctag tccaacattt tttcccagtg agtcacatcc tgggatccag tgtataaatc | 1500 | |
| caatatcatg tcttgtgcat aattcttcca aaggatctta ttttgtgaac tatatcagta | 1560 | |
| gtgtacatta ccatataatg taaaagatc tacatacaaa caatgcaacc aactatccaa | 1620 | |
| gtgttatacc aactaaaacc cccaataaac cttgaacagt g | 1661 | |

<210> SEQ ID NO 49
<211> LENGTH: 1220
<212> TYPE: DNA
<213> ORGANISM: Homo sapiens

<400> SEQUENCE: 49

| | |
|---|---|
| ccttcagcgc ctcggctcca gcgccatggc gccctccagg aagttcttcg ttgggggaaa | 60 |
| ctggaagatg aacgggcgga agcagagtct ggggagctc atcggcactc tgaacgcggc | 120 |
| caaggtgccg gccgacaccg aggtggtttg tgctcccccct actgcctata tcgacttcgc | 180 |
| ccggcagaag ctagatccca agattgctgt ggctgcgcag aactgctaca agtgactaa | 240 |
| tggggctttt actggggaga tcagccctgg catgatcaaa gactgcggag ccacgtgggt | 300 |
| ggtcctgggg cactcagaga gaaggcatgt cttttgggag tcagatgagc tgattgggca | 360 |
| gaaagtggcc catgctctgg cagagggact cggagtaatc gcctgcattg gggagaagct | 420 |
| agatgaaagg gaagctggca tcactgagaa ggttgttttc gagcagacaa aggtcatcgc | 480 |
| agataacgtg aaggactgga gcaaggtcgt cctggcctat gagcctgtgt gggccattgg | 540 |
| tactggcaag actgcaacac cccaacaggc ccaggaagta cacgagaagc tccgaggatg | 600 |
| gctgaagtcc aacgtctctg atgcggtggc tcagagcacc cgtatcattt atggaggctc | 660 |
| tgtgactggg gcaacctgca aggagctggc cagccagcct gatgtggatg cttccttgt | 720 |
| gggtggtgct tccctcaagc ccgaattcgt ggacatcatc aatgccaaac aatgagcccc | 780 |
| atccatcttc cctaccttc ctgccaagcc agggactaag cagcccagaa gcccagtaac | 840 |
| tgccctttcc ctgcatatgc ttctgatggt gtcatctgct ccttcctgtg gcctcatcca | 900 |
| aactgtatct tcctttactg tttatatctt caccctgtaa tggttgggac caggccaatc | 960 |
| ccttctccac ttactataat ggttggaact aaacgtcacc aaggtggctt ctccttggct | 1020 |
| gagagatgga aggcgtggtg ggatttgctc ctgggttccc taggccctag tgagggcaga | 1080 |
| agagaaacca tcctctccct tcttacaccg tgaggccaag atcccctcag aaggcaggag | 1140 |
| tgctgccctc tcccatggtg cccgtgcctc tgtgctgtgt atgtgaacca cccatgtgag | 1200 |
| ggaataaacc tggcactagg | 1220 |

<210> SEQ ID NO 50
<211> LENGTH: 829
<212> TYPE: DNA
<213> ORGANISM: Homo sapiens

<400> SEQUENCE: 50

| | |
|---|---|
| cccccgagc gccgctccgg ctgcaccgcg ctcgctccga gtttcaggct cgtgctaagc | 60 |
| tagcgccgtc gtcgtctccc ttcagtcgcc atcatgatta tctaccggga cctcatcagc | 120 |
| cacgatgaga tgttctccga catctacaag atccgggaga tcgcggacgg gttgtgcctg | 180 |

| | |
|---|---|
| gaggtggagg ggaagatggt cagtaggaca gaaggtaaca ttgatgactc gctcattggt | 240 |
| ggaaatgcct ccgctgaagg ccccgagggc gaaggtaccg aaagcacagt aatcactggt | 300 |
| gtcgatattg tcatgaacca tcacctgcag gaaacaagtt tcacaaaaga agcctacaag | 360 |
| aagtacatca aagattacat gaaatcaatc aaagggaaac ttgaagaaca gagaccagaa | 420 |
| agagtaaaac cttttatgac aggggctgca gaacaaatca agcacatcct tgctaatttc | 480 |
| aaaaactacc agttctttat tggtgaaaac atgaatccag atggcatggt tgctctattg | 540 |
| gactaccgtg aggatggtgt gaccccatat atgattttct ttaaggatgg tttagaaatg | 600 |
| gaaaaatgtt aacaaatgtg gcaattattt tggatctatc acctgtcatc ataactggct | 660 |
| tctgcttgtc atccacacaa caccaggact taagacaaat gggactgatg tcatcttgag | 720 |
| ctcttcattt attttgactg tgatttattt ggagtggagg cattgttttt aagaaaaaca | 780 |
| tgtcatgtag gttgtctaaa ataaaatgc atttaaactc atttgagag | 829 |

<210> SEQ ID NO 51
<211> LENGTH: 769
<212> TYPE: DNA
<213> ORGANISM: Homo sapiens

<400> SEQUENCE: 51

| | |
|---|---|
| cccccgagc gccgctccgg ctgcaccgcg ctcgctccga gtttcaggct cgtgctaagc | 60 |
| tagcgccgtc gtcgtctccc ttcagtcgcc atcatgatta tctaccggga cctcatcagc | 120 |
| cacgatgaga tgttctccga catctacaag atccgggaga tcgcggacgg gttgtgcctg | 180 |
| gaggtggagg ggaagatggt cagtaggaca gaaggtaaca ttgatgactc gctcattggt | 240 |
| ggaaatgcct ccgctgaagg ccccgagggc gaaggtaccg aaagcacagt aatcactggt | 300 |
| gtcgatattg tcatgaacca tcacctgcag gaaacaagtt tcacaaaaga agcctacaag | 360 |
| aagtacatca aagattacat gaaatcaatc aaagggaaac ttgaagaaca gagaccagaa | 420 |
| aaaaactacc agttctttat tggtgaaaac atgaatccag atggcatggt tgctctattg | 480 |
| gactaccgtg aggatggtgt gaccccatat atgattttct ttaaggatgg tttagaaatg | 540 |
| gaaaaatgtt aacaaatgtg gcaattattt tggatctatc acctgtcatc ataactggct | 600 |
| tctgcttgtc atccacacaa caccaggact taagacaaat gggactgatg tcatcttgag | 660 |
| ctcttcattt attttgactg tgatttattt ggagtggagg cattgttttt aagaaaaaca | 720 |
| tgtcatgtag gttgtctaaa ataaaatgc atttaaactc atttgagag | 769 |

<210> SEQ ID NO 52
<211> LENGTH: 829
<212> TYPE: DNA
<213> ORGANISM: Homo sapiens

<400> SEQUENCE: 52

| | |
|---|---|
| cccccgagc gccgctccgg ctgcaccgcg ctcgctccga gtttcaggct cgtgctaagc | 60 |
| tagcgccgtc gtcgtctccc ttcagtcgcc atcatgatta tctaccggga cctcatcagc | 120 |
| cacgatgaga tgttctccga catctacaag atccgggaga tcgcggacgg gttgtgcctg | 180 |
| gaggtggagg ggaagatggt cagtaggaca gaaggtaaca ttgatgactc gctcattggt | 240 |
| ggaaatgcct ccgctgaagg ccccgagggc gaaggtaccg aaagcacagt aatcactggt | 300 |
| gtcgatattg tcatgaacca tcacctgcag gaaacaagtt tcacaaaaga agcctacaag | 360 |
| aagtacatca aagattacat gaaatcaatc aaagggaaac ttgaagaaca gagaccagaa | 420 |
| agagtaaaac cttttatgac aggggctgca gaacaaatca agcacatcct tgctaatttc | 480 |

```
aaaaactacc agttctttat tggtgaaaac atgaatccag atggcatggt tgctctattg    540
gactaccgtg aggatggtgt gaccccatat atgattttct ttaaggatgg tttagaaatg    600
gaaaaatgtt aacaaatgtg gcaattattt tggatctatc acctgtcatc ataactggct    660
tctgcttgtc atccacacaa caccaggact aagacaaat gggactgatg tcatcttgag    720
ctcttcattt attttgactg tgatttattt ggagtggagg cattgttttt aagaaaaaca    780
tgtcatgtag gttgtctaaa aataaaatgc atttaaactc atttgagag                829
```

<210> SEQ ID NO 53
<211> LENGTH: 829
<212> TYPE: DNA
<213> ORGANISM: Homo sapiens

<400> SEQUENCE: 53

```
ccccccgagc gccgctccgg ctgcaccgcg ctcgctccga gtttcaggct cgtgctaagc     60
tagcgccgtc gtcgtctccc ttcagtcgcc atcatgatta tctaccggga cctcatcagc    120
cacgatgaga tgttctccga catctacaag atccgggaga tcgcggacgg gttgtgcctg    180
gaggtggagg ggaagatggt cagtaggaca gaaggtaaca ttgatgactc gctcattggt    240
ggaaatgcct ccgctgaagg ccccgagggc gaaggtaccg aaagcacagt aatcactggt    300
gtcgatattg tcatgaacca tcacctgcag gaaacaagtt tcacaaaara agcctacaag    360
aagtacatca agattacat gaaatcaatc aaagggaaac ttgaagaaca gagaccagaa    420
agagtaaaac cttttatgac aggggctgca gaacaaatca agcacatcct tgctaatttc    480
aaaaactacc agttctttat tggtgaaaac atgaatccag atggcatggt tgctctattg    540
gactaccgtg aggatggtgt gaccccatat atgattttct ttaaggatgg tttagaaatg    600
gaaaaatgtt aacaaatgtg gcaattattt tggatctatc acctgtcatc ataactggct    660
tctgcttgtc atccacacaa caccaggact aagacaaat gggactgatg tcatcttgag    720
ctcttcattt attttgactg tgatttattt ggagtggagg cattgttttt aagaaaaaca    780
tgtcatgtag gttgtctaaa aataaaatgc atttaaactc atttgagag                829
```

<210> SEQ ID NO 54
<211> LENGTH: 318
<212> TYPE: DNA
<213> ORGANISM: Homo sapiens

<400> SEQUENCE: 54

```
aaagaagcct acaagaagta catcaaagat tacatgaaat caatcaaagg gaaacttgaa     60
gaacagagac cagaaagagt aaaacctttt atgacagggg ctgcagaaca aatcaagcac    120
atccttgcta atttcaaaaa ctaccagttc tttattggtg aaaacatgaa tccagatggc    180
atggttgctc tattggacta ccgtgaggat ggtgtgaccc catatatgat tttctttaag    240
gatggtttag aaatggaaaa atgttaacaa atgtggcaat tattttggat ctatcacctg    300
tcatcataac tggcttct                                                  318
```

<210> SEQ ID NO 55
<211> LENGTH: 317
<212> TYPE: DNA
<213> ORGANISM: Homo sapiens

<400> SEQUENCE: 55

```
aaagaagcat acaagaagta catcaaagat acatgaaatc aatcaaaggg aaacttgaag     60
aacagagacc agaaagagta aaacctttta tgacaggggc tgcagaacaa atcaagcaca    120
```

```
tccttgctaa tttcaaaaac taccagttct ttattggtga aaacatgaat ccagatggca    180
tggttgctct attgggctac cgtgaggatg gtgtgacccc atatatgatt ttctttaagg    240
atggtttaga atggaaaaa tgttaacaaa tgtggcaatt atttgggatc tatcacctgt    300
catcataact ggcttct                                                  317
```

```
<210> SEQ ID NO 56
<211> LENGTH: 319
<212> TYPE: DNA
<213> ORGANISM: Homo sapiens

<400> SEQUENCE: 56
aaaagaagcc tacaagaagt acatcaaaga ttacatgaaa tcaatcaaag ggaaacttga    60
agaacagaga ccagaaagag taaaaccttt tatgacaggg gctgcagaac aaatcaagca    120
catccttgct aatttcaaaa actaccagtt ctttattggt gaaaacatga atccagatgg    180
catggttgct ctattggact accgtgagga tggtgtgacc ccatatatga ttttctttaa    240
ggatggttta gaaatggaaa atgttaaca atgtggcaa ttattttgga tctatcacct    300
gtcatcataa ctggcttct                                               319
```

```
<210> SEQ ID NO 57
<211> LENGTH: 320
<212> TYPE: DNA
<213> ORGANISM: Homo sapiens

<400> SEQUENCE: 57
aaaagaagcc tacaagaacg tacatcagtt gattacatga atcaatcaaa gggaaacttg    60
aagaacagag accagaaaga gtaaaaccttt ttatgacagg gctgcagaa caaatcaagc    120 acatccttgc taatttcaaa aactaccagt tctttattgg tgaaaacatg aatccagatg    180
gcatggttgc tctattggac taccgtgagg atggtgtgac cccatatatg attttcttta    240
aggatggttt agaaatggaa aatgttaac aaatgtggca attattttgg atctatcacc    300
tgtcatcata actggcttct                                               320
```

```
<210> SEQ ID NO 58
<211> LENGTH: 140
<212> TYPE: DNA
<213> ORGANISM: Homo sapiens

<400> SEQUENCE: 58
agaacaaatc aagcacatcc ttgctaattt caaaaactac cagttcttta ttggtgaaaa    60
catgaatcca gatggcatgg ttgctctatt ggactaccgt gaggatggtg tgaccccata    120
tatgattttc tttaaggatg                                               140
```

```
<210> SEQ ID NO 59
<211> LENGTH: 21
<212> TYPE: DNA
<213> ORGANISM: Homo sapiens

<400> SEQUENCE: 59
tgtcaatcgg taccctgaat g                                             21
```

```
<210> SEQ ID NO 60
<211> LENGTH: 20
<212> TYPE: DNA
<213> ORGANISM: Homo sapiens

<400> SEQUENCE: 60
```

| tgtcaatcgg accctgaatg | 20 |

<210> SEQ ID NO 61
<211> LENGTH: 1847
<212> TYPE: DNA
<213> ORGANISM: Homo sapiens

<400> SEQUENCE: 61

| gtccccgcgc cagagacgca gccgcgctcc caccacccac acccaccgcg ccctcgttcg | 60 |
| cctcttctcc gggagccagt ccgcgccacc gccgccgccc aggccatcgc caccctccgc | 120 |
| agccatgtcc accaggtccg tgtcctcgtc ctcctaccgc aggatgttcg gcggcccggg | 180 |
| caccgcgagc cggccgagct ccagccggag ctacgtgact acgtccaccc gcacctacag | 240 |
| cctgggcagc gcgctgcgcc ccagcaccag ccgcagcctc tacgcctcgt ccccgggcgg | 300 |
| cgtgtatgcc acgcgctcct ctgccgtgcg cctgcggagc agcgtgcccg gggtgcggct | 360 |
| cctgcaggac tcggtggact ctcgctggcc gacgccatc aacaccgagt tcaagaacac | 420 |
| ccgcaccaac gagaaggtgg agctgcagga gctgaatgac cgcttcgcca actacatcga | 480 |
| caaggtgcgc ttcctggagc agcagaataa gatcctgctg gccgagctcg agcagctcaa | 540 |
| gggccaaggc aagtcgcgcc tgggggacct ctacgaggag gagatgcggg agctgcgccg | 600 |
| gcaggtggac cagctaacca acgacaaagc ccgcgtcgag gtggagcgcg acaacctggc | 660 |
| cgaggacatc atgcgcctcc gggagaaatt gcaggaggag atgcttcaga gagaggaagc | 720 |
| cgaaaacacc ctgcaatctt tcagacagga tgttgacaat gcgtctctgg cacgtcttga | 780 |
| ccttgaacgc aaagtggaat cttttgcaaga agagattgcc ttttttgaaga aactccacga | 840 |
| agaggaaatc caggagctgc aggctcagat tcaggaacag catgtccaaa tcgatgtgga | 900 |
| tgtttccaag cctgacctca cggctgccct gcgtgacgta cgtcagcaat atgaaagtgt | 960 |
| ggctgccaag aacctgcagg aggcagaaga atggtacaaa tccaagtttg ctgacctctc | 1020 |
| tgaggctgcc aaccggaaca atgacgccct gcgccaggca aagcaggagt ccactgagta | 1080 |
| ccggagacag gtgcagtccc tcacctgtga agtggatgcc cttaaaggaa ccaatgagtc | 1140 |
| cctggaacgc cagatgcgtg aaatggaaga gaactttgcc gttgaagctg ctaactacca | 1200 |
| agacactatt ggccgcctgc aggatgagat tcagaatatg aaggaggaaa tggctcgtca | 1260 |
| ccttcgtgaa taccaagacc tgctcaatgt taagatggcc cttgacattg agattgccac | 1320 |
| ctacaggaag ctgctggaag gcgaggagag caggatttct ctgcctcttc caaacttttc | 1380 |
| ctccctgaac ctgagggaaa ctaatctgga ttcactccct ctggttgata cccactcaaa | 1440 |
| aaggacactt ctgattaaga cggttgaaac tagagatgga caggttatca acgaaacttc | 1500 |
| tcagcatcac gatgaccttg aataaaaatt gcacacactc agtgcagcaa tatattacca | 1560 |
| gcaagaataa aaagaaatc catatcttaa agaaacagct ttcaagtgcc tttctgcagt | 1620 |
| ttttcaggag cgcaagatag atttggaata ggaataagct ctagttctta acaaccgaca | 1680 |
| ctcctacaag atttagaaaa aagtttacaa cataatctag tttacagaaa atcttgtgc | 1740 |
| tagaatactt tttaaaaggt attttgaata ccattaaaac tgcttttttt tttccagcaa | 1800 |
| gtatccaacc aacttggttc tgcttcaata atctttgga aaaactc | 1847 |

<210> SEQ ID NO 62
<211> LENGTH: 1847
<212> TYPE: DNA
<213> ORGANISM: Homo sapiens

<400> SEQUENCE: 62

```
gtccccgcgc cagagacgca gccgcgctcc caccacccac acccaccgcg ccctcgttcg      60
cctcttcttc gggagccagt ccgcgccacc gccgccgccc aggccatcgc caccctccgc     120
agccatgtcc accaggtccg tgtcctcgtc ctcctaccgc aggatgttcg gcggcccggg     180
caccgcgagc cggccgagct ccagccggag ctacgtgact acgtccaccc gcacctacag     240
cctgtgcagc gcgctgcgcc ccagcaccag ccgcagcctc tacgcctcgt ccccgggcgg     300
cgtgtatgcc acgcgctcct ctgccgggcg cctgcggagc agcgtgcccg gggtgcggct     360
cctgcaggac tcggtggact ctctcgctgg cgacgccatc cacaccgagc tcacgaacac     420
ccggaccaac gacaaagtgg agctgccgga cctgactgac cgcttcgcca actacatcga     480
caaagggcgc ttcctggagc agcagactcc gatcctgctg ccaaactcc agcacctcca     540
aggccaaggg aagtcccgcc tggggggaact ctaccaagag gaaatgcggg aactgggccg     600
gccaggggac cagttaaaca agaacaagc ccgcgtcgaa gggaagcgcg aaaaactggg     660
cgaagacctc atgcgcctcg gggaaccccg gcccaagcca agcccccaa aaaaggcag     720
ccgccaacgc cgggcacctg cccgacccgc cggcgccccg gggcccgggg ccggctggg     780
actgtgccgc cgggggggcc cccggccaac caaaaagggc ctgggggaag cacccccccca     840
aaagggactc ccggaactgc aggctccaat cccggaacag cctgtcccaa tccaggggga     900
ggtttcccgg gctgaactcc cgggtggcct ggggacgta cgtcacccat atgcaggggg     960
ggctgccaag aacctggagg aggcagaaaa atggtacaaa tcccaggtgg ctgaactctc    1020
tgaggctggc aaccggaaca atgacgccct gggccaggct tagcgggagt ccactgagta    1080
ccggagacag gtgcagtccc tcacctgtga aggggatgcc cttaagggaa ccagtgagtt    1140
cctggaacgc cagatgcgtg aaatgggaga gaacttggcc ggtgaggctg ctaactacca    1200
agaaactatg gggcgcctgc aggatgagat tcagtatatg aaggaggaaa tggctcgtca    1260
ccttcgtgaa taccaagaac tgctcaatgt tcagctggcc cttgacatcg agaacggcac    1320
ctacaggaag ctgctggagg cgaggagag caggatatct ctggctcttc ccaacttttc    1380
ctccctgaac ctgagggaga ataatctgga ttcactccct ctggttgata cccagtccaa    1440
gaggacactt ttgatttaga cggtggacac tagagatggc caggttatcc acgaaacttc    1500
ttagcgtcac gatgaacttg atttcaaatt gcccacactc agtgcagcca tatattaccc    1560
ggcagaaaac caaaaagatc cctatctttg aaaaccaggt ttcaagggcc cttctgcagt    1620
ttttcaagaa cgccagataa atccggaata ggaataagct ctagttctta acaaccgcac    1680
ctcctccaag attttgaaaa aagtttccca cattatctag tttcccgaaa aatttggtgg    1740
tagaaaactt tttacaaggt atccggaaaa cccttacacc tgctcttttt tttccagcaa    1800
gtatccaacc aactgggttc tgcttcaata aatcttggga aaaactc                 1847
```

<210> SEQ ID NO 63
<211> LENGTH: 466
<212> TYPE: PRT
<213> ORGANISM: Homo sapiens

<400> SEQUENCE: 63

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45
```

```
Ser Arg Ser Leu Tyr Ala Ser Ser Pro Gly Gly Val Tyr Ala Thr Arg
 50                  55                  60

Ser Ser Ala Val Arg Leu Arg Ser Ser Val Pro Gly Val Arg Leu Leu
 65                  70                  75                  80

Gln Asp Ser Val Asp Phe Ser Leu Ala Asp Ala Ile Asn Thr Glu Phe
                 85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
                195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
                275                 280                 285

Glu Trp Tyr Lys Ser Lys Phe Ala Asp Leu Ser Glu Ala Ala Asn Arg
                290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Gly Arg Leu Gln Asp Glu
                355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
                420                 425                 430

Leu Val Asp Thr His Ser Lys Arg Thr Leu Leu Ile Lys Thr Val Glu
                435                 440                 445

Thr Arg Asp Gly Gln Val Ile Asn Glu Thr Ser Gln His His Asp Asp
450                 455                 460

Leu Glu
465
```

<210> SEQ ID NO 64
<211> LENGTH: 565
<212> TYPE: PRT
<213> ORGANISM: Homo sapiens

<400> SEQUENCE: 64

```
Met Ser Thr Arg Ser Val Ser Ser Ser Tyr Arg Arg Met Phe Gly
1               5                   10                  15

Gly Pro Gly Thr Ala Ser Arg Pro Ser Ser Arg Ser Tyr Val Thr
            20                  25                  30

Thr Ser Thr Arg Thr Tyr Ser Leu Cys Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Gly Arg Leu Arg Ser Ser Val Pro Gly Val Arg Leu Leu
65                  70                  75                  80

Gln Asp Ser Val Asp Phe Ser Leu Ala Asp Ala Ile His Thr Glu Leu
                85                  90                  95

Thr Asn Thr Arg Thr Asn Asp Lys Val Glu Leu Pro Asp Leu Thr Asp
            100                 105                 110

Arg Phe Ala Asn Tyr Ile Asp Lys Gly Arg Phe Leu Glu Gln Gln Thr
        115                 120                 125

Pro Ile Leu Leu Ala Lys Leu Gln His Leu Gln Gly Gln Gly Lys Ser
    130                 135                 140

Arg Leu Gly Glu Leu Tyr Gln Glu Glu Met Arg Glu Leu Gly Arg Pro
145                 150                 155                 160

Gly Asp Gln Leu Asn Lys Glu Gln Ala Arg Val Glu Gly Lys Arg Glu
                165                 170                 175

Lys Leu Gly Glu Asp Leu Met Arg Leu Gly Glu Pro Arg Pro Lys Pro
            180                 185                 190

Lys Pro Pro Lys Lys Gly Ser Arg Gln Arg Arg Ala Pro Ala Arg Pro
        195                 200                 205

Ala Gly Ala Pro Gly Pro Arg Gly Arg Leu Gly Leu Cys Arg Pro Gly
    210                 215                 220

Gly Pro Ala Pro Thr Lys Lys Gly Leu Gly Glu Ala Pro Pro Gln Lys
225                 230                 235                 240

Gly Leu Pro Glu Leu Gln Ala Pro Ile Pro Glu Gln Pro Val Pro Ile
                245                 250                 255

Gln Gly Glu Val Ser Arg Ala Glu Leu Pro Gly Gly Leu Gly Asp Val
            260                 265                 270

Arg His Pro Tyr Asp Arg Gly Ala Ala Lys Asn Leu Glu Glu Ala Glu
        275                 280                 285

Lys Trp Tyr Lys Ser Gln Val Ala Glu Leu Ser Glu Ala Gly Asn Arg
    290                 295                 300

Asn Asn Asp Ala Leu Gly Gln Ala Arg Glu Ser Thr Glu Tyr Arg Arg
305                 310                 315                 320

Gln Val Gln Ser Leu Thr Cys Glu Gly Asp Ala Leu Lys Gly Thr Ser
                325                 330                 335

Glu Phe Leu Glu Arg Gln Met Arg Glu Met Gly Glu Asn Leu Ala Gly
            340                 345                 350

Glu Ala Ala Asn Tyr Gln Glu Thr Met Gly Arg Leu Gln Asp Glu Ile
        355                 360                 365

Gln Tyr Met Lys Glu Glu Met Ala Arg His Leu Arg Glu Tyr Gln Glu
    370                 375                 380
```

```
Leu Leu Asn Val Gln Leu Ala Leu Asp Ile Glu Asn Gly Thr Tyr Arg
385                 390                 395                 400

Lys Leu Glu Gly Glu Ser Arg Ile Ser Leu Ala Leu Pro Asn
            405                 410                 415

Phe Ser Ser Leu Asn Leu Arg Glu Asn Asn Leu Asp Ser Leu Pro Leu
                420                 425                 430

Val Asp Thr Gln Ser Lys Arg Thr Leu Leu Ile Thr Val Asp Thr Arg
                435                 440                 445

Asp Gly Gln Val Ile His Glu Thr Ser Arg His Asp Glu Leu Asp Phe
            450                 455                 460

Lys Leu Pro Thr Leu Ser Ala Ala Ile Tyr Tyr Pro Ala Glu Asn Gln
465                 470                 475                 480

Lys Asp Pro Tyr Leu Lys Pro Gly Glu Lys Gly Ser Ala Val Phe Gln
                485                 490                 495

Glu Arg Gln Ile Asn Pro Glu Glu Ala Leu Val Leu Asn Asn Arg Thr
            500                 505                 510

Ser Ser Lys Ile Leu Lys Lys Val Ser His Ile Ile Phe Pro Glu Lys
                515                 520                 525

Phe Gly Gly Arg Lys Leu Phe Thr Arg Tyr Pro Glu Asn Pro Tyr Thr
530                 535                 540

Cys Ser Phe Phe Ser Ser Lys Tyr Pro Thr Asn Trp Val Leu Leu Gln
545                 550                 555                 560

Ile Leu Gly Lys Thr
                565

<210> SEQ ID NO 65
<211> LENGTH: 185
<212> TYPE: PRT
<213> ORGANISM: Homo sapiens

<400> SEQUENCE: 65

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Glu Gly Thr Glu Ser
        50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
                100                 105                 110

Pro Phe Met Thr Gly Ala Ala Glu Gln Ile Lys His Ile Leu Ala Asn
            115                 120                 125

Phe Lys Asn Tyr Gln Phe Phe Ile Gly Glu Asn Met Asn Pro Asp Gly
        130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys Gln Met Trp Gln
                165                 170                 175

Leu Phe Trp Ile Tyr His Leu Ser Ser
                180                 185
```

```
<210> SEQ ID NO 66
<211> LENGTH: 480
<212> TYPE: PRT
<213> ORGANISM: Homo sapiens

<400> SEQUENCE: 66

Met Ser Thr Arg Ser Val Ser Ser Ser Tyr Arg Arg Met Phe Gly
1               5                   10                  15

Gly Pro Gly Thr Ala Ser Arg Pro Ser Ser Arg Ser Tyr Val Thr
                20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380
```

```
Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
            405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
            450                 455                 460

Leu Glu Lys Leu His Thr Leu Ser Ala Ala Ile Tyr Tyr Gln Gln Glu
465                 470                 475                 480

<210> SEQ ID NO 67
<211> LENGTH: 255
<212> TYPE: PRT
<213> ORGANISM: Homo sapiens

<400> SEQUENCE: 67

Met Lys Leu Asn Ile Ser Phe Pro Ala Thr Gly Cys Gln Lys Leu Ile
1               5                   10                  15

Glu Val Asp Asp Glu Arg Lys Leu Arg Thr Phe Tyr Glu Lys Arg Met
            20                  25                  30

Ala Thr Glu Val Ala Ala Asp Ala Leu Gly Glu Glu Trp Lys Gly Tyr
        35                  40                  45

Val Val Arg Ile Ser Gly Gly Asn Asp Lys Gln Gly Phe Pro Met Lys
    50                  55                  60

Gln Gly Val Leu Thr His Gly Arg Val Arg Leu Leu Leu Ser Lys Gly
65                  70                  75                  80

His Ser Cys Tyr Arg Pro Arg Arg Thr Gly Glu Arg Lys Arg Lys Ser
                85                  90                  95

Val Arg Gly Cys Ile Val Asp Ala Asn Leu Ser Val Leu Asn Leu Val
            100                 105                 110

Ile Val Lys Lys Gly Glu Lys Asp Ile Pro Gly Leu Thr Asp Thr Thr
        115                 120                 125

Val Pro Arg Arg Leu Gly Pro Lys Arg Ala Ser Arg Ile Arg Lys Leu
    130                 135                 140

Phe Asn Leu Ser Lys Glu Asp Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
            180                 185                 190

Ala Leu Lys Lys Gln Arg Thr Lys Lys Asn Lys Glu Glu Ala Ala Glu
        195                 200                 205

Tyr Ala Lys Leu Leu Ala Lys Arg Met Lys Glu Ala Lys Glu Lys Arg
    210                 215                 220

Gln Glu Gln Ile Ala Lys Arg Arg Arg Leu Ser Ser Leu Arg Ala Ser
225                 230                 235                 240

Thr Ser Lys Ser Glu Ser Ser Gln Lys Asp Phe Leu Ser Asn Lys
                245                 250                 255

<210> SEQ ID NO 68
<211> LENGTH: 276
<212> TYPE: PRT
<213> ORGANISM: Homo sapiens
```

<400> SEQUENCE: 68

```
Met Pro Lys Gly Lys Lys Ala Lys Gly Lys Lys Val Ala Pro Ala Pro
1               5                   10                  15

Ala Val Val Lys Lys Gln Glu Ala Lys Lys Val Val Asn Pro Leu Phe
            20                  25                  30

Glu Lys Arg Pro Lys Asn Phe Gly Ile Gly Gln Asp Ile Gln Pro Lys
        35                  40                  45

Arg Asp Leu Thr Arg Phe Val Lys Trp Pro Arg Tyr Ile Arg Leu Gln
    50                  55                  60

Arg Gln Arg Ala Ile Leu Tyr Lys Arg Leu Lys Val Pro Pro Ala Ile
65                  70                  75                  80

Asn Gln Phe Thr Gln Ala Leu Asp Arg Gln Thr Ala Thr Gln Leu Leu
                85                  90                  95

Lys Leu Ala His Lys Tyr Arg Pro Glu Thr Lys Gln Glu Lys Lys Gln
            100                 105                 110

Arg Leu Leu Ala Arg Ala Glu Lys Ala Ala Gly Lys Gly Asp Val
        115                 120                 125

Pro Thr Lys Arg Pro Pro Val Leu Arg Ala Gly Val Asn Thr Val Thr
    130                 135                 140

Thr Leu Val Glu Asn Lys Lys Ala Gln Leu Val Val Ile Ala His Asp
145                 150                 155                 160

Val Asp Pro Ile Glu Leu Val Val Phe Leu Pro Ala Leu Cys Arg Lys
                165                 170                 175

Met Gly Val Pro Tyr Cys Ile Ile Lys Gly Lys Ala Arg Leu Gly Arg
            180                 185                 190

Leu Val His Arg Lys Thr Cys Thr Thr Val Ala Phe Thr Gln Val Asn
        195                 200                 205

Ser Glu Asp Lys Gly Ala Leu Ala Lys Leu Val Glu Ala Ile Arg Thr
    210                 215                 220

Asn Tyr Asn Asp Arg Tyr Asp Glu Ile Arg Arg His Trp Gly Gly Asn
225                 230                 235                 240

Val Leu Gly Pro Lys Ser Val Ala Arg Ile Ala Lys Leu Glu Lys Ala
                245                 250                 255

Lys Ala Lys Glu Leu Ala Thr Lys Leu Gly Met Tyr Thr Val Glu Phe
            260                 265                 270

Ser Val His Lys
        275
```

<210> SEQ ID NO 69
<211> LENGTH: 275
<212> TYPE: PRT
<213> ORGANISM: Homo sapiens

<400> SEQUENCE: 69

```
Met Ala Arg Gly Pro Lys Lys His Leu Lys Arg Val Ala Ala Pro Lys
1               5                   10                  15

His Trp Met Leu Asp Lys Leu Thr Gly Val Phe Ala Pro Arg Pro Ser
            20                  25                  30

Thr Gly Pro His Lys Leu Arg Glu Cys Leu Pro Leu Ile Ile Phe Leu
        35                  40                  45

Arg Asn Arg Leu Lys Tyr Ala Leu Thr Gly Asp Glu Val Lys Lys Ile
    50                  55                  60

Cys Met Gln Arg Phe Ile Lys Ile Asp Gly Lys Val Arg Thr Asp Ile
65                  70                  75                  80
```

```
Thr Tyr Pro Ala Gly Phe Met Asp Val Ile Ser Ile Asp Lys Thr Gly
                85                  90                  95

Glu Asn Phe Arg Leu Ile Tyr Asp Thr Lys Gly Arg Phe Ala Val His
            100                 105                 110

Arg Ile Thr Pro Glu Glu Ala Lys Tyr Lys Leu Cys Lys Val Arg Lys
        115                 120                 125

Ile Phe Val Gly Thr Lys Gly Ile Pro His Leu Val Thr His Asp Ala
    130                 135                 140

Arg Thr Ile Arg Tyr Pro Asp Pro Leu Ile Lys Val Asn Asp Thr Ile
145                 150                 155                 160

Gln Ile Asp Leu Glu Thr Gly Lys Ile Thr Phe Ile Lys Phe Asp
                165                 170                 175

Thr Gly Asn Leu Cys Met Val Thr Gly Gly Ala Asn Leu Gly Arg Ile
            180                 185                 190

Gly Val Ile Thr Asn Arg Glu Arg His Pro Gly Ser Phe Asp Val Val
        195                 200                 205

His Val Lys Asp Ala Asn Gly Asn Ser Phe Ala Thr Arg Leu Ser Asn
    210                 215                 220

Ile Phe Val Ile Gly Lys Gly Asn Lys Pro Trp Ile Ser Leu Pro Arg
225                 230                 235                 240

Gly Lys Gly Ile Arg Leu Thr Ile Ala Glu Glu Arg Asp Lys Arg Leu
                245                 250                 255

Ala Ala Lys Gln Ser Ser Gly Asn Gly Ser Leu Gly Asp Met Ser Asp
            260                 265                 270

Leu Cys Thr
    275

<210> SEQ ID NO 70
<211> LENGTH: 186
<212> TYPE: PRT
<213> ORGANISM: Homo sapiens

<400> SEQUENCE: 70

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175
```

Gly Asp Ser Asp Asn Glu Ser Ala Ser Gly
            180                 185

<210> SEQ ID NO 71
<211> LENGTH: 183
<212> TYPE: PRT
<213> ORGANISM: Homo sapiens

<400> SEQUENCE: 71

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp Glu
                165                 170                 175

Pro Ser Glu Pro Ser Asp Phe
            180

<210> SEQ ID NO 72
<211> LENGTH: 401
<212> TYPE: PRT
<213> ORGANISM: Homo sapiens

<400> SEQUENCE: 72

Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu

```
            130                 135                 140
Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu Asp
                325                 330                 335

Pro Trp Thr Thr Ser Pro Ser Lys Ser Thr Arg Gly Arg Glu Arg Pro
            340                 345                 350

Ser Leu Leu Gly Ser Pro Cys His Thr Gln Ser Pro Thr Thr Leu Asn
        355                 360                 365

Leu Pro Ser Ser Gln Leu Pro Cys Arg Pro Leu Glu Glu Gly Arg Gly
    370                 375                 380

Leu Gly Ser Arg Thr Leu Ser Cys Thr Ile Asn Lys Val Pro Cys Ala
385                 390                 395                 400

Gln

<210> SEQ ID NO 73
<211> LENGTH: 302
<212> TYPE: PRT
<213> ORGANISM: Homo sapiens

<400> SEQUENCE: 73

Met Ala Pro Ser Arg Lys Phe Phe Val Gly Gly Asn Trp Lys Met Asn
1               5                   10                  15

Gly Arg Lys Gln Ser Leu Gly Glu Leu Ile Gly Thr Leu Asn Ala Ala
            20                  25                  30

Lys Val Pro Ala Asp Thr Glu Val Val Cys Ala Pro Pro Thr Ala Tyr
        35                  40                  45

Ile Asp Phe Ala Arg Gln Lys Leu Asp Pro Lys Ile Ala Val Ala Ala
    50                  55                  60

Gln Asn Cys Tyr Lys Val Thr Asn Gly Ala Phe Thr Gly Glu Ile Ser
65                  70                  75                  80

Pro Gly Met Ile Lys Asp Cys Gly Ala Thr Trp Val Val Leu Gly His
                85                  90                  95

Ser Glu Arg Arg His Val Phe Gly Glu Ser Asp Glu Leu Ile Gly Gln
            100                 105                 110
```

```
Lys Val Ala His Ala Leu Ala Glu Gly Leu Gly Val Ile Ala Cys Ile
            115                 120                 125
Gly Glu Lys Leu Asp Glu Arg Glu Ala Gly Ile Thr Glu Lys Val Val
        130                 135                 140
Phe Glu Gln Thr Lys Val Ile Ala Asp Asn Val Lys Asp Trp Ser Lys
145                 150                 155                 160
Val Val Leu Ala Tyr Glu Pro Val Trp Ala Ile Gly Thr Gly Lys Thr
                165                 170                 175
Ala Thr Pro Gln Gln Ala Gln Glu Val His Glu Lys Leu Arg Gly Trp
            180                 185                 190
Leu Lys Ser Asn Val Ser Asp Ala Val Ala Gln Ser Thr Arg Ile Ile
        195                 200                 205
Tyr Gly Gly Ser Val Thr Gly Ala Thr Cys Lys Glu Leu Ala Ser Gln
    210                 215                 220
Pro Asp Val Asp Gly Phe Leu Val Gly Gly Ala Ser Leu Lys Pro Glu
225                 230                 235                 240
Phe Val Asp Ile Ile Asn Ala Lys Gln Ala Pro Ser Ile Phe Pro Thr
                245                 250                 255
Leu Pro Ala Lys Pro Gly Thr Lys Gln Pro Arg Ser Pro Val Thr Ala
            260                 265                 270
Leu Ser Leu His Leu Leu Met Val Ser Ser Ala Pro Ser Cys Gly Leu
        275                 280                 285
Ile Gln Thr Val Ser Ser Phe Thr Val Tyr Ile Phe Thr Leu
    290                 295                 300

<210> SEQ ID NO 74
<211> LENGTH: 1283
<212> TYPE: DNA
<213> ORGANISM: Homo sapiens
<400> SEQUENCE: 74
ctctctgctc tcctgttcg acagtcagcc gcatcttctt ttgcgtcgcc agccgagcca      60
catcgctcag acaccatggg gaaggtgaag gtcggagtca acggatttgg tcgtattggg     120
cgcctggtca ccagggctgc ttttaactct ggtaaagtgg atattgttgc catcaatgac     180
cccttcattg acctcaacta catggtttac atgttccaat atgattccac ccatggcaaa     240
ttccatggca ccgtcaaggc tgagaacggg aagcttgtca tcaatggaaa tcccatcacc     300
atcttccagg agcgagatcc ctccaaaatc aagtggggcg atgctggcgc tgagtacgtc     360
gtggagtcca ctggcgtctt caccaccatg gagaaggctg ggctcatttt caggggggga     420
gccaaagggt catcatctc tgcccctct gctgatgccc ccatgttcgt catgggtgtg     480
aaccatgaga agtatgacaa cagcctcaag atcatcagca atgcctcctg caccaccaac     540
tgcttagcac ccctggccaa ggtcatccat gacaactttg gtatcgtgga aggactcatg     600
accacagtcc atgccatcac tgccacccag aagactgtgg atggcccctc cgggaaactg     660
tggcgtgatg gccgcggggc tctccagaac atcatccctg cctctactgg cgctgccaag     720
gctgtgggca aggtcatccc tgagctgaac gggaagctca ctggcatggc cttccgtgtc     780
cccactgcca acgtgtcagt ggtggacctg acctgccgtc tagaaaaacc tgccaaatat     840
gatgacatca gaaggtggt gaagcaggcg tcggagggcc ccctcaaggg catcctgggc     900
tacactgagc accaggtggt ctcctctgac ttcaacagcg acacccactc ctccacctt      960
gacgctgggg ctggcattgc cctcaacgac cactttgtca agctcatttc tggtatgac     1020
aacgaatttg gctacagcaa caggtggtg gacctcatgg cccacatggc ctccaaggag    1080
```

| | | | | |
|---|---|---|---|---|
| taagacccct | ggaccaccag | ccccagcaag | agcacaagag | gaagagagag | accctcactg | 1140 |
| ctggggagtc | cctgccacac | tcagtccccc | accacactga | atctcccctc | ctcacagttg | 1200 |
| ccatgtagac | cccttgaaga | ggggaggggc | ctagggagcc | gcaccttgtc | atgtaccatc | 1260 |
| aataaagtac | cctgtgctca | acc | | | | 1283 |

<210> SEQ ID NO 75
<211> LENGTH: 1812
<212> TYPE: DNA
<213> ORGANISM: Homo sapiens

<400> SEQUENCE: 75

| | | | | | | |
|---|---|---|---|---|---|---|
| tagctaggca | ggaagtcggc | gcgggcggcg | cggacagtat | ctgtgggtac | ccggagcacg | 60 |
| gagatctcgc | cggctttacg | ttcacctcgg | tgtctgcagc | accctccgct | tcctctccta | 120 |
| ggcgacgaga | cccagtggct | agaagttcac | catgtctatt | ctcaagatcc | atgccaggga | 180 |
| gatctttgac | tctcgcggga | atcccactgt | tgaggttgat | ctcttcacct | caaaaggtct | 240 |
| cttcagagct | gctgtgccca | gtggtgcttc | aactggtatc | tatgaggccc | tagagctccg | 300 |
| ggacaatgat | aagactcgct | atatggggaa | gggtgtctca | aaggctgttg | agcacatcaa | 360 |
| taaaactatt | gcgcctgccc | tggttagcaa | gaaactgaac | gtcacagaac | aagagaagat | 420 |
| tgacaaactg | atgatcgaga | tggatggaac | agaaaataaa | tctaagtttg | gtgcgaacgc | 480 |
| cattctgggg | gtgtcccttg | ccgtctgcaa | agctggtgcc | gttgagaagg | ggtcccct | 540 |
| gtaccgccac | atcgctgact | ggctggcaa | ctctgaagtc | atcctgccag | tcccggcgtt | 600 |
| caatgtcatc | aatggcggtt | ctcatgctgg | caacaagctg | gccatgcagg | agttcatgat | 660 |
| cctcccagtc | ggtgcagcaa | acttcaggga | agccatgcgc | attggagcag | aggtttacca | 720 |
| caacctgaag | aatgtcatca | aggagaaata | tgggaaagat | gccaccaatg | tggggatga | 780 |
| aggcgggttt | gctcccaaca | tcctggagaa | taagaaggc | ctggagctgc | tgaagactgc | 840 |
| tattgggaaa | gctggctaca | ctgataaggt | ggtcatcggc | atggacgtag | cggcctccga | 900 |
| gttcttcagg | tctgggaagt | atgacctgga | cttcaagtct | cccgatgacc | cagcaggta | 960 |
| catctcgcct | gaccagctgg | ctgacctgta | caagtccttc | atcaaggact | acccagtggt | 1020 |
| gtctatcgaa | gatccctttg | accaggatga | ctggggagc | tggcagaagt | tcacagccag | 1080 |
| tgcaggaatc | caggtagtgg | gggatgatct | cacagtgacc | aacccaaaga | ggatcgccaa | 1140 |
| ggccgtgaac | gagaagtcct | gcaactgcct | cctgctcaaa | gtcaaccaga | ttggctccgt | 1200 |
| gaccgagtct | cttcaggcgt | gcaagctggc | ccaggccaat | ggttgggcg | tcatggtgtc | 1260 |
| tcatcgttcg | gggagactg | aagataccttt | catcgctgac | ctggttgtgg | ggctgtgcac | 1320 |
| tgggcagatc | aagactggtg | cccttgccg | atctgagcgc | ttggccaagt | acaaccagct | 1380 |
| cctcagaatt | gaagaggagc | tgggcagcaa | ggctaagttt | gccggcagga | acttcagaaa | 1440 |
| ccccttggcc | aagtaagctg | tgggcaggca | agcccttcgg | tcacctgttg | gctacacaga | 1500 |
| cccctcccct | cgtgtcagct | caggcagctc | gaggccccg | accaacactt | gcagggtcc | 1560 |
| ctgctagtta | gcgccccacc | gccgtggagt | tcgtaccgct | tccttagaac | ttctacagaa | 1620 |
| gccaagctcc | ctggagccct | gttggcagct | ctagctttgc | agtcgtgtaa | ttggcccaag | 1680 |
| tcattgtttt | tctcgcctca | cttttccacca | agtgtctaga | gtcatgtgag | cctcgtgtca | 1740 |
| tctccggggt | ggccacaggc | tagatccccg | gtggttttgt | gctcaaaata | aaaagcctca | 1800 |
| gtgacccatg | ag | | | | | 1812 |

<210> SEQ ID NO 76
<211> LENGTH: 627
<212> TYPE: DNA
<213> ORGANISM: Homo sapiens

<400> SEQUENCE: 76

```
acaactcggt ggtggccact gcgcagacca gacttcgctc gtactcgtgc gcctcgcttc    60
gcttttcctc cgcaaccatg tctgacaaac ccgatatggc tgagatcgag aaattcgata   120
agtcgaaact gaagaagaca gagacgcaag agaaaaatcc actgccttcc aaagaaacga   180
ttgaacagga gaagcaagca ggcgaatcgt aatgaggcgt gcgccgccaa tatgcactgt   240
acattccaca agcattgcct tcttatttta cttcttttag ctgtttaact ttgtaagatg   300
caaagaggtt ggatcaagtt taaatgactg tgctgcccct ttcacatcaa agaactactg   360
acaacgaagg ccgcgcctgc ctttcccatc tgtctatcta tctggctggc agggaaggaa   420
agaacttgca tgttggtgaa ggaagaagtg gggtggaaga agtggggtgg acgacagtg    480
aaatctagag taaaaccaag ctggcccaag gtgtcctgca ggctgtaatg cagtttaatc   540
agagtgccat tttttttttt gttcaaatga ttttaattat tggaatgcac aatttttta    600
atatgcaaat aaaaagttta aaaactt                                       627
```

<210> SEQ ID NO 77
<211> LENGTH: 296
<212> TYPE: PRT
<213> ORGANISM: Homo sapiens

<400> SEQUENCE: 77

```
Arg Leu Arg Glu Gly Gly Pro Pro Arg Pro Phe Arg Met Lys Ala Ala
1               5                   10                  15

Val Leu Thr Leu Ala Val Leu Phe Leu Thr Gly Ser Gln Ala Arg His
            20                  25                  30

Phe Trp Gln Gln Asp Glu Pro Pro Gln Ser Pro Trp Asp Arg Val Lys
        35                  40                  45

Asp Leu Ala Thr Val Tyr Val Asp Val Leu Lys Asp Ser Gly Arg Asp
    50                  55                  60

Tyr Val Ser Gln Phe Glu Gly Ser Ala Leu Gly Lys Gln Leu Asn Leu
65                  70                  75                  80

Lys Leu Leu Asp Asn Trp Asp Ser Val Thr Ser Thr Phe Ser Lys Leu
                85                  90                  95

Arg Glu Gln Leu Gly Pro Val Thr Gln Glu Phe Trp Asp Asn Leu Glu
            100                 105                 110

Lys Glu Thr Glu Gly Leu Arg Gln Glu Met Ser Lys Asp Leu Glu Glu
        115                 120                 125

Val Lys Ala Lys Val Gln Pro Tyr Leu Asp Asp Phe Gln Lys Lys Trp
    130                 135                 140

Gln Glu Glu Met Glu Leu Tyr Arg Gln Lys Val Glu Pro Leu Arg Ala
145                 150                 155                 160

Glu Leu Gln Glu Gly Ala Arg Gln Lys Leu His Glu Leu Gln Glu Lys
                165                 170                 175

Leu Ser Pro Leu Gly Glu Glu Met Arg Asp Arg Ala Arg Ala His Val
            180                 185                 190

Asp Ala Leu Arg Thr His Leu Ala Pro Tyr Ser Asp Glu Leu Arg Gln
        195                 200                 205

Arg Leu Ala Ala Arg Leu Glu Ala Leu Lys Glu Asn Gly Gly Ala Arg
    210                 215                 220

Leu Ala Glu Tyr His Ala Lys Ala Thr Glu His Leu Ser Thr Leu Ser
```

```
                    225                 230                 235                 240

Glu Lys Ala Lys Pro Ala Leu Glu Asp Leu Arg Gln Gly Leu Leu Pro
                245                 250                 255

Val Leu Glu Ser Phe Lys Val Ser Phe Leu Ser Ala Leu Glu Glu Tyr
                260                 265                 270

Thr Lys Leu Asn Thr Gln Gly Ala Arg Arg Pro Ser Arg
                275                 280                 285

Cys Ser Glu Thr Phe Pro Lys Trp
                290                 295

<210> SEQ ID NO 78
<211> LENGTH: 153
<212> TYPE: PRT
<213> ORGANISM: Homo sapiens

<400> SEQUENCE: 78

Gly Thr Asp Thr Lys Asp Arg Asp Ala Gly Ala Leu Pro Thr Val
1               5                   10                  15

Thr Asn Met Lys Leu Leu Ala Ala Thr Val Leu Leu Leu Thr Ile Cys
                20                  25                  30

Ser Leu Glu Gly Ala Leu Val Arg Arg Gln Ala Lys Glu Pro Cys Val
            35                  40                  45

Glu Ser Leu Val Ser Gln Tyr Phe Gln Thr Val Thr Asp Tyr Gly Lys
        50                  55                  60

Asp Leu Met Glu Lys Val Lys Ser Pro Glu Leu Gln Ala Glu Ala Lys
65                  70                  75                  80

Ser Tyr Phe Glu Lys Ser Lys Glu Gln Leu Thr Pro Leu Ile Lys Lys
                85                  90                  95

Ala Gly Thr Glu Leu Val Asn Phe Leu Ser Tyr Phe Val Glu Leu Gly
            100                 105                 110

Thr Gln Pro Ala Thr Gln Ser Val Gln Thr Ile Val Phe Gln Pro Gln
        115                 120                 125

Leu Ala Ser Arg Thr Pro Thr Gly Gln Ser Ser Cys Pro Tyr Pro
            130                 135                 140

Leu Phe Ala Thr Ile Asn Ala Glu Ile
145                 150

<210> SEQ ID NO 79
<211> LENGTH: 236
<212> TYPE: PRT
<213> ORGANISM: Homo sapiens

<400> SEQUENCE: 79

Leu Trp Leu Trp Ser Gly Ser Gly Ser Gln Pro Leu Ile Leu Ser Val
1               5                   10                  15

Pro Val Arg Ser Trp Gly Gln Pro Ala Arg Val Trp Ser Leu Asp Thr
                20                  25                  30

Met Gly Thr Arg Leu Leu Pro Ala Leu Phe Leu Val Leu Val Leu
            35                  40                  45

Gly Phe Glu Val Gln Gly Thr Gln Gln Pro Gln Gln Asp Glu Met Pro
        50                  55                  60

Ser Pro Thr Phe Leu Thr Gln Val Lys Glu Ser Leu Ser Ser Tyr Trp
65                  70                  75                  80

Glu Ser Ala Lys Thr Ala Ala Gln Asn Leu Tyr Glu Lys Thr Tyr Leu
                85                  90                  95

Pro Ala Val Asp Glu Lys Leu Arg Asp Leu Tyr Ser Lys Ser Thr Ala
            100                 105                 110
```

Ala Met Ser Thr Tyr Thr Gly Ile Phe Thr Asp Gln Val Leu Ser Val
            115                 120                 125

Leu Lys Gly Glu Glu Gln Pro Asp Pro Pro Ser Val Asp Lys Gly Arg
130                 135                 140

Val Pro Tyr Ser Pro Asp Pro Pro Gly Ser Asp Ala Pro Pro Ser Gln
145                 150                 155                 160

Leu Leu His Pro Pro Asn Ser Ser Leu Asn Ser Phe Gln Lys Ile
            165                 170                 175

Gln Phe Lys Leu Leu Met Asp Gly Thr Ala Phe Leu Arg Thr Gln
            180                 185                 190

Gly Pro Arg Trp Arg Gly Leu Ser Pro Ala Asn Ile Ala Pro Thr Leu
            195                 200                 205

Cys Met Glu Leu Pro Met Gly Pro Trp Glu Ser Glu Gln Ile Ile
210                 215                 220

Val Thr Lys Lys Lys Lys Lys Lys Lys Lys
225                 230                 235

<210> SEQ ID NO 80
<211> LENGTH: 436
<212> TYPE: PRT
<213> ORGANISM: Homo sapiens

<400> SEQUENCE: 80

Met Lys Ser Leu Val Leu Leu Cys Leu Ala Gln Leu Trp Gly Cys
1               5                   10                  15

His Ser Ala Pro His Gly Pro Gly Leu Ile Tyr Arg Gln Pro Asn Cys
            20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
            85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
            115                 120                 125

Tyr Ala Lys Cys Asp Ser Ser Pro Asp Ser Ala Glu Asp Val Arg Lys
130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
            165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
            195                 200                 205

Val Ala Lys Glu Ala Thr Glu Ala Ala Lys Cys Asn Leu Leu Ala Glu
            210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
            245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
            275                 280                 285

Pro Pro Ala Gly Ser Pro Pro Asp Ser His Val Leu Leu Ala Ala Pro
290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
            325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val Ala
            355                 360                 365

Arg His Gly Arg Asp Glu Glu Val Trp His Arg Lys His Ser His His
            370                 375                 380

Phe Val Gln Ala Trp Ala Trp Val Gly Gly Leu Val Cys Trp Pro Arg
385                 390                 395                 400

Lys Cys His Met Arg Ser Thr Leu Ile Ser Ser Leu Asp Ser Leu Leu
            405                 410                 415

Pro Val Ile Pro His Arg Thr Glu Ala Glu Trp Val Val Met Phe
            420                 425                 430

Asp Arg Arg His
            435

<210> SEQ ID NO 81
<211> LENGTH: 653
<212> TYPE: PRT
<213> ORGANISM: Homo sapiens

<400> SEQUENCE: 81

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

```
Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Thr Cys Cys Cys Lys Ser Ser Cys Leu Arg
        595                 600                 605

Leu Ile Thr Ser His Leu Lys Ala Ser Gln Pro Thr Met Arg Ile Arg
```

```
                    610                 615                 620
Glu Arg Lys Arg Ser Lys Ala Tyr Ser Ser Val Phe Leu Phe Arg Trp
625                 630                 635                 640

Cys Lys Ala Asn Thr Leu Ser Lys Lys His Lys Phe Leu
                645                 650

<210> SEQ ID NO 82
<211> LENGTH: 237
<212> TYPE: PRT
<213> ORGANISM: Homo sapiens

<400> SEQUENCE: 82

Met Asn Lys Pro Leu Trp Ile Ser Val Leu Thr Ser Leu Leu Glu
1               5                   10                  15

Ala Phe Ala His Thr Asp Leu Ser Gly Lys Val Phe Val Phe Pro Arg
                20                  25                  30

Glu Ser Val Thr Asp His Val Asn Leu Ile Thr Pro Leu Glu Lys Pro
            35                  40                  45

Leu Gln Asn Phe Thr Leu Cys Phe Arg Ala Tyr Ser Asp Leu Ser Arg
        50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Gly Ile Ala Glu Phe Trp Ile
        115                 120                 125

Asn Gly Thr Pro Leu Val Lys Lys Gly Leu Arg Gln Gly Tyr Phe Val
    130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
        195                 200                 205

Tyr Glu Ile Arg Gly Tyr Val Ile Ile Lys Pro Leu Val Trp Val Gly
210                 215                 220

Leu Asp Ser Thr Arg Ala Leu Glu Asn Glu Met Thr Val
225                 230                 235

<210> SEQ ID NO 83
<211> LENGTH: 279
<212> TYPE: PRT
<213> ORGANISM: Homo sapiens

<400> SEQUENCE: 83

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60
```

```
Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Gly Ala Arg Arg Arg
            260                 265                 270

Pro Pro Ser Arg Cys Ser Glu
            275

<210> SEQ ID NO 84
<211> LENGTH: 120
<212> TYPE: PRT
<213> ORGANISM: Homo sapiens

<400> SEQUENCE: 84

Met Lys Leu Leu Ala Ala Thr Val Leu Leu Thr Ile Cys Ser Leu
1               5                   10                  15

Glu Gly Ala Leu Val Arg Arg Gln Ala Lys Glu Pro Cys Val Glu Ser
                20                  25                  30

Leu Val Ser Gln Tyr Phe Gln Thr Val Thr Asp Tyr Gly Lys Asp Leu
            35                  40                  45

Met Glu Lys Val Lys Ser Pro Glu Leu Gln Ala Glu Ala Lys Ser Tyr
        50                  55                  60

Phe Glu Lys Ser Lys Glu Gln Leu Thr Pro Leu Ile Lys Lys Ala Gly
 65                 70                  75                  80

Thr Glu Leu Val Asn Phe Leu Ser Tyr Phe Val Glu Leu Gly Thr Gln
                85                  90                  95

Pro Ala Thr Gln Ser Val Gln Thr Ile Val Phe Gln Pro Gln Leu Ala
            100                 105                 110

Ser Arg Thr Pro Thr Gly Gln Ser
        115                 120

<210> SEQ ID NO 85
<211> LENGTH: 123
<212> TYPE: PRT
<213> ORGANISM: Homo sapiens
```

<400> SEQUENCE: 85

Met Gly Thr Arg Leu Leu Pro Ala Leu Phe Leu Val Leu Leu Val Leu
1               5                   10                  15

Gly Phe Glu Val Gln Gly Thr Gln Gln Pro Gln Gln Asp Glu Met Pro
            20                  25                  30

Ser Pro Thr Phe Leu Thr Gln Val Lys Glu Ser Leu Ser Ser Tyr Trp
        35                  40                  45

Glu Ser Ala Lys Thr Ala Ala Gln Asn Leu Tyr Glu Lys Thr Tyr Leu
    50                  55                  60

Pro Ala Val Asp Glu Lys Leu Arg Asp Leu Tyr Ser Lys Ser Thr Ala
65                  70                  75                  80

Ala Met Ser Thr Tyr Thr Gly Ile Phe Thr Asp Gln Val Leu Ser Val
                85                  90                  95

Leu Lys Gly Glu Glu Gln Pro Asp Pro Pro Ser Val Asp Lys Gly Arg
            100                 105                 110

Val Pro Tyr Ser Pro Asp Pro Pro Gly Ser Asp
            115                 120

<210> SEQ ID NO 86
<211> LENGTH: 153
<212> TYPE: PRT
<213> ORGANISM: Homo sapiens

<400> SEQUENCE: 86

Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala Asp Leu Asn Thr Pro Ser Pro Pro Ala Tyr Pro Ser Cys
            100                 105                 110

Glu Leu Leu Gly Ser Cys Asn Leu Gln Gly Cys Pro Cys Arg Leu Leu
        115                 120                 125

Lys Arg Asp Ser Ile Leu Ser Ala Leu Leu Pro His Leu Met Pro Gly
    130                 135                 140

Pro Pro Pro Gly Met Leu Ala Ser Gln
145                 150

<210> SEQ ID NO 87
<211> LENGTH: 225
<212> TYPE: PRT
<213> ORGANISM: Homo sapiens

<400> SEQUENCE: 87

Met Val Met Leu Leu Leu Leu Leu Ser Ala Leu Ala Gly Leu Phe Gly
1               5                   10                  15

Ala Ala Glu Gly Gln Ala Phe His Leu Gly Lys Cys Pro Asn Pro Pro
            20                  25                  30

Val Gln Glu Asn Phe Asp Val Asn Lys Tyr Leu Gly Arg Trp Tyr Glu

```
                35                  40                  45
Ile Glu Lys Ile Pro Thr Thr Phe Glu Asn Gly Arg Cys Ile Gln Ala
 50                  55                  60

Asn Tyr Ser Leu Met Glu Asn Gly Lys Ile Lys Val Leu Asn Gln Glu
 65                  70                  75                  80

Leu Arg Ala Asp Gly Thr Val Asn Gln Ile Glu Gly Glu Ala Thr Pro
                 85                  90                  95

Val Asn Leu Thr Glu Pro Ala Lys Leu Glu Val Lys Phe Ser Trp Phe
                100                 105                 110

Met Pro Ser Ala Pro Tyr Trp Ile Leu Ala Thr Asp Tyr Glu Asn Tyr
                115                 120                 125

Ala Leu Val Tyr Ser Cys Thr Cys Ile Ile Gln Leu Phe His Val Asp
            130                 135                 140

Phe Ala Trp Ile Leu Ala Arg Asn Pro Asn Leu Pro Pro Glu Thr Val
145                 150                 155                 160

Asp Ser Leu Lys Asn Ile Leu Thr Ser Asn Asn Ile Asp Val Lys Lys
                165                 170                 175

Met Thr Val Thr Asp Gln Val Asn Cys Pro Lys Leu Ser Pro Gly Ser
                180                 185                 190

Thr Gly Arg Leu His Pro Leu His Val Thr Ser Ala Ser Leu Ser Pro
            195                 200                 205

Thr Pro Pro Pro His Lys Asp Lys Pro Ile Asn His Asp Lys Gly
        210                 215                 220

Ser
225

<210> SEQ ID NO 88
<211> LENGTH: 354
<212> TYPE: PRT
<213> ORGANISM: Homo sapiens

<400> SEQUENCE: 88

Met Lys Val Leu Trp Ala Ala Leu Leu Val Thr Phe Leu Ala Gly Cys
 1               5                  10                  15

Gln Ala Lys Val Glu Gln Ala Val Glu Thr Glu Pro Glu Pro Glu Leu
                 20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
 50                  55                  60

Val Gln Glu Glu Leu Leu Ser Ser Gln Val Thr Gln Glu Leu Arg Ala
 65                  70                  75                  80

Leu Met Asp Glu Thr Met Lys Glu Leu Lys Ala Tyr Lys Ser Glu Leu
                 85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
```

```
                        180                 185                 190
Ser Ala Ile Arg Glu Arg Leu Gly Pro Leu Val Glu Gln Gly Arg Val
                195                 200                 205

Arg Ala Ala Thr Val Gly Ser Leu Ala Gly Gln Pro Leu Gln Glu Arg
            210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His Thr Pro Lys
305                 310                 315                 320

Pro Ala Ala Met Arg Pro His Ala Thr Pro Cys Leu Leu Pro Pro Arg
                325                 330                 335

Ser Leu Gln Arg Glu Thr Leu Ser Pro Pro Gln Pro Ser Ser Trp Gly
            340                 345                 350

Gly Pro

<210> SEQ ID NO 89
<211> LENGTH: 315
<212> TYPE: PRT
<213> ORGANISM: Homo sapiens

<400> SEQUENCE: 89

Met Trp Ala Ser Met Ser Arg Met Leu Pro Val Leu Ser Leu Leu Leu
1               5                   10                  15

Leu Leu Leu Gly Pro Ala Val Pro Gln Glu Asn Gln Asp Gly Arg Tyr
                20                  25                  30

Ser Leu Thr Tyr Ile Tyr Thr Gly Leu Ser Lys His Val Glu Asp Val
            35                  40                  45

Pro Ala Phe Gln Ala Leu Gly Ser Leu Asn Asp Leu Gln Phe Phe Arg
        50                  55                  60

Tyr Asn Ser Lys Asp Arg Lys Ser Gln Pro Met Gly Leu Trp Arg Gln
65                  70                  75                  80

Val Glu Gly Met Glu Asp Trp Lys Gln Asp Ser Gln Leu Gln Lys Ala
                85                  90                  95

Arg Glu Asp Ile Phe Met Glu Thr Leu Lys Asp Ile Val Glu Tyr Tyr
            100                 105                 110

Asn Asp Ser Asn Gly Ser His Val Leu Gln Gly Arg Phe Gly Cys Glu
        115                 120                 125

Ile Glu Asn Asn Arg Ser Ser Gly Ala Phe Trp Lys Tyr Tyr Tyr Asp
    130                 135                 140

Gly Lys Asp Tyr Ile Glu Phe Asn Lys Glu Ile Pro Ala Trp Val Pro
145                 150                 155                 160

Phe Asp Pro Ala Ala Gln Ile Thr Lys Gln Lys Trp Glu Ala Glu Pro
                165                 170                 175

Val Tyr Val Gln Arg Ala Lys Ala Tyr Leu Glu Glu Glu Cys Pro Ala
            180                 185                 190

Thr Leu Arg Lys Tyr Leu Lys Tyr Ser Lys Asn Ile Leu Asp Arg Gln
        195                 200                 205
```

Asp Pro Pro Ser Val Val Thr Ser His Gln Ala Pro Gly Glu Lys
    210                 215                 220

Lys Lys Leu Lys Cys Leu Ala Tyr Asp Phe Tyr Pro Gly Lys Ile Asp
225                 230                 235                 240

Val His Trp Thr Arg Ala Gly Glu Val Gln Glu Pro Glu Leu Arg Gly
                245                 250                 255

Asp Val Leu His Asn Gly Asn Gly Thr Tyr Gln Ser Trp Val Val Val
                260                 265                 270

Ala Val Pro Pro Gln Asp Thr Ala Pro Tyr Ser Cys His Val Gln His
                275                 280                 285

Ser Ser Leu Ala Gln Pro Leu Val Val Pro Trp Glu Ala Ser Glu Ala
    290                 295                 300

Arg Val Gly Gly Asn Val Gly Ser Gln Thr Gln
305                 310                 315

<210> SEQ ID NO 90
<211> LENGTH: 412
<212> TYPE: PRT
<213> ORGANISM: Homo sapiens

<400> SEQUENCE: 90

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
                275                 280                 285

Lys Glu Ala Gly Thr Leu Ala Tyr Tyr Glu Ile Cys Asp Phe Leu Arg
            290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
                355                 360                 365

Arg Phe Pro Leu Thr Asn Ala Ile Lys Asp Ala Leu Ala Ala Thr Pro
            370                 375                 380

Ser Val Leu His Thr Ala Arg Gly Pro Arg Met Pro Arg Pro Pro Leu
385                 390                 395                 400

Ala Pro Ala Gly Arg Glu Pro Asp His Leu Pro Cys
                405                 410

<210> SEQ ID NO 91
<211> LENGTH: 573
<212> TYPE: PRT
<213> ORGANISM: Homo sapiens

<400> SEQUENCE: 91

Met Gln Val Cys Ser Gln Pro Gln Arg Gly Cys Val Arg Glu Gln Ser
1               5                   10                  15

Ala Ile Asn Thr Ala Pro Pro Ser Ala His Asn Ala Ala Ser Pro Gly
            20                  25                  30

Gly Ala Arg Gly His Arg Val Pro Leu Thr Glu Ala Cys Lys Asp Ser
        35                  40                  45

Arg Ile Gly Gly Met Met Lys Thr Leu Leu Leu Phe Val Gly Leu Leu
    50                  55                  60

Leu Thr Trp Glu Ser Gly Gln Val Leu Gly Asp Gln Thr Val Ser Asp
65                  70                  75                  80

Asn Glu Leu Gln Glu Met Ser Asn Gln Gly Ser Lys Tyr Val Asn Lys
                85                  90                  95

Glu Ile Gln Asn Ala Val Asn Gly Val Lys Gln Ile Lys Thr Leu Ile
            100                 105                 110

Glu Lys Thr Asn Glu Glu Arg Lys Thr Leu Leu Ser Asn Leu Glu Glu
        115                 120                 125

Ala Lys Lys Lys Lys Glu Asp Ala Leu Asn Glu Thr Arg Glu Ser Glu
    130                 135                 140

Thr Lys Leu Lys Glu Leu Pro Gly Val Cys Asn Glu Thr Met Met Ala
145                 150                 155                 160

Leu Trp Glu Glu Cys Lys Pro Cys Leu Lys Gln Thr Cys Met Lys Phe
                165                 170                 175

Tyr Ala Arg Val Cys Arg Ser Gly Ser Gly Leu Val Gly Arg Gln Leu
            180                 185                 190

Glu Glu Phe Leu Asn Gln Ser Ser Pro Phe Tyr Phe Trp Met Asn Gly
        195                 200                 205

Asp Arg Ile Asp Ser Leu Leu Glu Asn Asp Arg Gln Gln Thr His Met
    210                 215                 220

Leu Asp Val Met Gln Asp His Phe Ser Arg Ala Ser Ser Ile Ile Asp
225                 230                 235                 240

```
Glu Leu Phe Gln Asp Arg Phe Thr Arg Glu Pro Gln Asp Thr Tyr
            245                 250                 255

His Tyr Leu Pro Phe Ser Leu Pro His Arg Arg Pro His Phe Phe
            260                 265                 270

Pro Lys Ser Arg Ile Val Arg Ser Leu Met Pro Phe Ser Pro Tyr Glu
            275                 280                 285

Pro Leu Asn Phe His Ala Met Phe Gln Pro Phe Leu Glu Met Ile His
            290                 295                 300

Glu Ala Gln Gln Ala Met Asp Ile His Phe His Ser Pro Ala Phe Gln
305                 310                 315                 320

His Pro Pro Thr Glu Phe Ile Arg Glu Gly Asp Asp Arg Thr Val
            325                 330                 335

Cys Arg Glu Ile Arg His Asn Ser Thr Gly Cys Leu Arg Met Lys Asp
            340                 345                 350

Gln Cys Asp Lys Cys Arg Glu Ile Leu Ser Val Asp Cys Ser Thr Asn
            355                 360                 365

Asn Pro Ser Gln Ala Lys Leu Arg Arg Glu Leu Asp Glu Ser Leu Gln
            370                 375                 380

Val Ala Glu Arg Leu Thr Arg Lys Tyr Asn Glu Leu Leu Lys Ser Tyr
385                 390                 395                 400

Gln Trp Lys Met Leu Asn Thr Ser Ser Leu Leu Glu Gln Leu Asn Glu
            405                 410                 415

Gln Phe Asn Trp Val Ser Arg Leu Ala Asn Leu Thr Gln Gly Glu Asp
            420                 425                 430

Gln Tyr Tyr Leu Arg Val Thr Thr Val Ala Ser His Thr Ser Asp Ser
            435                 440                 445

Asp Val Pro Ser Gly Val Thr Glu Val Val Lys Leu Phe Asp Ser
            450                 455                 460

Asp Pro Ile Thr Val Thr Val Pro Val Glu Val Ser Arg Lys Asn Pro
465                 470                 475                 480

Lys Phe Met Glu Thr Val Ala Glu Lys Ala Leu Gln Glu Tyr Arg Lys
            485                 490                 495

Lys His Arg Glu Glu Asp Val Asp Val Ala Phe Ala Pro Thr Gly Ala
            500                 505                 510

Ser Glu Ser Ser Pro Gln Asp Glu Leu Gln Pro Pro Arg Glu Ser
            515                 520                 525

Ser Ala Arg His Gln Val Thr Arg Pro Gln Pro Gly Pro Gln Leu
            530                 535                 540

Arg Pro Ala Ser Pro Arg Ser Gly Ser Cys Thr Leu Thr Leu Asp Ser
545                 550                 555                 560

Ala Ala His Gly Lys Asn Arg Ile Ala Pro Ala Cys Asn
            565                 570

<210> SEQ ID NO 92
<211> LENGTH: 539
<212> TYPE: PRT
<213> ORGANISM: Homo sapiens

<400> SEQUENCE: 92

Met Lys Ala Leu Ile Ala Ala Leu Leu Leu Ile Thr Leu Gln Tyr Ser
1               5                   10                  15

Cys Ala Val Ser Pro Thr Asp Cys Ser Ala Val Glu Pro Glu Ala Glu
            20                  25                  30

Lys Ala Leu Asp Leu Ile Asn Lys Arg Arg Arg Asp Gly Tyr Leu Phe
            35                  40                  45
```

```
Gln Leu Leu Arg Ile Ala Asp Ala His Leu Asp Arg Val Glu Asn Thr
 50                  55                  60
Thr Val Tyr Tyr Leu Val Leu Asp Val Gln Glu Ser Asp Cys Ser Val
 65                  70                  75                  80
Leu Ser Arg Lys Tyr Trp Asn Asp Cys Glu Pro Pro Asp Ser Arg Arg
                 85                  90                  95
Pro Ser Glu Ile Val Ile Gly Gln Cys Lys Val Ile Ala Thr Arg His
            100                 105                 110
Ser His Glu Ser Gln Asp Leu Arg Val Ile Asp Phe Asn Cys Thr Thr
        115                 120                 125
Ser Ser Val Ser Ser Ala Leu Ala Asn Thr Lys Asp Ser Pro Val Leu
    130                 135                 140
Ile Asp Phe Phe Glu Asp Thr Glu Arg Tyr Arg Lys Gln Ala Asn Lys
145                 150                 155                 160
Ala Leu Glu Lys Tyr Lys Glu Glu Asn Asp Asp Phe Ala Ser Phe Arg
                165                 170                 175
Val Asp Arg Ile Glu Arg Val Ala Arg Val Arg Gly Gly Glu Gly Thr
            180                 185                 190
Gly Tyr Phe Val Asp Phe Ser Val Arg Asn Cys Pro Arg His His Phe
        195                 200                 205
Pro Arg His Pro Asn Val Phe Gly Phe Cys Arg Ala Asp Leu Phe Tyr
210                 215                 220
Asp Val Glu Ala Leu Asp Leu Glu Ser Pro Lys Asn Leu Val Ile Asn
225                 230                 235                 240
Cys Glu Val Phe Asp Pro Gln Glu His Glu Asn Ile Asn Gly Val Pro
                245                 250                 255
Pro His Leu Gly His Pro Phe His Trp Gly Gly His Glu Arg Ser Ser
            260                 265                 270
Thr Thr Lys Pro Pro Phe Lys Pro His Gly Ser Arg Asp His His His
        275                 280                 285
Pro His Lys Pro His Glu His Gly Pro Pro Pro Pro Asp Glu Arg
    290                 295                 300
Asp His Ser His Gly Pro Pro Leu Pro Gln Gly Pro Pro Pro Leu Leu
305                 310                 315                 320
Pro Met Ser Cys Ser Ser Cys Gln His Ala Thr Phe Gly Thr Asn Gly
                325                 330                 335
Ala Gln Arg His Ser His Asn Asn Ser Ser Asp Leu His Pro His
            340                 345                 350
Lys His His Ser His Glu Gln His Pro His Gly His Pro His Ala
        355                 360                 365
His His Pro His Glu His Asp Thr His Arg Gln His Pro His Gly His
    370                 375                 380
His Pro His Gly His His Pro His Gly His His Pro His Gly His His
385                 390                 395                 400
Pro His Gly His His Pro His Cys His Asp Phe Gln Asp Tyr Gly Pro
                405                 410                 415
Cys Asp Pro Pro Pro His Asn Gln Gly His Cys Cys His Gly His Gly
            420                 425                 430
Pro Pro Pro Gly His Leu Arg Arg Gly Pro Gly Lys Gly Pro Arg
        435                 440                 445
Pro Phe His Cys Arg Gln Ile Gly Ser Val Tyr Arg Leu Pro Pro Leu
    450                 455                 460
Arg Lys Gly Glu Val Leu Pro Leu Pro Glu Ala Asn Phe Pro Ser Phe
```

```
                465                 470                 475                 480
        Pro Leu Pro His His Lys His Pro Leu Lys Pro Asp Asn Gln Pro Phe
                        485                 490                 495

Pro Gln Ser Val Ser Glu Ser Cys Pro Gly Lys Phe Lys Ser Gly Phe
                        500                 505                 510

Pro Gln Val Ser Met Phe Phe Thr His Thr Phe Pro Lys Asn Val Ile
                        515                 520                 525

Pro Leu Lys Arg Lys Met Asn Asn Thr Leu Asn
                        530                 535

<210> SEQ ID NO 93
        <211> LENGTH: 330
        <212> TYPE: PRT
        <213> ORGANISM: Homo sapiens

<400> SEQUENCE: 93

Met Gln Arg Ala Arg Pro Thr Leu Trp Ala Ala Leu Thr Leu Leu
        1               5                   10                  15

Val Leu Leu Arg Gly Pro Pro Val Ala Arg Ala Gly Ala Ser Ser Ala
                        20                  25                  30

Gly Leu Gly Pro Val Val Arg Cys Glu Pro Cys Asp Ala Arg Ala Leu
                        35                  40                  45

Ala Gln Cys Ala Pro Pro Ala Val Cys Ala Glu Leu Val Arg Glu
            50                  55                  60

Pro Gly Cys Gly Cys Cys Leu Thr Cys Ala Leu Ser Glu Gly Gln Pro
        65                  70                  75                  80

Cys Gly Ile Tyr Thr Glu Arg Cys Gly Ser Gly Leu Arg Cys Gln Pro
                        85                  90                  95

Ser Pro Asp Glu Ala Arg Pro Leu Gln Ala Leu Leu Asp Gly Arg Gly
                        100                 105                 110

Leu Cys Val Asn Ala Ser Ala Val Ser Arg Leu Arg Ala Tyr Leu Leu
                        115                 120                 125

Pro Ala Pro Pro Ala Pro Gly Asn Ala Ser Glu Ser Glu Glu Asp Arg
            130                 135                 140

Ser Ala Gly Ser Val Glu Ser Pro Ser Val Ser Ser Thr His Arg Val
        145                 150                 155                 160

Ser Asp Pro Lys Phe His Pro Leu His Ser Lys Ile Ile Ile Lys
                        165                 170                 175

Lys Gly His Ala Lys Asp Ser Gln Arg Tyr Lys Val Asp Tyr Glu Ser
                        180                 185                 190

Gln Ser Thr Asp Thr Gln Asn Phe Ser Ser Glu Ser Lys Arg Glu Thr
                        195                 200                 205

Glu Tyr Gly Pro Cys Arg Arg Glu Met Glu Asp Thr Leu Asn His Leu
            210                 215                 220

Lys Phe Leu Asn Val Leu Ser Pro Arg Gly Val His Ile Pro Asn Cys
        225                 230                 235                 240

Asp Lys Lys Gly Phe Tyr Lys Lys Gln Cys Arg Pro Ser Lys Gly
                        245                 250                 255

Arg Lys Arg Gly Phe Cys Trp Cys Val Asp Lys Tyr Gly Gln Pro Leu
                        260                 265                 270

Pro Gly Tyr Thr Thr Lys Gly Lys Glu Asp Val His Cys Tyr Ser Met
                        275                 280                 285

Gln Ser Lys Thr Pro Ala Ala Arg Leu Met Trp Ser Ser Asn Met Pro
            290                 295                 300

Tyr Phe Ala Gln Lys Thr Ala Lys Asp Met Thr Ser Ser Trp Leu Gln
```

Pro Arg Phe Ile Phe Leu Phe Val Val Asn
            325             330

<210> SEQ ID NO 94
<211> LENGTH: 419
<212> TYPE: PRT
<213> ORGANISM: Homo sapiens

<400> SEQUENCE: 94

Met Val Leu His Leu Leu Phe Leu Leu Thr Pro Gln Gly Gly
1               5                   10                  15

His Ser Cys Gln Gly Leu Glu Leu Ala Arg Glu Leu Val Leu Ala Lys
            20                  25                  30

Val Arg Ala Leu Phe Leu Asp Ala Leu Gly Pro Pro Ala Val Thr Arg
        35                  40                  45

Glu Gly Gly Asp Pro Gly Val Arg Arg Leu Pro Arg Arg His Ala Leu
50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Gly Leu Phe Arg
            100                 105                 110

Tyr Met Phe Arg Pro Ser Gln His Thr Arg Ser Arg Gln Val Thr Ser
        115                 120                 125

Ala Gln Leu Trp Phe His Thr Gly Leu Asp Arg Gln Gly Thr Ala Ala
130                 135                 140

Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
                165                 170                 175

Ala Val Leu His Leu Ala Thr Ser Ala Leu Ser Leu Leu Thr His Pro
            180                 185                 190

Val Leu Val Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
210                 215                 220

Ser Gly Gly Glu Arg Ala Arg Arg Ser Thr Pro Leu Met Ser Trp Pro
225                 230                 235                 240

Trp Ser Pro Ser Ala Leu Arg Leu Leu Gln Arg Pro Pro Glu Glu Pro
                245                 250                 255

Ala Ala His Ala Asn Cys His Arg Val Ala Leu Asn Ile Ser Phe Gln
            260                 265                 270

Glu Leu Gly Trp Glu Arg Trp Ile Val Tyr Pro Pro Ser Phe Ile Phe
        275                 280                 285

His Tyr Cys His Gly Gly Cys Gly Leu His Ile Pro Pro Asn Leu Ser
290                 295                 300

Leu Pro Val Pro Gly Ala Pro Pro Thr Pro Ala Gln Pro Tyr Ser Leu
305                 310                 315                 320

Leu Pro Gly Ala Gln Pro Cys Cys Ala Ala Leu Pro Gly Thr Met Arg
                325                 330                 335

Pro Leu His Val Arg Thr Thr Ser Asp Gly Gly Tyr Ser Phe Lys Tyr
            340                 345                 350

Glu Thr Val Pro Asn Leu Leu Thr Gln His Cys Ala Cys Ile Gly Trp

```
                 355                 360                 365
Gly Val Phe Leu Leu Asn Pro Met Ala Gly Gly His Ala Pro Thr Ile
            370                 375                 380
Ile Ser Trp Glu Glu Arg Gln Ser Trp Glu Ile Asp Gly Ser His Ser
385                 390                 395                 400
Ser Leu Leu Ser Leu Leu Cys Leu Trp Ala Thr Leu Pro Thr Pro Leu
                405                 410                 415
Leu Ser Gln

<210> SEQ ID NO 95
<211> LENGTH: 309
<212> TYPE: PRT
<213> ORGANISM: Homo sapiens

<400> SEQUENCE: 95

Met Gln Arg Leu Arg Trp Leu Arg Asp Trp Lys Ser Ser Gly Arg Gly
1               5                   10                  15
Leu Thr Ala Ala Lys Glu Pro Gly Ala Arg Ser Ser Pro Leu Gln Ala
            20                  25                  30
Met Arg Ile Leu Gln Leu Ile Leu Leu Ala Leu Ala Thr Gly Leu Val
        35                  40                  45
Gly Gly Glu Thr Arg Ile Ile Lys Gly Phe Glu Cys Lys Pro His Ser
    50                  55                  60
Gln Pro Trp Gln Ala Ala Leu Phe Glu Lys Thr Arg Leu Leu Cys Gly
65                  70                  75                  80
Ala Thr Leu Ile Ala Pro Arg Trp Leu Leu Thr Ala Ala His Cys Leu
                85                  90                  95
Lys Pro Arg Tyr Ile Val His Leu Gly Gln His Asn Leu Gln Lys Glu
            100                 105                 110
Glu Gly Cys Glu Gln Thr Arg Thr Ala Thr Glu Ser Phe Pro His Pro
        115                 120                 125
Gly Phe Asn Asn Ser Leu Pro Asn Lys Asp His Arg Asn Asp Ile Met
    130                 135                 140
Leu Val Lys Met Ala Ser Pro Val Ser Ile Thr Trp Ala Val Arg Pro
145                 150                 155                 160
Leu Thr Leu Ser Ser Arg Cys Val Thr Ala Gly Thr Ser Cys Leu Ile
                165                 170                 175
Ser Gly Trp Gly Ser Thr Ser Ser Pro Gln Leu Arg Leu Pro His Thr
            180                 185                 190
Leu Arg Cys Ala Asn Ile Thr Ile Ile Glu His Gln Lys Cys Glu Asn
        195                 200                 205
Ala Tyr Pro Gly Asn Ile Thr Asp Thr Met Val Cys Ala Ser Val Gln
    210                 215                 220
Glu Gly Gly Lys Asp Ser Cys Gln Gly Asp Ser Gly Gly Pro Leu Val
225                 230                 235                 240
Cys Asn Gln Ser Leu Gln Gly Ile Ile Ser Trp Gly Gln Asp Pro Cys
                245                 250                 255
Ala Ile Thr Arg Lys Pro Gly Val Tyr Thr Lys Val Cys Lys Tyr Val
            260                 265                 270
Asp Trp Ile Gln Glu Thr Met Lys Asn Asn Thr Gly Pro Thr His His
        275                 280                 285
Ser Pro Ser Pro Ser Ile Ser Thr Trp Cys Leu Val Pro Val His Ser
    290                 295                 300
Val Asn Lys Lys Pro
305
```

```
<210> SEQ ID NO 96
<211> LENGTH: 556
<212> TYPE: PRT
<213> ORGANISM: Homo sapiens

<400> SEQUENCE: 96

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380
```

```
Ala Glu Ala Ala Met Phe His Arg Lys Leu Phe Glu Glu Leu Val Arg
385                 390                 395                 400

Ala Ser Ser His Ser Thr Asp Leu Met Glu Ala Met Ala Met Gly Ser
            405                 410                 415

Val Glu Ala Ser Tyr Lys Cys Leu Ala Ala Leu Ile Val Leu Thr
        420                 425                 430

Glu Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Phe Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
        515                 520                 525

Pro Val Pro Trp Thr Pro Glu Pro Leu Leu Gln Pro Leu Ser His Pro
    530                 535                 540

Leu Pro Pro Ala His Pro Leu Gly Gln Gln Arg Leu
545                 550                 555

<210> SEQ ID NO 97
<211> LENGTH: 825
<212> TYPE: PRT
<213> ORGANISM: Homo sapiens

<400> SEQUENCE: 97

Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205
```

```
Trp Asp Ser Gln Ser Pro His Ala His Gly Tyr Ile Pro Ser Lys Phe
    210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                    245                 250                 255
Cys Asp Ile Pro Arg Cys Thr Thr Pro Pro Pro Ser Ser Gly Pro Thr
                260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
        290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                    325                 330                 335
Thr Thr Asn Ser Gln Val Arg Trp Glu Tyr Cys Lys Ile Pro Ser Cys
                340                 345                 350
Asp Ser Ser Pro Val Ser Thr Glu Gln Leu Ala Pro Thr Ala Pro Pro
            355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                    405                 410                 415
Pro Asn Ala Gly Leu Thr Met Asn Tyr Cys Arg Asn Pro Asp Ala Asp
                420                 425                 430
Lys Gly Pro Trp Cys Phe Thr Thr Asp Pro Ser Val Arg Trp Glu Tyr
            435                 440                 445
Cys Asn Leu Lys Lys Cys Ser Gly Thr Glu Ala Ser Val Val Ala Pro
        450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                    485                 490                 495
Val Thr Gly Thr Pro Cys Gln Asp Trp Ala Ala Gln Glu Pro His Arg
                500                 505                 510
His Ser Ile Phe Thr Pro Glu Thr Asn Pro Arg Ala Gly Leu Glu Lys
            515                 520                 525
Asn Tyr Cys Arg Asn Pro Asp Gly Asp Val Gly Gly Pro Trp Cys Tyr
        530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                    565                 570                 575
Cys Pro Gly Arg Val Val Gly Gly Cys Val Ala His Pro His Ser Trp
                580                 585                 590
Pro Trp Gln Val Ser Leu Arg Thr Arg Phe Gly Met His Phe Cys Gly
            595                 600                 605
Gly Thr Leu Ile Ser Pro Glu Trp Val Leu Thr Ala Ala His Cys Leu
        610                 615                 620
Glu Lys Ser Pro Arg Pro Ser Ser Tyr Lys Val Ile Leu Gly Ala His
```

```
                625                 630                 635                 640
Gln Glu Val Asn Leu Glu Pro His Val Gln Glu Ile Glu Val Ser Arg
                    645                 650                 655

Leu Phe Leu Glu Pro Thr Arg Lys Asp Ile Ala Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn Leu Asp Gly Arg Gln Ser
                805                 810                 815

Asp Ala Leu Thr Thr Trp Val Gly Ile
            820                 825

<210> SEQ ID NO 98
<211> LENGTH: 494
<212> TYPE: PRT
<213> ORGANISM: Homo sapiens

<400> SEQUENCE: 98

Met Glu Arg Met Leu Pro Leu Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
                100                 105                 110

Ala Glu Ile His Gln Ser Phe Gln His Leu Leu Arg Thr Leu Asn Gln
            115                 120                 125

Ser Ser Asp Glu Leu Gln Leu Ser Met Gly Asn Ala Met Phe Val Lys
        130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
```

```
                    180                 185                 190
Thr Asp Leu Ile Lys Asp Leu Asp Ser Gln Thr Met Met Val Leu Val
            195                 200                 205
Asn Tyr Ile Phe Phe Lys Ala Lys Trp Glu Met Pro Phe Asp Pro Gln
        210                 215                 220
Asp Thr His Gln Ser Arg Phe Tyr Leu Ser Lys Lys Trp Val Met
225                 230                 235                 240
Val Pro Met Met Ser Leu His His Leu Thr Ile Pro Tyr Phe Arg Asp
                245                 250                 255
Glu Glu Leu Ser Cys Thr Val Val Glu Leu Lys Tyr Thr Gly Asn Ala
            260                 265                 270
Ser Ala Leu Phe Ile Leu Pro Asp Gln Asp Lys Met Glu Glu Val Glu
        275                 280                 285
Ala Met Leu Leu Pro Glu Thr Leu Lys Arg Trp Arg Asp Ser Leu Glu
    290                 295                 300
Phe Arg Glu Ile Gly Glu Leu Tyr Leu Pro Lys Phe Ser Ile Ser Arg
305                 310                 315                 320
Asp Tyr Asn Leu Asn Asp Ile Leu Leu Gln Leu Gly Ile Glu Glu Ala
                325                 330                 335
Phe Thr Ser Lys Ala Asp Leu Ser Gly Ile Thr Gly Ala Arg Asn Leu
            340                 345                 350
Ala Val Ser Gln Val Val His Lys Ala Val Leu Asp Val Phe Glu Glu
        355                 360                 365
Gly Thr Glu Ala Ser Ala Ala Thr Ala Val Lys Ile Thr Leu Leu Ser
    370                 375                 380
Ala Leu Val Glu Thr Arg Thr Ile Val Arg Phe Asn Arg Pro Phe Leu
385                 390                 395                 400
Met Ile Ile Val Pro Thr Asp Thr Gln Asn Ile Phe Phe Met Ser Lys
                405                 410                 415
Val Thr Asn Pro Lys Gln Ala Ser Leu Pro Ser Ser Ser Gly Ala Leu
            420                 425                 430
Ser Lys Glu Leu Gly Met Gln Ala Gly Cys Leu Gly Leu Trp Ala Gln
        435                 440                 445
Pro Gly Pro Cys Ala Pro Ser Gly His Gly Met Cys Gly Pro Val Cys
    450                 455                 460
Leu Ser Leu Glu Gly Asp Ser Asp Ser Leu Cys Ser Ser His Met His
465                 470                 475                 480
Arg Gly Pro Trp Thr Leu Gln Ser Gly Gly Ser Trp Ala Ser
                485                 490

<210> SEQ ID NO 99
<211> LENGTH: 746
<212> TYPE: PRT
<213> ORGANISM: Homo sapiens

<400> SEQUENCE: 99

Met Arg Leu Ala Val Gly Ala Leu Leu Val Cys Ala Val Leu Gly Leu
1               5                   10                  15
Cys Leu Ala Val Pro Asp Lys Thr Val Arg Trp Cys Ala Val Ser Glu
            20                  25                  30
His Glu Ala Thr Lys Cys Gln Ser Phe Arg Asp His Met Lys Ser Val
        35                  40                  45
Ile Pro Ser Asp Gly Pro Ser Val Ala Cys Val Lys Lys Ala Ser Tyr
    50                  55                  60
Leu Asp Cys Ile Arg Ala Ile Ala Ala Asn Glu Ala Asp Ala Val Thr
```

-continued

|  |  |  |  |
|---|---|---|---|
| 65 | 70 | 75 | 80 |

Leu Asp Ala Gly Leu Val Tyr Asp Ala Tyr Leu Ala Pro Asn Asn Leu
              85                  90                  95

Lys Pro Val Val Ala Glu Phe Tyr Gly Ser Lys Glu Asp Pro Gln Thr
             100                 105                 110

Phe Tyr Tyr Ala Val Ala Val Lys Lys Asp Ser Gly Phe Gln Met
             115                 120                 125

Asn Gln Leu Arg Gly Lys Ser Cys His Thr Gly Leu Gly Arg Ser
         130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                 165                 170                 175

Cys Ala Pro Cys Ala Asp Gly Thr Asp Phe Pro Gln Leu Cys Gln Leu
                 180                 185                 190

Cys Pro Gly Cys Gly Cys Ser Thr Leu Asn Gln Tyr Phe Gly Tyr Ser
                 195                 200                 205

Gly Ala Phe Lys Cys Leu Lys Asp Gly Ala Gly Asp Val Ala Phe Val
         210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                 245                 250                 255

Tyr Lys Asp Cys His Leu Ala Gln Val Pro Ser His Thr Val Val Ala
                 260                 265                 270

Arg Ser Met Gly Gly Lys Glu Asp Leu Ile Trp Glu Leu Leu Asn Gln
         275                 280                 285

Ala Gln Glu His Phe Gly Lys Asp Lys Ser Lys Glu Phe Gln Leu Phe
         290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                 325                 330                 335

Glu Tyr Val Thr Ala Ile Arg Asn Leu Arg Glu Gly Thr Cys Pro Glu
                 340                 345                 350

Ala Pro Thr Asp Glu Cys Lys Pro Val Lys Trp Cys Ala Leu Ser His
                 355                 360                 365

His Glu Arg Leu Lys Cys Asp Glu Trp Ser Val Asn Ser Val Gly Lys
         370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                 405                 410                 415

Ile Ala Gly Lys Cys Gly Leu Val Pro Val Leu Ala Glu Asn Tyr Asn
                 420                 425                 430

Lys Ser Asp Asn Cys Glu Asp Thr Pro Glu Ala Gly Tyr Phe Ala Val
         435                 440                 445

Ala Val Val Lys Lys Ser Ala Ser Asp Leu Thr Trp Asp Asn Leu Lys
         450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                 485                 490                 495

```
Glu Phe Phe Ser Glu Gly Cys Ala Pro Gly Ser Lys Lys Asp Ser Ser
                500                 505                 510

Leu Cys Lys Leu Cys Met Gly Gly Leu Asn Leu Cys Glu Pro Asn
            515                 520                 525

Asn Lys Glu Gly Tyr Tyr Gly Tyr Thr Gly Ala Phe Arg Cys Leu Val
        530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
                580                 585                 590

Tyr Ala Asn Cys His Leu Ala Arg Ala Pro Asn His Ala Val Val Thr
                595                 600                 605

Arg Lys Asp Lys Glu Ala Cys Val His Lys Ile Leu Arg Gln Gln Gln
            610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro Asn Leu Arg Gly Arg Ala
690                 695                 700

Ala Thr Lys Val Lys Met Gly Thr Gln Met Ile His Glu Phe Ala Leu
705                 710                 715                 720

Val Ser Leu Ala Gln Val Val Cys Ala Asn His Val Cys Leu His Ser
                725                 730                 735

Ser Val Leu Pro Cys Val Leu Asn Lys Lys
                740                 745

<210> SEQ ID NO 100
<211> LENGTH: 490
<212> TYPE: PRT
<213> ORGANISM: Homo sapiens

<400> SEQUENCE: 100

Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
            115                 120                 125
```

```
His Ser Ile Tyr Met Phe Phe Asn Thr Ser Glu Leu Arg Glu Ala Val
            130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
370                 375                 380

Arg Ser Cys Lys Cys Ser Gly Pro Ala Pro Arg Pro Ala Pro Pro Ala
385                 390                 395                 400

Gly Pro Ala Pro Pro Arg Pro Ala Pro Ala Ala Leu Pro Met Gly Ala
                405                 410                 415

Val Phe Lys Asp Thr Arg Ala Pro Ser Pro Gly Ala Pro Leu Lys
            420                 425                 430

Met Glu Arg Gly Leu Arg Ile Ser Val Ser Leu Gly Ala Cys Leu Gly
        435                 440                 445

Ser Pro Ser Leu Thr Phe Pro His Ser His Ser Leu Ser Leu Pro Leu
450                 455                 460

Cys Leu Leu Leu Pro Val Cys Thr Ile Pro Leu Pro Gly Ile Lys Ala
465                 470                 475                 480

Gln Gly Thr Ser Gly Glu His Tyr Cys Ser
                485                 490

<210> SEQ ID NO 101
<211> LENGTH: 163
<212> TYPE: PRT
<213> ORGANISM: Homo sapiens

<400> SEQUENCE: 101

Met Ala Ser His Arg Leu Leu Leu Leu Cys Leu Ala Gly Leu Val Phe
1               5                   10                  15
```

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
        50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                    85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
        130                 135                 140

Pro Lys Glu Gly Thr Ser Pro Pro Val Asp Leu Lys Asp Glu Gly Trp
145                 150                 155                 160

Asp Phe Met

<210> SEQ ID NO 102
<211> LENGTH: 69
<212> TYPE: PRT
<213> ORGANISM: Homo sapiens

<400> SEQUENCE: 102

Ala Arg His Gly Arg Asp Glu Glu Val Trp His Arg Lys His Ser His
1               5                   10                  15

His Phe Val Gln Ala Trp Ala Trp Val Gly Gly Leu Val Cys Trp Pro
            20                  25                  30

Arg Lys Cys His Met Arg Ser Thr Leu Ile Ser Ser Leu Asp Ser Leu
            35                  40                  45

Leu Pro Val Ile Pro His Arg Thr Glu Ala Glu Trp Val Val Val Met
        50                  55                  60

Phe Asp Arg Arg His
65

<210> SEQ ID NO 103
<211> LENGTH: 26
<212> TYPE: PRT
<213> ORGANISM: Homo sapiens

<400> SEQUENCE: 103

Arg Ser Lys Ala Tyr Ser Ser Val Phe Leu Phe Arg Trp Cys Lys Ala
1               5                   10                  15

Asn Thr Leu Ser Lys Lys His Lys Phe Leu
            20                  25

<210> SEQ ID NO 104
<211> LENGTH: 14
<212> TYPE: PRT
<213> ORGANISM: Homo sapiens

<400> SEQUENCE: 104

Gly Leu Asp Ser Thr Arg Ala Leu Glu Asn Glu Met Thr Val
1               5                   10

<210> SEQ ID NO 105
<211> LENGTH: 12

```
<212> TYPE: PRT
<213> ORGANISM: Homo sapiens

<400> SEQUENCE: 105

Gly Ala Arg Arg Arg Pro Pro Ser Arg Cys Ser Glu
1               5                   10

<210> SEQ ID NO 106
<211> LENGTH: 20
<212> TYPE: PRT
<213> ORGANISM: Homo sapiens

<400> SEQUENCE: 106

Ser Val Gln Thr Ile Val Phe Gln Pro Gln Leu Ala Ser Arg Thr Pro
1               5                   10                  15

Thr Gly Gln Ser
            20

<210> SEQ ID NO 107
<211> LENGTH: 22
<212> TYPE: PRT
<213> ORGANISM: Homo sapiens

<400> SEQUENCE: 107

Gln Pro Asp Pro Pro Ser Val Asp Lys Gly Arg Val Pro Tyr Ser Pro
1               5                   10                  15

Asp Pro Pro Gly Ser Asp
            20

<210> SEQ ID NO 108
<211> LENGTH: 54
<212> TYPE: PRT
<213> ORGANISM: Homo sapiens

<400> SEQUENCE: 108

Asp Leu Asn Thr Pro Ser Pro Pro Ala Tyr Pro Ser Cys Glu Leu Leu
1               5                   10                  15

Gly Ser Cys Asn Leu Gln Gly Cys Pro Cys Arg Leu Leu Lys Arg Asp
                20                  25                  30

Ser Ile Leu Ser Ala Leu Leu Pro His Leu Met Pro Gly Pro Pro
        35                  40                  45

Gly Met Leu Ala Ser Gln
    50

<210> SEQ ID NO 109
<211> LENGTH: 36
<212> TYPE: PRT
<213> ORGANISM: Homo sapiens

<400> SEQUENCE: 109

Pro Gly Ser Thr Gly Arg Leu His Pro Leu His Val Thr Ser Ala Ser
1               5                   10                  15

Leu Ser Pro Thr Pro Pro Pro His Lys Asp Lys Pro Ile Asn His
                20                  25                  30

Asp Lys Gly Ser
        35

<210> SEQ ID NO 110
<211> LENGTH: 37
<212> TYPE: PRT
<213> ORGANISM: Homo sapiens
```

-continued

<400> SEQUENCE: 110

Thr Pro Lys Pro Ala Ala Met Arg Pro His Ala Thr Pro Cys Leu Leu
1               5                   10                  15

Pro Pro Arg Ser Leu Gln Arg Glu Thr Leu Ser Pro Pro Gln Pro Ser
                20                  25                  30

Ser Trp Gly Gly Pro
            35

<210> SEQ ID NO 111
<211> LENGTH: 13
<212> TYPE: PRT
<213> ORGANISM: Homo sapiens

<400> SEQUENCE: 111

Glu Ala Arg Val Gly Gly Asn Val Gly Ser Gln Thr Gln
1               5                   10

<210> SEQ ID NO 112
<211> LENGTH: 29
<212> TYPE: PRT
<213> ORGANISM: Homo sapiens

<400> SEQUENCE: 112

Pro Ser Val Leu His Thr Ala Arg Gly Pro Arg Met Pro Arg Pro Pro
1               5                   10                  15

Leu Ala Pro Ala Gly Arg Glu Pro Asp His Leu Pro Cys
                20                  25

<210> SEQ ID NO 113
<211> LENGTH: 72
<212> TYPE: PRT
<213> ORGANISM: Homo sapiens

<400> SEQUENCE: 113

Asp Val Asp Val Ala Phe Ala Pro Thr Gly Ala Ser Glu Ser Ser Ser
1               5                   10                  15

Pro Gln Asp Glu Leu Gln Pro Pro Arg Glu Ser Ser Ala Arg His Gln
                20                  25                  30

Val Thr Arg Pro Gln Pro Pro Gly Pro Gln Leu Arg Pro Ala Ser Pro
                35                  40                  45

Arg Ser Gly Ser Cys Thr Leu Thr Leu Asp Ser Ala Ala His Gly Lys
    50                  55                  60

Asn Arg Ile Ala Pro Ala Cys Asn
65                  70

<210> SEQ ID NO 114
<211> LENGTH: 14
<212> TYPE: PRT
<213> ORGANISM: Homo sapiens

<400> SEQUENCE: 114

Asn Val Ile Pro Leu Lys Arg Lys Met Asn Asn Thr Leu Asn
1               5                   10

<210> SEQ ID NO 115
<211> LENGTH: 39
<212> TYPE: PRT
<213> ORGANISM: Homo sapiens

```
<400> SEQUENCE: 115

Thr Pro Ala Ala Arg Leu Met Trp Ser Ser Asn Met Pro Tyr Phe Ala
1               5                   10                  15

Gln Lys Thr Ala Lys Asp Met Thr Ser Ser Trp Leu Gln Pro Arg Phe
            20                  25                  30

Ile Phe Leu Phe Val Val Asn
            35

<210> SEQ ID NO 116
<211> LENGTH: 53
<212> TYPE: PRT
<213> ORGANISM: Homo sapiens

<400> SEQUENCE: 116

Gly Trp Gly Val Phe Leu Leu Asn Pro Met Ala Gly His Ala Pro
1               5                   10                  15

Thr Ile Ile Ser Trp Glu Glu Arg Gln Ser Trp Glu Ile Asp Gly Ser
            20                  25                  30

His Ser Ser Leu Leu Ser Leu Leu Cys Leu Trp Ala Thr Leu Pro Thr
            35                  40                  45

Pro Leu Leu Ser Gln
            50

<210> SEQ ID NO 117
<211> LENGTH: 27
<212> TYPE: PRT
<213> ORGANISM: Homo sapiens

<400> SEQUENCE: 117

Thr Gly Pro Thr His His Ser Pro Ser Pro Ser Ile Ser Thr Trp Cys
1               5                   10                  15

Leu Val Pro Val His Ser Val Asn Lys Lys Pro
            20                  25

<210> SEQ ID NO 118
<211> LENGTH: 25
<212> TYPE: PRT
<213> ORGANISM: Homo sapiens

<400> SEQUENCE: 118

Trp Thr Pro Glu Pro Leu Leu Gln Pro Leu Ser His Pro Leu Pro Pro
1               5                   10                  15

Ala His Pro Leu Gly Gln Gln Arg Leu
            20                  25

<210> SEQ ID NO 119
<211> LENGTH: 20
<212> TYPE: PRT
<213> ORGANISM: Homo sapiens

<400> SEQUENCE: 119

Leu Asp Gly Arg Gln Ser Asp Ala Leu Thr His Leu Glu Ala Gly Thr
1               5                   10                  15

Trp Val Gly Ile
            20

<210> SEQ ID NO 120
<211> LENGTH: 71
<212> TYPE: PRT
<213> ORGANISM: Homo sapiens
```

<400> SEQUENCE: 120

Ser Leu Pro Ser Ser Gly Ala Leu Ser Lys Glu Leu Gly Met Gln
1               5                   10                  15

Ala Gly Cys Leu Gly Leu Trp Ala Gln Pro Gly Pro Cys Ala Pro Ser
                20                  25                  30

Gly His Gly Met Cys Gly Pro Val Cys Leu Ser Leu Glu Gly Asp Ser
                35                  40                  45

Asp Ser Leu Cys Ser Ser His Met His Arg Gly Pro Trp Thr Leu Gln
    50                  55                  60

Ser Gly Gly Ser Trp Ala Ser
65                  70

<210> SEQ ID NO 121
<211> LENGTH: 48
<212> TYPE: PRT
<213> ORGANISM: Homo sapiens

<400> SEQUENCE: 121

Asn Leu Arg Gly Arg Ala Ala Thr Lys Val Lys Met Gly Thr Gln Met
1               5                   10                  15

Ile His Glu Phe Ala Leu Val Ser Leu Ala Gln Val Val Cys Ala Asn
                20                  25                  30

His Val Cys Leu His Ser Ser Val Leu Pro Cys Val Leu Asn Lys Lys
                35                  40                  45

<210> SEQ ID NO 122
<211> LENGTH: 100
<212> TYPE: PRT
<213> ORGANISM: Homo sapiens

<400> SEQUENCE: 122

Gly Pro Ala Pro Pro Arg Pro Ala Pro Gly Pro Ala Pro Pro Arg
1               5                   10                  15

Pro Ala Pro Ala Ala Leu Pro Met Gly Ala Val Phe Lys Asp Thr Arg
                20                  25                  30

Ala Pro Ser Pro Pro Gly Ala Pro Leu Lys Met Glu Arg Gly Leu Arg
                35                  40                  45

Ile Ser Val Ser Leu Gly Ala Cys Leu Gly Ser Pro Ser Leu Thr Phe
    50                  55                  60

Pro His Ser His Ser Leu Ser Leu Pro Leu Cys Leu Leu Leu Pro Val
65                  70                  75                  80

Cys Thr Ile Pro Leu Pro Gly Ile Lys Ala Gln Gly Thr Ser Gly Glu
                85                  90                  95

His Tyr Cys Ser
            100

<210> SEQ ID NO 123
<211> LENGTH: 16
<212> TYPE: PRT
<213> ORGANISM: Homo sapiens

<400> SEQUENCE: 123

Gly Thr Ser Pro Pro Val Asp Leu Lys Asp Glu Gly Trp Asp Phe Met
1               5                   10                  15

<210> SEQ ID NO 124
<211> LENGTH: 25
<212> TYPE: DNA
<213> ORGANISM: Artificial sequence

```
<220> FEATURE:
<223> OTHER INFORMATION: Primer complement

<400> SEQUENCE: 124
gaaatgagct tgacaaagtg gtcgt                                              25

<210> SEQ ID NO 125
<211> LENGTH: 25
<212> TYPE: DNA
<213> ORGANISM: Artificial sequence
<220> FEATURE:
<223> OTHER INFORMATION: Primer complement

<400> SEQUENCE: 125
ctcatgggtc actgaggctt tttat                                              25

<210> SEQ ID NO 126
<211> LENGTH: 28
<212> TYPE: DNA
<213> ORGANISM: Artificial sequence
<220> FEATURE:
<223> OTHER INFORMATION: Primer complement

<400> SEQUENCE: 126
ttttatttgc atattaaaaa aattgtgc                                           28
```